US012807662B2

(12) United States Patent
Anderson

(10) Patent No.: US 12,807,662 B2
(45) Date of Patent: Nov. 24, 2026

(54) TARGETED TRANSLATION OF RNA WITH CRISPR-Cas13 TO ENHANCE PROTEIN SYNTHESIS

(71) Applicant: University of Rochester, Rochester, NY (US)

(72) Inventor: Douglas Matthew Anderson, Pittsford, NY (US)

(73) Assignee: University of Rochester, Rochester, NY (US)

( * ) Notice: Subject to any disclaimer, the term of this patent is extended or adjusted under 35 U.S.C. 154(b) by 937 days.

(21) Appl. No.: 17/760,222

(22) PCT Filed: Feb. 5, 2021

(86) PCT No.: PCT/US2021/016907
§ 371 (c)(1),
(2) Date: Aug. 5, 2022

(87) PCT Pub. No.: WO2021/158982
PCT Pub. Date: Aug. 12, 2021

(65) Prior Publication Data

US 2023/0078498 A1 Mar. 16, 2023

Related U.S. Application Data

(60) Provisional application No. 62/971,353, filed on Feb. 7, 2020.

(51) Int. Cl.
*C07K 14/47* (2006.01)
*C12N 9/14* (2006.01)
(Continued)

(52) U.S. Cl.
CPC ............ *C07K 14/4705* (2013.01); *C12N 9/14* (2013.01); *C12N 9/22* (2013.01); *C12N 15/11* (2013.01);
(Continued)

(58) Field of Classification Search
CPC ...................... C07K 2319/00; C07K 14/4705; C12N 15/62; C12N 2310/20; C12N 15/67; C12N 9/22
See application file for complete search history.

(56) References Cited

U.S. PATENT DOCUMENTS

2021/0340508 A1 11/2021 Anderson
2021/0363509 A1 11/2021 Anderson
(Continued)

FOREIGN PATENT DOCUMENTS

JP 2006518996 A 8/2006
JP 2019524072 A 9/2019
(Continued)

OTHER PUBLICATIONS

Hayward, Carl, et al. "Gene Therapy in Heart Failure." Circulation Journal, vol. 78, No. 11, 2014, pp. 2577-2587, https://doi.org/10.1253/circj.cj-14-1053. Accessed Jan. 12, 2022. (Year: 2014).*
(Continued)

*Primary Examiner* — Kimberly Chong
*Assistant Examiner* — Africa M Mcleod
(74) *Attorney, Agent, or Firm* — Riverside Law LLP

(57) ABSTRACT

The present disclosure provides proteins, nucleic acids, systems and methods for enhancing the synthesis of a protein.

10 Claims, 2 Drawing Sheets

Specification includes a Sequence Listing.

(51) Int. Cl.
*C12N 9/22* (2006.01)
*C12N 15/11* (2006.01)
*C12N 15/62* (2006.01)

(52) U.S. Cl.
CPC .... *C12N 15/625* (2013.01); *C12Y 306/03008* (2013.01); *C07K 2319/00* (2013.01); *C07K 2319/01* (2013.01); *C12N 2310/20* (2017.05); *C12N 2800/80* (2013.01)

(56) References Cited

U.S. PATENT DOCUMENTS

| | | | |
|---|---|---|---|
| 2022/0090088 | A1 | 3/2022 | Anderson |
| 2022/0267773 | A1 | 8/2022 | Anderson |
| 2023/0073250 | A1 | 3/2023 | Anderson |
| 2024/0218367 | A1 | 7/2024 | Anderson |

FOREIGN PATENT DOCUMENTS

| | | | |
|---|---|---|---|
| WO | 9632139 | 10/1996 | |
| WO | 2017219027 | 12/2017 | |
| WO | WO-2019204828 A1 * | 10/2019 | ............. C07K 14/47 |

OTHER PUBLICATIONS

He, Ziqi, et al. "Development and Application of the CRISPR-Dcas13d-EIF4G Translational Regulatory System to Inhibit Ferroptosis in Calcium Oxalate Crystal-Induced Kidney Injury." Advanced Science, vol. 11, No. 17, Feb. 21, 2024, https://doi.org/10.1002/advs.202309234. Accessed May 9, 2025. (Year: 2024).*

Marintchev, Assen, and Gerhard Wagner. "Translation Initiation: Structures, Mechanisms and Evolution." Quarterly Reviews of Biophysics, vol. 37, No. 3-4, Aug. 1, 2004, pp. 197-284, pubmed.ncbi.nlm.nih.gov/16194295/, https://doi.org/10.1017/S0033583505004026. (Year: 2004).*

Royall, Elizabeth, and Nicolas Locker. "Translational Control during Calicivirus Infection." Viruses, vol. 8, No. 4, Apr. 20, 2016, p. 104, https://doi.org/10.3390/v8040104. Accessed Oct. 29, 2020. (Year: 2016).*

"VPg [Feline Calicivirus]—Protein—NCBI." Nih.gov, Aug. 13, 2018, www.ncbi.nlm.nih.gov/protein/NP_783307.1. Accessed May 9, 2025. (Year: 2018).*

De Gregorio, E. "Translation Driven by an EIF4G Core Domain in Vivo." The EMBO Journal, vol. 18, No. 17, Sep. 1, 1999, pp. 4865-4874, https://doi.org/10.1093/emboj/18.17.4865. Accessed Nov. 25, 2021. (Year: 1999).*

UniProt. "Q04637 • IF4G1_HUMAN; Eukaryotic Translation Initiation Factor 4 Gamma 1." UniProt, Feb. 1, 1995, www.uniprot.org/uniprotkb/Q04637/entry. Accessed Nov. 24, 2025. (Year: 1995).*

De Gregorio E et al, "Translation driven by and elF4G core domain in vivo", The EMBO Journal / European Molecular Biology Organization, IRL Press, Oxford, (Jan. 1, 1999), vol. 18, No. 17, doi:10.1093/EMBOJ/18.17.4865, ISSN 0261-4189, pp. 4865-4874, XP002123172.

Goodfellow I. 2011. The genome-linked protein VPg of vertebrate viruses—a multifaceted protein. Curr Opin Virol 1: 355-362.

Laursen BS, Sorensen HP, Mortensen KK, Sperling-Petersen HU. 2005. Initiation of protein synthesis in bacteria. Microbiol Mol Biol Rev 69: 101-123.

Mazumder B et al., "Translational control by the 3'-UTR: the ends specify the means", Trends in Biochemical Sciences, Elsevier, Amsterdam, NL, (Feb. 1, 2003), vol. 28, No. 2, doi:10.1016/S0968-0004(03)00002-1, ISSN 0968-0004, pp. 91-98, XP004405616.

Mir MA, Panganiban AT. 2008. A protein that replaces the entire cellular elF4F complex. The EMBO journal 27:3129-3139.

* cited by examiner

1D

1E

1F

SEQUENCE LISTING

```
<160> NUMBER OF SEQ ID NOS: 95

<210> SEQ ID NO 1
<211> LENGTH: 1089
<212> TYPE: PRT
<213> ORGANISM: Artificial Sequence
<220> FEATURE:
<223> OTHER INFORMATION: Chemically synthesized

<400> SEQUENCE: 1

Asn Ile Pro Ala Leu Val Glu Asn Gln Lys Lys Tyr Phe Gly Thr Tyr
1               5                   10                  15

Ser Val Met Ala Met Leu Asn Ala Gln Thr Val Leu Asp His Ile Gln
            20                  25                  30

Lys Val Ala Asp Ile Glu Gly Glu Gln Asn Glu Asn Asn Glu Asn Leu
        35                  40                  45

Trp Phe His Pro Val Met Ser His Leu Tyr Asn Ala Lys Asn Gly Tyr
```

```
    50                  55                  60

Asp Lys Gln Pro Glu Lys Thr Met Phe Ile Ile Glu Arg Leu Gln Ser
65                  70                  75                  80

Tyr Phe Pro Phe Leu Lys Ile Met Ala Glu Asn Gln Arg Glu Tyr Ser
                85                  90                  95

Asn Gly Lys Tyr Lys Gln Asn Arg Val Glu Val Asn Ser Asn Asp Ile
            100                 105                 110

Phe Glu Val Leu Lys Arg Ala Phe Gly Val Leu Lys Met Tyr Arg Asp
        115                 120                 125

Leu Thr Asn His Tyr Lys Thr Tyr Glu Glu Lys Leu Asn Asp Gly Cys
    130                 135                 140

Glu Phe Leu Thr Ser Thr Glu Gln Pro Leu Ser Gly Met Ile Asn Asn
145                 150                 155                 160

Tyr Tyr Thr Val Ala Leu Arg Asn Met Asn Glu Arg Tyr Gly Tyr Lys
                165                 170                 175

Thr Glu Asp Leu Ala Phe Ile Gln Asp Lys Arg Phe Lys Phe Val Lys
            180                 185                 190

Asp Ala Tyr Gly Lys Lys Lys Ser Gln Val Asn Thr Gly Phe Phe Leu
        195                 200                 205

Ser Leu Gln Asp Tyr Asn Gly Asp Thr Gln Lys Lys Leu His Leu Ser
    210                 215                 220

Gly Val Gly Ile Ala Leu Leu Ile Cys Leu Phe Leu Asp Lys Gln Tyr
225                 230                 235                 240

Ile Asn Ile Phe Leu Ser Arg Leu Pro Ile Phe Ser Ser Tyr Asn Ala
                245                 250                 255

Gln Ser Glu Glu Arg Arg Ile Ile Ile Arg Ser Phe Gly Ile Asn Ser
            260                 265                 270

Ile Lys Leu Pro Lys Asp Arg Ile His Ser Glu Lys Ser Asn Lys Ser
        275                 280                 285

Val Ala Met Asp Met Leu Asn Glu Val Lys Arg Cys Pro Asp Glu Leu
    290                 295                 300

Phe Thr Thr Leu Ser Ala Glu Lys Gln Ser Arg Phe Arg Ile Ile Ser
305                 310                 315                 320

Asp Asp His Asn Glu Val Leu Met Lys Arg Ser Ser Asp Arg Phe Val
                325                 330                 335

Pro Leu Leu Leu Gln Tyr Ile Asp Tyr Gly Lys Leu Phe Asp His Ile
            340                 345                 350

Arg Phe His Val Asn Met Gly Lys Leu Arg Tyr Leu Leu Lys Ala Asp
        355                 360                 365

Lys Thr Cys Ile Asp Gly Gln Thr Arg Val Arg Val Ile Glu Gln Pro
    370                 375                 380

Leu Asn Gly Phe Gly Arg Leu Glu Glu Ala Glu Thr Met Arg Lys Gln
385                 390                 395                 400

Glu Asn Gly Thr Phe Gly Asn Ser Gly Ile Arg Ile Arg Asp Phe Glu
                405                 410                 415

Asn Met Lys Arg Asp Asp Ala Asn Pro Ala Asn Tyr Pro Tyr Ile Val
            420                 425                 430

Asp Thr Tyr Thr His Tyr Ile Leu Glu Asn Asn Lys Val Glu Met Phe
        435                 440                 445

Ile Asn Asp Lys Glu Asp Ser Ala Pro Leu Leu Pro Val Ile Glu Asp
    450                 455                 460

Asp Arg Tyr Val Val Lys Thr Ile Pro Ser Cys Arg Met Ser Thr Leu
465                 470                 475                 480
```

```
Glu Ile Pro Ala Met Ala Phe His Met Phe Leu Phe Gly Ser Lys Lys
                485                 490                 495

Thr Glu Lys Leu Ile Val Asp Val His Asn Arg Tyr Lys Arg Leu Phe
            500                 505                 510

Gln Ala Met Gln Lys Glu Glu Val Thr Ala Glu Asn Ile Ala Ser Phe
        515                 520                 525

Gly Ile Ala Glu Ser Asp Leu Pro Gln Lys Ile Leu Asp Leu Ile Ser
    530                 535                 540

Gly Asn Ala His Gly Lys Asp Val Asp Ala Phe Ile Arg Leu Thr Val
545                 550                 555                 560

Asp Asp Met Leu Thr Asp Thr Glu Arg Arg Ile Lys Arg Phe Lys Asp
                565                 570                 575

Asp Arg Lys Ser Ile Arg Ser Ala Asp Asn Lys Met Gly Lys Arg Gly
            580                 585                 590

Phe Lys Gln Ile Ser Thr Gly Lys Leu Ala Asp Phe Leu Ala Lys Asp
        595                 600                 605

Ile Val Leu Phe Gln Pro Ser Val Asn Asp Gly Glu Asn Lys Ile Thr
    610                 615                 620

Gly Leu Asn Tyr Arg Ile Met Gln Ser Ala Ile Ala Val Tyr Asp Ser
625                 630                 635                 640

Gly Asp Asp Tyr Glu Ala Lys Gln Gln Phe Lys Leu Met Phe Glu Lys
                645                 650                 655

Ala Arg Leu Ile Gly Lys Gly Thr Thr Glu Pro His Pro Phe Leu Tyr
            660                 665                 670

Lys Val Phe Ala Arg Ser Ile Pro Ala Asn Ala Val Glu Phe Tyr Glu
        675                 680                 685

Arg Tyr Leu Ile Glu Arg Lys Phe Tyr Leu Thr Gly Leu Ser Asn Glu
    690                 695                 700

Ile Lys Lys Gly Asn Arg Val Asp Val Pro Phe Ile Arg Arg Asp Gln
705                 710                 715                 720

Asn Lys Trp Lys Thr Pro Ala Met Lys Thr Leu Gly Arg Ile Tyr Ser
                725                 730                 735

Glu Asp Leu Pro Val Glu Leu Pro Arg Gln Met Phe Asp Asn Glu Ile
            740                 745                 750

Lys Ser His Leu Lys Ser Leu Pro Gln Met Glu Gly Ile Asp Phe Asn
        755                 760                 765

Asn Ala Asn Val Thr Tyr Leu Ile Ala Glu Tyr Met Lys Arg Val Leu
    770                 775                 780

Asp Asp Asp Phe Gln Thr Phe Tyr Gln Trp Asn Arg Asn Tyr Arg Tyr
785                 790                 795                 800

Met Asp Met Leu Lys Gly Glu Tyr Asp Arg Lys Gly Ser Leu Gln His
                805                 810                 815

Cys Phe Thr Ser Val Glu Glu Arg Glu Gly Leu Trp Lys Glu Arg Ala
            820                 825                 830

Ser Arg Thr Glu Arg Tyr Arg Lys Gln Ala Ser Asn Lys Ile Arg Ser
        835                 840                 845

Asn Arg Gln Met Arg Asn Ala Ser Ser Glu Glu Ile Glu Thr Ile Leu
    850                 855                 860

Asp Lys Arg Leu Ser Asn Ser Arg Asn Glu Tyr Gln Lys Ser Glu Lys
865                 870                 875                 880

Val Ile Arg Arg Tyr Arg Val Gln Asp Ala Leu Leu Phe Leu Leu Ala
                885                 890                 895
```

```
Lys Lys Thr Leu Thr Glu Leu Ala Asp Phe Asp Gly Glu Arg Phe Lys
            900                 905                 910

Leu Lys Glu Ile Met Pro Asp Ala Glu Lys Gly Ile Leu Ser Glu Ile
        915                 920                 925

Met Pro Met Ser Phe Thr Phe Glu Lys Gly Gly Lys Lys Tyr Thr Ile
    930                 935                 940

Thr Ser Glu Gly Met Lys Leu Lys Asn Tyr Gly Asp Phe Phe Val Leu
945                 950                 955                 960

Ala Ser Asp Lys Arg Ile Gly Asn Leu Leu Glu Leu Val Gly Ser Asp
                965                 970                 975

Ile Val Ser Lys Glu Asp Ile Met Glu Glu Phe Asn Lys Tyr Asp Gln
            980                 985                 990

Cys Arg Pro Glu Ile Ser Ser Ile  Val Phe Asn Leu Glu  Lys Trp Ala
        995                 1000                 1005

Phe Asp  Thr Tyr Pro Glu Leu  Ser Ala Arg Val Asp  Arg Glu Glu
    1010                 1015                 1020

Lys Val  Asp Phe Lys Ser Ile  Leu Lys Ile Leu Leu  Asn Asn Lys
    1025                 1030                 1035

Asn Ile  Asn Lys Glu Gln Ser  Asp Ile Leu Arg Lys  Ile Arg Asn
    1040                 1045                 1050

Ala Phe  Asp His Asn Asn Tyr  Pro Asp Lys Gly Val  Val Glu Ile
    1055                 1060                 1065

Lys Ala  Leu Pro Glu Ile Ala  Met Ser Ile Lys Lys  Ala Phe Gly
    1070                 1075                 1080

Glu Tyr  Ala Ile Met Lys
    1085
```

<210> SEQ ID NO 2
<211> LENGTH: 982
<212> TYPE: PRT
<213> ORGANISM: Artificial Sequence
<220> FEATURE:
<223> OTHER INFORMATION: Chemically synthesized

<400> SEQUENCE: 2

```
Asn Ile Pro Ala Leu Val Glu Asn Gln Lys Lys Tyr Phe Gly Thr Tyr
1               5                   10                  15

Ser Val Met Ala Met Leu Asn Ala Gln Thr Val Leu Asp His Ile Gln
            20                  25                  30

Lys Val Ala Asp Ile Glu Gly Glu Gln Asn Glu Asn Asn Glu Asn Leu
        35                  40                  45

Trp Phe His Pro Val Met Ser His Leu Tyr Asn Ala Lys Asn Gly Tyr
    50                  55                  60

Asp Lys Gln Pro Glu Lys Thr Met Phe Ile Ile Glu Arg Leu Gln Ser
65                  70                  75                  80

Tyr Phe Pro Phe Leu Lys Ile Met Ala Glu Asn Gln Arg Glu Tyr Ser
                85                  90                  95

Asn Gly Lys Tyr Lys Gln Asn Arg Val Glu Val Asn Ser Asn Asp Ile
            100                 105                 110

Phe Glu Val Leu Lys Arg Ala Phe Gly Val Leu Lys Met Tyr Arg Asp
        115                 120                 125

Leu Thr Asn His Tyr Lys Thr Tyr Glu Glu Lys Leu Asn Asp Gly Cys
    130                 135                 140

Glu Phe Leu Thr Ser Thr Glu Gln Pro Leu Ser Gly Met Ile Asn Asn
145                 150                 155                 160
```

-continued

```
Tyr Tyr Thr Val Ala Leu Arg Asn Met Asn Glu Arg Tyr Gly Tyr Lys
                165                 170                 175

Thr Glu Asp Leu Ala Phe Ile Gln Asp Lys Arg Phe Lys Phe Val Lys
            180                 185                 190

Asp Ala Tyr Gly Lys Lys Lys Ser Gln Val Asn Thr Gly Phe Phe Leu
        195                 200                 205

Ser Leu Gln Asp Tyr Asn Gly Asp Thr Gln Lys Lys Leu His Leu Ser
    210                 215                 220

Gly Val Gly Ile Ala Leu Leu Ile Cys Leu Phe Leu Asp Lys Gln Tyr
225                 230                 235                 240

Ile Asn Ile Phe Leu Ser Arg Leu Pro Ile Phe Ser Ser Tyr Asn Ala
                245                 250                 255

Gln Ser Glu Glu Arg Arg Ile Ile Ile Arg Ser Phe Gly Ile Asn Ser
            260                 265                 270

Ile Lys Leu Pro Lys Asp Arg Ile His Ser Glu Lys Ser Asn Lys Ser
        275                 280                 285

Val Ala Met Asp Met Leu Asn Glu Val Lys Arg Cys Pro Asp Glu Leu
    290                 295                 300

Phe Thr Thr Leu Ser Ala Glu Lys Gln Ser Arg Phe Arg Ile Ile Ser
305                 310                 315                 320

Asp Asp His Asn Glu Val Leu Met Lys Arg Ser Ser Asp Arg Phe Val
                325                 330                 335

Pro Leu Leu Leu Gln Tyr Ile Asp Tyr Gly Lys Leu Phe Asp His Ile
            340                 345                 350

Arg Phe His Val Asn Met Gly Lys Leu Arg Tyr Leu Leu Lys Ala Asp
        355                 360                 365

Lys Thr Cys Ile Asp Gly Gln Thr Arg Val Arg Val Ile Glu Gln Pro
    370                 375                 380

Leu Asn Gly Phe Gly Arg Leu Glu Glu Ala Glu Thr Met Arg Lys Gln
385                 390                 395                 400

Glu Asn Gly Thr Phe Gly Asn Ser Gly Ile Arg Ile Arg Asp Phe Glu
                405                 410                 415

Asn Met Lys Arg Asp Asp Ala Asn Pro Ala Asn Tyr Pro Tyr Ile Val
            420                 425                 430

Asp Thr Tyr Thr His Tyr Ile Leu Glu Asn Asn Lys Val Glu Met Phe
        435                 440                 445

Ile Asn Asp Lys Glu Asp Ser Ala Pro Leu Leu Pro Val Ile Glu Asp
    450                 455                 460

Asp Arg Tyr Val Val Lys Thr Ile Pro Ser Cys Arg Met Ser Thr Leu
465                 470                 475                 480

Glu Ile Pro Ala Met Ala Phe His Met Phe Leu Phe Gly Ser Lys Lys
                485                 490                 495

Thr Glu Lys Leu Ile Val Asp Val His Asn Arg Tyr Lys Arg Leu Phe
            500                 505                 510

Gln Ala Met Gln Lys Glu Glu Val Thr Ala Glu Asn Ile Ala Ser Phe
        515                 520                 525

Gly Ile Ala Glu Ser Asp Leu Pro Gln Lys Ile Leu Asp Leu Ile Ser
    530                 535                 540

Gly Asn Ala His Gly Lys Asp Val Asp Ala Phe Ile Arg Leu Thr Val
545                 550                 555                 560

Asp Asp Met Leu Thr Asp Thr Glu Arg Arg Ile Lys Arg Phe Lys Asp
                565                 570                 575

Asp Arg Lys Ser Ile Arg Ser Ala Asp Asn Lys Met Gly Lys Arg Gly
```

```
            580                 585                 590

Phe Lys Gln Ile Ser Thr Gly Lys Leu Ala Asp Phe Leu Ala Lys Asp
        595                 600                 605

Ile Val Leu Phe Gln Pro Ser Val Asn Asp Gly Glu Asn Lys Ile Thr
    610                 615                 620

Gly Leu Asn Tyr Arg Ile Met Gln Ser Ala Ile Ala Val Tyr Asp Ser
625                 630                 635                 640

Gly Asp Asp Tyr Glu Ala Lys Gln Gln Phe Lys Leu Met Phe Glu Lys
                645                 650                 655

Ala Arg Leu Ile Gly Lys Gly Thr Thr Glu Pro His Pro Phe Leu Tyr
            660                 665                 670

Lys Val Phe Ala Arg Ser Ile Pro Ala Asn Ala Val Glu Phe Tyr Glu
        675                 680                 685

Arg Tyr Leu Ile Glu Arg Lys Phe Tyr Leu Thr Gly Leu Ser Asn Glu
    690                 695                 700

Ile Lys Lys Gly Asn Arg Val Asp Val Pro Phe Ile Arg Arg Asp Gln
705                 710                 715                 720

Asn Lys Trp Lys Thr Pro Ala Met Lys Thr Leu Gly Arg Ile Tyr Ser
                725                 730                 735

Glu Asp Leu Pro Val Glu Leu Pro Arg Gln Met Phe Asp Asn Glu Ile
            740                 745                 750

Lys Ser His Leu Lys Ser Leu Pro Gln Met Glu Gly Ile Asp Phe Asn
        755                 760                 765

Asn Ala Asn Val Thr Tyr Leu Ile Ala Glu Tyr Met Lys Arg Val Leu
    770                 775                 780

Asp Asp Asp Phe Gln Thr Phe Tyr Gln Trp Asn Arg Asn Tyr Arg Tyr
785                 790                 795                 800

Met Asp Met Leu Lys Gly Glu Tyr Asp Arg Lys Gly Ser Leu Gln His
                805                 810                 815

Cys Phe Thr Ser Val Glu Glu Arg Glu Gly Leu Trp Lys Glu Arg Ala
            820                 825                 830

Ser Arg Thr Glu Arg Tyr Arg Lys Gln Ala Ser Asn Lys Ile Arg Ser
        835                 840                 845

Asn Arg Gln Met Arg Asn Ala Ser Ser Glu Glu Ile Glu Thr Ile Leu
    850                 855                 860

Asp Lys Arg Leu Ser Asn Ser Arg Asn Glu Tyr Gln Lys Ser Glu Lys
865                 870                 875                 880

Val Ile Arg Arg Tyr Arg Val Gln Asp Ala Leu Leu Phe Leu Leu Ala
                885                 890                 895

Lys Lys Thr Leu Thr Glu Leu Ala Asp Phe Asp Gly Glu Arg Phe Lys
            900                 905                 910

Leu Lys Glu Ile Met Pro Asp Ala Glu Lys Gly Ile Leu Ser Glu Ile
        915                 920                 925

Met Pro Met Ser Phe Thr Phe Glu Lys Gly Gly Lys Lys Tyr Thr Ile
    930                 935                 940

Thr Ser Glu Gly Met Lys Leu Lys Asn Tyr Gly Asp Phe Phe Val Leu
945                 950                 955                 960

Ala Ser Asp Lys Arg Ile Gly Asn Leu Leu Glu Leu Val Gly Ser Asp
                965                 970                 975

Ile Val Ser Lys Glu Asp
            980
```

<210> SEQ ID NO 3

<211> LENGTH: 953
<212> TYPE: PRT
<213> ORGANISM: Artificial Sequence
<220> FEATURE:
<223> OTHER INFORMATION: Chemically synthesized

<400> SEQUENCE: 3

```
Met Ser Asn Glu Ile Gly Ala Phe Arg Glu His Gln Phe Ala Tyr Ala
1               5                   10                  15

Pro Gly Asn Glu Lys Gln Glu Glu Ala Thr Phe Ala Thr Tyr Phe Asn
            20                  25                  30

Leu Ala Leu Ser Asn Val Glu Gly Met Met Phe Gly Glu Val Glu Ser
        35                  40                  45

Asn Pro Asp Lys Ile Glu Lys Ser Leu Asp Thr Leu Pro Pro Ala Ile
    50                  55                  60

Leu Arg Gln Ile Ala Ser Phe Ile Trp Leu Ser Lys Glu Asp His Pro
65                  70                  75                  80

Asp Lys Ala Tyr Ser Thr Glu Glu Val Lys Val Ile Val Thr Asp Leu
                85                  90                  95

Val Arg Arg Leu Cys Phe Tyr Arg Asn Tyr Phe Ser His Cys Phe Tyr
            100                 105                 110

Leu Asp Thr Gln Tyr Phe Tyr Ser Asp Glu Leu Val Asp Thr Thr Ala
        115                 120                 125

Ile Gly Glu Lys Leu Pro Tyr Asn Phe His His Phe Ile Thr Asn Arg
    130                 135                 140

Leu Phe Arg Tyr Ser Leu Pro Glu Ile Thr Leu Phe Arg Trp Asn Glu
145                 150                 155                 160

Gly Glu Arg Lys Tyr Glu Ile Leu Arg Asp Gly Leu Ile Phe Phe Cys
                165                 170                 175

Cys Leu Phe Leu Lys Arg Gly Gln Ala Glu Arg Phe Leu Asn Glu Leu
            180                 185                 190

Arg Phe Phe Lys Arg Thr Asp Glu Glu Gly Arg Ile Lys Arg Thr Ile
        195                 200                 205

Phe Thr Lys Tyr Cys Thr Arg Glu Ser His Lys His Ile Gly Ile Glu
    210                 215                 220

Glu Gln Asp Phe Leu Ile Phe Gln Asp Ile Ile Gly Asp Leu Asn Arg
225                 230                 235                 240

Val Pro Lys Val Cys Asp Gly Val Val Asp Leu Ser Lys Glu Asn Glu
                245                 250                 255

Arg Tyr Ile Lys Asn Arg Glu Thr Ser Asn Glu Ser Asp Glu Asn Lys
            260                 265                 270

Ala Arg Tyr Arg Leu Leu Ile Arg Glu Lys Asp Lys Phe Pro Tyr Tyr
        275                 280                 285

Leu Met Arg Tyr Ile Val Asp Phe Gly Val Leu Pro Cys Ile Thr Phe
    290                 295                 300

Lys Gln Asn Asp Tyr Ser Thr Lys Glu Gly Arg Gly Gln Phe His Tyr
305                 310                 315                 320

Gln Asp Ala Ala Val Ala Gln Glu Glu Arg Cys Tyr Asn Phe Val Val
                325                 330                 335

Arg Asn Gly Asn Val Tyr Tyr Ser Tyr Met Pro Gln Ala Gln Asn Val
            340                 345                 350

Val Arg Ile Ser Glu Leu Gln Gly Thr Ile Ser Val Glu Glu Leu Arg
        355                 360                 365

Asn Met Val Tyr Ala Ser Ile Asn Gly Lys Asp Val Asn Lys Ser Val
    370                 375                 380
```

```
Glu Gln Tyr Leu Tyr His Leu His Leu Leu Tyr Glu Lys Ile Leu Thr
385                 390                 395                 400

Ile Ser Gly Gln Thr Ile Lys Glu Gly Arg Val Asp Val Glu Asp Tyr
                405                 410                 415

Arg Pro Leu Leu Asp Lys Leu Leu Leu Arg Pro Ala Ser Asn Gly Glu
            420                 425                 430

Glu Leu Arg Arg Glu Leu Arg Lys Leu Leu Pro Lys Arg Val Cys Asp
        435                 440                 445

Leu Leu Ser Asn Arg Phe Asp Cys Ser Glu Gly Val Ser Ala Val Glu
    450                 455                 460

Lys Arg Leu Lys Ala Ile Leu Leu Arg His Glu Gln Leu Leu Leu Ser
465                 470                 475                 480

Gln Asn Pro Ala Leu His Ile Asp Lys Ile Lys Ser Val Ile Asp Tyr
                485                 490                 495

Leu Tyr Leu Phe Phe Ser Asp Asp Glu Lys Phe Arg Gln Gln Pro Thr
            500                 505                 510

Glu Lys Ala His Arg Gly Leu Lys Asp Glu Glu Phe Gln Met Tyr His
        515                 520                 525

Tyr Leu Val Gly Asp Tyr Asp Ser His Pro Leu Ala Leu Trp Lys Glu
    530                 535                 540

Leu Glu Ala Ser Gly Arg Leu Lys Pro Glu Met Arg Lys Leu Thr Ser
545                 550                 555                 560

Ala Thr Ser Leu His Gly Leu Tyr Met Leu Cys Leu Lys Gly Thr Val
                565                 570                 575

Glu Trp Cys Arg Lys Gln Leu Met Ser Ile Gly Lys Gly Thr Ala Lys
            580                 585                 590

Val Glu Ala Ile Ala Asp Arg Val Gly Leu Lys Leu Tyr Asp Lys Leu
        595                 600                 605

Lys Glu Tyr Thr Pro Glu Gln Leu Glu Arg Glu Val Lys Leu Val Val
    610                 615                 620

Met His Gly Tyr Ala Ala Ala Ala Thr Pro Lys Pro Lys Ala Gln Ala
625                 630                 635                 640

Ala Ile Pro Ser Lys Leu Thr Glu Leu Arg Phe Tyr Ser Phe Leu Gly
                645                 650                 655

Lys Arg Glu Met Ser Phe Ala Ala Phe Ile Arg Gln Asp Lys Lys Ala
            660                 665                 670

Gln Lys Leu Trp Leu Arg Asn Phe Tyr Thr Val Glu Asn Ile Lys Thr
        675                 680                 685

Leu Gln Lys Arg Gln Ala Ala Ala Asp Ala Ala Cys Lys Lys Leu Tyr
    690                 695                 700

Asn Leu Val Gly Glu Val Glu Arg Val His Thr Asn Asp Lys Val Leu
705                 710                 715                 720

Val Leu Val Ala Gln Arg Tyr Arg Glu Arg Leu Leu Asn Val Gly Ser
                725                 730                 735

Lys Cys Ala Val Thr Leu Asp Asn Pro Glu Arg Gln Gln Lys Leu Ala
            740                 745                 750

Asp Val Tyr Glu Val Gln Asn Ala Trp Leu Ser Ile Arg Phe Asp Asp
        755                 760                 765

Leu Asp Phe Thr Leu Thr His Val Asn Leu Ser Asn Leu Arg Lys Ala
    770                 775                 780

Tyr Asn Leu Ile Pro Arg Lys His Ile Leu Ala Phe Lys Glu Tyr Leu
785                 790                 795                 800
```

```
Asp Asn Arg Val Lys Gln Lys Leu Cys Glu Glu Cys Arg Asn Val Arg
                805                 810                 815

Arg Lys Glu Asp Leu Cys Thr Cys Cys Ser Pro Arg Tyr Ser Asn Leu
            820                 825                 830

Thr Ser Trp Leu Lys Glu Asn His Ser Glu Ser Ser Ile Glu Arg Glu
        835                 840                 845

Ala Ala Thr Met Met Leu Leu Asp Val Glu Arg Lys Leu Leu Ser Phe
    850                 855                 860

Leu Leu Asp Glu Arg Arg Lys Ala Ile Ile Glu Tyr Gly Lys Phe Ile
865                 870                 875                 880

Pro Phe Ser Ala Leu Val Lys Glu Cys Arg Leu Ala Asp Ala Gly Leu
                885                 890                 895

Cys Gly Ile Arg Asn Asp Val Leu His Asp Asn Val Ile Ser Tyr Ala
            900                 905                 910

Asp Ala Ile Gly Lys Leu Ser Ala Tyr Phe Pro Lys Glu Ala Ser Glu
        915                 920                 925

Ala Val Glu Tyr Ile Arg Arg Thr Lys Glu Val Arg Glu Gln Arg Arg
    930                 935                 940

Glu Glu Leu Met Ala Asn Ser Ser Gln
945                 950


<210> SEQ ID NO 4
<211> LENGTH: 1111
<212> TYPE: PRT
<213> ORGANISM: Artificial Sequence
<220> FEATURE:
<223> OTHER INFORMATION: Chemically synthesized

<400> SEQUENCE: 4

Met Lys Ser Gly Arg Arg Glu Lys Ala Lys Ser Asn Lys Ser Ser Ile
1               5                   10                  15

Val Arg Val Ile Ile Ser Asn Phe Asp Asp Lys Gln Val Lys Glu Ile
            20                  25                  30

Lys Val Leu Tyr Thr Lys Gln Gly Gly Ile Asp Val Ile Lys Phe Lys
        35                  40                  45

Ser Thr Glu Lys Asp Glu Lys Gly Arg Met Lys Phe Asn Phe Asp Cys
    50                  55                  60

Ala Tyr Asn Arg Leu Glu Glu Glu Glu Phe Asn Ser Phe Gly Gly Lys
65                  70                  75                  80

Gly Lys Gln Ser Phe Phe Val Thr Thr Asn Glu Asp Leu Thr Glu Leu
                85                  90                  95

His Val Thr Lys Arg His Lys Thr Thr Gly Glu Ile Ile Lys Asp Tyr
            100                 105                 110

Thr Ile Gln Gly Lys Tyr Thr Pro Ile Lys Gln Asp Arg Thr Lys Val
        115                 120                 125

Thr Val Ser Ile Thr Asp Asn Lys Asp His Phe Asp Ser Asn Asp Leu
    130                 135                 140

Gly Asp Lys Ile Arg Leu Ser Arg Ser Leu Thr Gln Tyr Thr Asn Arg
145                 150                 155                 160

Ile Leu Leu Asp Ala Asp Val Met Lys Asn Tyr Arg Glu Ile Val Cys
                165                 170                 175

Ser Asp Ser Glu Lys Val Asp Glu Thr Ile Asn Ile Asp Ser Gln Glu
            180                 185                 190

Ile Tyr Lys Ile Asn Arg Phe Leu Ser Tyr Arg Ser Asn Met Ile Ile
        195                 200                 205
```

```
Tyr Tyr Gln Met Ile Asn Asn Phe Leu Leu His Tyr Asp Gly Glu Glu
    210                 215                 220

Asp Lys Gly Gly Asn Asp Ser Ile Asn Leu Ile Asn Glu Ile Trp Lys
225                 230                 235                 240

Tyr Glu Asn Lys Lys Asn Asp Glu Lys Glu Lys Ile Ile Glu Arg Ser
                245                 250                 255

Tyr Lys Ser Ile Glu Lys Ser Ile Asn Gln Tyr Ile Leu Asn His Asn
            260                 265                 270

Thr Glu Val Glu Ser Gly Asp Lys Glu Lys Lys Ile Asp Ile Ser Glu
        275                 280                 285

Glu Arg Ile Lys Glu Asp Leu Lys Lys Thr Phe Ile Leu Phe Ser Arg
    290                 295                 300

Leu Arg His Tyr Met Val His Tyr Asn Tyr Lys Phe Tyr Glu Asn Leu
305                 310                 315                 320

Tyr Ser Gly Lys Asn Phe Ile Ile Tyr Asn Lys Asp Lys Ser Lys Ser
                325                 330                 335

Arg Arg Phe Ser Glu Leu Leu Asp Leu Asn Ile Phe Lys Glu Leu Ser
            340                 345                 350

Lys Ile Lys Leu Val Lys Asn Arg Ala Val Ser Asn Tyr Leu Asp Lys
        355                 360                 365

Lys Thr Thr Ile His Val Leu Asn Lys Asn Ile Asn Ala Ile Lys Leu
    370                 375                 380

Leu Asp Ile Tyr Arg Asp Ile Cys Glu Thr Lys Asn Gly Phe Asn Asn
385                 390                 395                 400

Phe Ile Asn Asn Met Met Thr Ile Ser Gly Glu Glu Asp Lys Glu Tyr
                405                 410                 415

Lys Glu Met Val Thr Lys His Phe Asn Glu Asn Met Asn Lys Leu Ser
            420                 425                 430

Ile Tyr Leu Glu Asn Phe Lys Lys His Ser Asp Phe Lys Thr Asn Asn
        435                 440                 445

Lys Lys Lys Glu Thr Tyr Asn Leu Leu Lys Gln Glu Leu Asp Glu Gln
    450                 455                 460

Lys Lys Leu Arg Leu Trp Phe Asn Ala Pro Tyr Val Tyr Asp Ile His
465                 470                 475                 480

Ser Ser Lys Lys Tyr Lys Glu Leu Tyr Val Glu Arg Lys Lys Tyr Val
                485                 490                 495

Asp Ile His Ser Lys Leu Ile Glu Ala Gly Ile Asn Asn Asp Asn Lys
            500                 505                 510

Lys Lys Leu Asn Glu Ile Asn Val Lys Leu Cys Glu Leu Asn Thr Glu
        515                 520                 525

Met Lys Glu Met Thr Lys Leu Asn Ser Lys Tyr Arg Leu Gln Tyr Lys
    530                 535                 540

Leu Gln Leu Ala Phe Gly Phe Ile Leu Glu Glu Phe Asn Leu Asp Ile
545                 550                 555                 560

Asp Lys Phe Val Ser Ala Phe Asp Lys Asp Asn Asn Leu Thr Ile Ser
                565                 570                 575

Lys Phe Met Glu Lys Arg Glu Thr Tyr Leu Ser Lys Ser Leu Asp Arg
            580                 585                 590

Arg Asp Asn Arg Phe Lys Lys Leu Ile Lys Asp Tyr Lys Phe Arg Asp
        595                 600                 605

Thr Glu Asp Ile Phe Cys Ser Asp Arg Glu Asn Asn Leu Val Lys Leu
    610                 615                 620

Tyr Ile Leu Met Tyr Ile Leu Leu Pro Val Glu Ile Arg Gly Asp Phe
```

-continued 625 630 635 640

Leu Gly Phe Val Lys Lys Asn Tyr Tyr Asp Leu Lys His Val Asp Phe
645 650 655

Ile Asp Lys Arg Asn Asn Asp Asn Lys Asp Thr Phe Phe His Asp Leu
660 665 670

Arg Leu Phe Glu Lys Asn Val Lys Arg Leu Glu Val Thr Ser Tyr Ser
675 680 685

Leu Ser Asp Gly Phe Leu Gly Lys Lys Ser Arg Glu Lys Phe Gly Lys
690 695 700

Glu Leu Glu Lys Phe Ile Tyr Lys Asn Val Ser Ile Ala Leu Pro Thr
705 710 715 720

Asn Ile Asp Ile Lys Glu Phe Asn Lys Ser Leu Val Leu Pro Met Met
725 730 735

Lys Asn Tyr Gln Ile Ile Phe Lys Leu Leu Asn Asp Ile Glu Ile Ser
740 745 750

Ala Leu Phe Leu Ile Ala Lys Lys Glu Gly Asn Glu Gly Ser Ile Thr
755 760 765

Phe Lys Lys Val Ile Asp Lys Val Arg Lys Glu Asp Met Asn Gly Asn
770 775 780

Ile Asn Phe Ser Gln Val Met Lys Met Ala Leu Asn Glu Lys Val Asn
785 790 795 800

Cys Gln Ile Arg Asn Ser Ile Ala His Ile Asn Met Lys Gln Leu Tyr
805 810 815

Ile Glu Pro Leu Asn Ile Tyr Ile Asn Asn Asn Gln Asn Lys Lys Thr
820 825 830

Ile Ser Glu Gln Met Glu Glu Ile Ile Asp Ile Cys Ile Thr Lys Gly
835 840 845

Leu Thr Gly Lys Glu Leu Asn Lys Asn Ile Ile Asn Asp Tyr Tyr Met
850 855 860

Lys Lys Glu Lys Leu Val Phe Asn Leu Lys Leu Arg Lys Arg Asn Asn
865 870 875 880

Leu Val Ser Ile Asp Ala Gln Gln Lys Asn Met Lys Glu Lys Ser Ile
885 890 895

Leu Asn Lys Tyr Asp Leu Asn Tyr Lys Asp Glu Asn Leu Asn Ile Lys
900 905 910

Glu Ile Ile Leu Lys Val Asn Asp Leu Asn Asn Lys Gln Lys Leu Leu
915 920 925

Lys Glu Thr Thr Glu Gly Glu Ser Asn Tyr Lys Asn Ala Leu Ser Lys
930 935 940

Asp Ile Leu Leu Leu Asn Gly Ile Ile Arg Lys Asn Ile Asn Phe Lys
945 950 955 960

Ile Lys Glu Met Ile Leu Gly Ile Ile Gln Gln Asn Glu Tyr Arg Tyr
965 970 975

Val Asn Ile Asn Ile Tyr Asp Lys Ile Arg Lys Glu Asp His Asn Ile
980 985 990

Asp Leu Lys Ile Asn Asn Lys Tyr Ile Glu Ile Ser Cys Tyr Glu Asn
995 1000 1005

Lys Ser Asn Glu Ser Thr Asp Glu Arg Ile Asn Phe Lys Ile Lys
1010 1015 1020

Tyr Met Asp Leu Lys Val Lys Asn Glu Leu Leu Val Pro Ser Cys
1025 1030 1035

Tyr Glu Asp Ile Tyr Ile Lys Lys Lys Ile Asp Leu Glu Ile Arg
1040 1045 1050

Tyr Ile Glu Asn Cys Lys Val Val Tyr Ile Asp Ile Tyr Tyr Lys
    1055 1060 1065

Lys Tyr Asn Ile Asn Leu Glu Phe Asp Gly Lys Thr Leu Phe Val
    1070 1075 1080

Lys Phe Asn Lys Asp Val Lys Lys Asn Asn Gln Lys Val Asn Leu
    1085 1090 1095

Glu Ser Asn Tyr Ile Gln Asn Ile Lys Phe Ile Val Ser
    1100 1105 1110

<210> SEQ ID NO 5
<211> LENGTH: 1276
<212> TYPE: PRT
<213> ORGANISM: Artificial Sequence
<220> FEATURE:
<223> OTHER INFORMATION: Chemically synthesized

<400> SEQUENCE: 5

Met Lys Ile Ser Lys Val Asp His Val Lys Ser Gly Ile Asp Gln Lys
1 5 10 15

Leu Ser Ser Gln Arg Gly Met Leu Tyr Lys Gln Pro Gln Lys Lys Tyr
20 25 30

Glu Gly Lys Gln Leu Glu Glu His Val Arg Asn Leu Ser Arg Lys Ala
35 40 45

Lys Ala Leu Tyr Gln Val Phe Pro Val Ser Gly Asn Ser Lys Met Glu
50 55 60

Lys Glu Leu Gln Ile Ile Asn Ser Phe Ile Lys Asn Ile Leu Leu Arg
65 70 75 80

Leu Asp Ser Gly Lys Thr Ser Glu Glu Ile Val Gly Tyr Ile Asn Thr
85 90 95

Tyr Ser Val Ala Ser Gln Ile Ser Gly Asp His Ile Gln Glu Leu Val
100 105 110

Asp Gln His Leu Lys Glu Ser Leu Arg Lys Tyr Thr Cys Val Gly Asp
115 120 125

Lys Arg Ile Tyr Val Pro Asp Ile Ile Val Ala Leu Leu Lys Ser Lys
130 135 140

Phe Asn Ser Glu Thr Leu Gln Tyr Asp Asn Ser Glu Leu Lys Ile Leu
145 150 155 160

Ile Asp Phe Ile Arg Glu Asp Tyr Leu Lys Glu Lys Gln Ile Lys Gln
165 170 175

Ile Val His Ser Ile Glu Asn Asn Ser Thr Pro Leu Arg Ile Ala Glu
180 185 190

Ile Asn Gly Gln Lys Arg Leu Ile Pro Ala Asn Val Asp Asn Pro Lys
195 200 205

Lys Ser Tyr Ile Phe Glu Phe Leu Lys Glu Tyr Ala Gln Ser Asp Pro
210 215 220

Lys Gly Gln Glu Ser Leu Leu Gln His Met Arg Tyr Leu Ile Leu Leu
225 230 235 240

Tyr Leu Tyr Gly Pro Asp Lys Ile Thr Asp Asp Tyr Cys Glu Glu Ile
245 250 255

Glu Ala Trp Asn Phe Gly Ser Ile Val Met Asp Asn Glu Gln Leu Phe
260 265 270

Ser Glu Glu Ala Ser Met Leu Ile Gln Asp Arg Ile Tyr Val Asn Gln
275 280 285

Gln Ile Glu Glu Gly Arg Gln Ser Lys Asp Thr Ala Lys Val Lys Lys
290 295 300

```
Asn Lys Ser Lys Tyr Arg Met Leu Gly Asp Lys Ile Glu His Ser Ile
305                 310                 315                 320

Asn Glu Ser Val Val Lys His Tyr Gln Glu Ala Cys Lys Ala Val Glu
                325                 330                 335

Glu Lys Asp Ile Pro Trp Ile Lys Tyr Ile Ser Asp His Val Met Ser
            340                 345                 350

Val Tyr Ser Ser Lys Asn Arg Val Asp Leu Asp Lys Leu Ser Leu Pro
        355                 360                 365

Tyr Leu Ala Lys Asn Thr Trp Asn Thr Trp Ile Ser Phe Ile Ala Met
    370                 375                 380

Lys Tyr Val Asp Met Gly Lys Gly Val Tyr His Phe Ala Met Ser Asp
385                 390                 395                 400

Val Asp Lys Val Gly Lys Gln Asp Asn Leu Ile Ile Gly Gln Ile Asp
                405                 410                 415

Pro Lys Phe Ser Asp Gly Ile Ser Ser Phe Asp Tyr Glu Arg Ile Lys
            420                 425                 430

Ala Glu Asp Asp Leu His Arg Ser Met Ser Gly Tyr Ile Ala Phe Ala
        435                 440                 445

Val Asn Asn Phe Ala Arg Ala Ile Cys Ser Asp Glu Phe Arg Lys Lys
    450                 455                 460

Asn Arg Lys Glu Asp Val Leu Thr Val Gly Leu Asp Glu Ile Pro Leu
465                 470                 475                 480

Tyr Asp Asn Val Lys Arg Lys Leu Leu Gln Tyr Phe Gly Gly Ala Ser
                485                 490                 495

Asn Trp Asp Asp Ser Ile Ile Asp Ile Ile Asp Asp Lys Asp Leu Val
            500                 505                 510

Ala Cys Ile Lys Glu Asn Leu Tyr Val Ala Arg Asn Val Asn Phe His
        515                 520                 525

Phe Ala Gly Ser Glu Lys Val Gln Lys Lys Gln Asp Asp Ile Leu Glu
    530                 535                 540

Glu Ile Val Arg Lys Glu Thr Arg Asp Ile Gly Lys His Tyr Arg Lys
545                 550                 555                 560

Val Phe Tyr Ser Asn Asn Val Ala Val Phe Tyr Cys Asp Glu Asp Ile
                565                 570                 575

Ile Lys Leu Met Asn His Leu Tyr Gln Arg Glu Lys Pro Tyr Gln Ala
            580                 585                 590

Gln Ile Pro Ser Tyr Asn Lys Val Ile Ser Lys Thr Tyr Leu Pro Asp
        595                 600                 605

Leu Ile Phe Met Leu Leu Lys Gly Lys Asn Arg Thr Lys Ile Ser Asp
    610                 615                 620

Pro Ser Ile Met Asn Met Phe Arg Gly Thr Phe Tyr Phe Leu Leu Lys
625                 630                 635                 640

Glu Ile Tyr Tyr Asn Asp Phe Leu Gln Ala Ser Asn Leu Lys Glu Met
                645                 650                 655

Phe Cys Glu Gly Leu Lys Asn Asn Val Lys Asn Lys Lys Ser Glu Lys
            660                 665                 670

Pro Tyr Gln Asn Phe Met Arg Arg Phe Glu Glu Leu Glu Asn Met Gly
        675                 680                 685

Met Asp Phe Gly Glu Ile Cys Gln Gln Ile Met Thr Asp Tyr Glu Gln
    690                 695                 700

Gln Asn Lys Gln Lys Lys Lys Thr Ala Thr Ala Val Met Ser Glu Lys
705                 710                 715                 720
```

```
Asp Lys Lys Ile Arg Thr Leu Asp Asn Asp Thr Gln Lys Tyr Lys His
                725                 730                 735

Phe Arg Thr Leu Leu Tyr Ile Gly Leu Arg Glu Ala Phe Ile Ile Tyr
            740                 745                 750

Leu Lys Asp Glu Lys Asn Lys Glu Trp Tyr Glu Phe Leu Arg Glu Pro
        755                 760                 765

Val Lys Arg Glu Gln Pro Glu Glu Lys Glu Phe Val Asn Lys Trp Lys
    770                 775                 780

Leu Asn Gln Tyr Ser Asp Cys Ser Glu Leu Ile Leu Lys Asp Ser Leu
785                 790                 795                 800

Ala Ala Ala Trp Tyr Val Val Ala His Phe Ile Asn Gln Ala Gln Leu
                805                 810                 815

Asn His Leu Ile Gly Asp Ile Lys Asn Tyr Ile Gln Phe Ile Ser Asp
            820                 825                 830

Ile Asp Arg Arg Ala Lys Ser Thr Gly Asn Pro Val Ser Glu Ser Thr
        835                 840                 845

Glu Ile Gln Ile Glu Arg Tyr Arg Lys Ile Leu Arg Val Leu Glu Phe
    850                 855                 860

Ala Lys Phe Phe Cys Gly Gln Ile Thr Asn Val Leu Thr Asp Tyr Tyr
865                 870                 875                 880

Gln Asp Glu Asn Asp Phe Ser Thr His Val Gly His Tyr Val Lys Phe
                885                 890                 895

Glu Lys Lys Asn Met Glu Pro Ala His Ala Leu Gln Ala Phe Ser Asn
            900                 905                 910

Ser Leu Tyr Ala Cys Gly Lys Glu Lys Lys Lys Ala Gly Phe Tyr Tyr
        915                 920                 925

Asp Gly Met Asn Pro Ile Val Asn Arg Asn Ile Thr Leu Ala Ser Met
    930                 935                 940

Tyr Gly Asn Lys Lys Leu Leu Glu Asn Ala Met Asn Pro Val Thr Glu
945                 950                 955                 960

Gln Asp Ile Arg Lys Tyr Tyr Ser Leu Met Ala Glu Leu Asp Ser Val
                965                 970                 975

Leu Lys Asn Gly Ala Val Cys Lys Ser Glu Asp Glu Gln Lys Asn Leu
            980                 985                 990

Arg His Phe Gln Asn Leu Lys Asn  Arg Ile Glu Leu Val  Asp Val Leu
        995                 1000                1005

Thr Leu  Ser Glu Leu Val Asn  Asp Leu Val Ala Gln  Leu Ile Gly
    1010                1015                1020

Trp Val  Tyr Ile Arg Glu Arg  Asp Met Met Tyr Leu  Gln Leu Gly
    1025                1030                1035

Leu His  Tyr Ile Lys Leu Tyr  Phe Thr Asp Ser Val  Ala Glu Asp
    1040                1045                1050

Ser Tyr  Leu Arg Thr Leu Asp  Leu Glu Glu Gly Ser  Ile Ala Asp
    1055                1060                1065

Gly Ala  Val Leu Tyr Gln Ile  Ala Ser Leu Tyr Ser  Phe Asn Leu
    1070                1075                1080

Pro Met  Tyr Val Lys Pro Asn  Lys Ser Ser Val Tyr  Cys Lys Lys
    1085                1090                1095

His Val  Asn Ser Val Ala Thr  Lys Phe Asp Ile Phe  Glu Lys Glu
    1100                1105                1110

Tyr Cys  Asn Gly Asp Glu Thr  Val Ile Glu Asn Gly  Leu Arg Leu
    1115                1120                1125

Phe Glu  Asn Ile Asn Leu His  Lys Asp Met Val Lys  Phe Arg Asp
```

```
    1130                1135                1140

Tyr Leu  Ala His Phe Lys Tyr  Phe Ala Lys Leu Asp  Glu Ser Ile
    1145                1150                1155

Leu Glu  Leu Tyr Ser Lys Ala  Tyr Asp Phe Phe Phe  Ser Tyr Asn
    1160                1165                1170

Ile Lys  Leu Lys Lys Ser Val  Ser Tyr Val Leu Thr  Asn Val Leu
    1175                1180                1185

Leu Ser  Tyr Phe Ile Asn Ala  Lys Leu Ser Phe Ser  Thr Tyr Lys
    1190                1195                1200

Ser Ser  Gly Asn Lys Thr Val  Gln His Arg Thr Thr  Lys Ile Ser
    1205                1210                1215

Val Val  Ala Gln Thr Asp Tyr  Phe Thr Tyr Lys Leu  Arg Ser Ile
    1220                1225                1230

Val Lys  Asn Lys Asn Gly Val  Glu Ser Ile Glu Asn  Asp Asp Arg
    1235                1240                1245

Arg Cys  Glu Val Val Asn Ile  Ala Ala Arg Asp Lys  Glu Phe Val
    1250                1255                1260

Asp Glu  Val Cys Asn Val Ile  Asn Tyr Asn Ser Asp  Lys
    1265                1270                1275


<210> SEQ ID NO 6
<211> LENGTH: 1224
<212> TYPE: PRT
<213> ORGANISM: Artificial Sequence
<220> FEATURE:
<223> OTHER INFORMATION: Chemically synthesized

<400> SEQUENCE: 6

Met Glu Asn Lys Thr Ser Leu Gly Asn Asn Ile Tyr Tyr Asn Pro Phe
1               5                   10                  15

Lys Pro Gln Asp Lys Ser Tyr Phe Ala Gly Tyr Phe Asn Ala Ala Met
            20                  25                  30

Glu Asn Thr Asp Ser Val Phe Arg Glu Leu Gly Lys Arg Leu Lys Gly
        35                  40                  45

Lys Glu Tyr Thr Ser Glu Asn Phe Phe Asp Ala Ile Phe Lys Glu Asn
    50                  55                  60

Ile Ser Leu Val Glu Tyr Glu Arg Tyr Val Lys Leu Leu Ser Asp Tyr
65                  70                  75                  80

Phe Pro Met Ala Arg Leu Leu Asp Lys Lys Glu Val Pro Ile Lys Glu
                85                  90                  95

Arg Lys Glu Asn Phe Lys Lys Asn Phe Lys Gly Ile Ile Lys Ala Val
            100                 105                 110

Arg Asp Leu Arg Asn Phe Tyr Thr His Lys Glu His Gly Glu Val Glu
        115                 120                 125

Ile Thr Asp Glu Ile Phe Gly Val Leu Asp Glu Met Leu Lys Ser Thr
    130                 135                 140

Val Leu Thr Val Lys Lys Lys Lys Val Lys Thr Asp Lys Thr Lys Glu
145                 150                 155                 160

Ile Leu Lys Lys Ser Ile Glu Lys Gln Leu Asp Ile Leu Cys Gln Lys
                165                 170                 175

Lys Leu Glu Tyr Leu Arg Asp Thr Ala Arg Lys Ile Glu Glu Lys Arg
            180                 185                 190

Arg Asn Gln Arg Glu Arg Gly Glu Lys Glu Leu Val Ala Pro Phe Lys
        195                 200                 205

Tyr Ser Asp Lys Arg Asp Asp Leu Ile Ala Ala Ile Tyr Asn Asp Ala
```

```
    210                 215                 220

Phe Asp Val Tyr Ile Asp Lys Lys Lys Asp Ser Leu Lys Glu Ser Ser
225                 230                 235                 240

Lys Ala Lys Tyr Asn Thr Lys Ser Asp Pro Gln Gln Glu Glu Gly Asp
                245                 250                 255

Leu Lys Ile Pro Ile Ser Lys Asn Gly Val Val Phe Leu Leu Ser Leu
            260                 265                 270

Phe Leu Thr Lys Gln Glu Ile His Ala Phe Lys Ser Lys Ile Ala Gly
        275                 280                 285

Phe Lys Ala Thr Val Ile Asp Glu Ala Thr Val Ser Glu Ala Thr Val
    290                 295                 300

Ser His Gly Lys Asn Ser Ile Cys Phe Met Ala Thr His Glu Ile Phe
305                 310                 315                 320

Ser His Leu Ala Tyr Lys Lys Leu Lys Arg Lys Val Arg Thr Ala Glu
                325                 330                 335

Ile Asn Tyr Gly Glu Ala Glu Asn Ala Glu Gln Leu Ser Val Tyr Ala
            340                 345                 350

Lys Glu Thr Leu Met Met Gln Met Leu Asp Glu Leu Ser Lys Val Pro
        355                 360                 365

Asp Val Val Tyr Gln Asn Leu Ser Glu Asp Val Gln Lys Thr Phe Ile
    370                 375                 380

Glu Asp Trp Asn Glu Tyr Leu Lys Glu Asn Asn Gly Asp Val Gly Thr
385                 390                 395                 400

Met Glu Glu Glu Gln Val Ile His Pro Val Ile Arg Lys Arg Tyr Glu
                405                 410                 415

Asp Lys Phe Asn Tyr Phe Ala Ile Arg Phe Leu Asp Glu Phe Ala Gln
            420                 425                 430

Phe Pro Thr Leu Arg Phe Gln Val His Leu Gly Asn Tyr Leu His Asp
        435                 440                 445

Ser Arg Pro Lys Glu Asn Leu Ile Ser Asp Arg Arg Ile Lys Glu Lys
    450                 455                 460

Ile Thr Val Phe Gly Arg Leu Ser Glu Leu Glu His Lys Lys Ala Leu
465                 470                 475                 480

Phe Ile Lys Asn Thr Glu Thr Asn Glu Asp Arg Glu His Tyr Trp Glu
                485                 490                 495

Ile Phe Pro Asn Pro Asn Tyr Asp Phe Pro Lys Glu Asn Ile Ser Val
            500                 505                 510

Asn Asp Lys Asp Phe Pro Ile Ala Gly Ser Ile Leu Asp Arg Glu Lys
        515                 520                 525

Gln Pro Val Ala Gly Lys Ile Gly Ile Lys Val Lys Leu Leu Asn Gln
    530                 535                 540

Gln Tyr Val Ser Glu Val Asp Lys Ala Val Lys Ala His Gln Leu Lys
545                 550                 555                 560

Gln Arg Lys Ala Ser Lys Pro Ser Ile Gln Asn Ile Ile Glu Glu Ile
                565                 570                 575

Val Pro Ile Asn Glu Ser Asn Pro Lys Glu Ala Ile Val Phe Gly Gly
            580                 585                 590

Gln Pro Thr Ala Tyr Leu Ser Met Asn Asp Ile His Ser Ile Leu Tyr
        595                 600                 605

Glu Phe Phe Asp Lys Trp Glu Lys Lys Lys Glu Lys Leu Glu Lys Lys
    610                 615                 620

Gly Glu Lys Glu Leu Arg Lys Glu Ile Gly Lys Glu Leu Glu Lys Lys
625                 630                 635                 640
```

```
Ile Val Gly Lys Ile Gln Ala Gln Ile Gln Gln Ile Ile Asp Lys Asp
                645                 650                 655

Thr Asn Ala Lys Ile Leu Lys Pro Tyr Gln Asp Gly Asn Ser Thr Ala
            660                 665                 670

Ile Asp Lys Glu Lys Leu Ile Lys Asp Leu Lys Gln Glu Gln Asn Ile
        675                 680                 685

Leu Gln Lys Leu Lys Asp Glu Gln Thr Val Arg Glu Lys Glu Tyr Asn
    690                 695                 700

Asp Phe Ile Ala Tyr Gln Asp Lys Asn Arg Glu Ile Asn Lys Val Arg
705                 710                 715                 720

Asp Arg Asn His Lys Gln Tyr Leu Lys Asp Asn Leu Lys Arg Lys Tyr
                725                 730                 735

Pro Glu Ala Pro Ala Arg Lys Glu Val Leu Tyr Tyr Arg Glu Lys Gly
            740                 745                 750

Lys Val Ala Val Trp Leu Ala Asn Asp Ile Lys Arg Phe Met Pro Thr
        755                 760                 765

Asp Phe Lys Asn Glu Trp Lys Gly Glu Gln His Ser Leu Leu Gln Lys
    770                 775                 780

Ser Leu Ala Tyr Tyr Glu Gln Cys Lys Glu Glu Leu Lys Asn Leu Leu
785                 790                 795                 800

Pro Glu Lys Val Phe Gln His Leu Pro Phe Lys Leu Gly Gly Tyr Phe
                805                 810                 815

Gln Gln Lys Tyr Leu Tyr Gln Phe Tyr Thr Cys Tyr Leu Asp Lys Arg
            820                 825                 830

Leu Glu Tyr Ile Ser Gly Leu Val Gln Gln Ala Glu Asn Phe Lys Ser
        835                 840                 845

Glu Asn Lys Val Phe Lys Lys Val Glu Asn Glu Cys Phe Lys Phe Leu
    850                 855                 860

Lys Lys Gln Asn Tyr Thr His Lys Glu Leu Asp Ala Arg Val Gln Ser
865                 870                 875                 880

Ile Leu Gly Tyr Pro Ile Phe Leu Glu Arg Gly Phe Met Asp Glu Lys
                885                 890                 895

Pro Thr Ile Ile Lys Gly Lys Thr Phe Lys Gly Asn Glu Ala Leu Phe
            900                 905                 910

Ala Asp Trp Phe Arg Tyr Tyr Lys Glu Tyr Gln Asn Phe Gln Thr Phe
        915                 920                 925

Tyr Asp Thr Glu Asn Tyr Pro Leu Val Glu Leu Glu Lys Lys Gln Ala
    930                 935                 940

Asp Arg Lys Arg Lys Thr Lys Ile Tyr Gln Gln Lys Lys Asn Asp Val
945                 950                 955                 960

Phe Thr Leu Leu Met Ala Lys His Ile Phe Lys Ser Val Phe Lys Gln
                965                 970                 975

Asp Ser Ile Asp Gln Phe Ser Leu Glu Asp Leu Tyr Gln Ser Arg Glu
            980                 985                 990

Glu Arg Leu Gly Asn Gln Glu Arg  Ala Arg Gln Thr Gly  Glu Arg Asn
        995                 1000                1005

Thr Asn  Tyr Ile Trp Asn Lys  Thr Val Asp Leu Lys  Leu Cys Asp
    1010                1015                1020

Gly Lys  Ile Thr Val Glu Asn  Val Lys Leu Lys Asn  Val Gly Asp
    1025                1030                1035

Phe Ile  Lys Tyr Glu Tyr Asp  Gln Arg Val Gln Ala  Phe Leu Lys
    1040                1045                1050
```

Tyr Glu Glu Asn Ile Glu Trp Gln Ala Phe Leu Ile Lys Glu Ser
1055 1060 1065

Lys Glu Glu Glu Asn Tyr Pro Tyr Val Val Glu Arg Glu Ile Glu
1070 1075 1080

Gln Tyr Glu Lys Val Arg Arg Glu Glu Leu Leu Lys Glu Val His
1085 1090 1095

Leu Ile Glu Glu Tyr Ile Leu Glu Lys Val Lys Asp Lys Glu Ile
1100 1105 1110

Leu Lys Lys Gly Asp Asn Gln Asn Phe Lys Tyr Tyr Ile Leu Asn
1115 1120 1125

Gly Leu Leu Lys Gln Leu Lys Asn Glu Asp Val Glu Ser Tyr Lys
1130 1135 1140

Val Phe Asn Leu Asn Thr Glu Pro Glu Asp Val Asn Ile Asn Gln
1145 1150 1155

Leu Lys Gln Glu Ala Thr Asp Leu Glu Gln Lys Ala Phe Val Leu
1160 1165 1170

Thr Tyr Ile Arg Asn Lys Phe Ala His Asn Gln Leu Pro Lys Lys
1175 1180 1185

Glu Phe Trp Asp Tyr Cys Gln Glu Lys Tyr Gly Lys Ile Glu Lys
1190 1195 1200

Glu Lys Thr Tyr Ala Glu Tyr Phe Ala Glu Val Phe Lys Lys Glu
1205 1210 1215

Lys Glu Ala Leu Ile Lys
1220

<210> SEQ ID NO 7
<211> LENGTH: 1385
<212> TYPE: PRT
<213> ORGANISM: Artificial Sequence
<220> FEATURE:
<223> OTHER INFORMATION: Chemically synthesized

<400> SEQUENCE: 7

Met Lys Phe Ser Lys Val Asp His Thr Arg Ser Ala Val Gly Ile Gln
1 5 10 15

Lys Ala Thr Asp Ser Val His Gly Met Leu Tyr Thr Asp Pro Lys Lys
20 25 30

Gln Glu Val Asn Asp Leu Asp Lys Arg Phe Asp Gln Leu Asn Val Lys
35 40 45

Ala Lys Arg Leu Tyr Asn Val Phe Asn Gln Ser Lys Ala Glu Glu Asp
50 55 60

Asp Asp Glu Lys Arg Phe Gly Lys Val Val Lys Lys Leu Asn Arg Glu
65 70 75 80

Leu Lys Asp Leu Leu Phe His Arg Glu Val Ser Arg Tyr Asn Ser Ile
85 90 95

Gly Asn Ala Lys Tyr Asn Tyr Tyr Gly Ile Lys Ser Asn Pro Glu Glu
100 105 110

Ile Val Ser Asn Leu Gly Met Val Glu Ser Leu Lys Gly Glu Arg Asp
115 120 125

Pro Gln Lys Val Ile Ser Lys Leu Leu Leu Tyr Tyr Leu Arg Lys Gly
130 135 140

Leu Lys Pro Gly Thr Asp Gly Leu Arg Met Ile Leu Glu Ala Ser Cys
145 150 155 160

Gly Leu Arg Lys Leu Ser Gly Asp Glu Lys Glu Leu Lys Val Phe Leu
165 170 175

```
Gln Thr Leu Asp Glu Asp Phe Glu Lys Lys Thr Phe Lys Lys Asn Leu
            180                 185                 190

Ile Arg Ser Ile Glu Asn Gln Asn Met Ala Val Gln Pro Ser Asn Glu
        195                 200                 205

Gly Asp Pro Ile Ile Gly Ile Thr Gln Gly Arg Phe Asn Ser Gln Lys
    210                 215                 220

Asn Glu Glu Lys Ser Ala Ile Glu Arg Met Met Ser Met Tyr Ala Asp
225                 230                 235                 240

Leu Asn Glu Asp His Arg Glu Asp Val Leu Arg Lys Leu Arg Arg Leu
                245                 250                 255

Asn Val Leu Tyr Phe Asn Val Asp Thr Glu Lys Thr Glu Glu Pro Thr
            260                 265                 270

Leu Pro Gly Glu Val Asp Thr Asn Pro Val Phe Glu Val Trp His Asp
        275                 280                 285

His Glu Lys Gly Lys Glu Asn Asp Arg Gln Phe Ala Thr Phe Ala Lys
    290                 295                 300

Ile Leu Thr Glu Asp Arg Glu Thr Arg Lys Lys Glu Lys Leu Ala Val
305                 310                 315                 320

Lys Glu Ala Leu Asn Asp Leu Lys Ser Ala Ile Arg Asp His Asn Ile
                325                 330                 335

Met Ala Tyr Arg Cys Ser Ile Lys Val Thr Glu Gln Asp Lys Asp Gly
            340                 345                 350

Leu Phe Phe Glu Asp Gln Arg Ile Asn Arg Phe Trp Ile His His Ile
        355                 360                 365

Glu Ser Ala Val Glu Arg Ile Leu Ala Ser Ile Asn Pro Glu Lys Leu
    370                 375                 380

Tyr Lys Leu Arg Ile Gly Tyr Leu Gly Glu Lys Val Trp Lys Asp Leu
385                 390                 395                 400

Leu Asn Tyr Leu Ser Ile Lys Tyr Ile Ala Val Gly Lys Ala Val Phe
                405                 410                 415

His Phe Ala Met Glu Asp Leu Gly Lys Thr Gly Gln Asp Ile Glu Leu
            420                 425                 430

Gly Lys Leu Ser Asn Ser Val Ser Gly Gly Leu Thr Ser Phe Asp Tyr
        435                 440                 445

Glu Gln Ile Arg Ala Asp Glu Thr Leu Gln Arg Gln Leu Ser Val Glu
    450                 455                 460

Val Ala Phe Ala Ala Asn Asn Leu Phe Arg Ala Val Val Gly Gln Thr
465                 470                 475                 480

Gly Lys Lys Ile Glu Gln Ser Lys Ser Glu Glu Asn Glu Glu Asp Phe
                485                 490                 495

Leu Leu Trp Lys Ala Glu Lys Ile Ala Glu Ser Ile Lys Lys Glu Gly
            500                 505                 510

Glu Gly Asn Thr Leu Lys Ser Ile Leu Gln Phe Phe Gly Gly Ala Ser
        515                 520                 525

Ser Trp Asp Leu Asn His Phe Cys Ala Ala Tyr Gly Asn Glu Ser Ser
    530                 535                 540

Ala Leu Gly Tyr Glu Thr Lys Phe Ala Asp Asp Leu Arg Lys Ala Ile
545                 550                 555                 560

Tyr Ser Leu Arg Asn Glu Thr Phe His Phe Thr Thr Leu Asn Lys Gly
                565                 570                 575

Ser Phe Asp Trp Asn Ala Lys Leu Ile Gly Asp Met Phe Ser His Glu
            580                 585                 590

Ala Ala Thr Gly Ile Ala Val Glu Arg Thr Arg Phe Tyr Ser Asn Asn
```

```
        595                 600                 605

Leu Pro Met Phe Tyr Arg Glu Ser Asp Leu Lys Arg Ile Met Asp His
    610                 615                 620

Leu Tyr Asn Thr Tyr His Pro Arg Ala Ser Gln Val Pro Ser Phe Asn
625                 630                 635                 640

Ser Val Phe Val Arg Lys Asn Phe Arg Leu Phe Leu Ser Asn Thr Leu
                645                 650                 655

Asn Thr Asn Thr Ser Phe Asp Thr Glu Val Tyr Gln Lys Trp Glu Ser
            660                 665                 670

Gly Val Tyr Tyr Leu Phe Lys Glu Ile Tyr Tyr Asn Ser Phe Leu Pro
        675                 680                 685

Ser Gly Asp Ala His His Leu Phe Phe Glu Gly Leu Arg Arg Ile Arg
    690                 695                 700

Lys Glu Ala Asp Asn Leu Pro Ile Val Gly Lys Glu Ala Lys Lys Arg
705                 710                 715                 720

Asn Ala Val Gln Asp Phe Gly Arg Arg Cys Asp Glu Leu Lys Asn Leu
                725                 730                 735

Ser Leu Ser Ala Ile Cys Gln Met Ile Met Thr Glu Tyr Asn Glu Gln
            740                 745                 750

Asn Asn Gly Asn Arg Lys Val Lys Ser Thr Arg Glu Asp Lys Arg Lys
        755                 760                 765

Pro Asp Ile Phe Gln His Tyr Lys Met Leu Leu Leu Arg Thr Leu Gln
    770                 775                 780

Glu Ala Phe Ala Ile Tyr Ile Arg Arg Glu Glu Phe Lys Phe Ile Phe
785                 790                 795                 800

Asp Leu Pro Lys Thr Leu Tyr Val Met Lys Pro Val Glu Glu Phe Leu
                805                 810                 815

Pro Asn Trp Lys Ser Gly Met Phe Asp Ser Leu Val Glu Arg Val Lys
            820                 825                 830

Gln Ser Pro Asp Leu Gln Arg Trp Tyr Val Leu Cys Lys Phe Leu Asn
        835                 840                 845

Gly Arg Leu Leu Asn Gln Leu Ser Gly Val Ile Arg Ser Tyr Ile Gln
    850                 855                 860

Phe Ala Gly Asp Ile Gln Arg Arg Ala Lys Ala Asn His Asn Arg Leu
865                 870                 875                 880

Tyr Met Asp Asn Thr Gln Arg Val Glu Tyr Tyr Ser Asn Val Leu Glu
                885                 890                 895

Val Val Asp Phe Cys Ile Lys Gly Thr Ser Arg Phe Ser Asn Val Phe
            900                 905                 910

Ser Asp Tyr Phe Arg Asp Glu Asp Ala Tyr Ala Asp Tyr Leu Asp Asn
        915                 920                 925

Tyr Leu Gln Phe Lys Asp Glu Lys Ile Ala Glu Val Ser Ser Phe Ala
    930                 935                 940

Ala Leu Lys Thr Phe Cys Asn Glu Glu Glu Val Lys Ala Gly Ile Tyr
945                 950                 955                 960

Met Asp Gly Glu Asn Pro Val Met Gln Arg Asn Ile Val Met Ala Lys
                965                 970                 975

Leu Phe Gly Pro Asp Glu Val Leu Lys Asn Val Val Pro Lys Val Thr
            980                 985                 990

Arg Glu Glu Ile Glu Glu Tyr Tyr  Gln Leu Glu Lys Gln  Ile Ala Pro
        995                 1000                1005

Tyr Arg  Gln Asn Gly Tyr Cys  Lys Ser Glu Glu Asp  Gln Lys Lys
    1010                1015                1020
```

```
Leu Leu  Arg Phe Gln Arg Ile  Lys Asn Arg Val Glu  Phe Gln Thr
    1025                 1030                 1035

Ile Thr  Glu Phe Ser Glu Ile  Ile Asn Glu Leu Leu  Gly Gln Leu
    1040                 1045                 1050

Ile Ser  Trp Ser Phe Leu Arg  Glu Arg Asp Leu Leu  Tyr Phe Gln
    1055                 1060                 1065

Leu Gly  Phe His Tyr Leu Cys  Leu His Asn Asp Thr  Glu Lys Pro
    1070                 1075                 1080

Ala Glu  Tyr Lys Glu Ile Ser  Arg Glu Asp Gly Thr  Val Ile Arg
    1085                 1090                 1095

Asn Ala  Ile Leu His Gln Val  Ala Ala Met Tyr Val  Gly Gly Leu
    1100                 1105                 1110

Pro Val  Tyr Thr Leu Ala Asp  Lys Lys Leu Ala Ala  Phe Glu Lys
    1115                 1120                 1125

Gly Glu  Ala Asp Cys Lys Leu  Ser Ile Ser Lys Asp  Thr Ala Gly
    1130                 1135                 1140

Ala Gly  Lys Lys Ile Lys Asp  Phe Phe Arg Tyr Ser  Lys Tyr Val
    1145                 1150                 1155

Leu Ile  Lys Asp Arg Met Leu  Thr Asp Gln Asn Gln  Lys Tyr Thr
    1160                 1165                 1170

Ile Tyr  Leu Ala Gly Leu Glu  Leu Phe Glu Asn Thr  Asp Glu His
    1175                 1180                 1185

Asp Asn  Ile Thr Asp Val Arg  Lys Tyr Val Asp His  Phe Lys Tyr
    1190                 1195                 1200

Tyr Ala  Thr Ser Asp Glu Asn  Ala Met Ser Ile Leu  Asp Leu Tyr
    1205                 1210                 1215

Ser Glu  Ile His Asp Arg Phe  Phe Thr Tyr Asp Met  Lys Tyr Gln
    1220                 1225                 1230

Lys Asn  Val Ala Asn Met Leu  Glu Asn Ile Leu Leu  Arg His Phe
    1235                 1240                 1245

Val Leu  Ile Arg Pro Glu Phe  Phe Thr Gly Ser Lys  Lys Val Gly
    1250                 1255                 1260

Glu Gly  Lys Lys Ile Thr Cys  Lys Ala Arg Ala Gln  Ile Glu Ile
    1265                 1270                 1275

Ala Glu  Asn Gly Met Arg Ser  Glu Asp Phe Thr Tyr  Lys Leu Ser
    1280                 1285                 1290

Asp Gly  Lys Lys Asn Ile Ser  Thr Cys Met Ile Ala  Ala Arg Asp
    1295                 1300                 1305

Gln Lys  Tyr Leu Asn Thr Val  Ala Arg Leu Leu Tyr  Tyr Pro His
    1310                 1315                 1320

Glu Ala  Lys Lys Ser Ile Val  Asp Thr Arg Glu Lys  Lys Asn Asn
    1325                 1330                 1335

Lys Lys  Thr Asn Arg Gly Asp  Gly Thr Phe Asn Lys  Gln Lys Gly
    1340                 1345                 1350

Thr Ala  Arg Lys Glu Lys Asp  Asn Gly Pro Arg Glu  Phe Asn Asp
    1355                 1360                 1365

Thr Gly  Phe Ser Asn Thr Pro  Phe Ala Gly Phe Asp  Pro Phe Arg
    1370                 1375                 1380

Asn Ser
    1385
```

<210> SEQ ID NO 8
<211> LENGTH: 1199

<212> TYPE: PRT
<213> ORGANISM: Artificial Sequence
<220> FEATURE:
<223> OTHER INFORMATION: Chemically synthesized

<400> SEQUENCE: 8

```
Met Lys Asn Ile Gln Arg Leu Gly Lys Gly Asn Glu Phe Ser Pro Phe
1               5                   10                  15

Lys Lys Glu Asp Lys Phe Tyr Phe Gly Gly Phe Leu Asn Leu Ala Asn
            20                  25                  30

Asn Asn Ile Glu Asp Phe Phe Lys Glu Ile Ile Thr Arg Phe Gly Ile
        35                  40                  45

Val Ile Thr Asp Glu Asn Lys Lys Pro Lys Glu Thr Phe Gly Glu Lys
    50                  55                  60

Ile Leu Asn Glu Ile Phe Lys Lys Asp Ile Ser Ile Val Asp Tyr Glu
65                  70                  75                  80

Lys Trp Val Asn Ile Phe Ala Asp Tyr Phe Pro Phe Thr Lys Tyr Leu
                85                  90                  95

Ser Leu Tyr Leu Glu Glu Met Gln Phe Lys Asn Arg Val Ile Cys Phe
            100                 105                 110

Arg Asp Val Met Lys Glu Leu Leu Lys Thr Val Glu Ala Leu Arg Asn
        115                 120                 125

Phe Tyr Thr His Tyr Asp His Glu Pro Ile Lys Ile Glu Asp Arg Val
    130                 135                 140

Phe Tyr Phe Leu Asp Lys Val Leu Leu Asp Val Ser Leu Thr Val Lys
145                 150                 155                 160

Asn Lys Tyr Leu Lys Thr Asp Lys Thr Lys Glu Phe Leu Asn Gln His
                165                 170                 175

Ile Gly Glu Glu Leu Lys Glu Leu Cys Lys Gln Arg Lys Asp Tyr Leu
            180                 185                 190

Val Gly Lys Gly Lys Arg Ile Asp Lys Glu Ser Glu Ile Ile Asn Gly
        195                 200                 205

Ile Tyr Asn Asn Ala Phe Lys Asp Phe Ile Cys Lys Arg Glu Lys Gln
    210                 215                 220

Asp Asp Lys Glu Asn His Asn Ser Val Glu Lys Ile Leu Cys Asn Lys
225                 230                 235                 240

Glu Pro Gln Asn Lys Lys Gln Lys Ser Ser Ala Thr Val Trp Glu Leu
                245                 250                 255

Cys Ser Lys Ser Ser Ser Lys Tyr Thr Glu Lys Ser Phe Pro Asn Arg
            260                 265                 270

Glu Asn Asp Lys His Cys Leu Glu Val Pro Ile Ser Gln Lys Gly Ile
        275                 280                 285

Val Phe Leu Leu Ser Phe Phe Leu Asn Lys Gly Glu Ile Tyr Ala Leu
    290                 295                 300

Thr Ser Asn Ile Lys Gly Phe Lys Ala Lys Ile Thr Lys Glu Glu Pro
305                 310                 315                 320

Val Thr Tyr Asp Lys Asn Ser Ile Arg Tyr Met Ala Thr His Arg Met
                325                 330                 335

Phe Ser Phe Leu Ala Tyr Lys Gly Leu Lys Arg Lys Ile Arg Thr Ser
            340                 345                 350

Glu Ile Asn Tyr Asn Glu Asp Gly Gln Ala Ser Ser Thr Tyr Glu Lys
        355                 360                 365

Glu Thr Leu Met Leu Gln Met Leu Asp Glu Leu Asn Lys Val Pro Asp
    370                 375                 380
```

```
Val Val Tyr Gln Asn Leu Ser Glu Asp Val Gln Lys Thr Phe Ile Glu
385                 390                 395                 400

Asp Trp Asn Glu Tyr Leu Lys Glu Asn Asn Gly Asp Val Gly Thr Met
                405                 410                 415

Glu Glu Glu Gln Val Ile His Pro Val Ile Arg Lys Arg Tyr Glu Asp
            420                 425                 430

Lys Phe Asn Tyr Phe Ala Ile Arg Phe Leu Asp Glu Phe Ala Gln Phe
        435                 440                 445

Pro Thr Leu Arg Phe Gln Val His Leu Gly Asn Tyr Leu Cys Asp Lys
    450                 455                 460

Arg Thr Lys Gln Ile Cys Asp Thr Thr Thr Glu Arg Glu Val Lys Lys
465                 470                 475                 480

Lys Ile Thr Val Phe Gly Arg Leu Ser Glu Leu Glu Asn Lys Lys Ala
                485                 490                 495

Ile Phe Leu Asn Glu Arg Glu Glu Ile Lys Gly Trp Glu Val Phe Pro
            500                 505                 510

Asn Pro Ser Tyr Asp Phe Pro Lys Glu Asn Ile Ser Val Asn Tyr Lys
        515                 520                 525

Asp Phe Pro Ile Val Gly Ser Ile Leu Asp Arg Glu Lys Gln Pro Val
    530                 535                 540

Ser Asn Lys Ile Gly Ile Arg Val Lys Ile Ala Asp Glu Leu Gln Arg
545                 550                 555                 560

Glu Ile Asp Lys Ala Ile Lys Glu Lys Lys Leu Arg Asn Pro Lys Asn
                565                 570                 575

Arg Lys Ala Asn Gln Asp Glu Lys Gln Lys Glu Arg Leu Val Asn Glu
            580                 585                 590

Ile Val Ser Thr Asn Ser Asn Glu Gln Gly Glu Pro Val Val Phe Ile
        595                 600                 605

Gly Gln Pro Thr Ala Tyr Leu Ser Met Asn Asp Ile His Ser Val Leu
    610                 615                 620

Tyr Glu Phe Leu Ile Asn Lys Ile Ser Gly Glu Ala Leu Glu Thr Lys
625                 630                 635                 640

Ile Val Glu Lys Ile Glu Thr Gln Ile Lys Gln Ile Ile Gly Lys Asp
                645                 650                 655

Ala Thr Thr Lys Ile Leu Lys Pro Tyr Thr Asn Ala Asn Ser Asn Ser
            660                 665                 670

Ile Asn Arg Glu Lys Leu Leu Arg Asp Leu Glu Gln Glu Gln Gln Ile
        675                 680                 685

Leu Lys Thr Leu Leu Glu Glu Gln Gln Gln Arg Glu Lys Asp Lys Lys
    690                 695                 700

Asp Lys Lys Ser Lys Arg Lys His Glu Leu Tyr Pro Ser Glu Lys Gly
705                 710                 715                 720

Lys Val Ala Val Trp Leu Ala Asn Asp Ile Lys Arg Phe Met Pro Lys
                725                 730                 735

Ala Phe Lys Glu Gln Trp Arg Gly Tyr His His Ser Leu Leu Gln Lys
            740                 745                 750

Tyr Leu Ala Tyr Tyr Glu Gln Ser Lys Glu Glu Leu Lys Asn Leu Leu
        755                 760                 765

Pro Lys Glu Val Phe Lys His Phe Pro Phe Lys Leu Lys Gly Tyr Phe
    770                 775                 780

Gln Gln Gln Tyr Leu Asn Gln Phe Tyr Thr Asp Tyr Leu Lys Arg Arg
785                 790                 795                 800

Leu Ser Tyr Val Asn Glu Leu Leu Leu Asn Ile Gln Asn Phe Lys Asn
```

```
                805                 810                 815

Asp Lys Asp Ala Leu Lys Ala Thr Glu Lys Glu Cys Phe Lys Phe Phe
            820                 825                 830

Arg Lys Gln Asn Tyr Ile Ile Asn Pro Ile Asn Ile Gln Ile Gln Ser
        835                 840                 845

Ile Leu Val Tyr Pro Ile Phe Leu Lys Arg Gly Phe Leu Asp Glu Lys
    850                 855                 860

Pro Thr Met Ile Asp Arg Glu Lys Phe Lys Glu Asn Lys Asp Thr Glu
865                 870                 875                 880

Leu Ala Asp Trp Phe Met His Tyr Lys Asn Tyr Lys Glu Asp Asn Tyr
                885                 890                 895

Gln Lys Phe Tyr Ala Tyr Pro Leu Glu Lys Val Glu Glu Lys Glu Lys
            900                 905                 910

Phe Lys Arg Asn Lys Gln Ile Asn Lys Gln Lys Lys Asn Asp Val Tyr
        915                 920                 925

Thr Leu Met Met Val Glu Tyr Ile Ile Gln Lys Ile Phe Gly Asp Lys
    930                 935                 940

Phe Val Glu Glu Asn Pro Leu Val Leu Lys Gly Ile Phe Gln Ser Lys
945                 950                 955                 960

Ala Glu Arg Gln Gln Asn Asn Thr His Ala Ala Thr Thr Gln Glu Arg
                965                 970                 975

Asn Leu Asn Gly Ile Leu Asn Gln Pro Lys Asp Ile Lys Ile Gln Gly
            980                 985                 990

Lys Ile Thr Val Lys Gly Val Lys  Leu Lys Asp Ile Gly  Asn Phe Arg
        995                 1000                1005

Lys Tyr  Glu Ile Asp Gln Arg  Val Asn Thr Phe Leu  Asp Tyr Glu
    1010                1015                1020

Pro Arg  Lys Glu Trp Met Ala  Tyr Leu Pro Asn Asp  Trp Lys Glu
    1025                1030                1035

Lys Glu  Lys Gln Gly Gln Leu  Pro Pro Asn Asn Val  Ile Asp Arg
    1040                1045                1050

Gln Ile  Ser Lys Tyr Glu Thr  Val Arg Ser Lys Ile  Leu Leu Lys
    1055                1060                1065

Asp Val  Gln Glu Leu Glu Lys  Ile Ile Ser Asp Glu  Ile Lys Glu
    1070                1075                1080

Glu His  Arg His Asp Leu Lys  Gln Gly Lys Tyr Tyr  Asn Phe Lys
    1085                1090                1095

Tyr Tyr  Ile Leu Asn Gly Leu  Leu Arg Gln Leu Lys  Asn Glu Asn
    1100                1105                1110

Val Glu  Asn Tyr Lys Val Phe  Lys Leu Asn Thr Asn  Pro Glu Lys
    1115                1120                1125

Val Asn  Ile Thr Gln Leu Lys  Gln Glu Ala Thr Asp  Leu Glu Gln
    1130                1135                1140

Lys Ala  Phe Val Leu Thr Tyr  Ile Arg Asn Lys Phe  Ala His Asn
    1145                1150                1155

Gln Leu  Pro Lys Lys Glu Phe  Trp Asp Tyr Cys Gln  Glu Lys Tyr
    1160                1165                1170

Gly Lys  Ile Glu Lys Glu Lys  Thr Tyr Ala Glu Tyr  Phe Ala Glu
    1175                1180                1185

Val Phe  Lys Arg Glu Lys Glu  Ala Leu Ile Lys
    1190                1195
```

<210> SEQ ID NO 9

<211> LENGTH: 1164
<212> TYPE: PRT
<213> ORGANISM: Artificial Sequence
<220> FEATURE:
<223> OTHER INFORMATION: Chemically synthesized

<400> SEQUENCE: 9

```
Met Arg Met Thr Lys Val Lys Ile Asn Gly Ser Pro Val Ser Met Asn
1               5                   10                  15

Arg Ser Lys Leu Asn Gly His Leu Val Trp Asn Gly Thr Thr Asn Thr
            20                  25                  30

Val Asn Ile Leu Thr Lys Lys Glu Gln Ser Phe Ala Ala Ser Phe Leu
        35                  40                  45

Asn Lys Thr Leu Val Lys Ala Asp Gln Val Lys Gly Tyr Lys Val Leu
    50                  55                  60

Ala Glu Asn Ile Phe Ile Ile Phe Glu Gln Leu Glu Lys Ser Asn Ser
65                  70                  75                  80

Glu Lys Pro Ser Val Tyr Leu Asn Asn Ile Arg Arg Leu Lys Glu Ala
                85                  90                  95

Gly Leu Lys Arg Phe Phe Lys Ser Lys Tyr His Glu Glu Ile Lys Tyr
            100                 105                 110

Thr Ser Glu Lys Asn Gln Ser Val Pro Thr Lys Leu Asn Leu Ile Pro
        115                 120                 125

Leu Phe Phe Asn Ala Val Asp Arg Ile Gln Glu Asp Lys Phe Asp Glu
    130                 135                 140

Lys Asn Trp Ser Tyr Phe Cys Lys Glu Met Ser Pro Tyr Leu Asp Tyr
145                 150                 155                 160

Lys Lys Ser Tyr Leu Asn Arg Lys Lys Glu Ile Leu Ala Asn Ser Ile
                165                 170                 175

Gln Gln Asn Arg Gly Phe Ser Met Pro Thr Ala Glu Glu Pro Asn Leu
            180                 185                 190

Leu Ser Lys Arg Lys Gln Leu Phe Gln Gln Trp Ala Met Lys Phe Gln
        195                 200                 205

Glu Ser Pro Leu Ile Gln Gln Asn Asn Phe Ala Val Glu Gln Phe Asn
    210                 215                 220

Lys Glu Phe Ala Asn Lys Ile Asn Glu Leu Ala Ala Val Tyr Asn Val
225                 230                 235                 240

Asp Glu Leu Cys Thr Ala Ile Thr Glu Lys Leu Met Asn Phe Asp Lys
                245                 250                 255

Asp Lys Ser Asn Lys Thr Arg Asn Phe Glu Ile Lys Lys Leu Trp Lys
            260                 265                 270

Gln His Pro His Asn Lys Asp Lys Ala Leu Ile Lys Leu Phe Asn Gln
        275                 280                 285

Glu Gly Asn Glu Ala Leu Asn Gln Phe Asn Ile Glu Leu Gly Lys Tyr
    290                 295                 300

Phe Glu His Tyr Phe Pro Lys Thr Gly Lys Lys Glu Ser Ala Glu Ser
305                 310                 315                 320

Tyr Tyr Leu Asn Pro Gln Thr Ile Ile Lys Thr Val Gly Tyr Gln Leu
                325                 330                 335

Arg Asn Ala Phe Val Gln Tyr Leu Leu Gln Val Gly Lys Leu His Gln
            340                 345                 350

Tyr Asn Lys Gly Val Leu Asp Ser Gln Thr Leu Gln Glu Ile Gly Met
        355                 360                 365

Tyr Glu Gly Phe Gln Thr Lys Phe Met Asp Ala Cys Val Phe Ala Ser
    370                 375                 380
```

```
Ser Ser Leu Arg Asn Ile Ile Gln Ala Thr Thr Asn Glu Asp Ile Leu
385                 390                 395                 400

Thr Arg Glu Lys Phe Lys Lys Glu Leu Glu Lys Asn Val Glu Leu Lys
                405                 410                 415

His Asp Leu Phe Phe Lys Thr Glu Ile Val Glu Glu Arg Asp Glu Asn
            420                 425                 430

Pro Ala Lys Lys Ile Ala Met Thr Pro Asn Glu Leu Asp Leu Trp Ala
        435                 440                 445

Ile Arg Gly Ala Val Gln Arg Val Arg Asn Gln Ile Phe His Gln Gln
    450                 455                 460

Ile Asn Lys Arg His Glu Pro Asn Gln Leu Lys Val Gly Ser Phe Glu
465                 470                 475                 480

Asn Gly Asp Leu Gly Asn Val Ser Tyr Gln Lys Thr Ile Tyr Gln Lys
                485                 490                 495

Leu Phe Asp Ala Glu Ile Lys Asp Ile Glu Ile Tyr Phe Ala Glu Lys
            500                 505                 510

Ile Lys Ser Ser Gly Ala Leu Glu Gln Tyr Ser Met Lys Asp Leu Glu
        515                 520                 525

Lys Leu Phe Ser Asn Lys Glu Leu Thr Leu Ser Leu Gly Gly Gln Val
    530                 535                 540

Val Ala Phe Ala Pro Ser Tyr Lys Lys Leu Tyr Lys Gln Gly Tyr Phe
545                 550                 555                 560

Tyr Gln Asn Glu Lys Thr Ile Glu Leu Glu Gln Phe Thr Asp Tyr Asp
                565                 570                 575

Phe Ser Asn Asp Val Phe Lys Ala Asn Tyr Tyr Leu Ile Lys Leu Ile
            580                 585                 590

Tyr His Tyr Val Phe Leu Pro Gln Phe Ser Gln Ala Asn Asn Lys Leu
        595                 600                 605

Phe Lys Asp Thr Val His Tyr Val Ile Gln Gln Asn Lys Glu Leu Asn
    610                 615                 620

Thr Thr Glu Lys Asp Lys Lys Asn Asn Lys Lys Ile Arg Lys Tyr Ala
625                 630                 635                 640

Phe Glu Gln Val Lys Leu Met Lys Asn Glu Ser Pro Glu Lys Tyr Met
                645                 650                 655

Gln Tyr Leu Gln Arg Glu Met Gln Glu Glu Arg Thr Ile Lys Glu Ala
            660                 665                 670

Lys Lys Thr Asn Glu Glu Lys Pro Asn Tyr Asn Phe Glu Lys Leu Leu
        675                 680                 685

Ile Gln Ile Phe Ile Lys Gly Phe Asp Thr Phe Leu Arg Asn Phe Asp
    690                 695                 700

Leu Asn Leu Asn Pro Ala Glu Glu Leu Val Gly Thr Val Lys Glu Lys
705                 710                 715                 720

Ala Glu Gly Leu Arg Lys Arg Lys Glu Arg Ile Ala Lys Ile Leu Asn
                725                 730                 735

Val Asp Glu Gln Ile Lys Thr Gly Asp Glu Glu Ile Ala Phe Trp Ile
            740                 745                 750

Phe Ala Lys Leu Leu Asp Ala Arg His Leu Ser Glu Leu Arg Asn Glu
        755                 760                 765

Met Ile Lys Phe Lys Gln Ser Ser Val Lys Lys Gly Leu Ile Lys Asn
    770                 775                 780

Gly Asp Leu Ile Glu Gln Met Gln Pro Ile Leu Glu Leu Cys Ile Leu
785                 790                 795                 800
```

```
Ser Asn Asp Ser Glu Ser Met Glu Lys Glu Ser Phe Asp Lys Ile Glu
                805                 810                 815

Val Phe Leu Glu Lys Val Glu Leu Ala Lys Asn Glu Pro Tyr Met Gln
            820                 825                 830

Glu Asp Lys Leu Thr Pro Val Lys Phe Arg Phe Met Lys Gln Leu Glu
        835                 840                 845

Lys Tyr Gln Thr Arg Asn Phe Ile Glu Asn Leu Val Ile Glu Asn Pro
    850                 855                 860

Glu Phe Lys Val Ser Glu Lys Ile Val Leu Asn Trp His Glu Glu Lys
865                 870                 875                 880

Glu Lys Ile Ala Asp Leu Val Asp Lys Arg Thr Lys Leu His Glu Glu
                885                 890                 895

Trp Ala Ser Lys Ala Arg Glu Ile Glu Glu Tyr Asn Glu Lys Ile Lys
            900                 905                 910

Lys Asn Lys Ser Lys Lys Leu Asp Lys Pro Ala Glu Phe Ala Lys Phe
        915                 920                 925

Ala Glu Tyr Lys Ile Ile Cys Glu Ala Ile Glu Asn Phe Asn Arg Leu
    930                 935                 940

Asp His Lys Val Arg Leu Thr Tyr Leu Lys Asn Leu His Tyr Leu Met
945                 950                 955                 960

Ile Asp Leu Met Gly Arg Met Val Gly Phe Ser Val Leu Phe Glu Arg
                965                 970                 975

Asp Phe Val Tyr Met Gly Arg Ser Tyr Ser Ala Leu Lys Lys Gln Ser
            980                 985                 990

Ile Tyr Leu Asn Asp Tyr Asp Thr  Phe Ala Asn Ile Arg  Asp Trp Glu
        995                 1000                1005

Val Asn  Glu Asn Lys His Leu  Phe Gly Thr Ser Ser  Ser Asp Leu
    1010                1015                1020

Thr Phe  Gln Glu Thr Ala Glu  Phe Lys Asn Leu Lys  Lys Pro Met
    1025                1030                1035

Glu Asn  Gln Leu Lys Ala Leu  Leu Gly Val Thr Asn  His Ser Phe
    1040                1045                1050

Glu Ile  Arg Asn Asn Ile Ala  His Leu His Val Leu  Arg Asn Asp
    1055                1060                1065

Gly Lys  Gly Glu Gly Val Ser  Leu Leu Ser Cys Met  Asn Asp Leu
    1070                1075                1080

Arg Lys  Leu Met Ser Tyr Asp  Arg Lys Leu Lys Asn  Ala Val Thr
    1085                1090                1095

Lys Ala  Ile Ile Lys Ile Leu  Asp Lys His Gly Met  Ile Leu Lys
    1100                1105                1110

Leu Thr  Asn Asn Asp His Thr  Lys Pro Phe Glu Ile  Glu Ser Leu
    1115                1120                1125

Lys Pro  Lys Lys Ile Ile His  Leu Glu Lys Ser Asn  His Ser Phe
    1130                1135                1140

Pro Met  Asp Gln Val Ser Gln  Glu Tyr Cys Asp Leu  Val Lys Lys
    1145                1150                1155

Met Leu  Val Phe Thr Asn
    1160
```

<210> SEQ ID NO 10
<211> LENGTH: 1175
<212> TYPE: PRT
<213> ORGANISM: Artificial Sequence
<220> FEATURE:
<223> OTHER INFORMATION: Chemically synthesized

<400> SEQUENCE: 10

Met Arg Ile Thr Lys Val Lys Ile Lys Leu Asp Asn Lys Leu Tyr Gln
1 5 10 15

Val Thr Met Gln Lys Glu Glu Lys Tyr Gly Thr Leu Lys Leu Asn Glu
20 25 30

Glu Ser Arg Lys Ser Thr Ala Glu Ile Leu Arg Leu Lys Lys Ala Ser
35 40 45

Phe Asn Lys Ser Phe His Ser Lys Thr Ile Asn Ser Gln Lys Glu Asn
50 55 60

Lys Asn Ala Thr Ile Lys Lys Asn Gly Asp Tyr Ile Ser Gln Ile Phe
65 70 75 80

Glu Lys Leu Val Gly Val Asp Thr Asn Lys Asn Ile Arg Lys Pro Lys
85 90 95

Met Ser Leu Thr Asp Leu Lys Asp Leu Pro Lys Lys Asp Leu Ala Leu
100 105 110

Phe Ile Lys Arg Lys Phe Lys Asn Asp Asp Ile Val Glu Ile Lys Asn
115 120 125

Leu Asp Leu Ile Ser Leu Phe Tyr Asn Ala Leu Gln Lys Val Pro Gly
130 135 140

Glu His Phe Thr Asp Glu Ser Trp Ala Asp Phe Cys Gln Glu Met Met
145 150 155 160

Pro Tyr Arg Glu Tyr Lys Asn Lys Phe Ile Glu Arg Lys Ile Ile Leu
165 170 175

Leu Ala Asn Ser Ile Glu Gln Asn Lys Gly Phe Ser Ile Asn Pro Glu
180 185 190

Thr Phe Ser Lys Arg Lys Arg Val Leu His Gln Trp Ala Ile Glu Val
195 200 205

Gln Glu Arg Gly Asp Phe Ser Ile Leu Asp Glu Lys Leu Ser Lys Leu
210 215 220

Ala Glu Ile Tyr Asn Phe Lys Lys Met Cys Lys Arg Val Gln Asp Glu
225 230 235 240

Leu Asn Asp Leu Glu Lys Ser Met Lys Lys Gly Lys Asn Pro Glu Lys
245 250 255

Glu Lys Glu Ala Tyr Lys Lys Gln Lys Asn Phe Lys Ile Lys Thr Ile
260 265 270

Trp Lys Asp Tyr Pro Tyr Lys Thr His Ile Gly Leu Ile Glu Lys Ile
275 280 285

Lys Glu Asn Glu Glu Leu Asn Gln Phe Asn Ile Glu Ile Gly Lys Tyr
290 295 300

Phe Glu His Tyr Phe Pro Ile Lys Lys Glu Arg Cys Thr Glu Asp Glu
305 310 315 320

Pro Tyr Tyr Leu Asn Ser Glu Thr Ile Ala Thr Thr Val Asn Tyr Gln
325 330 335

Leu Lys Asn Ala Leu Ile Ser Tyr Leu Met Gln Ile Gly Lys Tyr Lys
340 345 350

Gln Phe Gly Leu Glu Asn Gln Val Leu Asp Ser Lys Lys Leu Gln Glu
355 360 365

Ile Gly Ile Tyr Glu Gly Phe Gln Thr Lys Phe Met Asp Ala Cys Val
370 375 380

Phe Ala Thr Ser Ser Leu Lys Asn Ile Ile Glu Pro Met Arg Ser Gly
385 390 395 400

Asp Ile Leu Gly Lys Arg Glu Phe Lys Glu Ala Ile Ala Thr Ser Ser

```
                405                 410                 415

Phe Val Asn Tyr His His Phe Phe Pro Tyr Phe Pro Phe Glu Leu Lys
            420                 425                 430

Gly Met Lys Asp Arg Glu Ser Glu Leu Ile Pro Phe Gly Glu Gln Thr
        435                 440                 445

Glu Ala Lys Gln Met Gln Asn Ile Trp Ala Leu Arg Gly Ser Val Gln
    450                 455                 460

Gln Ile Arg Asn Glu Ile Phe His Ser Phe Asp Lys Asn Gln Lys Phe
465                 470                 475                 480

Asn Leu Pro Gln Leu Asp Lys Ser Asn Phe Glu Phe Asp Ala Ser Glu
                485                 490                 495

Asn Ser Thr Gly Lys Ser Gln Ser Tyr Ile Glu Thr Asp Tyr Lys Phe
            500                 505                 510

Leu Phe Glu Ala Glu Lys Asn Gln Leu Glu Gln Phe Phe Ile Glu Arg
        515                 520                 525

Ile Lys Ser Ser Gly Ala Leu Glu Tyr Tyr Pro Leu Lys Ser Leu Glu
    530                 535                 540

Lys Leu Phe Ala Lys Lys Glu Met Lys Phe Ser Leu Gly Ser Gln Val
545                 550                 555                 560

Val Ala Phe Ala Pro Ser Tyr Lys Lys Leu Val Lys Lys Gly His Ser
                565                 570                 575

Tyr Gln Thr Ala Thr Glu Gly Thr Ala Asn Tyr Leu Gly Leu Ser Tyr
            580                 585                 590

Tyr Asn Arg Tyr Glu Leu Lys Glu Glu Ser Phe Gln Ala Gln Tyr Tyr
        595                 600                 605

Leu Leu Lys Leu Ile Tyr Gln Tyr Val Phe Leu Pro Asn Phe Ser Gln
    610                 615                 620

Gly Asn Ser Pro Ala Phe Arg Glu Thr Val Lys Ala Ile Leu Arg Ile
625                 630                 635                 640

Asn Lys Asp Glu Ala Arg Lys Lys Met Lys Lys Asn Lys Lys Phe Leu
                645                 650                 655

Arg Lys Tyr Ala Phe Glu Gln Val Arg Glu Met Glu Phe Lys Glu Thr
            660                 665                 670

Pro Asp Gln Tyr Met Ser Tyr Leu Gln Ser Glu Met Arg Glu Glu Lys
        675                 680                 685

Val Arg Lys Ala Glu Lys Asn Asp Lys Gly Phe Glu Lys Asn Ile Thr
    690                 695                 700

Met Asn Phe Glu Lys Leu Leu Met Gln Ile Phe Val Lys Gly Phe Asp
705                 710                 715                 720

Val Phe Leu Thr Thr Phe Ala Gly Lys Glu Leu Leu Leu Ser Ser Glu
                725                 730                 735

Glu Lys Val Ile Lys Glu Thr Glu Ile Ser Leu Ser Lys Lys Ile Asn
            740                 745                 750

Glu Arg Glu Lys Thr Leu Lys Ala Ser Ile Gln Val Glu His Gln Leu
        755                 760                 765

Val Ala Thr Asn Ser Ala Ile Ser Tyr Trp Leu Phe Cys Lys Leu Leu
    770                 775                 780

Asp Ser Arg His Leu Asn Glu Leu Arg Asn Glu Met Ile Lys Phe Lys
785                 790                 795                 800

Gln Ser Arg Ile Lys Phe Asn His Thr Gln His Ala Glu Leu Ile Gln
                805                 810                 815

Asn Leu Leu Pro Ile Val Glu Leu Thr Ile Leu Ser Asn Asp Tyr Asp
            820                 825                 830
```

```
Glu Lys Asn Asp Ser Gln Asn Val Asp Val Ser Ala Tyr Phe Glu Asp
        835                 840                 845

Lys Ser Leu Tyr Glu Thr Ala Pro Tyr Val Gln Thr Asp Asp Arg Thr
    850                 855                 860

Arg Val Ser Phe Arg Pro Ile Leu Lys Leu Glu Lys Tyr His Thr Lys
865                 870                 875                 880

Ser Leu Ile Glu Ala Leu Leu Lys Asp Asn Pro Gln Phe Arg Val Ala
                885                 890                 895

Ala Thr Asp Ile Gln Glu Trp Met His Lys Arg Glu Glu Ile Gly Glu
            900                 905                 910

Leu Val Glu Lys Arg Lys Asn Leu His Thr Glu Trp Ala Glu Gly Gln
        915                 920                 925

Gln Thr Leu Gly Ala Glu Lys Arg Glu Glu Tyr Arg Asp Tyr Cys Lys
    930                 935                 940

Lys Ile Asp Arg Phe Asn Trp Lys Ala Asn Lys Val Thr Leu Thr Tyr
945                 950                 955                 960

Leu Ser Gln Leu His Tyr Leu Ile Thr Asp Leu Leu Gly Arg Met Val
                965                 970                 975

Gly Phe Ser Ala Leu Phe Glu Arg Asp Leu Val Tyr Phe Ser Arg Ser
            980                 985                 990

Phe Ser Glu Leu Gly Gly Glu Thr  Tyr His Ile Ser Asp  Tyr Lys Asn
        995                 1000                1005

Leu Ser  Gly Val Leu Arg Leu  Asn Ala Glu Val Lys  Pro Ile Lys
    1010                1015                1020

Ile Lys  Asn Ile Lys Val Ile  Asp Asn Glu Glu Asn  Pro Tyr Lys
    1025                1030                1035

Gly Asn  Glu Pro Glu Val Lys  Pro Phe Leu Asp Arg  Leu His Ala
    1040                1045                1050

Tyr Leu  Glu Asn Val Ile Gly  Ile Lys Ala Val His  Gly Lys Ile
    1055                1060                1065

Arg Asn  Gln Thr Ala His Leu  Ser Val Leu Gln Leu  Glu Leu Ser
    1070                1075                1080

Met Ile  Glu Ser Met Asn Asn  Leu Arg Asp Leu Met  Ala Tyr Asp
    1085                1090                1095

Arg Lys  Leu Lys Asn Ala Val  Thr Lys Ser Met Ile  Lys Ile Leu
    1100                1105                1110

Asp Lys  His Gly Met Ile Leu  Lys Leu Lys Ile Asp  Glu Asn His
    1115                1120                1125

Lys Asn  Phe Glu Ile Glu Ser  Leu Ile Pro Lys Glu  Ile Ile His
    1130                1135                1140

Leu Lys  Asp Lys Ala Ile Lys  Thr Asn Gln Val Ser  Glu Glu Tyr
    1145                1150                1155

Cys Gln  Leu Val Leu Ala Leu  Leu Thr Thr Asn Pro  Gly Asn Gln
    1160                1165                1170

Leu Asn
    1175
```

<210> SEQ ID NO 11
<211> LENGTH: 1373
<212> TYPE: PRT
<213> ORGANISM: Artificial Sequence
<220> FEATURE:
<223> OTHER INFORMATION: Chemically synthesized

<400> SEQUENCE: 11

```
Met Lys Ile Ser Lys Glu Ser His Lys Arg Thr Ala Val Ala Val Met
1               5                   10                  15

Glu Asp Arg Val Gly Gly Val Val Tyr Val Pro Gly Gly Ser Gly Ile
            20                  25                  30

Asp Leu Ser Asn Asn Leu Lys Lys Arg Ser Met Asp Thr Lys Ser Leu
        35                  40                  45

Tyr Asn Val Phe Asn Gln Ile Gln Ala Gly Thr Ala Pro Ser Glu Tyr
    50                  55                  60

Glu Trp Lys Asp Tyr Leu Ser Glu Ala Glu Asn Lys Lys Arg Glu Ala
65                  70                  75                  80

Gln Lys Met Ile Gln Lys Ala Asn Tyr Glu Leu Arg Arg Glu Cys Glu
                85                  90                  95

Asp Tyr Ala Lys Lys Ala Asn Leu Ala Val Ser Arg Ile Ile Phe Ser
            100                 105                 110

Lys Lys Pro Lys Lys Ile Phe Ser Asp Asp Asp Ile Ile Ser His Met
        115                 120                 125

Lys Lys Gln Arg Leu Ser Lys Phe Lys Gly Arg Met Glu Asp Phe Val
    130                 135                 140

Leu Ile Ala Leu Arg Lys Ser Leu Val Val Ser Thr Tyr Asn Gln Glu
145                 150                 155                 160

Val Phe Asp Ser Arg Lys Ala Ala Thr Val Phe Leu Lys Asn Ile Gly
                165                 170                 175

Lys Lys Asn Ile Ser Ala Asp Asp Glu Arg Gln Ile Lys Gln Leu Met
            180                 185                 190

Ala Leu Ile Arg Glu Asp Tyr Asp Lys Trp Asn Pro Asp Lys Asp Ser
        195                 200                 205

Ser Asp Lys Lys Glu Ser Ser Gly Thr Lys Val Ile Arg Ser Ile Glu
    210                 215                 220

His Gln Asn Met Val Ile Gln Pro Glu Lys Asn Lys Leu Ser Leu Ser
225                 230                 235                 240

Lys Ile Ser Asn Val Gly Lys Lys Thr Lys Thr Lys Gln Lys Glu Lys
                245                 250                 255

Ala Gly Leu Asp Ala Phe Leu Lys Glu Tyr Ala Gln Ile Asp Glu Asn
            260                 265                 270

Ser Arg Met Glu Tyr Leu Lys Lys Leu Arg Arg Leu Leu Asp Thr Tyr
        275                 280                 285

Phe Ala Ala Pro Ser Ser Tyr Ile Lys Gly Ala Ala Val Ser Leu Pro
    290                 295                 300

Glu Asn Ile Asn Phe Ser Ser Glu Leu Asn Val Trp Glu Arg His Glu
305                 310                 315                 320

Ala Ala Lys Lys Val Asn Ile Asn Phe Val Glu Ile Pro Glu Ser Leu
                325                 330                 335

Leu Asn Ala Glu Gln Asn Asn Asn Lys Ile Asn Lys Val Glu Gln Glu
            340                 345                 350

His Ser Leu Glu Gln Leu Arg Thr Asp Ile Arg Arg Arg Asn Ile Thr
        355                 360                 365

Cys Tyr His Phe Ala Asn Ala Leu Ala Ala Asp Glu Arg Tyr His Thr
    370                 375                 380

Leu Phe Phe Glu Asn Met Ala Met Asn Gln Phe Trp Ile His His Met
385                 390                 395                 400

Glu Asn Ala Val Glu Arg Ile Leu Lys Lys Cys Asn Val Gly Thr Leu
                405                 410                 415
```

```
Phe Lys Leu Arg Ile Gly Tyr Leu Ser Glu Lys Val Trp Lys Asp Met
            420                 425                 430

Leu Asn Leu Leu Ser Ile Lys Tyr Ile Ala Leu Gly Lys Ala Val Tyr
        435                 440                 445

His Phe Ala Leu Asp Asp Ile Trp Lys Ala Asp Ile Trp Lys Asp Ala
    450                 455                 460

Ser Asp Lys Asn Ser Gly Lys Ile Asn Asp Leu Thr Leu Lys Gly Ile
465                 470                 475                 480

Ser Ser Phe Asp Tyr Glu Met Val Lys Ala Gln Glu Asp Leu Gln Arg
                485                 490                 495

Glu Met Ala Val Gly Val Ala Phe Ser Thr Asn Asn Leu Ala Arg Val
            500                 505                 510

Thr Cys Lys Met Asp Asp Leu Ser Asp Ala Glu Ser Asp Phe Leu Leu
        515                 520                 525

Trp Asn Lys Glu Ala Ile Arg Arg His Val Lys Tyr Thr Glu Lys Gly
    530                 535                 540

Glu Ile Leu Ser Ala Ile Leu Gln Phe Phe Gly Gly Arg Ser Leu Trp
545                 550                 555                 560

Asp Glu Ser Leu Phe Glu Lys Ala Tyr Ser Asp Ser Asn Tyr Glu Leu
                565                 570                 575

Lys Phe Leu Asp Asp Leu Lys Arg Ala Ile Tyr Ala Ala Arg Asn Glu
            580                 585                 590

Thr Phe His Phe Lys Thr Ala Ala Ile Asp Gly Gly Ser Trp Asn Thr
        595                 600                 605

Arg Leu Phe Gly Ser Leu Phe Glu Lys Glu Ala Gly Leu Cys Leu Asn
    610                 615                 620

Val Glu Lys Asn Lys Phe Tyr Ser Asn Asn Leu Val Leu Phe Tyr Lys
625                 630                 635                 640

Gln Glu Asp Leu Arg Val Phe Leu Asp Lys Leu Tyr Gly Lys Glu Cys
                645                 650                 655

Ser Arg Ala Ala Gln Ile Pro Ser Tyr Asn Thr Ile Leu Pro Arg Lys
            660                 665                 670

Ser Phe Ser Asp Phe Met Lys Gln Leu Leu Gly Leu Lys Glu Pro Val
        675                 680                 685

Tyr Gly Ser Ala Ile Leu Asp Gln Trp Tyr Ser Ala Cys Tyr Tyr Leu
    690                 695                 700

Phe Lys Glu Val Tyr Tyr Asn Leu Phe Leu Gln Asp Ser Ser Ala Lys
705                 710                 715                 720

Ala Leu Phe Glu Lys Ala Val Lys Ala Leu Lys Gly Ala Asp Lys Lys
                725                 730                 735

Gln Glu Lys Ala Val Glu Ser Phe Arg Lys Arg Tyr Trp Glu Ile Ser
            740                 745                 750

Lys Asn Ala Ser Leu Ala Glu Ile Cys Gln Ser Tyr Ile Thr Glu Tyr
        755                 760                 765

Asn Gln Gln Asn Asn Lys Glu Arg Lys Val Arg Ser Ala Asn Asp Gly
    770                 775                 780

Met Phe Asn Glu Pro Ile Tyr Gln His Tyr Lys Met Leu Leu Lys Glu
785                 790                 795                 800

Ala Leu Lys Met Ala Phe Ala Ser Tyr Ile Lys Asn Asp Lys Glu Leu
                805                 810                 815

Lys Phe Val Tyr Lys Pro Thr Glu Lys Leu Phe Glu Val Ser Gln Asp
            820                 825                 830

Asn Phe Leu Pro Asn Trp Asn Ser Glu Lys Tyr Asn Thr Leu Ile Ser
```

```
        835                 840                 845

Glu Val Lys Asn Ser Pro Asp Leu Gln Lys Trp Tyr Ile Val Gly Lys
    850                 855                 860

Phe Met Asn Ala Arg Met Leu Asn Leu Leu Leu Gly Ser Met Arg Ser
865                 870                 875                 880

Tyr Leu Gln Tyr Val Ser Asp Ile Gln Lys Arg Ala Ala Gly Leu Gly
                885                 890                 895

Glu Asn Gln Leu His Leu Ser Ala Glu Asn Val Gly Gln Val Lys Lys
            900                 905                 910

Trp Ile Gln Val Leu Glu Val Cys Leu Leu Leu Ser Val Arg Ile Ser
        915                 920                 925

Asp Lys Phe Thr Asp Tyr Phe Lys Asp Glu Glu Glu Tyr Ala Ser Tyr
    930                 935                 940

Leu Lys Glu Tyr Val Asp Phe Glu Asp Ser Ala Met Pro Ser Asp Tyr
945                 950                 955                 960

Ser Ala Leu Leu Ala Phe Ser Asn Glu Gly Lys Ile Asp Leu Tyr Val
                965                 970                 975

Asp Ala Ser Asn Pro Lys Val Asn Arg Asn Ile Ile Gln Ala Lys Leu
            980                 985                 990

Tyr Ala Pro Asp Met Val Leu Lys  Lys Val Val Lys Lys  Ile Ser Gln
        995                 1000                1005

Asp Glu  Cys Lys Glu Phe Asn  Glu Lys Lys Glu Gln  Ile Met Gln
    1010                1015                1020

Phe Lys  Asn Lys Gly Asp Glu  Val Ser Trp Glu Glu  Gln Gln Lys
    1025                1030                1035

Ile Leu  Glu Tyr Gln Lys Leu  Lys Asn Arg Val Glu  Leu Arg Asp
    1040                1045                1050

Leu Ser  Glu Tyr Gly Glu Leu  Ile Asn Glu Leu Leu  Gly Gln Leu
    1055                1060                1065

Ile Asn  Trp Ser Tyr Leu Arg  Glu Arg Asp Leu Leu  Tyr Phe Gln
    1070                1075                1080

Leu Gly  Phe His Tyr Ser Cys  Leu Met Asn Glu Ser  Lys Lys Pro
    1085                1090                1095

Asp Ala  Tyr Lys Thr Ile Arg  Arg Gly Thr Val Ser  Ile Glu Asn
    1100                1105                1110

Ala Val  Leu Tyr Gln Ile Ile  Ala Met Tyr Ile Asn  Gly Phe Pro
    1115                1120                1125

Val Tyr  Ala Pro Glu Lys Gly  Glu Leu Lys Pro Gln  Cys Lys Thr
    1130                1135                1140

Gly Ser  Ala Gly Gln Lys Ile  Arg Ala Phe Cys Gln  Trp Ala Ser
    1145                1150                1155

Met Val  Glu Lys Lys Lys Tyr  Glu Leu Tyr Asn Ala  Gly Leu Glu
    1160                1165                1170

Leu Phe  Glu Val Val Lys Glu  His Asp Asn Ile Ile  Asp Leu Arg
    1175                1180                1185

Asn Lys  Ile Asp His Phe Lys  Tyr Tyr Gln Gly Asn  Asp Ser Ile
    1190                1195                1200

Leu Ala  Leu Tyr Gly Glu Ile  Phe Asp Arg Phe Phe  Thr Tyr Asp
    1205                1210                1215

Met Lys  Tyr Arg Asn Asn Val  Leu Asn His Leu Gln  Asn Ile Leu
    1220                1225                1230

Leu Arg  His Asn Val Ile Ile  Lys Pro Ile Ile Ser  Lys Asp Lys
    1235                1240                1245
```

```
Lys Glu  Val Gly Arg Gly Lys  Met Lys Asp Arg Ala  Ala Phe Leu
    1250                1255                1260

Leu Glu  Glu Val Ser Ser Asp  Arg Phe Thr Tyr Lys  Val Lys Glu
    1265                1270                1275

Gly Glu  Arg Lys Ile Asp Ala  Lys Asn Arg Leu Tyr  Leu Glu Thr
    1280                1285                1290

Val Arg  Asp Ile Leu Tyr Phe  Pro Asn Arg Ala Val  Asn Asp Lys
    1295                1300                1305

Gly Glu  Asp Val Ile Ile Cys  Ser Lys Lys Ala Gln  Asp Leu Asn
    1310                1315                1320

Glu Lys  Lys Ala Asp Arg Asp  Lys Asn His Asp Lys  Ser Lys Asp
    1325                1330                1335

Thr Asn  Gln Lys Lys Glu Gly  Lys Asn Gln Glu Glu  Lys Ser Glu
    1340                1345                1350

Asn Lys  Glu Pro Tyr Ser Asp  Arg Met Thr Trp Lys  Pro Phe Ala
    1355                1360                1365

Gly Ile  Lys Leu Glu
    1370


<210> SEQ ID NO 12
<211> LENGTH: 1344
<212> TYPE: PRT
<213> ORGANISM: Artificial Sequence
<220> FEATURE:
<223> OTHER INFORMATION: Chemically synthesized

<400> SEQUENCE: 12

Met Leu Arg Arg Asp Lys Glu Val Lys Lys Leu Tyr Asn Val Phe Asn
1               5                   10                  15

Gln Ile Gln Val Gly Thr Lys Pro Lys Lys Trp Asn Asn Asp Glu Lys
            20                  25                  30

Leu Ser Pro Glu Glu Asn Glu Arg Arg Ala Gln Gln Lys Asn Ile Lys
        35                  40                  45

Met Lys Asn Tyr Lys Trp Arg Glu Ala Cys Ser Lys Tyr Val Glu Ser
    50                  55                  60

Ser Gln Arg Ile Ile Asn Asp Val Ile Phe Tyr Ser Tyr Arg Lys Ala
65                  70                  75                  80

Lys Asn Lys Leu Arg Tyr Met Arg Lys Asn Glu Asp Ile Leu Lys Lys
                85                  90                  95

Met Gln Glu Ala Glu Lys Leu Ser Lys Phe Ser Gly Gly Lys Leu Glu
            100                 105                 110

Asp Phe Val Ala Tyr Thr Leu Arg Lys Ser Leu Val Val Ser Lys Tyr
        115                 120                 125

Asp Thr Gln Glu Phe Asp Ser Leu Ala Ala Met Val Val Phe Leu Glu
    130                 135                 140

Cys Ile Gly Lys Asn Asn Ile Ser Asp His Glu Arg Glu Ile Val Cys
145                 150                 155                 160

Lys Leu Leu Glu Leu Ile Arg Lys Asp Phe Ser Lys Leu Asp Pro Asn
                165                 170                 175

Val Lys Gly Ser Gln Gly Ala Asn Ile Val Arg Ser Val Arg Asn Gln
            180                 185                 190

Asn Met Ile Val Gln Pro Gln Gly Asp Arg Phe Leu Phe Pro Gln Val
        195                 200                 205

Tyr Ala Lys Glu Asn Glu Thr Val Thr Asn Lys Asn Val Glu Lys Glu
    210                 215                 220
```

-continued

```
Gly Leu Asn Glu Phe Leu Leu Asn Tyr Ala Asn Leu Asp Asp Glu Lys
225                 230                 235                 240

Arg Ala Glu Ser Leu Arg Lys Leu Arg Arg Ile Leu Asp Val Tyr Phe
                245                 250                 255

Ser Ala Pro Asn His Tyr Glu Lys Asp Met Asp Ile Thr Leu Ser Asp
            260                 265                 270

Asn Ile Glu Lys Glu Lys Phe Asn Val Trp Glu Lys His Glu Cys Gly
        275                 280                 285

Lys Lys Glu Thr Gly Leu Phe Val Asp Ile Pro Asp Val Leu Met Glu
    290                 295                 300

Ala Glu Ala Glu Asn Ile Lys Leu Asp Ala Val Val Glu Lys Arg Glu
305                 310                 315                 320

Arg Lys Val Leu Asn Asp Arg Val Arg Lys Gln Asn Ile Ile Cys Tyr
                325                 330                 335

Arg Tyr Thr Arg Ala Val Val Glu Lys Tyr Asn Ser Asn Glu Pro Leu
            340                 345                 350

Phe Phe Glu Asn Asn Ala Ile Asn Gln Tyr Trp Ile His His Ile Glu
        355                 360                 365

Asn Ala Val Glu Arg Ile Leu Lys Asn Cys Lys Ala Gly Lys Leu Phe
    370                 375                 380

Lys Leu Arg Lys Gly Tyr Leu Ala Glu Lys Val Trp Lys Asp Ala Ile
385                 390                 395                 400

Asn Leu Ile Ser Ile Lys Tyr Ile Ala Leu Gly Lys Ala Val Tyr Asn
                405                 410                 415

Phe Ala Leu Asp Asp Ile Trp Lys Asp Lys Lys Asn Lys Glu Leu Gly
            420                 425                 430

Ile Val Asp Glu Arg Ile Arg Asn Gly Ile Thr Ser Phe Asp Tyr Glu
        435                 440                 445

Met Ile Lys Ala His Glu Asn Leu Gln Arg Glu Leu Ala Val Asp Ile
    450                 455                 460

Ala Phe Ser Val Asn Asn Leu Ala Arg Ala Val Cys Asp Met Ser Asn
465                 470                 475                 480

Leu Gly Asn Lys Glu Ser Asp Phe Leu Leu Trp Lys Arg Asn Asp Ile
                485                 490                 495

Ala Asp Lys Leu Lys Asn Lys Asp Asp Met Ala Ser Val Ser Ala Val
            500                 505                 510

Leu Gln Phe Phe Gly Gly Lys Ser Ser Trp Asp Ile Asn Ile Phe Lys
        515                 520                 525

Asp Ala Tyr Lys Gly Lys Lys Lys Tyr Asn Tyr Glu Val Arg Phe Ile
    530                 535                 540

Asp Asp Leu Arg Lys Ala Ile Tyr Cys Ala Arg Asn Glu Asn Phe His
545                 550                 555                 560

Phe Lys Thr Ala Leu Val Asn Asp Glu Lys Trp Asn Thr Glu Leu Phe
                565                 570                 575

Gly Lys Ile Phe Glu Arg Glu Thr Glu Phe Cys Leu Asn Val Glu Lys
            580                 585                 590

Asp Arg Phe Tyr Ser Asn Asn Leu Tyr Met Phe Tyr Gln Val Ser Glu
        595                 600                 605

Leu Arg Asn Met Leu Asp His Leu Tyr Ser Arg Ser Val Ser Arg Ala
    610                 615                 620

Ala Gln Val Pro Ser Tyr Asn Ser Val Ile Val Arg Thr Ala Phe Pro
625                 630                 635                 640
```

```
Glu Tyr Ile Thr Asn Val Leu Gly Tyr Gln Lys Pro Ser Tyr Asp Ala
                645                 650                 655

Asp Thr Leu Gly Lys Trp Tyr Ser Ala Cys Tyr Tyr Leu Leu Lys Glu
            660                 665                 670

Ile Tyr Tyr Asn Ser Phe Leu Gln Ser Asp Arg Ala Leu Gln Leu Phe
        675                 680                 685

Glu Lys Ser Val Lys Thr Leu Ser Trp Asp Asp Lys Lys Gln Gln Arg
    690                 695                 700

Ala Val Asp Asn Phe Lys Asp His Phe Ser Asp Ile Lys Ser Ala Cys
705                 710                 715                 720

Thr Ser Leu Ala Gln Val Cys Gln Ile Tyr Met Thr Glu Tyr Asn Gln
                725                 730                 735

Gln Asn Asn Gln Ile Lys Lys Val Arg Ser Ser Asn Asp Ser Ile Phe
            740                 745                 750

Asp Gln Pro Val Tyr Gln His Tyr Lys Val Leu Leu Lys Lys Ala Ile
        755                 760                 765

Ala Asn Ala Phe Ala Asp Tyr Leu Lys Asn Asn Lys Asp Leu Phe Gly
    770                 775                 780

Phe Ile Gly Lys Pro Phe Lys Ala Asn Glu Ile Arg Glu Ile Asp Lys
785                 790                 795                 800

Glu Gln Phe Leu Pro Asp Trp Thr Ser Arg Lys Tyr Glu Ala Leu Cys
                805                 810                 815

Ile Glu Val Ser Gly Ser Gln Glu Leu Gln Lys Trp Tyr Ile Val Gly
            820                 825                 830

Lys Phe Leu Asn Ala Arg Ser Leu Asn Leu Met Val Gly Ser Met Arg
        835                 840                 845

Ser Tyr Ile Gln Tyr Val Thr Asp Ile Lys Arg Arg Ala Ala Ser Ile
    850                 855                 860

Gly Asn Glu Leu His Val Ser Val His Asp Val Glu Lys Val Glu Lys
865                 870                 875                 880

Trp Val Gln Val Ile Glu Val Cys Ser Leu Leu Ala Ser Arg Thr Ser
                885                 890                 895

Asn Gln Phe Glu Asp Tyr Phe Asn Asp Lys Asp Asp Tyr Ala Arg Tyr
            900                 905                 910

Leu Lys Ser Tyr Val Asp Phe Ser Asn Val Asp Met Pro Ser Glu Tyr
        915                 920                 925

Ser Ala Leu Val Asp Phe Ser Asn Glu Glu Gln Ser Asp Leu Tyr Val
    930                 935                 940

Asp Pro Lys Asn Pro Lys Val Asn Arg Asn Ile Val His Ser Lys Leu
945                 950                 955                 960

Phe Ala Ala Asp His Ile Leu Arg Asp Ile Val Glu Pro Val Ser Lys
                965                 970                 975

Asp Asn Ile Glu Glu Phe Tyr Ser Gln Lys Ala Glu Ile Ala Tyr Cys
            980                 985                 990

Lys Ile Lys Gly Lys Glu Ile Thr  Ala Glu Glu Gln Lys  Ala Val Leu
        995                 1000                 1005

Lys Tyr  Gln Lys Leu Lys Asn  Arg Val Glu Leu Arg  Asp Ile Val
    1010                 1015                 1020

Glu Tyr  Gly Glu Ile Ile Asn  Glu Leu Leu Gly Gln  Leu Ile Asn
    1025                 1030                 1035

Trp Ser  Phe Met Arg Glu Arg  Asp Leu Leu Tyr Phe  Gln Leu Gly
    1040                 1045                 1050

Phe His  Tyr Asp Cys Leu Arg  Asn Asp Ser Lys Lys  Pro Glu Gly
```

1055 1060 1065

Tyr Lys Asn Ile Lys Val Asp Glu Asn Ser Ile Lys Asp Ala Ile
1070 1075 1080

Leu Tyr Gln Ile Ile Gly Met Tyr Val Asn Gly Val Thr Val Tyr
1085 1090 1095

Ala Pro Glu Lys Asp Gly Asp Lys Leu Lys Glu Gln Cys Val Lys
1100 1105 1110

Gly Gly Val Gly Val Lys Val Ser Ala Phe His Arg Tyr Ser Lys
1115 1120 1125

Tyr Leu Gly Leu Asn Glu Lys Thr Leu Tyr Asn Ala Gly Leu Glu
1130 1135 1140

Ile Phe Glu Val Val Ala Glu His Glu Asp Ile Ile Asn Leu Arg
1145 1150 1155

Asn Gly Ile Asp His Phe Lys Tyr Tyr Leu Gly Asp Tyr Arg Ser
1160 1165 1170

Met Leu Ser Ile Tyr Ser Glu Val Phe Asp Arg Phe Phe Thr Tyr
1175 1180 1185

Asp Ile Lys Tyr Gln Lys Asn Val Leu Asn Leu Leu Gln Asn Ile
1190 1195 1200

Leu Leu Arg His Asn Val Ile Val Glu Pro Ile Leu Glu Ser Gly
1205 1210 1215

Phe Lys Thr Ile Gly Glu Gln Thr Lys Pro Gly Ala Lys Leu Ser
1220 1225 1230

Ile Arg Ser Ile Lys Ser Asp Thr Phe Gln Tyr Lys Val Lys Gly
1235 1240 1245

Gly Thr Leu Ile Thr Asp Ala Lys Asp Glu Arg Tyr Leu Glu Thr
1250 1255 1260

Ile Arg Lys Ile Leu Tyr Tyr Ala Glu Asn Glu Glu Asp Asn Leu
1265 1270 1275

Lys Lys Ser Val Val Val Thr Asn Ala Asp Lys Tyr Glu Lys Asn
1280 1285 1290

Lys Glu Ser Asp Asp Gln Asn Lys Gln Lys Glu Lys Lys Asn Lys
1295 1300 1305

Asp Asn Lys Gly Lys Lys Asn Glu Glu Thr Lys Ser Asp Ala Glu
1310 1315 1320

Lys Asn Asn Asn Glu Arg Leu Ser Tyr Asn Pro Phe Ala Asn Leu
1325 1330 1335

Asn Phe Lys Leu Ser Asn
1340

<210> SEQ ID NO 13
<211> LENGTH: 954
<212> TYPE: PRT
<213> ORGANISM: Artificial Sequence
<220> FEATURE:
<223> OTHER INFORMATION: Chemically synthesized

<400> SEQUENCE: 13

Met Gly Lys Lys Ile His Ala Arg Asp Leu Arg Glu Gln Arg Lys Thr
1 5 10 15

Asp Arg Thr Glu Lys Phe Ala Asp Gln Asn Lys Lys Arg Glu Ala Glu
20 25 30

Arg Ala Val Pro Lys Lys Asp Ala Ala Val Ser Val Lys Ser Val Ser
35 40 45

Ser Val Ser Ser Lys Lys Asp Asn Val Thr Lys Ser Met Ala Lys Ala

```
    50                  55                  60

Ala Gly Val Lys Ser Val Phe Ala Val Gly Asn Thr Val Tyr Met Thr
65                  70                  75                  80

Ser Phe Gly Arg Gly Asn Asp Ala Val Leu Glu Gln Lys Ile Val Asp
                85                  90                  95

Thr Ser His Glu Pro Leu Asn Ile Asp Asp Pro Ala Tyr Gln Leu Asn
            100                 105                 110

Val Val Thr Met Asn Gly Tyr Ser Val Thr Gly His Arg Gly Glu Thr
        115                 120                 125

Val Ser Ala Val Thr Asp Asn Pro Leu Arg Arg Phe Asn Gly Arg Lys
    130                 135                 140

Lys Asp Glu Pro Glu Gln Ser Val Pro Thr Asp Met Leu Cys Leu Lys
145                 150                 155                 160

Pro Thr Leu Glu Lys Lys Phe Phe Gly Lys Glu Phe Asp Asp Asn Ile
                165                 170                 175

His Ile Gln Leu Ile Tyr Asn Ile Leu Asp Ile Glu Lys Ile Leu Ala
            180                 185                 190

Val Tyr Ser Thr Asn Ala Ile Tyr Ala Leu Asn Asn Met Ser Ala Asp
        195                 200                 205

Glu Asn Ile Glu Asn Ser Asp Phe Phe Met Lys Arg Thr Thr Asp Glu
    210                 215                 220

Thr Phe Asp Asp Phe Glu Lys Lys Lys Glu Ser Thr Asn Ser Arg Glu
225                 230                 235                 240

Lys Ala Asp Phe Asp Ala Phe Glu Lys Phe Ile Gly Asn Tyr Arg Leu
                245                 250                 255

Ala Tyr Phe Ala Asp Ala Phe Tyr Val Asn Lys Lys Asn Pro Lys Gly
            260                 265                 270

Lys Ala Lys Asn Val Leu Arg Glu Asp Lys Glu Leu Tyr Ser Val Leu
        275                 280                 285

Thr Leu Ile Gly Lys Leu Arg His Trp Cys Val His Ser Glu Glu Gly
    290                 295                 300

Arg Ala Glu Phe Trp Leu Tyr Lys Leu Asp Glu Leu Lys Asp Asp Phe
305                 310                 315                 320

Lys Asn Val Leu Asp Val Val Tyr Asn Arg Pro Val Glu Glu Ile Asn
                325                 330                 335

Asn Arg Phe Ile Glu Asn Asn Lys Val Asn Ile Gln Ile Leu Gly Ser
            340                 345                 350

Val Tyr Lys Asn Thr Asp Ile Ala Glu Leu Val Arg Ser Tyr Tyr Glu
        355                 360                 365

Phe Leu Ile Thr Lys Lys Tyr Lys Asn Met Gly Phe Ser Ile Lys Lys
    370                 375                 380

Leu Arg Glu Ser Met Leu Glu Gly Lys Gly Tyr Ala Asp Lys Glu Tyr
385                 390                 395                 400

Asp Ser Val Arg Asn Lys Leu Tyr Gln Met Thr Asp Phe Ile Leu Tyr
                405                 410                 415

Thr Gly Tyr Ile Asn Glu Asp Ser Asp Arg Ala Asp Asp Leu Val Asn
            420                 425                 430

Thr Leu Arg Ser Ser Leu Lys Glu Asp Asp Lys Thr Thr Val Tyr Cys
        435                 440                 445

Lys Glu Ala Asp Tyr Leu Trp Lys Lys Tyr Arg Glu Ser Ile Arg Glu
    450                 455                 460

Val Ala Asp Ala Leu Asp Gly Asp Asn Ile Lys Lys Leu Ser Lys Ser
465                 470                 475                 480
```

```
Asn Ile Glu Ile Gln Glu Asp Lys Leu Arg Lys Cys Phe Ile Ser Tyr
                485                 490                 495

Ala Asp Ser Val Ser Glu Phe Thr Lys Leu Ile Tyr Leu Leu Thr Arg
            500                 505                 510

Phe Leu Ser Gly Lys Glu Ile Asn Asp Leu Val Thr Thr Leu Ile Asn
        515                 520                 525

Lys Phe Asp Asn Ile Arg Ser Phe Leu Glu Ile Met Asp Glu Leu Gly
    530                 535                 540

Leu Asp Arg Thr Phe Thr Ala Glu Tyr Ser Phe Phe Glu Gly Ser Thr
545                 550                 555                 560

Lys Tyr Leu Ala Glu Leu Val Glu Leu Asn Ser Phe Val Lys Ser Cys
                565                 570                 575

Ser Phe Asp Ile Asn Ala Lys Arg Thr Met Tyr Arg Asp Ala Leu Asp
            580                 585                 590

Ile Leu Gly Ile Glu Ser Asp Lys Thr Glu Glu Asp Ile Glu Lys Met
        595                 600                 605

Ile Asp Asn Ile Leu Gln Ile Asp Ala Asn Gly Asp Lys Lys Leu Lys
    610                 615                 620

Lys Asn Asn Gly Leu Arg Asn Phe Ile Ala Ser Asn Val Ile Asp Ser
625                 630                 635                 640

Asn Arg Phe Lys Tyr Leu Val Arg Tyr Gly Asn Pro Lys Lys Ile Arg
                645                 650                 655

Glu Thr Ala Lys Cys Lys Pro Ala Val Arg Phe Val Leu Asn Glu Ile
            660                 665                 670

Pro Asp Ala Gln Ile Glu Arg Tyr Tyr Glu Ala Cys Cys Pro Lys Asn
        675                 680                 685

Thr Ala Leu Cys Ser Ala Asn Lys Arg Arg Glu Lys Leu Ala Asp Met
    690                 695                 700

Ile Ala Glu Ile Lys Phe Glu Asn Phe Ser Asp Ala Gly Asn Tyr Gln
705                 710                 715                 720

Lys Ala Asn Val Thr Ser Arg Thr Ser Glu Ala Glu Ile Lys Arg Lys
                725                 730                 735

Asn Gln Ala Ile Ile Arg Leu Tyr Leu Thr Val Met Tyr Ile Met Leu
            740                 745                 750

Lys Asn Leu Val Asn Val Asn Ala Arg Tyr Val Ile Ala Phe His Cys
        755                 760                 765

Val Glu Arg Asp Thr Lys Leu Tyr Ala Glu Ser Gly Leu Glu Val Gly
    770                 775                 780

Asn Ile Glu Lys Asn Lys Thr Asn Leu Thr Met Ala Val Met Gly Val
785                 790                 795                 800

Lys Leu Glu Asn Gly Ile Ile Lys Thr Glu Phe Asp Lys Ser Phe Ala
                805                 810                 815

Glu Asn Ala Ala Asn Arg Tyr Leu Arg Asn Ala Arg Trp Tyr Lys Leu
            820                 825                 830

Ile Leu Asp Asn Leu Lys Lys Ser Glu Arg Ala Val Val Asn Glu Phe
        835                 840                 845

Arg Asn Thr Val Cys His Leu Asn Ala Ile Arg Asn Ile Asn Ile Asn
    850                 855                 860

Ile Lys Glu Ile Lys Glu Val Glu Asn Tyr Phe Ala Leu Tyr His Tyr
865                 870                 875                 880

Leu Ile Gln Lys His Leu Glu Asn Arg Phe Ala Asp Lys Lys Val Glu
                885                 890                 895
```

```
Arg Asp Thr Gly Asp Phe Ile Ser Lys Leu Glu Glu His Lys Thr Tyr
            900                 905                 910

Cys Lys Asp Phe Val Lys Ala Tyr Cys Thr Pro Phe Gly Tyr Asn Leu
        915                 920                 925

Val Arg Tyr Lys Asn Leu Thr Ile Asp Gly Leu Phe Asp Lys Asn Tyr
    930                 935                 940

Pro Gly Lys Asp Asp Ser Asp Glu Gln Lys
945                 950


<210> SEQ ID NO 14
<211> LENGTH: 1150
<212> TYPE: PRT
<213> ORGANISM: Artificial Sequence
<220> FEATURE:
<223> OTHER INFORMATION: Chemically synthesized

<400> SEQUENCE: 14

Met Glu Asn Leu Asn Lys Ile Leu Asp Lys Glu Asn Glu Ile Cys Ile
1               5                   10                  15

Ser Lys Ile Phe Asn Thr Lys Gly Ile Ala Ala Pro Ile Thr Glu Lys
            20                  25                  30

Ala Leu Asp Asn Ile Lys Ser Lys Gln Lys Asn Asp Leu Asn Lys Glu
        35                  40                  45

Ala Arg Leu His Tyr Phe Ser Ile Gly His Ser Phe Lys Gln Ile Asp
    50                  55                  60

Thr Lys Lys Val Phe Asp Tyr Val Leu Ile Glu Glu Leu Lys Asp Glu
65                  70                  75                  80

Lys Pro Leu Lys Phe Ile Thr Leu Gln Lys Asp Phe Phe Thr Lys Glu
                85                  90                  95

Phe Ser Ile Lys Leu Gln Lys Leu Ile Asn Ser Ile Arg Asn Ile Asn
            100                 105                 110

Asn His Tyr Val His Asn Phe Asn Asp Ile Asn Leu Asn Lys Ile Asp
        115                 120                 125

Ser Asn Val Phe His Phe Leu Lys Glu Ser Phe Glu Leu Ala Ile Ile
    130                 135                 140

Glu Lys Tyr Tyr Lys Val Asn Lys Lys Tyr Pro Leu Asp Asn Glu Ile
145                 150                 155                 160

Val Leu Phe Leu Lys Glu Leu Phe Ile Lys Asp Glu Asn Thr Ala Leu
                165                 170                 175

Leu Asn Tyr Phe Thr Asn Leu Ser Lys Asp Glu Ala Ile Glu Tyr Ile
            180                 185                 190

Leu Thr Phe Thr Ile Thr Glu Asn Lys Ile Trp Asn Ile Asn Asn Glu
        195                 200                 205

His Asn Ile Leu Asn Ile Glu Lys Gly Lys Tyr Leu Thr Phe Glu Ala
    210                 215                 220

Met Leu Phe Leu Ile Thr Ile Phe Leu Tyr Lys Asn Glu Ala Asn His
225                 230                 235                 240

Leu Leu Pro Lys Leu Tyr Asp Phe Lys Asn Asn Lys Ser Lys Gln Glu
                245                 250                 255

Leu Phe Thr Phe Phe Ser Lys Lys Phe Thr Ser Gln Asp Ile Asp Ala
            260                 265                 270

Glu Glu Gly His Leu Ile Lys Phe Arg Asp Met Ile Gln Tyr Leu Asn
        275                 280                 285

His Tyr Pro Thr Ala Trp Asn Asn Asp Leu Lys Leu Glu Ser Glu Asn
    290                 295                 300
```

-continued

```
Lys Asn Lys Ile Met Thr Thr Lys Leu Ile Asp Ser Ile Ile Glu Phe
305                 310                 315                 320

Glu Leu Asn Ser Asn Tyr Pro Ser Phe Ala Thr Asp Ile Gln Phe Lys
                325                 330                 335

Lys Glu Ala Lys Ala Phe Leu Phe Ala Ser Asn Lys Lys Arg Asn Gln
            340                 345                 350

Thr Ser Phe Ser Asn Lys Ser Tyr Asn Glu Glu Ile Arg His Asn Pro
        355                 360                 365

His Ile Lys Gln Tyr Arg Asp Glu Ile Ala Ser Ala Leu Thr Pro Ile
    370                 375                 380

Ser Phe Asn Val Lys Glu Asp Lys Phe Lys Ile Phe Val Lys Lys His
385                 390                 395                 400

Val Leu Glu Glu Tyr Phe Pro Asn Ser Ile Gly Tyr Glu Lys Phe Leu
                405                 410                 415

Glu Tyr Asn Asp Phe Thr Glu Lys Glu Lys Glu Asp Phe Gly Leu Lys
            420                 425                 430

Leu Tyr Ser Asn Pro Lys Thr Asn Lys Leu Ile Glu Arg Ile Asp Asn
        435                 440                 445

His Lys Leu Val Lys Ser His Gly Arg Asn Gln Asp Arg Phe Met Asp
    450                 455                 460

Phe Ser Met Arg Phe Leu Ala Glu Asn Asn Tyr Phe Gly Lys Asp Ala
465                 470                 475                 480

Phe Phe Lys Cys Tyr Lys Phe Tyr Asp Thr Gln Glu Gln Asp Glu Phe
                485                 490                 495

Leu Gln Ser Asn Glu Asn Asn Asp Asp Val Lys Phe His Lys Gly Lys
            500                 505                 510

Val Thr Thr Tyr Ile Lys Tyr Glu Glu His Leu Lys Asn Tyr Ser Tyr
        515                 520                 525

Trp Asp Cys Pro Phe Val Glu Glu Asn Asn Ser Met Ser Val Lys Ile
    530                 535                 540

Ser Ile Gly Ser Glu Glu Lys Ile Leu Lys Ile Gln Arg Asn Leu Met
545                 550                 555                 560

Ile Tyr Phe Leu Glu Asn Ala Leu Tyr Asn Glu Asn Val Glu Asn Gln
                565                 570                 575

Gly Tyr Lys Leu Val Asn Asn Tyr Tyr Arg Glu Leu Lys Lys Asp Val
            580                 585                 590

Glu Glu Ser Ile Ala Ser Leu Asp Leu Ile Lys Ser Asn Pro Asp Phe
        595                 600                 605

Lys Ser Lys Tyr Lys Lys Ile Leu Pro Lys Arg Leu Leu His Asn Tyr
    610                 615                 620

Ala Pro Ala Lys Gln Asp Lys Ala Pro Glu Asn Ala Phe Glu Thr Leu
625                 630                 635                 640

Leu Lys Lys Ala Asp Phe Arg Glu Glu Gln Tyr Lys Lys Leu Leu Lys
                645                 650                 655

Lys Ala Glu His Glu Lys Asn Lys Glu Asp Phe Val Lys Arg Asn Lys
            660                 665                 670

Gly Lys Gln Phe Lys Leu His Phe Ile Arg Lys Ala Cys Gln Met Met
        675                 680                 685

Tyr Phe Lys Glu Lys Tyr Asn Thr Leu Lys Glu Gly Asn Ala Ala Phe
    690                 695                 700

Glu Lys Lys Asp Pro Val Ile Glu Lys Arg Lys Asn Lys Glu His Glu
705                 710                 715                 720

Phe Gly His His Lys Asn Leu Asn Ile Thr Arg Glu Glu Phe Asn Asp
```

```
                725                 730                 735

Tyr Cys Lys Trp Met Phe Ala Phe Asn Gly Asn Asp Ser Tyr Lys Lys
            740                 745                 750

Tyr Leu Arg Asp Leu Phe Ser Glu Lys His Phe Phe Asp Asn Gln Glu
        755                 760                 765

Tyr Lys Asn Leu Phe Glu Ser Ser Val Asn Leu Glu Ala Phe Tyr Ala
    770                 775                 780

Lys Thr Lys Glu Leu Phe Lys Lys Trp Ile Glu Thr Asn Lys Pro Thr
785                 790                 795                 800

Asn Asn Glu Asn Arg Tyr Thr Leu Glu Asn Tyr Lys Asn Leu Ile Leu
                805                 810                 815

Gln Lys Gln Val Phe Ile Asn Val Tyr His Phe Ser Lys Tyr Leu Ile
            820                 825                 830

Asp Lys Asn Leu Leu Asn Ser Glu Asn Asn Val Ile Gln Tyr Lys Ser
        835                 840                 845

Leu Glu Asn Val Glu Tyr Leu Ile Ser Asp Phe Tyr Phe Gln Ser Lys
    850                 855                 860

Leu Ser Ile Asp Gln Tyr Lys Thr Cys Gly Lys Leu Phe Asn Lys Leu
865                 870                 875                 880

Lys Ser Asn Lys Leu Glu Asp Cys Leu Leu Tyr Glu Ile Ala Tyr Asn
                885                 890                 895

Tyr Ile Asp Lys Lys Asn Val His Lys Ile Asp Ile Gln Lys Ile Leu
            900                 905                 910

Thr Ser Lys Ile Ile Leu Thr Ile Asn Asp Ala Asn Thr Pro Tyr Lys
        915                 920                 925

Ile Ser Val Pro Phe Asn Lys Leu Glu Arg Tyr Thr Glu Met Ile Ala
    930                 935                 940

Ile Lys Asn Gln Asn Asn Leu Lys Ala Arg Phe Leu Ile Asp Leu Pro
945                 950                 955                 960

Leu Tyr Leu Ser Lys Asn Lys Ile Lys Lys Gly Lys Asp Ser Ala Gly
                965                 970                 975

Tyr Glu Ile Ile Ile Lys Asn Asp Leu Glu Ile Glu Asp Ile Asn Thr
            980                 985                 990

Ile Asn Asn Lys Ile Ile Asn Asp  Ser Val Lys Phe Thr  Glu Val Leu
        995                 1000                1005

Met Glu  Leu Glu Lys Tyr Phe  Ile Leu Lys Asp Lys  Cys Ile Leu
    1010                1015                1020

Ser Lys  Asn Tyr Ile Asp Asn  Ser Glu Ile Pro Ser  Leu Lys Gln
    1025                1030                1035

Phe Ser  Lys Val Trp Ile Lys  Glu Asn Glu Asn Glu  Ile Ile Asn
    1040                1045                1050

Tyr Arg  Asn Ile Ala Cys His  Phe His Leu Pro Leu  Leu Glu Thr
    1055                1060                1065

Phe Asp  Asn Leu Leu Leu Asn  Val Glu Gln Lys Phe  Ile Lys Glu
    1070                1075                1080

Glu Leu  Gln Asn Val Ser Thr  Ile Asn Asp Leu Ser  Lys Pro Gln
    1085                1090                1095

Glu Tyr  Leu Ile Leu Leu Phe  Ile Lys Phe Lys His  Asn Asn Phe
    1100                1105                1110

Tyr Leu  Asn Leu Phe Asn Lys  Asn Glu Ser Lys Thr  Ile Lys Asn
    1115                1120                1125

Asp Lys  Glu Val Lys Lys Asn  Arg Val Leu Gln Lys  Phe Ile Asn
    1130                1135                1140
```

```
Gln Val  Ile Leu Lys Lys Lys
    1145                 1150


<210> SEQ ID NO 15
<211> LENGTH: 1110
<212> TYPE: PRT
<213> ORGANISM: Artificial Sequence
<220> FEATURE:
<223> OTHER INFORMATION: Chemically synthesized

<400> SEQUENCE: 15

Met Lys Val Arg Tyr Arg Lys Gln Ala Gln Leu Asp Thr Phe Ile Ile
1               5                   10                  15

Lys Thr Glu Ile Val Asn Asn Asp Ile Phe Ile Lys Ser Ile Ile Glu
            20                  25                  30

Lys Ala Arg Glu Lys Tyr Arg Tyr Ser Phe Leu Phe Asp Gly Glu Glu
        35                  40                  45

Lys Tyr His Phe Lys Asn Lys Ser Ser Val Glu Ile Val Lys Asn Asp
    50                  55                  60

Ile Phe Ser Gln Thr Pro Asp Asn Met Ile Arg Asn Tyr Lys Ile Thr
65                  70                  75                  80

Leu Lys Ile Ser Glu Lys Asn Pro Arg Val Val Glu Ala Glu Ile Glu
                85                  90                  95

Asp Leu Met Asn Ser Thr Ile Leu Lys Asp Gly Arg Arg Ser Ala Arg
            100                 105                 110

Arg Glu Lys Ser Met Thr Glu Arg Lys Leu Ile Glu Glu Lys Val Ala
        115                 120                 125

Glu Asn Tyr Ser Leu Leu Ala Asn Cys Pro Ile Glu Glu Val Asp Ser
    130                 135                 140

Ile Lys Ile Tyr Lys Ile Lys Arg Phe Leu Thr Tyr Arg Ser Asn Met
145                 150                 155                 160

Leu Leu Tyr Phe Ala Ser Ile Asn Ser Phe Leu Cys Glu Gly Ile Lys
                165                 170                 175

Gly Lys Asp Asn Glu Thr Glu Glu Ile Trp His Leu Lys Asp Asn Asp
            180                 185                 190

Val Arg Lys Glu Lys Val Lys Glu Asn Phe Lys Asn Lys Leu Ile Gln
        195                 200                 205

Ser Thr Glu Asn Tyr Asn Ser Ser Leu Lys Asn Gln Ile Glu Glu Lys
    210                 215                 220

Glu Lys Leu Ser Ser Lys Glu Phe Lys Lys Gly Ala Phe Tyr Arg Thr
225                 230                 235                 240

Ile Ile Lys Lys Leu Gln Gln Glu Arg Ile Lys Glu Leu Ser Glu Lys
                245                 250                 255

Ser Leu Thr Glu Asp Cys Glu Lys Ile Ile Lys Leu Tyr Ser Glu Leu
            260                 265                 270

Arg His Pro Leu Met His Tyr Asp Tyr Gln Tyr Phe Glu Asn Leu Phe
        275                 280                 285

Glu Asn Lys Glu Asn Ser Glu Leu Thr Lys Asn Leu Asn Leu Asp Ile
    290                 295                 300

Phe Lys Ser Leu Pro Leu Val Arg Lys Met Lys Leu Asn Asn Lys Val
305                 310                 315                 320

Asn Tyr Leu Glu Asp Asn Asp Thr Leu Phe Val Leu Gln Lys Thr Lys
                325                 330                 335

Lys Ala Lys Thr Leu Tyr Gln Ile Tyr Asp Ala Leu Cys Glu Gln Lys
            340                 345                 350
```

```
Asn Gly Phe Asn Lys Phe Ile Asn Asp Phe Phe Val Ser Asp Gly Glu
        355                 360                 365

Glu Asn Thr Val Phe Lys Gln Ile Ile Asn Glu Lys Phe Gln Ser Glu
    370                 375                 380

Met Glu Phe Leu Glu Lys Arg Ile Ser Glu Ser Glu Lys Lys Asn Glu
385                 390                 395                 400

Lys Leu Lys Lys Lys Leu Asp Ser Met Lys Ala His Phe Arg Asn Ile
                405                 410                 415

Asn Ser Glu Asp Thr Lys Glu Ala Tyr Phe Trp Asp Ile His Ser Ser
            420                 425                 430

Arg Asn Tyr Lys Thr Lys Tyr Asn Glu Arg Lys Asn Leu Val Asn Glu
        435                 440                 445

Tyr Thr Lys Leu Leu Gly Ser Ser Lys Glu Lys Lys Leu Leu Arg Glu
    450                 455                 460

Glu Ile Thr Lys Ile Asn Arg Gln Leu Leu Lys Leu Lys Gln Glu Met
465                 470                 475                 480

Glu Glu Ile Thr Lys Lys Asn Ser Leu Phe Arg Leu Glu Tyr Lys Met
                485                 490                 495

Lys Ile Ala Phe Gly Phe Leu Phe Cys Glu Phe Asp Gly Asn Ile Ser
            500                 505                 510

Lys Phe Lys Asp Glu Phe Asp Ala Ser Asn Gln Glu Lys Ile Ile Gln
        515                 520                 525

Tyr His Lys Asn Gly Glu Lys Tyr Leu Thr Ser Phe Leu Lys Glu Glu
    530                 535                 540

Glu Lys Glu Lys Phe Asn Leu Glu Lys Met Gln Lys Ile Ile Gln Lys
545                 550                 555                 560

Thr Glu Glu Glu Asp Trp Leu Leu Pro Glu Thr Lys Asn Asn Leu Phe
                565                 570                 575

Lys Phe Tyr Leu Leu Thr Tyr Leu Leu Leu Pro Tyr Glu Leu Lys Gly
            580                 585                 590

Asp Phe Leu Gly Phe Val Lys Lys His Tyr Tyr Asp Ile Lys Asn Val
        595                 600                 605

Asp Phe Met Asp Glu Asn Gln Asn Asn Ile Gln Val Ser Gln Thr Val
    610                 615                 620

Glu Lys Gln Glu Asp Tyr Phe Tyr His Lys Ile Arg Leu Phe Glu Lys
625                 630                 635                 640

Asn Thr Lys Lys Tyr Glu Ile Val Lys Tyr Ser Ile Val Pro Asn Glu
                645                 650                 655

Lys Leu Lys Gln Tyr Phe Glu Asp Leu Gly Ile Asp Ile Lys Tyr Leu
            660                 665                 670

Thr Gly Ser Val Glu Ser Gly Glu Lys Trp Leu Gly Glu Asn Leu Gly
        675                 680                 685

Ile Asp Ile Lys Tyr Leu Thr Val Glu Gln Lys Ser Glu Val Ser Glu
    690                 695                 700

Glu Lys Asn Lys Lys Val Ser Leu Lys Asn Asn Gly Met Phe Asn Lys
705                 710                 715                 720

Thr Ile Leu Leu Phe Val Phe Lys Tyr Tyr Gln Ile Ala Phe Lys Leu
                725                 730                 735

Phe Asn Asp Ile Glu Leu Tyr Ser Leu Phe Phe Leu Arg Glu Lys Ser
            740                 745                 750

Glu Lys Pro Phe Glu Val Phe Leu Glu Glu Leu Lys Asp Lys Met Ile
        755                 760                 765
```

```
Gly Lys Gln Leu Asn Phe Gly Gln Leu Leu Tyr Val Val Tyr Glu Val
    770                 775                 780

Leu Val Lys Asn Lys Asp Leu Asp Lys Ile Leu Ser Lys Lys Ile Asp
785                 790                 795                 800

Tyr Arg Lys Asp Lys Ser Phe Ser Pro Glu Ile Ala Tyr Leu Arg Asn
                805                 810                 815

Phe Leu Ser His Leu Asn Tyr Ser Lys Phe Leu Asp Asn Phe Met Lys
            820                 825                 830

Ile Asn Thr Asn Lys Ser Asp Glu Asn Lys Glu Val Leu Ile Pro Ser
        835                 840                 845

Ile Lys Ile Gln Lys Met Ile Gln Phe Ile Glu Lys Cys Asn Leu Gln
    850                 855                 860

Asn Gln Ile Asp Phe Asp Phe Asn Phe Val Asn Asp Phe Tyr Met Arg
865                 870                 875                 880

Lys Glu Lys Met Phe Phe Ile Gln Leu Lys Gln Ile Phe Pro Asp Ile
                885                 890                 895

Asn Ser Thr Glu Lys Gln Lys Lys Ser Glu Lys Glu Glu Ile Leu Arg
            900                 905                 910

Lys Arg Tyr His Leu Ile Asn Lys Lys Asn Glu Gln Ile Lys Asp Glu
        915                 920                 925

His Glu Ala Gln Ser Gln Leu Tyr Glu Lys Ile Leu Ser Leu Gln Lys
    930                 935                 940

Ile Phe Ser Cys Asp Lys Asn Asn Phe Tyr Arg Arg Leu Lys Glu Glu
945                 950                 955                 960

Lys Leu Leu Phe Leu Glu Lys Gln Gly Lys Lys Lys Ile Ser Met Lys
                965                 970                 975

Glu Ile Lys Asp Lys Ile Ala Ser Asp Ile Ser Asp Leu Leu Gly Ile
            980                 985                 990

Leu Lys Lys Glu Ile Thr Arg Asp  Ile Lys Asp Lys Leu  Thr Glu Lys
        995                 1000                1005

Phe Arg  Tyr Cys Glu Glu Lys  Leu Leu Asn Ile Ser  Phe Tyr Asn
    1010                1015                1020

His Gln  Asp Lys Lys Lys Glu  Glu Gly Ile Arg Val  Phe Leu Ile
    1025                1030                1035

Arg Asp  Lys Asn Ser Asp Asn  Phe Lys Phe Glu Ser  Ile Leu Asp
    1040                1045                1050

Asp Gly  Ser Asn Lys Ile Phe  Ile Ser Lys Asn Gly  Lys Glu Ile
    1055                1060                1065

Thr Ile  Gln Cys Cys Asp Lys  Val Leu Glu Thr Leu  Met Ile Glu
    1070                1075                1080

Lys Asn  Thr Leu Lys Ile Ser  Ser Asn Gly Lys Ile  Ile Ser Leu
    1085                1090                1095

Ile Pro  His Tyr Ser Tyr Ser  Ile Asp Val Lys Tyr
    1100                1105                1110


<210> SEQ ID NO 16
<211> LENGTH: 1111
<212> TYPE: PRT
<213> ORGANISM: Artificial Sequence
<220> FEATURE:
<223> OTHER INFORMATION: Chemically synthesized

<400> SEQUENCE: 16

Met Glu Lys Phe Arg Arg Gln Asn Arg Ser Ser Ile Ile Lys Ile Ile
1               5                   10                  15
```

```
Ile Ser Asn Tyr Asp Thr Lys Gly Ile Lys Glu Leu Lys Val Arg Tyr
            20                  25                  30

Arg Lys Gln Ala Gln Leu Asp Thr Phe Ile Ile Lys Thr Glu Ile Val
        35                  40                  45

Asn Asn Asp Ile Phe Ile Lys Ser Ile Ile Glu Lys Ala Arg Glu Lys
    50                  55                  60

Tyr Arg Tyr Ser Phe Leu Phe Asp Gly Glu Glu Lys Tyr His Phe Lys
65                  70                  75                  80

Asn Lys Ser Ser Val Glu Ile Val Lys Lys Asp Ile Phe Ser Gln Thr
                85                  90                  95

Pro Asp Asn Met Ile Arg Asn Tyr Lys Ile Thr Leu Lys Ile Ser Glu
            100                 105                 110

Lys Asn Pro Arg Val Val Glu Ala Glu Ile Glu Asp Leu Met Asn Ser
        115                 120                 125

Thr Ile Leu Lys Asp Gly Arg Arg Ser Ala Arg Arg Glu Lys Ser Met
    130                 135                 140

Thr Glu Arg Lys Leu Ile Glu Glu Lys Val Ala Glu Asn Tyr Ser Leu
145                 150                 155                 160

Leu Ala Asn Cys Pro Met Glu Glu Val Asp Ser Ile Lys Ile Tyr Lys
                165                 170                 175

Ile Lys Arg Phe Leu Thr Tyr Arg Ser Asn Met Leu Leu Tyr Phe Ala
            180                 185                 190

Ser Ile Asn Ser Phe Leu Cys Glu Gly Ile Lys Gly Lys Asp Asn Glu
        195                 200                 205

Thr Glu Glu Ile Trp His Leu Lys Asp Asn Asp Val Arg Lys Glu Lys
    210                 215                 220

Val Lys Glu Asn Phe Lys Asn Lys Leu Ile Gln Ser Thr Glu Asn Tyr
225                 230                 235                 240

Asn Ser Ser Leu Lys Asn Gln Ile Glu Glu Lys Glu Lys Leu Leu Arg
                245                 250                 255

Lys Glu Ser Lys Lys Gly Ala Phe Tyr Arg Thr Ile Ile Lys Lys Leu
            260                 265                 270

Gln Gln Glu Arg Ile Lys Glu Leu Ser Glu Lys Ser Leu Thr Glu Asp
        275                 280                 285

Cys Glu Lys Ile Ile Lys Leu Tyr Ser Glu Leu Arg His Pro Leu Met
    290                 295                 300

His Tyr Asp Tyr Gln Tyr Phe Glu Asn Leu Phe Glu Asn Lys Glu Asn
305                 310                 315                 320

Ser Glu Leu Thr Lys Asn Leu Asn Leu Asp Ile Phe Lys Ser Leu Pro
                325                 330                 335

Leu Val Arg Lys Met Lys Leu Asn Asn Lys Val Asn Tyr Leu Glu Asp
            340                 345                 350

Asn Asp Thr Leu Phe Val Leu Gln Lys Thr Lys Lys Ala Lys Thr Leu
        355                 360                 365

Tyr Gln Ile Tyr Asp Ala Leu Cys Glu Gln Lys Asn Gly Phe Asn Lys
    370                 375                 380

Phe Ile Asn Asp Phe Phe Val Ser Asp Gly Glu Glu Asn Thr Val Phe
385                 390                 395                 400

Lys Gln Ile Ile Asn Glu Lys Phe Gln Ser Glu Ile Glu Phe Leu Glu
                405                 410                 415

Lys Arg Ile Ser Glu Ser Glu Lys Lys Asn Glu Lys Leu Lys Lys Lys
            420                 425                 430

Leu Asp Ser Met Lys Ala His Phe Arg Asn Ile Asn Ser Glu Asp Thr
```

```
        435                 440                 445

Lys Glu Ala Tyr Phe Trp Asp Ile His Ser Ser Arg Asn Tyr Lys Thr
    450                 455                 460

Lys Tyr Asn Glu Arg Lys Asn Leu Val Asn Glu Tyr Thr Glu Leu Leu
465                 470                 475                 480

Gly Ser Ser Lys Glu Lys Lys Leu Leu Arg Glu Glu Ile Thr Lys Ile
                485                 490                 495

Asn Arg Gln Leu Leu Lys Leu Lys Gln Glu Met Glu Glu Ile Thr Lys
            500                 505                 510

Lys Asn Ser Leu Phe Arg Leu Glu Tyr Lys Met Lys Met Ala Phe Gly
        515                 520                 525

Phe Leu Phe Cys Glu Phe Asp Gly Asn Ile Ser Arg Phe Lys Asp Glu
    530                 535                 540

Phe Asp Ala Ser Asn Gln Glu Lys Ile Ile Gln Tyr His Lys Asn Gly
545                 550                 555                 560

Glu Lys Tyr Leu Thr Tyr Phe Leu Lys Glu Glu Glu Lys Glu Lys Phe
                565                 570                 575

Asn Leu Lys Lys Leu Gln Glu Thr Ile Gln Lys Thr Gly Glu Glu Asn
            580                 585                 590

Trp Leu Leu Pro Gln Asn Lys Asn Asn Leu Phe Lys Phe Tyr Leu Leu
        595                 600                 605

Thr Tyr Leu Leu Leu Pro Tyr Glu Leu Lys Gly Asp Phe Leu Gly Phe
    610                 615                 620

Val Lys Lys His Tyr Tyr Asp Ile Lys Asn Val Asp Phe Met Asp Glu
625                 630                 635                 640

Asn Gln Ser Ser Lys Ile Ile Glu Ser Lys Glu Asp Asp Phe Tyr His
                645                 650                 655

Lys Ile Arg Leu Phe Glu Lys Asn Thr Lys Lys Tyr Glu Ile Val Lys
            660                 665                 670

Tyr Ser Ile Val Pro Asp Lys Lys Leu Lys Gln Tyr Phe Lys Asp Leu
        675                 680                 685

Gly Ile Asp Thr Lys Tyr Leu Ile Leu Asp Gln Lys Ser Glu Val Ser
    690                 695                 700

Gly Glu Lys Asn Lys Lys Val Ser Leu Lys Asn Asn Gly Met Phe Asn
705                 710                 715                 720

Lys Thr Ile Leu Leu Phe Val Phe Lys Tyr Tyr Gln Ile Ala Phe Lys
                725                 730                 735

Leu Phe Asn Asp Ile Glu Leu Tyr Ser Leu Phe Phe Leu Arg Glu Lys
            740                 745                 750

Ser Gly Lys Pro Phe Glu Val Phe Leu Lys Glu Leu Lys Asp Lys Met
        755                 760                 765

Ile Gly Lys Gln Leu Asn Phe Gly Gln Leu Leu Tyr Val Val Tyr Glu
    770                 775                 780

Val Leu Val Lys Asn Lys Asp Leu Ser Glu Ile Leu Ser Glu Arg Ile
785                 790                 795                 800

Asp Tyr Arg Lys Asp Met Cys Phe Ser Ala Glu Ile Ala Asp Leu Arg
                805                 810                 815

Asn Phe Leu Ser His Leu Asn Tyr Ser Lys Phe Leu Asp Asn Phe Met
            820                 825                 830

Lys Ile Asn Thr Asn Lys Ser Asp Glu Asn Lys Glu Val Leu Ile Pro
        835                 840                 845

Ser Ile Lys Ile Gln Lys Met Ile Lys Phe Ile Glu Glu Cys Asn Leu
    850                 855                 860
```

Gln Ser Gln Ile Asp Phe Asp Phe Asn Phe Val Asn Asp Phe Tyr Met
865 870 875 880

Arg Lys Glu Lys Met Phe Phe Ile Gln Leu Lys Gln Ile Phe Pro Asp
885 890 895

Ile Asn Ser Thr Glu Lys Gln Lys Met Asn Glu Lys Glu Glu Ile Leu
900 905 910

Arg Asn Arg Tyr His Leu Thr Asp Lys Lys Asn Glu Gln Ile Lys Asp
915 920 925

Glu His Glu Ala Gln Ser Gln Leu Tyr Glu Lys Ile Leu Ser Leu Gln
930 935 940

Lys Ile Tyr Ser Ser Asp Lys Asn Asn Phe Tyr Gly Arg Leu Lys Glu
945 950 955 960

Glu Lys Leu Leu Phe Leu Glu Lys Gln Glu Lys Lys Lys Leu Ser Met
965 970 975

Glu Glu Ile Lys Asp Lys Ile Ala Gly Asp Ile Ser Asp Leu Leu Gly
980 985 990

Ile Leu Lys Lys Glu Ile Thr Arg Asp Ile Lys Asp Lys Leu Thr Glu
995 1000 1005

Lys Phe Arg Tyr Cys Glu Glu Lys Leu Leu Asn Leu Ser Phe Tyr
1010 1015 1020

Asn His Gln Asp Lys Lys Lys Glu Glu Ser Ile Arg Val Phe Leu
1025 1030 1035

Ile Arg Asp Lys Asn Ser Asp Asn Phe Lys Phe Glu Ser Ile Leu
1040 1045 1050

Asp Asp Gly Ser Asn Lys Ile Phe Ile Ser Lys Asn Gly Lys Glu
1055 1060 1065

Ile Thr Ile Gln Cys Cys Asp Lys Val Leu Glu Thr Leu Ile Ile
1070 1075 1080

Glu Lys Asn Thr Leu Lys Ile Ser Ser Asn Gly Lys Ile Ile Ser
1085 1090 1095

Leu Ile Pro His Tyr Ser Tyr Ser Ile Asp Val Lys Tyr
1100 1105 1110

<210> SEQ ID NO 17
<211> LENGTH: 668
<212> TYPE: PRT
<213> ORGANISM: Artificial Sequence
<220> FEATURE:
<223> OTHER INFORMATION: Chemically synthesized

<400> SEQUENCE: 17

Met Thr Glu Lys Lys Ser Ile Ile Phe Lys Asn Lys Ser Ser Val Glu
1 5 10 15

Ile Val Lys Lys Asp Ile Phe Ser Gln Thr Pro Asp Asn Met Ile Arg
20 25 30

Asn Tyr Lys Ile Thr Leu Lys Ile Ser Glu Lys Asn Pro Arg Val Val
35 40 45

Glu Ala Glu Ile Glu Asp Leu Met Asn Ser Thr Ile Leu Lys Asp Gly
50 55 60

Arg Arg Ser Ala Arg Arg Glu Lys Ser Met Thr Glu Arg Lys Leu Ile
65 70 75 80

Glu Glu Lys Val Ala Glu Asn Tyr Ser Leu Leu Ala Asn Cys Pro Met
85 90 95

Glu Glu Val Asp Ser Ile Lys Ile Tyr Lys Ile Lys Arg Phe Leu Thr
100 105 110

```
Tyr Arg Ser Asn Met Leu Leu Tyr Phe Ala Ser Ile Asn Ser Phe Leu
        115                 120                 125

Cys Glu Gly Ile Lys Gly Lys Asp Asn Glu Thr Glu Glu Ile Trp His
    130                 135                 140

Leu Lys Asp Asn Asp Val Arg Lys Glu Lys Val Lys Glu Asn Phe Lys
145                 150                 155                 160

Asn Lys Leu Ile Gln Ser Thr Glu Asn Tyr Asn Ser Ser Leu Lys Asn
                165                 170                 175

Gln Ile Glu Glu Lys Glu Lys Leu Leu Arg Lys Glu Ser Lys Lys Gly
            180                 185                 190

Ala Phe Tyr Arg Thr Ile Ile Lys Lys Leu Gln Gln Glu Arg Ile Lys
        195                 200                 205

Glu Leu Ser Glu Lys Ser Leu Thr Glu Asp Cys Glu Lys Ile Ile Lys
    210                 215                 220

Leu Tyr Ser Glu Leu Arg His Pro Leu Met His Tyr Asp Tyr Gln Tyr
225                 230                 235                 240

Phe Glu Asn Leu Phe Glu Asn Lys Glu Asn Ser Glu Leu Thr Lys Asn
                245                 250                 255

Leu Asn Leu Asp Ile Phe Lys Ser Leu Pro Leu Val Arg Lys Met Lys
            260                 265                 270

Leu Asn Asn Lys Val Asn Tyr Leu Glu Asp Asn Asp Thr Leu Phe Val
        275                 280                 285

Leu Gln Lys Thr Lys Lys Ala Lys Thr Leu Tyr Gln Ile Tyr Asp Ala
    290                 295                 300

Leu Cys Glu Gln Lys Asn Gly Phe Asn Lys Phe Ile Asn Asp Phe Phe
305                 310                 315                 320

Val Ser Asp Gly Glu Glu Asn Thr Val Phe Lys Gln Ile Ile Asn Glu
                325                 330                 335

Lys Phe Gln Ser Glu Met Glu Phe Leu Glu Lys Arg Ile Ser Glu Ser
            340                 345                 350

Glu Lys Lys Asn Glu Lys Leu Lys Lys Lys Phe Asp Ser Met Lys Ala
        355                 360                 365

His Phe His Asn Ile Asn Ser Glu Asp Thr Lys Glu Ala Tyr Phe Trp
    370                 375                 380

Asp Ile His Ser Ser Ser Asn Tyr Lys Thr Lys Tyr Asn Glu Arg Lys
385                 390                 395                 400

Asn Leu Val Asn Glu Tyr Thr Glu Leu Leu Gly Ser Ser Lys Glu Lys
                405                 410                 415

Lys Leu Leu Arg Glu Glu Ile Thr Gln Ile Asn Arg Lys Leu Leu Lys
            420                 425                 430

Leu Lys Gln Glu Met Glu Glu Ile Thr Lys Lys Asn Ser Leu Phe Arg
        435                 440                 445

Leu Glu Tyr Lys Met Lys Ile Ala Phe Gly Phe Leu Phe Cys Glu Phe
    450                 455                 460

Asp Gly Asn Ile Ser Lys Phe Lys Asp Glu Phe Asp Ala Ser Asn Gln
465                 470                 475                 480

Glu Lys Ile Ile Gln Tyr His Lys Asn Gly Glu Lys Tyr Leu Thr Tyr
                485                 490                 495

Phe Leu Lys Glu Glu Glu Lys Glu Lys Phe Asn Leu Glu Lys Met Gln
            500                 505                 510

Lys Ile Ile Gln Lys Thr Glu Glu Glu Asp Trp Leu Leu Pro Glu Thr
        515                 520                 525
```

```
Lys Asn Asn Leu Phe Lys Phe Tyr Leu Leu Thr Tyr Leu Leu Leu Pro
    530                 535                 540

Tyr Glu Leu Lys Gly Asp Phe Leu Gly Phe Val Lys Lys His Tyr Tyr
545                 550                 555                 560

Asp Ile Lys Asn Val Asp Phe Met Asp Glu Asn Gln Asn Asn Ile Gln
                565                 570                 575

Val Ser Gln Thr Val Glu Lys Gln Glu Asp Tyr Phe Tyr His Lys Ile
            580                 585                 590

Arg Leu Phe Glu Lys Asn Thr Lys Lys Tyr Glu Ile Val Lys Tyr Ser
        595                 600                 605

Ile Val Pro Asn Glu Lys Leu Lys Gln Tyr Phe Glu Asp Leu Gly Ile
    610                 615                 620

Asp Ile Lys Tyr Leu Thr Gly Ser Val Glu Ser Gly Glu Lys Trp Leu
625                 630                 635                 640

Gly Glu Asn Leu Gly Ile Asp Ile Lys Tyr Leu Thr Val Glu Gln Lys
                645                 650                 655

Ser Glu Val Ser Glu Glu Lys Ile Lys Lys Phe Leu
            660                 665


<210> SEQ ID NO 18
<211> LENGTH: 1115
<212> TYPE: PRT
<213> ORGANISM: Artificial Sequence
<220> FEATURE:
<223> OTHER INFORMATION: Chemically synthesized

<400> SEQUENCE: 18

Met Glu Lys Phe Arg Arg Gln Asn Arg Asn Ser Ile Ile Lys Ile Ile
1               5                   10                  15

Ile Ser Asn Tyr Asp Thr Lys Gly Ile Lys Glu Leu Lys Val Arg Tyr
            20                  25                  30

Arg Lys Gln Ala Gln Leu Asp Thr Phe Ile Ile Lys Thr Glu Ile Val
        35                  40                  45

Asn Asn Asp Ile Phe Ile Lys Ser Ile Ile Glu Lys Ala Arg Glu Lys
    50                  55                  60

Tyr Arg Tyr Ser Phe Leu Phe Asp Gly Glu Glu Lys Tyr His Phe Lys
65                  70                  75                  80

Asn Lys Ser Ser Val Glu Ile Val Lys Lys Asp Ile Phe Ser Gln Thr
                85                  90                  95

Pro Asp Asn Met Ile Arg Asn Tyr Lys Ile Thr Leu Lys Ile Ser Glu
            100                 105                 110

Lys Asn Pro Arg Val Val Glu Ala Glu Ile Glu Asp Leu Met Asn Ser
        115                 120                 125

Thr Ile Leu Lys Asp Gly Arg Arg Ser Ala Arg Arg Glu Lys Ser Met
    130                 135                 140

Thr Glu Arg Lys Leu Ile Glu Glu Lys Val Ala Lys Asn Tyr Ser Leu
145                 150                 155                 160

Leu Ala Asn Cys Pro Met Glu Glu Val Asp Ser Ile Lys Ile Tyr Lys
                165                 170                 175

Ile Lys Arg Phe Leu Thr Tyr Arg Ser Asn Met Leu Leu Tyr Phe Ala
            180                 185                 190

Ser Ile Asn Ser Phe Leu Cys Glu Gly Ile Lys Gly Lys Asp Asn Glu
        195                 200                 205

Thr Glu Glu Ile Trp His Leu Lys Asp Asn Asp Val Arg Lys Glu Lys
    210                 215                 220
```

```
Val Arg Glu Asn Phe Lys Asn Lys Leu Ile Gln Ser Thr Glu Asn Tyr
225                 230                 235                 240

Asn Ser Ser Leu Lys Asn Gln Ile Glu Glu Lys Glu Lys Leu Leu Arg
                245                 250                 255

Lys Glu Phe Lys Lys Gly Ala Phe Tyr Arg Thr Ile Ile Lys Lys Leu
            260                 265                 270

Gln Gln Glu Arg Ile Lys Glu Leu Ser Glu Lys Ser Leu Thr Glu Asp
        275                 280                 285

Cys Glu Lys Ile Ile Lys Leu Tyr Ser Lys Leu Arg His Ser Leu Met
    290                 295                 300

His Tyr Asp Tyr Gln Tyr Phe Glu Asn Leu Phe Glu Asn Lys Lys Asn
305                 310                 315                 320

Asp Asp Leu Met Lys Asp Leu Asn Leu Asp Leu Phe Lys Ser Leu Pro
                325                 330                 335

Leu Ile Arg Lys Met Lys Leu Asn Asn Lys Val Asn Tyr Leu Glu Asp
            340                 345                 350

Gly Asp Thr Leu Phe Val Leu Gln Lys Thr Lys Lys Ala Lys Thr Leu
        355                 360                 365

Tyr Gln Ile Tyr Asp Ala Leu Cys Glu Gln Lys Asn Gly Phe Asn Lys
    370                 375                 380

Phe Ile Asn Asp Phe Phe Val Ser Asp Gly Glu Glu Asn Thr Val Phe
385                 390                 395                 400

Lys Gln Ile Ile Asn Glu Lys Phe Gln Ser Glu Met Glu Phe Leu Glu
                405                 410                 415

Lys Arg Ile Ser Glu Ser Glu Lys Lys Asn Glu Lys Leu Lys Lys Lys
            420                 425                 430

Leu Asp Ser Met Lys Ala His Phe Arg Asn Ile Asn Ser Glu Asp Thr
        435                 440                 445

Lys Glu Ala Tyr Phe Trp Asp Ile His Ser Ser Arg Asn Tyr Lys Thr
    450                 455                 460

Lys Tyr Asn Glu Arg Lys Asn Leu Val Asn Glu Tyr Thr Glu Leu Leu
465                 470                 475                 480

Gly Ser Ser Lys Glu Lys Lys Leu Leu Arg Glu Glu Ile Thr Lys Ile
                485                 490                 495

Asn Arg Gln Leu Leu Lys Leu Lys Gln Glu Met Glu Glu Ile Thr Lys
            500                 505                 510

Lys Asn Ser Leu Phe Arg Leu Glu Tyr Lys Met Lys Ile Ala Phe Gly
        515                 520                 525

Phe Leu Phe Cys Glu Phe Asp Gly Asn Ile Ser Lys Phe Lys Asp Glu
    530                 535                 540

Phe Asp Ala Ser Asn Gln Glu Lys Ile Ile Gln Tyr His Lys Asn Gly
545                 550                 555                 560

Glu Lys Tyr Leu Thr Ser Phe Leu Lys Glu Glu Glu Lys Glu Lys Phe
                565                 570                 575

Asn Leu Glu Lys Met Gln Lys Ile Ile Gln Lys Thr Glu Glu Glu Asp
            580                 585                 590

Trp Leu Leu Pro Glu Thr Lys Asn Asn Leu Phe Lys Phe Tyr Leu Leu
        595                 600                 605

Thr Tyr Leu Leu Leu Pro Tyr Glu Leu Lys Gly Asp Phe Leu Gly Phe
    610                 615                 620

Val Lys Lys His Tyr Tyr Asp Ile Lys Asn Val Asp Phe Ile Asp Glu
625                 630                 635                 640

Asn Gln Asn Asn Ile Gln Val Ser Gln Thr Val Glu Lys Gln Glu Asp
```

```
                645                 650                 655

Tyr Phe Tyr His Lys Ile Arg Leu Phe Glu Lys Asn Thr Lys Lys Tyr
            660                 665                 670

Glu Ile Val Lys Tyr Ser Ile Val Pro Asn Glu Lys Leu Lys Gln Tyr
        675                 680                 685

Phe Glu Asp Leu Gly Ile Asp Ile Lys Tyr Leu Thr Val Glu Gln Lys
    690                 695                 700

Ser Glu Val Ser Glu Glu Lys Asn Lys Lys Val Ser Leu Lys Asn Asn
705                 710                 715                 720

Gly Met Phe Asn Lys Thr Ile Leu Leu Phe Val Phe Lys Tyr Tyr Gln
                725                 730                 735

Ile Ala Phe Lys Leu Phe Asn Asp Ile Glu Leu Tyr Ser Leu Phe Phe
            740                 745                 750

Leu Arg Glu Lys Ser Gly Lys Pro Leu Glu Ile Phe Arg Lys Glu Leu
        755                 760                 765

Glu Ser Lys Met Lys Asp Gly Tyr Leu Asn Phe Gly Gln Leu Leu Tyr
    770                 775                 780

Val Val Tyr Glu Val Leu Val Lys Asn Lys Asp Leu Asp Lys Ile Leu
785                 790                 795                 800

Ser Lys Lys Ile Asp Tyr Arg Lys Asp Lys Ser Phe Ser Pro Glu Ile
                805                 810                 815

Ala Tyr Leu Arg Asn Phe Leu Ser His Leu Asn Tyr Ser Lys Phe Leu
            820                 825                 830

Asp Asn Phe Met Lys Ile Asn Thr Asn Lys Ser Asp Glu Asn Lys Glu
        835                 840                 845

Val Leu Ile Pro Ser Ile Lys Ile Gln Lys Met Ile Gln Phe Ile Glu
    850                 855                 860

Lys Cys Asn Leu Gln Asn Gln Ile Asp Phe Asp Phe Asn Phe Val Asn
865                 870                 875                 880

Asp Phe Tyr Met Arg Lys Glu Lys Met Phe Phe Ile Gln Leu Lys Gln
                885                 890                 895

Ile Phe Pro Asp Ile Asn Ser Thr Glu Lys Gln Lys Met Asn Glu Lys
            900                 905                 910

Glu Glu Ile Leu Arg Asn Arg Tyr His Leu Thr Asp Lys Lys Asn Glu
        915                 920                 925

Gln Ile Lys Asp Glu His Glu Ala Gln Ser Gln Leu Tyr Glu Lys Ile
    930                 935                 940

Leu Ser Leu Gln Lys Ile Tyr Ser Ser Asp Lys Asn Asn Phe Tyr Gly
945                 950                 955                 960

Arg Leu Lys Glu Glu Lys Leu Leu Phe Leu Glu Lys Gln Gly Lys Lys
                965                 970                 975

Lys Leu Ser Met Glu Glu Ile Lys Asp Lys Ile Ala Gly Asp Ile Ser
            980                 985                 990

Asp Leu Leu Gly Ile Leu Lys Lys  Glu Ile Thr Arg Asp  Ile Lys Asp
        995                 1000                1005

Lys Leu  Thr Glu Lys Phe Arg  Tyr Cys Glu Glu Lys  Leu Leu Asn
    1010                1015                1020

Leu Ser  Phe Tyr Asn His Gln  Asp Lys Lys Lys Glu  Glu Ser Ile
    1025                1030                1035

Arg Val  Phe Leu Ile Arg Asp  Lys Asn Ser Asp Asn  Phe Lys Phe
    1040                1045                1050

Glu Ser  Ile Leu Asp Asp Gly  Ser Asn Lys Ile Phe  Ile Ser Lys
    1055                1060                1065
```

```
Asn Gly  Lys Glu Ile Thr Ile  Gln Cys Cys Asp Lys  Val Leu Glu
    1070                 1075                 1080

Thr Leu  Ile Ile Glu Lys Asn  Thr Leu Lys Ile Ser  Ser Asn Gly
    1085                 1090                 1095

Lys Ile  Ile Ser Leu Ile Pro  His Tyr Ser Tyr Ser  Ile Asp Val
    1100                 1105                 1110

Lys Tyr
    1115


<210> SEQ ID NO 19
<211> LENGTH: 1121
<212> TYPE: PRT
<213> ORGANISM: Artificial Sequence
<220> FEATURE:
<223> OTHER INFORMATION: Chemically synthesized

<400> SEQUENCE: 19

Met Gly Lys Pro Asn Arg Ser Ser Ile Ile Lys Ile Ile Ile Ser Asn
1               5                   10                  15

Tyr Asp Asn Lys Gly Ile Lys Glu Val Lys Val Arg Tyr Asn Lys Gln
            20                  25                  30

Ala Gln Leu Asp Thr Phe Leu Ile Lys Ser Glu Leu Lys Asp Gly Lys
        35                  40                  45

Phe Ile Leu Tyr Ser Ile Val Asp Lys Ala Arg Glu Lys Tyr Arg Tyr
    50                  55                  60

Ser Phe Glu Ile Asp Lys Thr Asn Ile Asn Lys Asn Glu Ile Leu Ile
65                  70                  75                  80

Ile Lys Lys Asp Ile Tyr Ser Asn Lys Glu Asp Lys Val Ile Arg Lys
                85                  90                  95

Tyr Ile Leu Ser Phe Glu Val Ser Glu Lys Asn Asp Arg Thr Ile Val
            100                 105                 110

Thr Lys Ile Lys Asp Cys Leu Glu Thr Gln Lys Lys Glu Lys Phe Glu
        115                 120                 125

Arg Glu Asn Thr Arg Arg Leu Ile Ser Glu Thr Glu Arg Lys Leu Leu
    130                 135                 140

Ser Glu Glu Thr Gln Lys Thr Tyr Ser Lys Ile Ala Cys Cys Ser Pro
145                 150                 155                 160

Glu Asp Ile Asp Ser Val Lys Ile Tyr Lys Ile Lys Arg Tyr Leu Ala
                165                 170                 175

Tyr Arg Ser Asn Met Leu Leu Phe Phe Ser Leu Ile Asn Asp Ile Phe
            180                 185                 190

Val Lys Gly Val Val Lys Asp Asn Gly Glu Glu Val Gly Glu Ile Trp
        195                 200                 205

Arg Ile Ile Asp Ser Lys Glu Ile Asp Glu Lys Lys Thr Tyr Asp Leu
    210                 215                 220

Leu Val Glu Asn Phe Lys Lys Arg Met Ser Gln Glu Phe Ile Asn Tyr
225                 230                 235                 240

Lys Gln Ser Ile Glu Asn Lys Ile Glu Lys Asn Thr Asn Lys Ile Lys
                245                 250                 255

Glu Ile Glu Gln Lys Leu Lys Lys Glu Lys Tyr Lys Lys Glu Ile Asn
            260                 265                 270

Arg Leu Lys Lys Gln Leu Ile Glu Leu Asn Arg Glu Asn Asp Leu Leu
        275                 280                 285

Glu Lys Asp Lys Ile Glu Leu Ser Asp Glu Glu Ile Arg Glu Asp Ile
    290                 295                 300
```

```
Glu Lys Ile Leu Lys Ile Tyr Ser Asp Leu Arg His Lys Leu Met His
305                 310                 315                 320

Tyr Asn Tyr Gln Tyr Phe Glu Asn Leu Phe Glu Asn Lys Lys Ile Ser
                325                 330                 335

Lys Glu Lys Asn Glu Asp Val Asn Leu Thr Glu Leu Leu Asp Leu Asn
            340                 345                 350

Leu Phe Arg Tyr Leu Pro Leu Val Arg Gln Leu Lys Leu Glu Asn Lys
        355                 360                 365

Thr Asn Tyr Leu Glu Lys Glu Asp Lys Ile Thr Val Leu Gly Val Ser
    370                 375                 380

Asp Ser Ala Ile Lys Tyr Tyr Ser Tyr Tyr Asn Phe Leu Cys Glu Gln
385                 390                 395                 400

Lys Asn Gly Phe Asn Asn Phe Ile Asn Ser Phe Phe Ser Asn Asp Gly
                405                 410                 415

Glu Glu Asn Lys Ser Phe Lys Glu Lys Ile Asn Leu Ser Leu Glu Lys
            420                 425                 430

Glu Ile Glu Ile Met Glu Lys Glu Thr Asn Glu Lys Ile Lys Glu Ile
        435                 440                 445

Asn Lys Asn Glu Leu Gln Leu Met Lys Glu Gln Lys Glu Leu Gly Thr
    450                 455                 460

Ala Tyr Val Leu Asp Ile His Ser Leu Asn Asp Tyr Lys Ile Ser His
465                 470                 475                 480

Asn Glu Arg Asn Lys Asn Val Lys Leu Gln Asn Asp Ile Met Asn Gly
                485                 490                 495

Asn Arg Asp Lys Asn Ala Leu Asp Lys Ile Asn Lys Lys Leu Val Glu
            500                 505                 510

Leu Lys Ile Lys Met Asp Lys Ile Thr Lys Arg Asn Ser Ile Leu Arg
        515                 520                 525

Leu Lys Tyr Lys Leu Gln Val Ala Tyr Gly Phe Leu Met Glu Glu Tyr
    530                 535                 540

Lys Gly Asn Ile Lys Lys Phe Lys Asp Glu Phe Asp Ile Ser Lys Glu
545                 550                 555                 560

Lys Ile Lys Ser Tyr Lys Ser Lys Gly Glu Lys Tyr Leu Glu Val Lys
                565                 570                 575

Ser Glu Lys Lys Tyr Ile Thr Lys Ile Leu Asn Ser Ile Glu Asp Ile
            580                 585                 590

His Asn Ile Thr Trp Leu Lys Asn Gln Glu Glu Asn Asn Leu Phe Lys
        595                 600                 605

Phe Tyr Val Leu Thr Tyr Ile Leu Leu Pro Phe Glu Phe Arg Gly Asp
    610                 615                 620

Phe Leu Gly Phe Val Lys Lys His Tyr Tyr Asp Ile Lys Asn Val Glu
625                 630                 635                 640

Phe Leu Asp Glu Asn Asn Asp Arg Leu Thr Pro Glu Gln Leu Glu Lys
                645                 650                 655

Met Lys Asn Asp Ser Phe Phe Asn Lys Ile Arg Leu Phe Glu Lys Asn
            660                 665                 670

Ser Lys Lys Tyr Asp Ile Leu Lys Glu Ser Ile Leu Thr Ser Glu Arg
        675                 680                 685

Ile Gly Lys Tyr Phe Ser Leu Leu Asn Thr Gly Ala Lys Tyr Phe Glu
    690                 695                 700

Tyr Gly Gly Glu Glu Asn Arg Gly Ile Phe Asn Lys Asn Ile Ile Ile
705                 710                 715                 720
```

```
Pro Ile Phe Lys Tyr Tyr Gln Ile Val Leu Lys Leu Tyr Asn Asp Val
                725                 730                 735

Glu Leu Ala Met Leu Leu Thr Leu Ser Glu Ser Asp Glu Lys Asp Ile
            740                 745                 750

Asn Lys Ile Lys Glu Leu Val Thr Leu Lys Glu Lys Val Ser Pro Lys
        755                 760                 765

Lys Ile Asp Tyr Glu Lys Lys Tyr Lys Phe Ser Val Leu Leu Asp Cys
    770                 775                 780

Phe Asn Arg Ile Ile Asn Leu Gly Lys Lys Asp Phe Leu Ala Ser Glu
785                 790                 795                 800

Glu Val Lys Glu Val Ala Lys Thr Phe Thr Asn Leu Ala Tyr Leu Arg
                805                 810                 815

Asn Lys Ile Cys His Leu Asn Tyr Ser Lys Phe Ile Asp Asp Leu Leu
            820                 825                 830

Thr Ile Asp Thr Asn Lys Ser Thr Thr Asp Ser Glu Gly Lys Leu Leu
        835                 840                 845

Ile Asn Asp Arg Ile Arg Lys Leu Ile Lys Phe Ile Arg Glu Asn Asn
    850                 855                 860

Gln Lys Met Asn Ile Ser Ile Asp Tyr Asn Tyr Ile Asn Asp Tyr Tyr
865                 870                 875                 880

Met Lys Lys Glu Lys Phe Ile Phe Gly Gln Arg Lys Gln Ala Lys Thr
                885                 890                 895

Ile Ile Asp Ser Gly Lys Lys Ala Asn Lys Arg Asn Lys Ala Glu Glu
            900                 905                 910

Leu Leu Lys Met Tyr Arg Val Lys Lys Glu Asn Ile Asn Leu Ile Tyr
        915                 920                 925

Glu Leu Ser Lys Lys Leu Asn Glu Leu Thr Lys Ser Glu Leu Phe Leu
    930                 935                 940

Leu Asp Lys Lys Leu Leu Lys Asp Ile Asp Phe Thr Asp Val Lys Ile
945                 950                 955                 960

Lys Asn Lys Ser Phe Phe Glu Leu Lys Asn Asp Val Lys Glu Val Ala
                965                 970                 975

Asn Ile Lys Gln Ala Leu Gln Lys His Ser Ser Glu Leu Ile Gly Ile
            980                 985                 990

Tyr Lys Lys Glu Val Ile Met Ala  Ile Lys Arg Ser Ile  Val Ser Lys
        995                 1000                1005

Leu Ile  Tyr Asp Glu Glu Lys  Val Leu Ser Ile Ile  Ile Tyr Asp
    1010                1015                1020

Lys Thr  Asn Lys Lys Tyr Glu  Asp Phe Leu Leu Glu  Ile Arg Arg
    1025                1030                1035

Glu Arg  Asp Ile Asn Lys Phe  Gln Phe Leu Ile Asp  Glu Lys Lys
    1040                1045                1050

Glu Lys  Leu Gly Tyr Glu Lys  Ile Ile Glu Thr Lys  Glu Lys Lys
    1055                1060                1065

Lys Val  Val Val Lys Ile Gln  Asn Asn Ser Glu Leu  Val Ser Glu
    1070                1075                1080

Pro Arg  Ile Ile Lys Asn Lys  Asp Lys Lys Lys Ala  Lys Thr Pro
    1085                1090                1095

Glu Glu  Ile Ser Lys Leu Gly  Ile Leu Asp Leu Thr  Asn His Tyr
    1100                1105                1110

Cys Phe  Asn Leu Lys Ile Thr  Leu
    1115                1120
```

<210> SEQ ID NO 20
<211> LENGTH: 897
<212> TYPE: PRT
<213> ORGANISM: Artificial Sequence
<220> FEATURE:
<223> OTHER INFORMATION: Chemically synthesized

<400> SEQUENCE: 20

Met Glu Asn Lys Gly Asn Asn Lys Lys Ile Asp Phe Asp Glu Asn Tyr
1 5 10 15

Asn Ile Leu Val Ala Gln Ile Lys Glu Tyr Phe Thr Lys Glu Ile Glu
20 25 30

Asn Tyr Asn Asn Arg Ile Asp Asn Ile Ile Asp Lys Lys Glu Leu Leu
35 40 45

Lys Tyr Ser Glu Lys Lys Glu Glu Ser Glu Lys Asn Lys Lys Leu Glu
50 55 60

Glu Leu Asn Lys Leu Lys Ser Gln Lys Leu Lys Ile Leu Thr Asp Glu
65 70 75 80

Glu Ile Lys Ala Asp Val Ile Lys Ile Ile Lys Ile Phe Ser Asp Leu
85 90 95

Arg His Ser Leu Met His Tyr Glu Tyr Lys Tyr Phe Glu Asn Leu Phe
100 105 110

Glu Asn Lys Lys Asn Glu Glu Leu Ala Glu Leu Leu Asn Leu Asn Leu
115 120 125

Phe Lys Asn Leu Thr Leu Leu Arg Gln Met Lys Ile Glu Asn Lys Thr
130 135 140

Asn Tyr Leu Glu Gly Arg Glu Glu Phe Asn Ile Ile Gly Lys Asn Ile
145 150 155 160

Lys Ala Lys Glu Val Leu Gly His Tyr Asn Leu Leu Ala Glu Gln Lys
165 170 175

Asn Gly Phe Asn Asn Phe Ile Asn Ser Phe Phe Val Gln Asp Gly Thr
180 185 190

Glu Asn Leu Glu Phe Lys Lys Leu Ile Asp Glu His Phe Val Asn Ala
195 200 205

Lys Lys Arg Leu Glu Arg Asn Ile Lys Lys Ser Lys Lys Leu Glu Lys
210 215 220

Glu Leu Glu Lys Met Glu Gln His Tyr Gln Arg Leu Asn Cys Ala Tyr
225 230 235 240

Val Trp Asp Ile His Thr Ser Thr Thr Tyr Lys Lys Leu Tyr Asn Lys
245 250 255

Arg Lys Ser Leu Ile Glu Glu Tyr Asn Lys Gln Ile Asn Glu Ile Lys
260 265 270

Asp Lys Glu Val Ile Thr Ala Ile Asn Val Glu Leu Leu Arg Ile Lys
275 280 285

Lys Glu Met Glu Glu Ile Thr Lys Ser Asn Ser Leu Phe Arg Leu Lys
290 295 300

Tyr Lys Met Gln Ile Ala Tyr Ala Phe Leu Glu Ile Glu Phe Gly Gly
305 310 315 320

Asn Ile Ala Lys Phe Lys Asp Glu Phe Asp Cys Ser Lys Met Glu Glu
325 330 335

Val Gln Lys Tyr Leu Lys Lys Gly Val Lys Tyr Leu Lys Tyr Tyr Lys
340 345 350

Asp Lys Glu Ala Gln Lys Asn Tyr Glu Phe Pro Phe Glu Glu Ile Phe
355 360 365

Glu Asn Lys Asp Thr His Asn Glu Glu Trp Leu Glu Asn Thr Ser Glu

```
    370                 375                 380

Asn Asn Leu Phe Lys Phe Tyr Ile Leu Thr Tyr Leu Leu Leu Pro Met
385                 390                 395                 400

Glu Phe Lys Gly Asp Phe Leu Gly Val Val Lys Lys His Tyr Tyr Asp
                405                 410                 415

Ile Lys Asn Val Asp Phe Thr Asp Glu Ser Glu Lys Glu Leu Ser Gln
            420                 425                 430

Val Gln Leu Asp Lys Met Ile Gly Asp Ser Phe Phe His Lys Ile Arg
        435                 440                 445

Leu Phe Glu Lys Asn Thr Lys Arg Tyr Glu Ile Ile Lys Tyr Ser Ile
    450                 455                 460

Leu Thr Ser Asp Glu Ile Lys Arg Tyr Phe Arg Leu Leu Glu Leu Asp
465                 470                 475                 480

Val Pro Tyr Phe Glu Tyr Glu Lys Gly Thr Asp Glu Ile Gly Ile Phe
                485                 490                 495

Asn Lys Asn Ile Ile Leu Thr Ile Phe Lys Tyr Tyr Gln Ile Ile Phe
            500                 505                 510

Arg Leu Tyr Asn Asp Leu Glu Ile His Gly Leu Phe Asn Ile Ser Ser
        515                 520                 525

Asp Leu Asp Lys Ile Leu Arg Asp Leu Lys Ser Tyr Gly Asn Lys Asn
    530                 535                 540

Ile Asn Phe Arg Glu Phe Leu Tyr Val Ile Lys Gln Asn Asn Asn Ser
545                 550                 555                 560

Ser Thr Glu Glu Glu Tyr Arg Lys Ile Trp Glu Asn Leu Glu Ala Lys
                565                 570                 575

Tyr Leu Arg Leu His Leu Leu Thr Pro Glu Lys Glu Glu Ile Lys Thr
            580                 585                 590

Lys Thr Lys Glu Glu Leu Glu Lys Leu Asn Glu Ile Ser Asn Leu Arg
        595                 600                 605

Asn Gly Ile Cys His Leu Asn Tyr Lys Glu Ile Ile Glu Glu Ile Leu
    610                 615                 620

Lys Thr Glu Ile Ser Glu Lys Asn Lys Glu Ala Thr Leu Asn Glu Lys
625                 630                 635                 640

Ile Arg Lys Val Ile Asn Phe Ile Lys Glu Asn Glu Leu Asp Lys Val
                645                 650                 655

Glu Leu Gly Phe Asn Phe Ile Asn Asp Phe Phe Met Lys Lys Glu Gln
            660                 665                 670

Phe Met Phe Gly Gln Ile Lys Gln Val Lys Glu Gly Asn Ser Asp Ser
        675                 680                 685

Ile Thr Thr Glu Arg Glu Arg Lys Glu Lys Asn Asn Lys Lys Leu Lys
    690                 695                 700

Glu Thr Tyr Glu Leu Asn Cys Asp Asn Leu Ser Glu Phe Tyr Glu Thr
705                 710                 715                 720

Ser Asn Asn Leu Arg Glu Arg Ala Asn Ser Ser Ser Leu Leu Glu Asp
                725                 730                 735

Ser Ala Phe Leu Lys Lys Ile Gly Leu Tyr Lys Val Lys Asn Asn Lys
            740                 745                 750

Val Asn Ser Lys Val Lys Asp Glu Glu Lys Arg Ile Glu Asn Ile Lys
        755                 760                 765

Arg Lys Leu Leu Lys Asp Ser Ser Asp Ile Met Gly Met Tyr Lys Ala
    770                 775                 780

Glu Val Val Lys Lys Leu Lys Glu Lys Leu Ile Leu Ile Phe Lys His
785                 790                 795                 800
```

Asp Glu Glu Lys Arg Ile Tyr Val Thr Val Tyr Asp Thr Ser Lys Ala
805 810 815

Val Pro Glu Asn Ile Ser Lys Glu Ile Leu Val Lys Arg Asn Asn Ser
820 825 830

Lys Glu Glu Tyr Phe Phe Glu Asp Asn Asn Lys Lys Tyr Val Thr Glu
835 840 845

Tyr Tyr Thr Leu Glu Ile Thr Glu Thr Asn Glu Leu Lys Val Ile Pro
850 855 860

Ala Lys Lys Leu Glu Gly Lys Glu Phe Lys Thr Glu Lys Asn Lys Glu
865 870 875 880

Asn Lys Leu Met Leu Asn Asn His Tyr Cys Phe Asn Val Lys Ile Ile
885 890 895

Tyr

<210> SEQ ID NO 21
<211> LENGTH: 1285
<212> TYPE: PRT
<213> ORGANISM: Artificial Sequence
<220> FEATURE:
<223> OTHER INFORMATION: Chemically synthesized

<400> SEQUENCE: 21

Met Lys Leu Thr Arg Arg Arg Ile Ser Gly Asn Ser Val Asp Gln Lys
1 5 10 15

Ile Thr Ala Ala Phe Tyr Arg Asp Met Ser Gln Gly Leu Leu Tyr Tyr
20 25 30

Asp Ser Glu Asp Asn Asp Cys Thr Asp Lys Val Ile Glu Ser Met Asp
35 40 45

Phe Glu Arg Ser Trp Arg Gly Arg Ile Leu Lys Asn Gly Glu Asp Asp
50 55 60

Lys Asn Pro Phe Tyr Met Phe Val Lys Gly Leu Val Gly Ser Asn Asp
65 70 75 80

Lys Ile Val Cys Glu Pro Ile Asp Val Asp Ser Asp Pro Asp Asn Leu
85 90 95

Asp Ile Leu Ile Asn Lys Asn Leu Thr Gly Phe Gly Arg Asn Leu Lys
100 105 110

Ala Pro Asp Ser Asn Asp Thr Leu Glu Asn Leu Ile Arg Lys Ile Gln
115 120 125

Ala Gly Ile Pro Glu Glu Glu Val Leu Pro Glu Leu Lys Lys Ile Lys
130 135 140

Glu Met Ile Gln Lys Asp Ile Val Asn Arg Lys Glu Gln Leu Leu Lys
145 150 155 160

Ser Ile Lys Asn Asn Arg Ile Pro Phe Ser Leu Glu Gly Ser Lys Leu
165 170 175

Val Pro Ser Thr Lys Lys Met Lys Trp Leu Phe Lys Leu Ile Asp Val
180 185 190

Pro Asn Lys Thr Phe Asn Glu Lys Met Leu Glu Lys Tyr Trp Glu Ile
195 200 205

Tyr Asp Tyr Asp Lys Leu Lys Ala Asn Ile Thr Asn Arg Leu Asp Lys
210 215 220

Thr Asp Lys Lys Ala Arg Ser Ile Ser Arg Ala Val Ser Glu Glu Leu
225 230 235 240

Arg Glu Tyr His Lys Asn Leu Arg Thr Asn Tyr Asn Arg Phe Val Ser
245 250 255

```
Gly Asp Arg Pro Ala Ala Gly Leu Asp Asn Gly Gly Ser Ala Lys Tyr
            260                 265                 270

Asn Pro Asp Lys Glu Glu Phe Leu Leu Phe Leu Lys Glu Val Glu Gln
        275                 280                 285

Tyr Phe Lys Lys Tyr Phe Pro Val Lys Ser Lys His Ser Asn Lys Ser
    290                 295                 300

Lys Asp Lys Ser Leu Val Asp Lys Tyr Lys Asn Tyr Cys Ser Tyr Lys
305                 310                 315                 320

Val Val Lys Lys Glu Val Asn Arg Ser Ile Ile Asn Gln Leu Val Ala
                325                 330                 335

Gly Leu Ile Gln Gln Gly Lys Leu Leu Tyr Tyr Phe Tyr Tyr Asn Asp
            340                 345                 350

Thr Trp Gln Glu Asp Phe Leu Asn Ser Tyr Gly Leu Ser Tyr Ile Gln
        355                 360                 365

Val Glu Glu Ala Phe Lys Lys Ser Val Met Thr Ser Leu Ser Trp Gly
    370                 375                 380

Ile Asn Arg Leu Thr Ser Phe Phe Ile Asp Asp Ser Asn Thr Val Lys
385                 390                 395                 400

Phe Asp Asp Ile Thr Thr Lys Lys Ala Lys Glu Ala Ile Glu Ser Asn
                405                 410                 415

Tyr Phe Asn Lys Leu Arg Thr Cys Ser Arg Met Gln Asp His Phe Lys
            420                 425                 430

Glu Lys Leu Ala Phe Phe Tyr Pro Val Tyr Val Lys Asp Lys Lys Asp
        435                 440                 445

Arg Pro Asp Asp Asp Ile Glu Asn Leu Ile Val Leu Val Lys Asn Ala
    450                 455                 460

Ile Glu Ser Val Ser Tyr Leu Arg Asn Arg Thr Phe His Phe Lys Glu
465                 470                 475                 480

Ser Ser Leu Leu Glu Leu Leu Lys Glu Leu Asp Asp Lys Asn Ser Gly
                485                 490                 495

Gln Asn Lys Ile Asp Tyr Ser Val Ala Ala Glu Phe Ile Lys Arg Asp
            500                 505                 510

Ile Glu Asn Leu Tyr Asp Val Phe Arg Glu Gln Ile Arg Ser Leu Gly
        515                 520                 525

Ile Ala Glu Tyr Tyr Lys Ala Asp Met Ile Ser Asp Cys Phe Lys Thr
    530                 535                 540

Cys Gly Leu Glu Phe Ala Leu Tyr Ser Pro Lys Asn Ser Leu Met Pro
545                 550                 555                 560

Ala Phe Lys Asn Val Tyr Lys Arg Gly Ala Asn Leu Asn Lys Ala Tyr
                565                 570                 575

Ile Arg Asp Lys Gly Pro Lys Glu Thr Gly Asp Gln Gly Gln Asn Ser
            580                 585                 590

Tyr Lys Ala Leu Glu Glu Tyr Arg Glu Leu Thr Trp Tyr Ile Glu Val
        595                 600                 605

Lys Asn Asn Asp Gln Ser Tyr Asn Ala Tyr Lys Asn Leu Leu Gln Leu
    610                 615                 620

Ile Tyr Tyr His Ala Phe Leu Pro Glu Val Arg Glu Asn Glu Ala Leu
625                 630                 635                 640

Ile Thr Asp Phe Ile Asn Arg Thr Lys Glu Trp Asn Arg Lys Glu Thr
                645                 650                 655

Glu Glu Arg Leu Asn Thr Lys Asn Asn Lys Lys His Lys Asn Phe Asp
            660                 665                 670

Glu Asn Asp Asp Ile Thr Val Asn Thr Tyr Arg Tyr Glu Ser Ile Pro
```

```
        675                 680                 685

Asp Tyr Gln Gly Glu Ser Leu Asp Asp Tyr Leu Lys Val Leu Gln Arg
    690                 695                 700

Lys Gln Met Ala Arg Ala Lys Glu Val Asn Glu Lys Glu Glu Gly Asn
705                 710                 715                 720

Asn Asn Tyr Ile Gln Phe Ile Arg Asp Val Val Val Trp Ala Phe Gly
                725                 730                 735

Ala Tyr Leu Glu Asn Lys Leu Lys Asn Tyr Lys Asn Glu Leu Gln Pro
            740                 745                 750

Pro Leu Ser Lys Glu Asn Ile Gly Leu Asn Asp Thr Leu Lys Glu Leu
        755                 760                 765

Phe Pro Glu Glu Lys Val Lys Ser Pro Phe Asn Ile Lys Cys Arg Phe
    770                 775                 780

Ser Ile Ser Thr Phe Ile Asp Asn Lys Gly Lys Ser Thr Asp Asn Thr
785                 790                 795                 800

Ser Ala Glu Ala Val Lys Thr Asp Gly Lys Glu Asp Glu Lys Asp Lys
                805                 810                 815

Lys Asn Ile Lys Arg Lys Asp Leu Leu Cys Phe Tyr Leu Phe Leu Arg
            820                 825                 830

Leu Leu Asp Glu Asn Glu Ile Cys Lys Leu Gln His Gln Phe Ile Lys
        835                 840                 845

Tyr Arg Cys Ser Leu Lys Glu Arg Arg Phe Pro Gly Asn Arg Thr Lys
    850                 855                 860

Leu Glu Lys Glu Thr Glu Leu Leu Ala Glu Leu Glu Glu Leu Met Glu
865                 870                 875                 880

Leu Val Arg Phe Thr Met Pro Ser Ile Pro Glu Ile Ser Ala Lys Ala
                885                 890                 895

Glu Ser Gly Tyr Asp Thr Met Ile Lys Lys Tyr Phe Lys Asp Phe Ile
            900                 905                 910

Glu Lys Lys Val Phe Lys Asn Pro Lys Thr Ser Asn Leu Tyr Tyr His
        915                 920                 925

Ser Asp Ser Lys Thr Pro Val Thr Arg Lys Tyr Met Ala Leu Leu Met
    930                 935                 940

Arg Ser Ala Pro Leu His Leu Tyr Lys Asp Ile Phe Lys Gly Tyr Tyr
945                 950                 955                 960

Leu Ile Thr Lys Lys Glu Cys Leu Glu Tyr Ile Lys Leu Ser Asn Ile
                965                 970                 975

Ile Lys Asp Tyr Gln Asn Ser Leu Asn Glu Leu His Glu Gln Leu Glu
            980                 985                 990

Arg Ile Lys Leu Lys Ser Glu Lys  Gln Asn Gly Lys Asp  Ser Leu Tyr
        995                 1000                1005

Leu Asp  Lys Lys Asp Phe Tyr  Lys Val Lys Glu Tyr  Val Glu Asn
    1010                 1015                 1020

Leu Glu  Gln Val Ala Arg Tyr  Lys His Leu Gln His  Lys Ile Asn
    1025                 1030                 1035

Phe Glu  Ser Leu Tyr Arg Ile  Phe Arg Ile His Val  Asp Ile Ala
    1040                 1045                 1050

Ala Arg  Met Val Gly Tyr Thr  Gln Asp Trp Glu Arg  Asp Met His
    1055                 1060                 1065

Phe Leu  Phe Lys Ala Leu Val  Tyr Asn Gly Val Leu  Glu Glu Arg
    1070                 1075                 1080

Arg Phe  Glu Ala Ile Phe Asn  Asn Asn Asp Asp Asn  Asn Asp Gly
    1085                 1090                 1095
```

```
Arg Ile  Val Lys Lys Ile Gln  Asn Asn Leu Asn Asn  Lys Asn Arg
    1100                 1105                 1110

Glu Leu  Val Ser Met Leu Cys  Trp Asn Lys Lys Leu  Asn Lys Asn
    1115                 1120                 1125

Glu Phe  Gly Ala Ile Ile Trp  Lys Arg Asn Pro Ile  Ala His Leu
    1130                 1135                 1140

Asn His  Phe Thr Gln Thr Glu  Gln Asn Ser Lys Ser  Ser Leu Glu
    1145                 1150                 1155

Ser Leu  Ile Asn Ser Leu Arg  Ile Leu Leu Ala Tyr  Asp Arg Lys
    1160                 1165                 1170

Arg Gln  Asn Ala Val Thr Lys  Thr Ile Asn Asp Leu  Leu Leu Asn
    1175                 1180                 1185

Asp Tyr  His Ile Arg Ile Lys  Trp Glu Gly Arg Val  Asp Glu Gly
    1190                 1195                 1200

Gln Ile  Tyr Phe Asn Ile Lys  Glu Lys Glu Asp Ile  Glu Asn Glu
    1205                 1210                 1215

Pro Ile  Ile His Leu Lys His  Leu His Lys Lys Asp  Cys Tyr Ile
    1220                 1225                 1230

Tyr Lys  Asn Ser Tyr Met Phe  Asp Lys Gln Lys Glu  Trp Ile Cys
    1235                 1240                 1245

Asn Gly  Ile Lys Glu Glu Val  Tyr Asp Lys Ser Ile  Leu Lys Cys
    1250                 1255                 1260

Ile Gly  Asn Leu Phe Lys Phe  Asp Tyr Glu Asp Lys  Asn Lys Ser
    1265                 1270                 1275

Ser Ala  Asn Pro Lys His Thr
    1280                 1285
```

<210> SEQ ID NO 22
<211> LENGTH: 1051
<212> TYPE: PRT
<213> ORGANISM: Artificial Sequence
<220> FEATURE:
<223> OTHER INFORMATION: Chemically synthesized

<400> SEQUENCE: 22

```
Met Lys Ile Thr Lys Met Arg Val Asp Gly Arg Thr Ile Val Met Glu
1               5                   10                  15

Arg Thr Ser Lys Glu Gly Gln Leu Gly Tyr Glu Gly Ile Asp Gly Asn
            20                  25                  30

Lys Thr Thr Glu Ile Ile Phe Asp Lys Lys Lys Glu Ser Phe Tyr Lys
        35                  40                  45

Ser Ile Leu Asn Lys Thr Val Arg Lys Pro Asp Glu Lys Glu Lys Asn
    50                  55                  60

Arg Arg Lys Gln Ala Ile Asn Lys Ala Ile Asn Lys Glu Ile Thr Glu
65                  70                  75                  80

Leu Met Leu Ala Val Leu His Gln Glu Val Pro Ser Gln Lys Leu His
                85                  90                  95

Asn Leu Lys Ser Leu Asn Thr Glu Ser Leu Thr Lys Leu Phe Lys Pro
            100                 105                 110

Lys Phe Gln Asn Met Ile Ser Tyr Pro Pro Ser Lys Gly Ala Glu His
        115                 120                 125

Val Gln Phe Cys Leu Thr Asp Ile Ala Val Pro Ala Ile Arg Asp Leu
    130                 135                 140

Asp Glu Ile Lys Pro Asp Trp Gly Ile Phe Phe Glu Lys Leu Lys Pro
145                 150                 155                 160
```

```
Tyr Thr Asp Trp Ala Glu Ser Tyr Ile His Tyr Lys Gln Thr Thr Ile
                165                 170                 175

Gln Lys Ser Ile Glu Gln Asn Lys Ile Gln Ser Pro Asp Ser Pro Arg
            180                 185                 190

Lys Leu Val Leu Gln Lys Tyr Val Thr Ala Phe Leu Asn Gly Glu Pro
        195                 200                 205

Leu Gly Leu Asp Leu Val Ala Lys Lys Tyr Lys Leu Ala Asp Leu Ala
    210                 215                 220

Glu Ser Phe Lys Leu Val Asp Leu Asn Glu Asp Lys Ser Ala Asn Tyr
225                 230                 235                 240

Lys Ile Lys Ala Cys Leu Gln Gln His Gln Arg Asn Ile Leu Asp Glu
                245                 250                 255

Leu Lys Glu Asp Pro Glu Leu Asn Gln Tyr Gly Ile Glu Val Lys Lys
            260                 265                 270

Tyr Ile Gln Arg Tyr Phe Pro Ile Lys Arg Ala Pro Asn Arg Ser Lys
        275                 280                 285

His Ala Arg Ala Asp Phe Leu Lys Lys Glu Leu Ile Glu Ser Thr Val
    290                 295                 300

Glu Gln Gln Phe Lys Asn Ala Val Tyr His Tyr Val Leu Glu Gln Gly
305                 310                 315                 320

Lys Met Glu Ala Tyr Glu Leu Thr Asp Pro Lys Thr Lys Asp Leu Gln
                325                 330                 335

Asp Ile Arg Ser Gly Glu Ala Phe Ser Phe Lys Phe Ile Asn Ala Cys
            340                 345                 350

Ala Phe Ala Ser Asn Asn Leu Lys Met Ile Leu Asn Pro Glu Cys Glu
        355                 360                 365

Lys Asp Ile Leu Gly Lys Gly Asn Phe Lys Lys Asn Leu Pro Asn Ser
    370                 375                 380

Thr Thr Arg Ser Asp Val Val Lys Lys Met Ile Pro Phe Phe Ser Asp
385                 390                 395                 400

Glu Leu Gln Asn Val Asn Phe Asp Glu Ala Ile Trp Ala Ile Arg Gly
                405                 410                 415

Ser Ile Gln Gln Ile Arg Asn Glu Val Tyr His Cys Lys Lys His Ser
            420                 425                 430

Trp Lys Ser Ile Leu Lys Ile Lys Gly Phe Glu Phe Glu Pro Asn Asn
        435                 440                 445

Met Lys Tyr Ala Asp Ser Asp Met Gln Lys Leu Met Asp Lys Asp Ile
    450                 455                 460

Ala Lys Ile Pro Glu Phe Ile Glu Glu Lys Leu Lys Ser Ser Gly Val
465                 470                 475                 480

Val Arg Phe Tyr Arg His Asp Glu Leu Gln Ser Ile Trp Glu Met Lys
                485                 490                 495

Gln Gly Phe Ser Leu Leu Thr Thr Asn Ala Pro Phe Val Pro Ser Phe
            500                 505                 510

Lys Arg Val Tyr Ala Lys Gly His Asp Tyr Gln Thr Ser Lys Asn Arg
        515                 520                 525

Tyr Tyr Asn Leu Asp Leu Thr Thr Phe Asp Ile Leu Glu Tyr Gly Glu
    530                 535                 540

Glu Asp Phe Arg Ala Arg Tyr Phe Leu Thr Lys Leu Val Tyr Tyr Gln
545                 550                 555                 560

Gln Phe Met Pro Trp Phe Thr Ala Asp Asn Asn Ala Phe Arg Asp Ala
                565                 570                 575
```

```
Ala Asn Phe Val Leu Arg Leu Asn Lys Asn Arg Gln Gln Asp Ala Lys
            580                 585                 590

Ala Phe Ile Asn Ile Arg Glu Val Glu Glu Gly Glu Met Pro Arg Asp
        595                 600                 605

Tyr Met Gly Tyr Val Gln Gly Gln Ile Ala Ile His Glu Asp Ser Ile
    610                 615                 620

Glu Asp Thr Pro Asn His Phe Glu Lys Phe Ile Ser Gln Val Phe Ile
625                 630                 635                 640

Lys Gly Phe Asp Arg His Met Arg Ser Ala Asn Leu Lys Phe Ile Lys
                645                 650                 655

Asn Pro Arg Asn Gln Gly Leu Glu Gln Ser Glu Ile Glu Glu Met Ser
            660                 665                 670

Phe Asp Ile Lys Val Glu Pro Ser Phe Leu Lys Asn Lys Asp Asp Tyr
        675                 680                 685

Ile Ala Phe Trp Ile Phe Cys Lys Met Leu Asp Ala Arg His Leu Ser
    690                 695                 700

Glu Leu Arg Asn Glu Met Ile Lys Tyr Asp Gly His Leu Thr Gly Glu
705                 710                 715                 720

Gln Glu Ile Ile Gly Leu Ala Leu Leu Gly Val Asp Ser Arg Glu Asn
                725                 730                 735

Asp Trp Lys Gln Phe Phe Ser Ser Glu Arg Glu Tyr Glu Lys Ile Met
            740                 745                 750

Lys Gly Tyr Val Val Glu Glu Leu Tyr Gln Arg Glu Pro Tyr Arg Gln
        755                 760                 765

Ser Asp Gly Lys Thr Pro Ile Leu Phe Arg Gly Val Glu Gln Ala Arg
    770                 775                 780

Lys Tyr Gly Thr Glu Thr Val Ile Gln Arg Leu Phe Asp Ala Asn Pro
785                 790                 795                 800

Glu Phe Lys Val Ser Lys Cys Asn Leu Ala Glu Trp Glu Arg Gln Lys
                805                 810                 815

Glu Thr Ile Glu Glu Thr Ile Lys Arg Arg Lys Glu Leu His Asn Glu
            820                 825                 830

Trp Ala Lys Asn Pro Lys Lys Pro Gln Asn Asn Ala Phe Phe Lys Glu
        835                 840                 845

Tyr Lys Glu Cys Cys Asp Ala Ile Asp Ala Tyr Asn Trp His Lys Asn
    850                 855                 860

Lys Thr Thr Leu Ala Tyr Val Asn Glu Leu His His Leu Leu Ile Glu
865                 870                 875                 880

Ile Leu Gly Arg Tyr Val Gly Tyr Val Ala Ile Ala Asp Arg Asp Phe
                885                 890                 895

Gln Cys Met Ala Asn Gln Tyr Phe Lys His Ser Gly Ile Thr Glu Arg
            900                 905                 910

Val Glu Tyr Trp Gly Asp Asn Arg Leu Lys Ser Ile Lys Lys Leu Asp
        915                 920                 925

Thr Phe Leu Lys Lys Glu Gly Leu Phe Val Ser Glu Lys Asn Ala Arg
    930                 935                 940

Asn His Ile Ala His Leu Asn Tyr Leu Ser Leu Lys Ser Glu Cys Thr
945                 950                 955                 960

Leu Leu Tyr Leu Ser Glu Arg Leu Arg Glu Ile Phe Lys Tyr Asp Arg
                965                 970                 975

Lys Leu Lys Asn Ala Val Ser Lys Ser Leu Ile Asp Ile Leu Asp Arg
            980                 985                 990

His Gly Met Ser Val Val Phe Ala  Asn Leu Lys Glu Asn  Lys His Arg
```

```
        995                 1000                1005

Leu Val  Ile Lys Ser Leu Glu  Pro Lys Lys Leu Arg  His Leu Gly
    1010                 1015                1020

Gly Lys  Lys Ile Asp Gly Gly  Tyr Ile Glu Thr Asn  Gln Val Ser
    1025                 1030                1035

Glu Glu  Tyr Cys Gly Ile Val  Lys Arg Leu Leu Glu  Met
    1040                 1045                1050


<210> SEQ ID NO 23
<211> LENGTH: 1340
<212> TYPE: PRT
<213> ORGANISM: Artificial Sequence
<220> FEATURE:
<223> OTHER INFORMATION: Chemically synthesized

<400> SEQUENCE: 23

Met Gln Ile Ser Lys Val Asn His Lys His Val Ala Val Gly Gln Lys
1               5                   10                  15

Asp Arg Glu Arg Ile Thr Gly Phe Ile Tyr Asn Asp Pro Val Gly Asp
            20                  25                  30

Glu Lys Ser Leu Glu Asp Val Val Ala Lys Arg Ala Asn Asp Thr Lys
        35                  40                  45

Val Leu Phe Asn Val Phe Asn Thr Lys Asp Leu Tyr Asp Ser Gln Glu
    50                  55                  60

Ser Asp Lys Ser Glu Lys Asp Lys Glu Ile Ile Ser Lys Gly Ala Lys
65                  70                  75                  80

Phe Val Ala Lys Ser Phe Asn Ser Ala Ile Thr Ile Leu Lys Lys Gln
                85                  90                  95

Asn Lys Ile Tyr Ser Thr Leu Thr Ser Gln Gln Val Ile Lys Glu Leu
            100                 105                 110

Lys Asp Lys Phe Gly Gly Ala Arg Ile Tyr Asp Asp Asp Ile Glu Glu
        115                 120                 125

Ala Leu Thr Glu Thr Leu Lys Lys Ser Phe Arg Lys Glu Asn Val Arg
    130                 135                 140

Asn Ser Ile Lys Val Leu Ile Glu Asn Ala Ala Gly Ile Arg Ser Ser
145                 150                 155                 160

Leu Ser Lys Asp Glu Glu Glu Leu Ile Gln Glu Tyr Phe Val Lys Gln
                165                 170                 175

Leu Val Glu Glu Tyr Thr Lys Thr Lys Leu Gln Lys Asn Val Val Lys
            180                 185                 190

Ser Ile Lys Asn Gln Asn Met Val Ile Gln Pro Asp Ser Asp Ser Gln
        195                 200                 205

Val Leu Ser Leu Ser Glu Ser Arg Arg Glu Lys Gln Ser Ser Ala Val
    210                 215                 220

Ser Ser Asp Thr Leu Val Asn Cys Lys Glu Lys Asp Val Leu Lys Ala
225                 230                 235                 240

Phe Leu Thr Asp Tyr Ala Val Leu Asp Glu Asp Glu Arg Asn Ser Leu
                245                 250                 255

Leu Trp Lys Leu Arg Asn Leu Val Asn Leu Tyr Phe Tyr Gly Ser Glu
            260                 265                 270

Ser Ile Arg Asp Tyr Ser Tyr Thr Lys Glu Lys Ser Val Trp Lys Glu
        275                 280                 285

His Asp Glu Gln Lys Ala Asn Lys Thr Leu Phe Ile Asp Glu Ile Cys
    290                 295                 300

His Ile Thr Lys Ile Gly Lys Asn Gly Lys Glu Gln Lys Val Leu Asp
```

-continued

```
305                 310                 315                 320

Tyr Glu Glu Asn Arg Ser Arg Cys Arg Lys Gln Asn Ile Asn Tyr Tyr
                325                 330                 335

Arg Ser Ala Leu Asn Tyr Ala Lys Asn Asn Thr Ser Gly Ile Phe Glu
            340                 345                 350

Asn Glu Asp Ser Asn His Phe Trp Ile His Leu Ile Glu Asn Glu Val
        355                 360                 365

Glu Arg Leu Tyr Asn Gly Ile Glu Asn Gly Glu Glu Phe Lys Phe Glu
    370                 375                 380

Thr Gly Tyr Ile Ser Glu Lys Val Trp Lys Ala Val Ile Asn His Leu
385                 390                 395                 400

Ser Ile Lys Tyr Ile Ala Leu Gly Lys Ala Val Tyr Asn Tyr Ala Met
                405                 410                 415

Lys Glu Leu Ser Ser Pro Gly Asp Ile Glu Pro Gly Lys Ile Asp Asp
            420                 425                 430

Ser Tyr Ile Asn Gly Ile Thr Ser Phe Asp Tyr Glu Ile Ile Lys Ala
        435                 440                 445

Glu Glu Ser Leu Gln Arg Asp Ile Ser Met Asn Val Val Phe Ala Thr
    450                 455                 460

Asn Tyr Leu Ala Cys Ala Thr Val Asp Thr Asp Lys Asp Phe Leu Leu
465                 470                 475                 480

Phe Ser Lys Glu Asp Ile Arg Ser Cys Thr Lys Lys Asp Gly Asn Leu
                485                 490                 495

Cys Lys Asn Ile Met Gln Phe Trp Gly Gly Tyr Ser Thr Trp Lys Asn
            500                 505                 510

Phe Cys Glu Glu Tyr Leu Lys Asp Asp Lys Asp Ala Leu Glu Leu Leu
        515                 520                 525

Tyr Ser Leu Lys Ser Met Leu Tyr Ser Met Arg Asn Ser Ser Phe His
    530                 535                 540

Phe Ser Thr Glu Asn Val Asp Asn Gly Ser Trp Asp Thr Glu Leu Ile
545                 550                 555                 560

Gly Lys Leu Phe Glu Glu Asp Cys Asn Arg Ala Ala Arg Ile Glu Lys
                565                 570                 575

Glu Lys Phe Tyr Asn Asn Asn Leu His Met Phe Tyr Ser Ser Ser Leu
            580                 585                 590

Leu Glu Lys Val Leu Glu Arg Leu Tyr Ser Ser His His Glu Arg Ala
        595                 600                 605

Ser Gln Val Pro Ser Phe Asn Arg Val Phe Val Arg Lys Asn Phe Pro
    610                 615                 620

Ser Ser Leu Ser Glu Gln Arg Ile Thr Pro Lys Phe Thr Asp Ser Lys
625                 630                 635                 640

Asp Glu Gln Ile Trp Gln Ser Ala Val Tyr Tyr Leu Cys Lys Glu Ile
                645                 650                 655

Tyr Tyr Asn Asp Phe Leu Gln Ser Lys Glu Ala Tyr Lys Leu Phe Arg
            660                 665                 670

Glu Gly Val Lys Asn Leu Asp Lys Asn Asp Ile Asn Asn Gln Lys Ala
        675                 680                 685

Ala Asp Ser Phe Lys Gln Ala Val Val Tyr Tyr Gly Lys Ala Ile Gly
    690                 695                 700

Asn Ala Thr Leu Ser Gln Val Cys Gln Ala Ile Met Thr Glu Tyr Asn
705                 710                 715                 720

Arg Gln Asn Asn Asp Gly Leu Lys Lys Lys Ser Ala Tyr Ala Glu Lys
                725                 730                 735
```

```
Gln Asn Ser Asn Lys Tyr Lys His Tyr Pro Leu Phe Leu Lys Gln Val
            740                 745                 750

Leu Gln Ser Ala Phe Trp Glu Tyr Leu Asp Glu Asn Lys Glu Ile Tyr
        755                 760                 765

Gly Phe Ile Ser Ala Gln Ile His Lys Ser Asn Val Glu Ile Lys Ala
    770                 775                 780

Glu Asp Phe Ile Ala Asn Tyr Ser Ser Gln Gln Tyr Lys Lys Leu Val
785                 790                 795                 800

Asp Lys Val Lys Lys Thr Pro Glu Leu Gln Lys Trp Tyr Thr Leu Gly
                805                 810                 815

Arg Leu Ile Asn Pro Arg Gln Ala Asn Gln Phe Leu Gly Ser Ile Arg
            820                 825                 830

Asn Tyr Val Gln Phe Val Lys Asp Ile Gln Arg Arg Ala Lys Glu Asn
        835                 840                 845

Gly Asn Pro Ile Arg Asn Tyr Tyr Glu Val Leu Glu Ser Asp Ser Ile
    850                 855                 860

Ile Lys Ile Leu Glu Met Cys Thr Lys Leu Asn Gly Thr Thr Ser Asn
865                 870                 875                 880

Asp Ile His Asp Tyr Phe Arg Asp Glu Asp Glu Tyr Ala Glu Tyr Ile
                885                 890                 895

Ser Gln Phe Val Asn Phe Gly Asp Val His Ser Gly Ala Ala Leu Asn
            900                 905                 910

Ala Phe Cys Asn Ser Glu Ser Glu Gly Lys Lys Asn Gly Ile Tyr Tyr
        915                 920                 925

Asp Gly Ile Asn Pro Ile Val Asn Arg Asn Trp Val Leu Cys Lys Leu
    930                 935                 940

Tyr Gly Ser Pro Asp Leu Ile Ser Lys Ile Ile Ser Arg Val Asn Glu
945                 950                 955                 960

Asn Met Ile His Asp Phe His Lys Gln Glu Asp Leu Ile Arg Glu Tyr
                965                 970                 975

Gln Ile Lys Gly Ile Cys Ser Asn Lys Lys Glu Gln Gln Asp Leu Arg
            980                 985                 990

Thr Phe Gln Val Leu Lys Asn Arg  Val Glu Leu Arg Asp  Ile Val Glu
        995                 1000                1005

Tyr Ser  Glu Ile Ile Asn Glu  Leu Tyr Gly Gln Leu  Ile Lys Trp
    1010                1015                1020

Cys Tyr  Leu Arg Glu Arg Asp  Leu Met Tyr Phe Gln  Leu Gly Phe
    1025                1030                1035

His Tyr  Leu Cys Leu Asn Asn  Ala Ser Ser Lys Glu  Ala Asp Tyr
    1040                1045                1050

Ile Lys  Ile Asn Val Asp Asp  Arg Asn Ile Ser Gly  Ala Ile Leu
    1055                1060                1065

Tyr Gln  Ile Ala Ala Met Tyr  Ile Asn Gly Leu Pro  Val Tyr Tyr
    1070                1075                1080

Lys Lys  Asp Asp Met Tyr Val  Ala Leu Lys Ser Gly  Lys Lys Ala
    1085                1090                1095

Ser Asp  Glu Leu Asn Ser Asn  Glu Gln Thr Ser Lys  Lys Ile Asn
    1100                1105                1110

Tyr Phe  Leu Lys Tyr Gly Asn  Asn Ile Leu Gly Asp  Lys Lys Asp
    1115                1120                1125

Gln Leu  Tyr Leu Ala Gly Leu  Glu Leu Phe Glu Asn  Val Ala Glu
    1130                1135                1140
```

His Glu Asn Ile Ile Ile Phe Arg Asn Glu Ile Asp His Phe His
1145 1150 1155

Tyr Phe Tyr Asp Arg Asp Arg Ser Met Leu Asp Leu Tyr Ser Glu
1160 1165 1170

Val Phe Asp Arg Phe Phe Thr Tyr Asp Met Lys Leu Arg Lys Asn
1175 1180 1185

Val Val Asn Met Leu Tyr Asn Ile Leu Leu Asp His Asn Ile Val
1190 1195 1200

Ser Ser Phe Val Phe Glu Thr Gly Glu Lys Lys Val Gly Arg Gly
1205 1210 1215

Asp Ser Glu Val Ile Lys Pro Ser Ala Lys Ile Arg Leu Arg Ala
1220 1225 1230

Asn Asn Gly Val Ser Ser Asp Val Phe Thr Tyr Lys Val Gly Ser
1235 1240 1245

Lys Asp Glu Leu Lys Ile Ala Thr Leu Pro Ala Lys Asn Glu Glu
1250 1255 1260

Phe Leu Leu Asn Val Ala Arg Leu Ile Tyr Tyr Pro Asp Met Glu
1265 1270 1275

Ala Val Ser Glu Asn Met Val Arg Glu Gly Val Val Lys Val Glu
1280 1285 1290

Lys Ser Asn Asp Lys Lys Gly Lys Ile Ser Arg Gly Ser Asn Thr
1295 1300 1305

Arg Ser Ser Asn Gln Ser Lys Tyr Asn Asn Lys Ser Lys Asn Arg
1310 1315 1320

Met Asn Tyr Ser Met Gly Ser Ile Phe Glu Lys Met Asp Leu Lys
1325 1330 1335

Phe Asp
1340

<210> SEQ ID NO 24
<211> LENGTH: 1437
<212> TYPE: PRT
<213> ORGANISM: Artificial Sequence
<220> FEATURE:
<223> OTHER INFORMATION: Chemically synthesized

<400> SEQUENCE: 24

Met Lys Ile Ser Lys Val Arg Glu Glu Asn Arg Gly Ala Lys Leu Thr
1 5 10 15

Val Asn Ala Lys Thr Ala Val Val Ser Glu Asn Arg Ser Gln Glu Gly
20 25 30

Ile Leu Tyr Asn Asp Pro Ser Arg Tyr Gly Lys Ser Arg Lys Asn Asp
35 40 45

Glu Asp Arg Asp Arg Tyr Ile Glu Ser Arg Leu Lys Ser Ser Gly Lys
50 55 60

Leu Tyr Arg Ile Phe Asn Glu Asp Lys Asn Lys Arg Glu Thr Asp Glu
65 70 75 80

Leu Gln Trp Phe Leu Ser Glu Ile Val Lys Lys Ile Asn Arg Arg Asn
85 90 95

Gly Leu Val Leu Ser Asp Met Leu Ser Val Asp Asp Arg Ala Phe Glu
100 105 110

Lys Ala Phe Glu Lys Tyr Ala Glu Leu Ser Tyr Thr Asn Arg Arg Asn
115 120 125

Lys Val Ser Gly Ser Pro Ala Phe Glu Thr Cys Gly Val Asp Ala Ala
130 135 140

```
Thr Ala Glu Arg Leu Lys Gly Ile Ile Ser Glu Thr Asn Phe Ile Asn
145                 150                 155                 160

Arg Ile Lys Asn Asn Ile Asp Asn Lys Val Ser Glu Asp Ile Ile Asp
                165                 170                 175

Arg Ile Ile Ala Lys Tyr Leu Lys Lys Ser Leu Cys Arg Glu Arg Val
            180                 185                 190

Lys Arg Gly Leu Lys Lys Leu Leu Met Asn Ala Phe Asp Leu Pro Tyr
        195                 200                 205

Ser Asp Pro Asp Ile Asp Val Gln Arg Asp Phe Ile Asp Tyr Val Leu
    210                 215                 220

Glu Asp Phe Tyr His Val Arg Ala Lys Ser Gln Val Ser Arg Ser Ile
225                 230                 235                 240

Lys Asn Met Asn Met Pro Val Gln Pro Glu Gly Asp Gly Lys Phe Ala
                245                 250                 255

Ile Thr Val Ser Lys Gly Gly Thr Glu Ser Gly Asn Lys Arg Ser Ala
            260                 265                 270

Glu Lys Glu Ala Phe Lys Lys Phe Leu Ser Asp Tyr Ala Ser Leu Asp
        275                 280                 285

Glu Arg Val Arg Asp Asp Met Leu Arg Arg Met Arg Arg Leu Val Val
    290                 295                 300

Leu Tyr Phe Tyr Gly Ser Asp Asp Ser Lys Leu Ser Asp Val Asn Glu
305                 310                 315                 320

Lys Phe Asp Val Trp Glu Asp His Ala Ala Arg Arg Val Asp Asn Arg
                325                 330                 335

Glu Phe Ile Lys Leu Pro Leu Glu Asn Lys Leu Ala Asn Gly Lys Thr
            340                 345                 350

Asp Lys Asp Ala Glu Arg Ile Arg Lys Asn Thr Val Lys Glu Leu Tyr
        355                 360                 365

Arg Asn Gln Asn Ile Gly Cys Tyr Arg Gln Ala Val Lys Ala Val Glu
    370                 375                 380

Glu Asp Asn Asn Gly Arg Tyr Phe Asp Asp Lys Met Leu Asn Met Phe
385                 390                 395                 400

Phe Ile His Arg Ile Glu Tyr Gly Val Glu Lys Ile Tyr Ala Asn Leu
                405                 410                 415

Lys Gln Val Thr Glu Phe Lys Ala Arg Thr Gly Tyr Leu Ser Glu Lys
            420                 425                 430

Ile Trp Lys Asp Leu Ile Asn Tyr Ile Ser Ile Lys Tyr Ile Ala Met
        435                 440                 445

Gly Lys Ala Val Tyr Asn Tyr Ala Met Asp Glu Leu Asn Ala Ser Asp
    450                 455                 460

Lys Lys Glu Ile Glu Leu Gly Lys Ile Ser Glu Glu Tyr Leu Ser Gly
465                 470                 475                 480

Ile Ser Ser Phe Asp Tyr Glu Leu Ile Lys Ala Glu Glu Met Leu Gln
                485                 490                 495

Arg Glu Thr Ala Val Tyr Val Ala Phe Ala Ala Arg His Leu Ser Ser
            500                 505                 510

Gln Thr Val Glu Leu Asp Ser Glu Asn Ser Asp Phe Leu Leu Leu Lys
        515                 520                 525

Pro Lys Gly Thr Met Asp Lys Asn Asp Lys Asn Lys Leu Ala Ser Asn
    530                 535                 540

Asn Ile Leu Asn Phe Leu Lys Asp Lys Glu Thr Leu Arg Asp Thr Ile
545                 550                 555                 560

Leu Gln Tyr Phe Gly Gly His Ser Leu Trp Thr Asp Phe Pro Phe Asp
```

```
                565                 570                 575

Lys Tyr Leu Ala Gly Gly Lys Asp Asp Val Asp Phe Leu Thr Asp Leu
            580                 585                 590

Lys Asp Val Ile Tyr Ser Met Arg Asn Asp Ser Phe His Tyr Ala Thr
        595                 600                 605

Glu Asn His Asn Asn Gly Lys Trp Asn Lys Glu Leu Ile Ser Ala Met
    610                 615                 620

Phe Glu His Glu Thr Glu Arg Met Thr Val Val Met Lys Asp Lys Phe
625                 630                 635                 640

Tyr Ser Asn Asn Leu Pro Met Phe Tyr Lys Asn Asp Asp Leu Lys Lys
                645                 650                 655

Leu Leu Ile Asp Leu Tyr Lys Asp Asn Val Glu Arg Ala Ser Gln Val
            660                 665                 670

Pro Ser Phe Asn Lys Val Phe Val Arg Lys Asn Phe Pro Ala Leu Val
        675                 680                 685

Arg Asp Lys Asp Asn Leu Gly Ile Glu Leu Asp Leu Lys Ala Asp Ala
    690                 695                 700

Asp Lys Gly Glu Asn Glu Leu Lys Phe Tyr Asn Ala Leu Tyr Tyr Met
705                 710                 715                 720

Phe Lys Glu Ile Tyr Tyr Asn Ala Phe Leu Asn Asp Lys Asn Val Arg
                725                 730                 735

Glu Arg Phe Ile Thr Lys Ala Thr Lys Val Ala Asp Asn Tyr Asp Arg
            740                 745                 750

Asn Lys Glu Arg Asn Leu Lys Asp Arg Ile Lys Ser Ala Gly Ser Asp
        755                 760                 765

Glu Lys Lys Lys Leu Arg Glu Gln Leu Gln Asn Tyr Ile Ala Glu Asn
    770                 775                 780

Asp Phe Gly Gln Arg Ile Lys Asn Ile Val Gln Val Asn Pro Asp Tyr
785                 790                 795                 800

Thr Leu Ala Gln Ile Cys Gln Leu Ile Met Thr Glu Tyr Asn Gln Gln
                805                 810                 815

Asn Asn Gly Cys Met Gln Lys Lys Ser Ala Ala Arg Lys Asp Ile Asn
            820                 825                 830

Lys Asp Ser Tyr Gln His Tyr Lys Met Leu Leu Leu Val Asn Leu Arg
        835                 840                 845

Lys Ala Phe Leu Glu Phe Ile Lys Glu Asn Tyr Ala Phe Val Leu Lys
    850                 855                 860

Pro Tyr Lys His Asp Leu Cys Asp Lys Ala Asp Phe Val Pro Asp Phe
865                 870                 875                 880

Ala Lys Tyr Val Lys Pro Tyr Ala Gly Leu Ile Ser Arg Val Ala Gly
                885                 890                 895

Ser Ser Glu Leu Gln Lys Trp Tyr Ile Val Ser Arg Phe Leu Ser Pro
            900                 905                 910

Ala Gln Ala Asn His Met Leu Gly Phe Leu His Ser Tyr Lys Gln Tyr
        915                 920                 925

Val Trp Asp Ile Tyr Arg Arg Ala Ser Glu Thr Gly Thr Glu Ile Asn
    930                 935                 940

His Ser Ile Ala Glu Asp Lys Ile Ala Gly Val Asp Ile Thr Asp Val
945                 950                 955                 960

Asp Ala Val Ile Asp Leu Ser Val Lys Leu Cys Gly Thr Ile Ser Ser
                965                 970                 975

Glu Ile Ser Asp Tyr Phe Lys Asp Asp Glu Val Tyr Ala Glu Tyr Ile
            980                 985                 990
```

-continued

```
Ser Ser Tyr Leu Asp Phe Glu Tyr  Asp Gly Gly Asn Tyr  Lys Asp Ser
        995                 1000                 1005

Leu Asn  Arg Phe Cys Asn Ser  Asp Ala Val Asn Asp  Gln Lys Val
    1010                 1015                 1020

Ala Leu  Tyr Tyr Asp Gly Glu  His Pro Lys Leu Asn  Arg Asn Ile
    1025                 1030                 1035

Ile Leu  Ser Lys Leu Tyr Gly  Glu Arg Arg Phe Leu  Glu Lys Ile
    1040                 1045                 1050

Thr Asp  Arg Val Ser Arg Ser  Asp Ile Val Glu Tyr  Tyr Lys Leu
    1055                 1060                 1065

Lys Lys  Glu Thr Ser Gln Tyr  Gln Thr Lys Gly Ile  Phe Asp Ser
    1070                 1075                 1080

Glu Asp  Glu Gln Lys Asn Ile  Lys Lys Phe Gln Glu  Met Lys Asn
    1085                 1090                 1095

Ile Val  Glu Phe Arg Asp Leu  Met Asp Tyr Ser Glu  Ile Ala Asp
    1100                 1105                 1110

Glu Leu  Gln Gly Gln Leu Ile  Asn Trp Ile Tyr Leu  Arg Glu Arg
    1115                 1120                 1125

Asp Leu  Met Asn Phe Gln Leu  Gly Tyr His Tyr Ala  Cys Leu Asn
    1130                 1135                 1140

Asn Asp  Ser Asn Lys Gln Ala  Thr Tyr Val Thr Leu  Asp Tyr Gln
    1145                 1150                 1155

Gly Lys  Lys Asn Arg Lys Ile  Asn Gly Ala Ile Leu  Tyr Gln Ile
    1160                 1165                 1170

Cys Ala  Met Tyr Ile Asn Gly  Leu Pro Leu Tyr Tyr  Val Asp Lys
    1175                 1180                 1185

Asp Ser  Ser Glu Trp Thr Val  Ser Asp Gly Lys Glu  Ser Thr Gly
    1190                 1195                 1200

Ala Lys  Ile Gly Glu Phe Tyr  Arg Tyr Ala Lys Ser  Phe Glu Asn
    1205                 1210                 1215

Thr Ser  Asp Cys Tyr Ala Ser  Gly Leu Glu Ile Phe  Glu Asn Ile
    1220                 1225                 1230

Ser Glu  His Asp Asn Ile Thr  Glu Leu Arg Asn Tyr  Ile Glu His
    1235                 1240                 1245

Phe Arg  Tyr Tyr Ser Ser Phe  Asp Arg Ser Phe Leu  Gly Ile Tyr
    1250                 1255                 1260

Ser Glu  Val Phe Asp Arg Phe  Phe Thr Tyr Asp Leu  Lys Tyr Arg
    1265                 1270                 1275

Lys Asn  Val Pro Thr Ile Leu  Tyr Asn Ile Leu Leu  Gln His Phe
    1280                 1285                 1290

Val Asn  Val Arg Phe Glu Phe  Val Ser Gly Lys Lys  Met Ile Gly
    1295                 1300                 1305

Ile Asp  Lys Lys Asp Arg Lys  Ile Ala Lys Glu Lys  Glu Cys Ala
    1310                 1315                 1320

Arg Ile  Thr Ile Arg Glu Lys  Asn Gly Val Tyr Ser  Glu Gln Phe
    1325                 1330                 1335

Thr Tyr  Lys Leu Lys Asn Gly  Thr Val Tyr Val Asp  Ala Arg Asp
    1340                 1345                 1350

Lys Arg  Tyr Leu Gln Ser Ile  Ile Arg Leu Leu Phe  Tyr Pro Glu
    1355                 1360                 1365

Lys Val  Asn Met Asp Glu Met  Ile Glu Val Lys Glu  Lys Lys Lys
    1370                 1375                 1380
```

```
Pro Ser  Asp Asn Asn Thr Gly  Lys Gly Tyr Ser Lys  Arg Asp Arg
    1385                 1390                 1395

Gln Gln  Asp Arg Lys Glu Tyr  Asp Lys Tyr Lys Glu  Lys Lys Lys
    1400                 1405                 1410

Lys Glu  Gly Asn Phe Leu Ser  Gly Met Gly Gly Asn  Ile Asn Trp
    1415                 1420                 1425

Asp Glu  Ile Asn Ala Gln Leu  Lys Asn
    1430                 1435
```

<210> SEQ ID NO 25
<211> LENGTH: 1159
<212> TYPE: PRT
<213> ORGANISM: Artificial Sequence
<220> FEATURE:
<223> OTHER INFORMATION: Chemically synthesized

<400> SEQUENCE: 25

```
Met Lys Val Thr Lys Val Gly Gly Ile Ser His Lys Lys Tyr Thr Ser
1               5                   10                  15

Glu Gly Arg Leu Val Lys Ser Glu Ser Glu Glu Asn Arg Thr Asp Glu
            20                  25                  30

Arg Leu Ser Ala Leu Leu Asn Met Arg Leu Asp Met Tyr Ile Lys Asn
        35                  40                  45

Pro Ser Ser Thr Glu Thr Lys Glu Asn Gln Lys Arg Ile Gly Lys Leu
    50                  55                  60

Lys Lys Phe Phe Ser Asn Lys Met Val Tyr Leu Lys Asp Asn Thr Leu
65                  70                  75                  80

Ser Leu Lys Asn Gly Lys Lys Glu Asn Ile Asp Arg Glu Tyr Ser Glu
                85                  90                  95

Thr Asp Ile Leu Glu Ser Asp Val Arg Asp Lys Lys Asn Phe Ala Val
            100                 105                 110

Leu Lys Lys Ile Tyr Leu Asn Glu Asn Val Asn Ser Glu Glu Leu Glu
        115                 120                 125

Val Phe Arg Asn Asp Ile Lys Lys Lys Leu Asn Lys Ile Asn Ser Leu
    130                 135                 140

Lys Tyr Ser Phe Glu Lys Asn Lys Ala Asn Tyr Gln Lys Ile Asn Glu
145                 150                 155                 160

Asn Asn Ile Glu Lys Val Glu Gly Lys Ser Lys Arg Asn Ile Ile Tyr
                165                 170                 175

Asp Tyr Tyr Arg Glu Ser Ala Lys Arg Asp Ala Tyr Val Ser Asn Val
            180                 185                 190

Lys Glu Ala Phe Asp Lys Leu Tyr Lys Glu Glu Asp Ile Ala Lys Leu
        195                 200                 205

Val Leu Glu Ile Glu Asn Leu Thr Lys Leu Glu Lys Tyr Lys Ile Arg
    210                 215                 220

Glu Phe Tyr His Glu Ile Ile Gly Arg Lys Asn Asp Lys Glu Asn Phe
225                 230                 235                 240

Ala Lys Ile Ile Tyr Glu Glu Ile Gln Asn Val Asn Asn Met Lys Glu
                245                 250                 255

Leu Ile Glu Lys Val Pro Asp Met Ser Glu Leu Lys Lys Ser Gln Val
            260                 265                 270

Phe Tyr Lys Tyr Tyr Leu Asp Lys Glu Glu Leu Asn Asp Lys Asn Ile
        275                 280                 285

Lys Tyr Ala Phe Cys His Phe Val Glu Ile Glu Met Ser Gln Leu Leu
    290                 295                 300
```

```
Lys Asn Tyr Val Tyr Lys Arg Leu Ser Asn Ile Ser Asn Asp Lys Ile
305                 310                 315                 320

Lys Arg Ile Phe Glu Tyr Gln Asn Leu Lys Lys Leu Ile Glu Asn Lys
                325                 330                 335

Leu Leu Asn Lys Leu Asp Thr Tyr Val Arg Asn Cys Gly Lys Tyr Asn
            340                 345                 350

Tyr Tyr Leu Gln Asp Gly Glu Ile Ala Thr Ser Asp Phe Ile Ala Arg
        355                 360                 365

Asn Arg Gln Asn Glu Ala Phe Leu Arg Asn Ile Ile Gly Val Ser Ser
    370                 375                 380

Val Ala Tyr Phe Ser Leu Arg Asn Ile Leu Glu Thr Glu Asn Glu Asn
385                 390                 395                 400

Asp Ile Thr Gly Arg Met Arg Gly Lys Thr Val Lys Asn Asn Lys Gly
                405                 410                 415

Glu Glu Lys Tyr Val Ser Gly Glu Val Asp Lys Ile Tyr Asn Glu Asn
            420                 425                 430

Lys Lys Asn Glu Val Lys Glu Asn Leu Lys Met Phe Tyr Ser Tyr Asp
        435                 440                 445

Phe Asn Met Asp Asn Lys Asn Glu Ile Glu Asp Phe Phe Ala Asn Ile
    450                 455                 460

Asp Glu Ala Ile Ser Ser Ile Arg His Gly Ile Val His Phe Asn Leu
465                 470                 475                 480

Glu Leu Glu Gly Lys Asp Ile Phe Ala Phe Lys Asn Ile Ala Pro Ser
                485                 490                 495

Glu Ile Ser Lys Lys Met Phe Gln Asn Glu Ile Asn Glu Lys Lys Leu
            500                 505                 510

Lys Leu Lys Ile Phe Arg Gln Leu Asn Ser Ala Asn Val Phe Arg Tyr
        515                 520                 525

Leu Glu Lys Tyr Lys Ile Leu Asn Tyr Leu Lys Arg Thr Arg Phe Glu
    530                 535                 540

Phe Val Asn Lys Asn Ile Pro Phe Val Pro Ser Phe Thr Lys Leu Tyr
545                 550                 555                 560

Ser Arg Ile Asp Asp Leu Lys Asn Ser Leu Gly Ile Tyr Trp Lys Thr
                565                 570                 575

Pro Lys Thr Asn Asp Asp Asn Lys Thr Lys Glu Ile Ile Asp Ala Gln
            580                 585                 590

Ile Tyr Leu Leu Lys Asn Ile Tyr Tyr Gly Glu Phe Leu Asn Tyr Phe
        595                 600                 605

Met Ser Asn Asn Gly Asn Phe Phe Glu Ile Ser Lys Glu Ile Ile Glu
    610                 615                 620

Leu Asn Lys Asn Asp Lys Arg Asn Leu Lys Thr Gly Phe Tyr Lys Leu
625                 630                 635                 640

Gln Lys Phe Glu Asp Ile Gln Glu Lys Ile Pro Lys Glu Tyr Leu Ala
                645                 650                 655

Asn Ile Gln Ser Leu Tyr Met Ile Asn Ala Gly Asn Gln Asp Glu Glu
            660                 665                 670

Glu Lys Asp Thr Tyr Ile Asp Phe Ile Gln Lys Ile Phe Leu Lys Gly
        675                 680                 685

Phe Met Thr Tyr Leu Ala Asn Asn Gly Arg Leu Ser Leu Ile Tyr Ile
    690                 695                 700

Gly Ser Asp Glu Glu Thr Asn Thr Ser Leu Ala Glu Lys Lys Gln Glu
705                 710                 715                 720

Phe Asp Lys Phe Leu Lys Lys Tyr Glu Gln Asn Asn Asn Ile Lys Ile
```

```
                725                 730                 735

Pro Tyr Glu Ile Asn Glu Phe Leu Arg Glu Ile Lys Leu Gly Asn Ile
            740                 745                 750

Leu Lys Tyr Thr Glu Arg Leu Asn Met Phe Tyr Leu Ile Leu Lys Leu
        755                 760                 765

Leu Asn His Lys Glu Leu Thr Asn Leu Lys Gly Ser Leu Glu Lys Tyr
    770                 775                 780

Gln Ser Ala Asn Lys Glu Glu Ala Phe Ser Asp Gln Leu Glu Leu Ile
785                 790                 795                 800

Asn Leu Leu Asn Leu Asp Asn Asn Arg Val Thr Glu Asp Phe Glu Leu
                805                 810                 815

Glu Ala Asp Glu Ile Gly Lys Phe Leu Asp Phe Asn Gly Asn Lys Val
            820                 825                 830

Lys Asp Asn Lys Glu Leu Lys Lys Phe Asp Thr Asn Lys Ile Tyr Phe
        835                 840                 845

Asp Gly Glu Asn Ile Ile Lys His Arg Ala Phe Tyr Asn Ile Lys Lys
    850                 855                 860

Tyr Gly Met Leu Asn Leu Leu Glu Lys Ile Ala Asp Lys Ala Gly Tyr
865                 870                 875                 880

Lys Ile Ser Ile Glu Glu Leu Lys Lys Tyr Ser Asn Lys Lys Asn Glu
                885                 890                 895

Ile Glu Lys Asn His Lys Met Gln Glu Asn Leu His Arg Lys Tyr Ala
            900                 905                 910

Arg Pro Arg Lys Asp Glu Lys Phe Thr Asp Glu Asp Tyr Glu Ser Tyr
        915                 920                 925

Lys Gln Ala Ile Glu Asn Ile Glu Glu Tyr Thr His Leu Lys Asn Lys
    930                 935                 940

Val Glu Phe Asn Glu Leu Asn Leu Leu Gln Gly Leu Leu Leu Arg Ile
945                 950                 955                 960

Leu His Arg Leu Val Gly Tyr Thr Ser Ile Trp Glu Arg Asp Leu Arg
                965                 970                 975

Phe Arg Leu Lys Gly Glu Phe Pro Glu Asn Gln Tyr Ile Glu Glu Ile
            980                 985                 990

Phe Asn Phe Glu Asn Lys Lys Asn  Val Lys Tyr Lys Gly  Gly Gln Ile
        995                 1000                1005

Val Glu  Lys Tyr Ile Lys Phe  Tyr Lys Glu Leu His  Gln Asn Asp
    1010                1015                1020

Glu Val  Lys Ile Asn Lys Tyr  Ser Ser Ala Asn Ile  Lys Val Leu
    1025                1030                1035

Lys Gln  Glu Lys Lys Asp Leu  Tyr Ile Arg Asn Tyr  Ile Ala His
    1040                1045                1050

Phe Asn  Tyr Ile Pro His Ala  Glu Ile Ser Leu Leu  Glu Val Leu
    1055                1060                1065

Glu Asn  Leu Arg Lys Leu Leu  Ser Tyr Asp Arg Lys  Leu Lys Asn
    1070                1075                1080

Ala Val  Met Lys Ser Val Val  Asp Ile Leu Lys Glu  Tyr Gly Phe
    1085                1090                1095

Val Ala  Thr Phe Lys Ile Gly  Ala Asp Lys Lys Ile  Gly Ile Gln
    1100                1105                1110

Thr Leu  Glu Ser Glu Lys Ile  Val His Leu Lys Asn  Leu Lys Lys
    1115                1120                1125

Lys Lys  Leu Met Thr Asp Arg  Asn Ser Glu Glu Leu  Cys Lys Leu
    1130                1135                1140
```

```
Val Lys Ile Met Phe Glu Tyr Lys Met Glu Glu Lys Lys Ser Glu
    1145                1150                1155

Asn


<210> SEQ ID NO 26
<211> LENGTH: 1120
<212> TYPE: PRT
<213> ORGANISM: Artificial Sequence
<220> FEATURE:
<223> OTHER INFORMATION: Chemically synthesized

<400> SEQUENCE: 26

Met Trp Ile Ser Ile Lys Thr Leu Ile His His Leu Gly Val Leu Phe
1               5                   10                  15

Phe Cys Asp Tyr Met Tyr Asn Arg Arg Glu Lys Lys Ile Ile Glu Val
            20                  25                  30

Lys Thr Met Arg Ile Thr Lys Val Glu Val Asp Arg Lys Lys Val Leu
        35                  40                  45

Ile Ser Arg Asp Lys Asn Gly Gly Lys Leu Val Tyr Glu Asn Glu Met
    50                  55                  60

Gln Asp Asn Thr Glu Gln Ile Met His His Lys Lys Ser Ser Phe Tyr
65                  70                  75                  80

Lys Ser Val Val Asn Lys Thr Ile Cys Arg Pro Glu Gln Lys Gln Met
                85                  90                  95

Lys Lys Leu Val His Gly Leu Leu Gln Glu Asn Ser Gln Glu Lys Ile
            100                 105                 110

Lys Val Ser Asp Val Thr Lys Leu Asn Ile Ser Asn Phe Leu Asn His
        115                 120                 125

Arg Phe Lys Lys Ser Leu Tyr Tyr Phe Pro Glu Asn Ser Pro Asp Lys
    130                 135                 140

Ser Glu Glu Tyr Arg Ile Glu Ile Asn Leu Ser Gln Leu Leu Glu Asp
145                 150                 155                 160

Ser Leu Lys Lys Gln Gln Gly Thr Phe Ile Cys Trp Glu Ser Phe Ser
                165                 170                 175

Lys Asp Met Glu Leu Tyr Ile Asn Trp Ala Glu Asn Tyr Ile Ser Ser
            180                 185                 190

Lys Thr Lys Leu Ile Lys Lys Ser Ile Arg Asn Asn Arg Ile Gln Ser
        195                 200                 205

Thr Glu Ser Arg Ser Gly Gln Leu Met Asp Arg Tyr Met Lys Asp Ile
    210                 215                 220

Leu Asn Lys Asn Lys Pro Phe Asp Ile Gln Ser Val Ser Glu Lys Tyr
225                 230                 235                 240

Gln Leu Glu Lys Leu Thr Ser Ala Leu Lys Ala Thr Phe Lys Glu Ala
                245                 250                 255

Lys Lys Asn Asp Lys Glu Ile Asn Tyr Lys Leu Lys Ser Thr Leu Gln
            260                 265                 270

Asn His Glu Arg Gln Ile Ile Glu Glu Leu Lys Glu Asn Ser Glu Leu
        275                 280                 285

Asn Gln Phe Asn Ile Glu Ile Arg Lys His Leu Glu Thr Tyr Phe Pro
    290                 295                 300

Ile Lys Lys Thr Asn Arg Lys Val Gly Asp Ile Arg Asn Leu Glu Ile
305                 310                 315                 320

Gly Glu Ile Gln Lys Ile Val Asn His Arg Leu Lys Asn Lys Ile Val
                325                 330                 335
```

```
Gln Arg Ile Leu Gln Glu Gly Lys Leu Ala Ser Tyr Glu Ile Glu Ser
            340                 345                 350

Thr Val Asn Ser Asn Ser Leu Gln Lys Ile Lys Ile Glu Glu Ala Phe
        355                 360                 365

Ala Leu Lys Phe Ile Asn Ala Cys Leu Phe Ala Ser Asn Asn Leu Arg
    370                 375                 380

Asn Met Val Tyr Pro Val Cys Lys Lys Asp Ile Leu Met Ile Gly Glu
385                 390                 395                 400

Phe Lys Asn Ser Phe Lys Glu Ile Lys His Lys Lys Phe Ile Arg Gln
                405                 410                 415

Trp Ser Gln Phe Phe Ser Gln Glu Ile Thr Val Asp Asp Ile Glu Leu
            420                 425                 430

Ala Ser Trp Gly Leu Arg Gly Ala Ile Ala Pro Ile Arg Asn Glu Ile
        435                 440                 445

Ile His Leu Lys Lys His Ser Trp Lys Lys Phe Phe Asn Asn Pro Thr
    450                 455                 460

Phe Lys Val Lys Lys Ser Lys Ile Ile Asn Gly Lys Thr Lys Asp Val
465                 470                 475                 480

Thr Ser Glu Phe Leu Tyr Lys Glu Thr Leu Phe Lys Asp Tyr Phe Tyr
                485                 490                 495

Ser Glu Leu Asp Ser Val Pro Glu Leu Ile Ile Asn Lys Met Glu Ser
            500                 505                 510

Ser Lys Ile Leu Asp Tyr Tyr Ser Ser Asp Gln Leu Asn Gln Val Phe
        515                 520                 525

Thr Ile Pro Asn Phe Glu Leu Ser Leu Leu Thr Ser Ala Val Pro Phe
    530                 535                 540

Ala Pro Ser Phe Lys Arg Val Tyr Leu Lys Gly Phe Asp Tyr Gln Asn
545                 550                 555                 560

Gln Asp Glu Ala Gln Pro Asp Tyr Asn Leu Lys Leu Asn Ile Tyr Asn
                565                 570                 575

Glu Lys Ala Phe Asn Ser Glu Ala Phe Gln Ala Gln Tyr Ser Leu Phe
            580                 585                 590

Lys Met Val Tyr Tyr Gln Val Phe Leu Pro Gln Phe Thr Thr Asn Asn
        595                 600                 605

Asp Leu Phe Lys Ser Ser Val Asp Phe Ile Leu Thr Leu Asn Lys Glu
    610                 615                 620

Arg Lys Gly Tyr Ala Lys Ala Phe Gln Asp Ile Arg Lys Met Asn Lys
625                 630                 635                 640

Asp Glu Lys Pro Ser Glu Tyr Met Ser Tyr Ile Gln Ser Gln Leu Met
                645                 650                 655

Leu Tyr Gln Lys Lys Gln Glu Glu Lys Glu Lys Ile Asn His Phe Glu
            660                 665                 670

Lys Phe Ile Asn Gln Val Phe Ile Lys Gly Phe Asn Ser Phe Ile Glu
        675                 680                 685

Lys Asn Arg Leu Thr Tyr Ile Cys His Pro Thr Lys Asn Thr Val Pro
    690                 695                 700

Glu Asn Asp Asn Ile Glu Ile Pro Phe His Thr Asp Met Asp Asp Ser
705                 710                 715                 720

Asn Ile Ala Phe Trp Leu Met Cys Lys Leu Leu Asp Ala Lys Gln Leu
                725                 730                 735

Ser Glu Leu Arg Asn Glu Met Ile Lys Phe Ser Cys Ser Leu Gln Ser
            740                 745                 750

Thr Glu Glu Ile Ser Thr Phe Thr Lys Ala Arg Glu Val Ile Gly Leu
```

```
        755                 760                 765

Ala Leu Leu Asn Gly Glu Lys Gly Cys Asn Asp Trp Lys Glu Leu Phe
    770                 775                 780

Asp Asp Lys Glu Ala Trp Lys Lys Asn Met Ser Leu Tyr Val Ser Glu
785                 790                 795                 800

Glu Leu Leu Gln Ser Leu Pro Tyr Thr Gln Glu Asp Gly Gln Thr Pro
                805                 810                 815

Val Ile Asn Arg Ser Ile Asp Leu Val Lys Lys Tyr Gly Thr Glu Thr
            820                 825                 830

Ile Leu Glu Lys Leu Phe Ser Ser Ser Asp Asp Tyr Lys Val Ser Ala
        835                 840                 845

Lys Asp Ile Ala Lys Leu His Glu Tyr Asp Val Thr Glu Lys Ile Ala
    850                 855                 860

Gln Gln Glu Ser Leu His Lys Gln Trp Ile Glu Lys Pro Gly Leu Ala
865                 870                 875                 880

Arg Asp Ser Ala Trp Thr Lys Lys Tyr Gln Asn Val Ile Asn Asp Ile
                885                 890                 895

Ser Asn Tyr Gln Trp Ala Lys Thr Lys Val Glu Leu Thr Gln Val Arg
            900                 905                 910

His Leu His Gln Leu Thr Ile Asp Leu Leu Ser Arg Leu Ala Gly Tyr
        915                 920                 925

Met Ser Ile Ala Asp Arg Asp Phe Gln Phe Ser Ser Asn Tyr Ile Leu
    930                 935                 940

Glu Arg Glu Asn Ser Glu Tyr Arg Val Thr Ser Trp Ile Leu Leu Ser
945                 950                 955                 960

Glu Asn Lys Asn Lys Asn Lys Tyr Asn Asp Tyr Glu Leu Tyr Asn Leu
                965                 970                 975

Lys Asn Ala Ser Ile Lys Val Ser Ser Lys Asn Asp Pro Gln Leu Lys
            980                 985                 990

Val Asp Leu Lys Gln Leu Arg Leu  Thr Leu Glu Tyr Leu  Glu Leu Phe
        995                 1000                 1005

Asp Asn  Arg Leu Lys Glu Lys  Arg Asn Asn Ile Ser  His Phe Asn
    1010                 1015                 1020

Tyr Leu  Asn Gly Gln Leu Gly  Asn Ser Ile Leu Glu  Leu Phe Asp
    1025                 1030                 1035

Asp Ala  Arg Asp Val Leu Ser  Tyr Asp Arg Lys Leu  Lys Asn Ala
    1040                 1045                 1050

Val Ser  Lys Ser Leu Lys Glu  Ile Leu Ser Ser His  Gly Met Glu
    1055                 1060                 1065

Val Thr  Phe Lys Pro Leu Tyr  Gln Thr Asn His His  Leu Lys Ile
    1070                 1075                 1080

Asp Lys  Leu Gln Pro Lys Lys  Ile His His Leu Gly  Glu Lys Ser
    1085                 1090                 1095

Thr Val  Ser Ser Asn Gln Val  Ser Asn Glu Tyr Cys  Gln Leu Val
    1100                 1105                 1110

Arg Thr  Leu Leu Thr Met Lys
    1115                 1120
```

<210> SEQ ID NO 27
<211> LENGTH: 1389
<212> TYPE: PRT
<213> ORGANISM: Artificial Sequence
<220> FEATURE:
<223> OTHER INFORMATION: Chemically synthesized

<400> SEQUENCE: 27

Met Gly Asn Leu Phe Gly His Lys Arg Trp Tyr Glu Val Arg Asp Lys
1               5                   10                  15

Lys Asp Phe Lys Ile Lys Arg Lys Val Lys Val Lys Arg Asn Tyr Asp
            20                  25                  30

Gly Asn Lys Tyr Ile Leu Asn Ile Asn Glu Asn Asn Asn Lys Glu Lys
        35                  40                  45

Ile Asp Asn Asn Lys Phe Ile Arg Lys Tyr Ile Asn Tyr Lys Lys Asn
    50                  55                  60

Asp Asn Ile Leu Lys Glu Phe Thr Arg Lys Phe His Ala Gly Asn Ile
65                  70                  75                  80

Leu Phe Lys Leu Lys Gly Lys Glu Gly Ile Ile Arg Ile Glu Asn Asn
                85                  90                  95

Asp Asp Phe Leu Glu Thr Glu Glu Val Val Leu Tyr Ile Glu Ala Tyr
            100                 105                 110

Gly Lys Ser Glu Lys Leu Lys Ala Leu Gly Ile Thr Lys Lys Lys Ile
        115                 120                 125

Ile Asp Glu Ala Ile Arg Gln Gly Ile Thr Lys Asp Asp Lys Lys Ile
    130                 135                 140

Glu Ile Lys Arg Gln Glu Asn Glu Glu Glu Ile Glu Ile Asp Ile Arg
145                 150                 155                 160

Asp Glu Tyr Thr Asn Lys Thr Leu Asn Asp Cys Ser Ile Ile Leu Arg
                165                 170                 175

Ile Ile Glu Asn Asp Glu Leu Glu Thr Lys Lys Ser Ile Tyr Glu Ile
            180                 185                 190

Phe Lys Asn Ile Asn Met Ser Leu Tyr Lys Ile Ile Glu Lys Ile Ile
        195                 200                 205

Glu Asn Glu Thr Glu Lys Val Phe Glu Asn Arg Tyr Tyr Glu Glu His
    210                 215                 220

Leu Arg Glu Lys Leu Leu Lys Asp Asp Lys Ile Asp Val Ile Leu Thr
225                 230                 235                 240

Asn Phe Met Glu Ile Arg Glu Lys Ile Lys Ser Asn Leu Glu Ile Leu
                245                 250                 255

Gly Phe Val Lys Phe Tyr Leu Asn Val Gly Gly Asp Lys Lys Lys Ser
            260                 265                 270

Lys Asn Lys Lys Met Leu Val Glu Lys Ile Leu Asn Ile Asn Val Asp
        275                 280                 285

Leu Thr Val Glu Asp Ile Ala Asp Phe Val Ile Lys Glu Leu Glu Phe
    290                 295                 300

Trp Asn Ile Thr Lys Arg Ile Glu Lys Val Lys Lys Val Asn Asn Glu
305                 310                 315                 320

Phe Leu Glu Lys Arg Arg Asn Arg Thr Tyr Ile Lys Ser Tyr Val Leu
                325                 330                 335

Leu Asp Lys His Glu Lys Phe Lys Ile Glu Arg Glu Asn Lys Lys Asp
            340                 345                 350

Lys Ile Val Lys Phe Phe Val Glu Asn Ile Lys Asn Asn Ser Ile Lys
        355                 360                 365

Glu Lys Ile Glu Lys Ile Leu Ala Glu Phe Lys Ile Asp Glu Leu Ile
    370                 375                 380

Lys Lys Leu Glu Lys Glu Leu Lys Lys Gly Asn Cys Asp Thr Glu Ile
385                 390                 395                 400

Phe Gly Ile Phe Lys Lys His Tyr Lys Val Asn Phe Asp Ser Lys Lys
                405                 410                 415

```
Phe Ser Lys Lys Ser Asp Glu Glu Lys Glu Leu Tyr Lys Ile Ile Tyr
            420                 425                 430

Arg Tyr Leu Lys Gly Arg Ile Glu Lys Ile Leu Val Asn Glu Gln Lys
        435                 440                 445

Val Arg Leu Lys Lys Met Glu Lys Ile Glu Ile Glu Lys Ile Leu Asn
    450                 455                 460

Glu Ser Ile Leu Ser Glu Lys Ile Leu Lys Arg Val Lys Gln Tyr Thr
465                 470                 475                 480

Leu Glu His Ile Met Tyr Leu Gly Lys Leu Arg His Asn Asp Ile Asp
                485                 490                 495

Met Thr Thr Val Asn Thr Asp Asp Phe Ser Arg Leu His Ala Lys Glu
            500                 505                 510

Glu Leu Asp Leu Glu Leu Ile Thr Phe Phe Ala Ser Thr Asn Met Glu
        515                 520                 525

Leu Asn Lys Ile Phe Ser Arg Glu Asn Ile Asn Asn Asp Glu Asn Ile
    530                 535                 540

Asp Phe Phe Gly Gly Asp Arg Glu Lys Asn Tyr Val Leu Asp Lys Lys
545                 550                 555                 560

Ile Leu Asn Ser Lys Ile Lys Ile Ile Arg Asp Leu Asp Phe Ile Asp
                565                 570                 575

Asn Lys Asn Asn Ile Thr Asn Asn Phe Ile Arg Lys Phe Thr Lys Ile
            580                 585                 590

Gly Thr Asn Glu Arg Asn Arg Ile Leu His Ala Ile Ser Lys Glu Arg
        595                 600                 605

Asp Leu Gln Gly Thr Gln Asp Asp Tyr Asn Lys Val Ile Asn Ile Ile
    610                 615                 620

Gln Asn Leu Lys Ile Ser Asp Glu Glu Val Ser Lys Ala Leu Asn Leu
625                 630                 635                 640

Asp Val Val Phe Lys Asp Lys Lys Asn Ile Ile Thr Lys Ile Asn Asp
                645                 650                 655

Ile Lys Ile Ser Glu Glu Asn Asn Asn Asp Ile Lys Tyr Leu Pro Ser
            660                 665                 670

Phe Ser Lys Val Leu Pro Glu Ile Leu Asn Leu Tyr Arg Asn Asn Pro
        675                 680                 685

Lys Asn Glu Pro Phe Asp Thr Ile Glu Thr Glu Lys Ile Val Leu Asn
    690                 695                 700

Ala Leu Ile Tyr Val Asn Lys Glu Leu Tyr Lys Lys Leu Ile Leu Glu
705                 710                 715                 720

Asp Asp Leu Glu Glu Asn Glu Ser Lys Asn Ile Phe Leu Gln Glu Leu
                725                 730                 735

Lys Lys Thr Leu Gly Asn Ile Asp Glu Ile Asp Glu Asn Ile Ile Glu
            740                 745                 750

Asn Tyr Tyr Lys Asn Ala Gln Ile Ser Ala Ser Lys Gly Asn Asn Lys
        755                 760                 765

Ala Ile Lys Lys Tyr Gln Lys Lys Val Ile Glu Cys Tyr Ile Gly Tyr
    770                 775                 780

Leu Arg Lys Asn Tyr Glu Glu Leu Phe Asp Phe Ser Asp Phe Lys Met
785                 790                 795                 800

Asn Ile Gln Glu Ile Lys Lys Gln Ile Lys Asp Ile Asn Asp Asn Lys
                805                 810                 815

Thr Tyr Glu Arg Ile Thr Val Lys Thr Ser Asp Lys Thr Ile Val Ile
            820                 825                 830
```

```
Asn Asp Asp Phe Glu Tyr Ile Ile Ser Ile Phe Ala Leu Leu Asn Ser
        835                 840                 845

Asn Ala Val Ile Asn Lys Ile Arg Asn Arg Phe Phe Ala Thr Ser Val
    850                 855                 860

Trp Leu Asn Thr Ser Glu Tyr Gln Asn Ile Ile Asp Ile Leu Asp Glu
865                 870                 875                 880

Ile Met Gln Leu Asn Thr Leu Arg Asn Glu Cys Ile Thr Glu Asn Trp
                885                 890                 895

Asn Leu Asn Leu Glu Glu Phe Ile Gln Lys Met Lys Glu Ile Glu Lys
            900                 905                 910

Asp Phe Asp Asp Phe Lys Ile Gln Thr Lys Lys Glu Ile Phe Asn Asn
        915                 920                 925

Tyr Tyr Glu Asp Ile Lys Asn Asn Ile Leu Thr Glu Phe Lys Asp Asp
    930                 935                 940

Ile Asn Gly Cys Asp Val Leu Glu Lys Lys Leu Glu Lys Ile Val Ile
945                 950                 955                 960

Phe Asp Asp Glu Thr Lys Phe Glu Ile Asp Lys Lys Ser Asn Ile Leu
                965                 970                 975

Gln Asp Glu Gln Arg Lys Leu Ser Asn Ile Asn Lys Lys Asp Leu Lys
            980                 985                 990

Lys Lys Val Asp Gln Tyr Ile Lys  Asp Lys Asp Gln Glu  Ile Lys Ser
        995                 1000                 1005

Lys Ile  Leu Cys Arg Ile Ile  Phe Asn Ser Asp Phe  Leu Lys Lys
    1010                 1015                 1020

Tyr Lys  Lys Glu Ile Asp Asn  Leu Ile Glu Asp Met  Glu Ser Glu
    1025                 1030                 1035

Asn Glu  Asn Lys Phe Gln Glu  Ile Tyr Tyr Pro Lys  Glu Arg Lys
    1040                 1045                 1050

Asn Glu  Leu Tyr Ile Tyr Lys  Lys Asn Leu Phe Leu  Asn Ile Gly
    1055                 1060                 1065

Asn Pro  Asn Phe Asp Lys Ile  Tyr Gly Leu Ile Ser  Asn Asp Ile
    1070                 1075                 1080

Lys Met  Ala Asp Ala Lys Phe  Leu Phe Asn Ile Asp  Gly Lys Asn
    1085                 1090                 1095

Ile Arg  Lys Asn Lys Ile Ser  Glu Ile Asp Ala Ile  Leu Lys Asn
    1100                 1105                 1110

Leu Asn  Asp Lys Leu Asn Gly  Tyr Ser Lys Glu Tyr  Lys Glu Lys
    1115                 1120                 1125

Tyr Ile  Lys Lys Leu Lys Glu  Asn Asp Asp Phe Phe  Ala Lys Asn
    1130                 1135                 1140

Ile Gln  Asn Lys Asn Tyr Lys  Ser Phe Glu Lys Asp  Tyr Asn Arg
    1145                 1150                 1155

Val Ser  Glu Tyr Lys Lys Ile  Arg Asp Leu Val Glu  Phe Asn Tyr
    1160                 1165                 1170

Leu Asn  Lys Ile Glu Ser Tyr  Leu Ile Asp Ile Asn  Trp Lys Leu
    1175                 1180                 1185

Ala Ile  Gln Met Ala Arg Phe  Glu Arg Asp Met His  Tyr Ile Val
    1190                 1195                 1200

Asn Gly  Leu Arg Glu Leu Gly  Ile Ile Lys Leu Ser  Gly Tyr Asn
    1205                 1210                 1215

Thr Gly  Ile Ser Arg Ala Tyr  Pro Lys Arg Asn Gly  Ser Asp Gly
    1220                 1225                 1230

Phe Tyr  Thr Thr Thr Ala Tyr  Tyr Lys Phe Phe Asp  Glu Glu Ser
```

1235 1240 1245

Tyr Lys Lys Phe Glu Lys Ile Cys Tyr Gly Phe Gly Ile Asp Leu
1250 1255 1260

Ser Glu Asn Ser Glu Ile Asn Lys Pro Glu Asn Glu Ser Ile Arg
1265 1270 1275

Asn Tyr Ile Ser His Phe Tyr Ile Val Arg Asn Pro Phe Ala Asp
1280 1285 1290

Tyr Ser Ile Ala Glu Gln Ile Asp Arg Val Ser Asn Leu Leu Ser
1295 1300 1305

Tyr Ser Thr Arg Tyr Asn Asn Ser Thr Tyr Ala Ser Val Phe Glu
1310 1315 1320

Val Phe Lys Lys Asp Val Asn Leu Asp Tyr Asp Glu Leu Lys Lys
1325 1330 1335

Lys Phe Lys Leu Ile Gly Asn Asn Asp Ile Leu Glu Arg Leu Met
1340 1345 1350

Lys Pro Lys Lys Val Ser Val Leu Glu Leu Glu Ser Tyr Asn Ser
1355 1360 1365

Asp Tyr Ile Lys Asn Leu Ile Ile Glu Leu Leu Thr Lys Ile Glu
1370 1375 1380

Asn Thr Asn Asp Thr Leu
1385

<210> SEQ ID NO 28
<211> LENGTH: 1385
<212> TYPE: PRT
<213> ORGANISM: Artificial Sequence
<220> FEATURE:
<223> OTHER INFORMATION: Chemically synthesized

<400> SEQUENCE: 28

Met Gly Asn Leu Phe Gly His Lys Arg Trp Tyr Glu Val Arg Asp Lys
1 5 10 15

Lys Asp Phe Lys Ile Lys Arg Lys Val Lys Val Lys Arg Asn Tyr Asp
20 25 30

Gly Asn Lys Tyr Ile Leu Asn Ile Asn Glu Asn Asn Asn Lys Glu Lys
35 40 45

Ile Asp Asn Asn Lys Phe Ile Gly Glu Phe Val Asn Tyr Lys Lys Asn
50 55 60

Asn Asn Val Leu Lys Glu Phe Lys Arg Lys Phe His Ala Gly Asn Ile
65 70 75 80

Leu Phe Lys Leu Lys Gly Lys Glu Glu Ile Ile Arg Ile Glu Asn Asn
85 90 95

Asp Asp Phe Leu Glu Thr Glu Glu Val Val Leu Tyr Ile Glu Val Tyr
100 105 110

Gly Lys Ser Glu Lys Leu Lys Ala Leu Glu Ile Thr Lys Lys Lys Ile
115 120 125

Ile Asp Glu Ala Ile Arg Gln Gly Ile Thr Lys Asp Asp Lys Lys Ile
130 135 140

Glu Ile Lys Arg Gln Glu Asn Glu Glu Glu Ile Glu Ile Asp Ile Arg
145 150 155 160

Asp Glu Tyr Thr Asn Lys Thr Leu Asn Asp Cys Ser Ile Ile Leu Arg
165 170 175

Ile Ile Glu Asn Asp Glu Leu Glu Thr Lys Lys Ser Ile Tyr Glu Ile
180 185 190

Phe Lys Asn Ile Asn Met Ser Leu Tyr Lys Ile Ile Glu Lys Ile Ile

```
        195                 200                 205

Glu Asn Glu Thr Glu Lys Val Phe Glu Asn Arg Tyr Tyr Glu Glu His
    210                 215                 220

Leu Arg Glu Lys Leu Leu Lys Asp Asn Lys Ile Asp Val Ile Leu Thr
225                 230                 235                 240

Asn Phe Met Glu Ile Arg Glu Lys Ile Lys Ser Asn Leu Glu Ile Met
                245                 250                 255

Gly Phe Val Lys Phe Tyr Leu Asn Val Ser Gly Asp Lys Lys Lys Ser
            260                 265                 270

Glu Asn Lys Lys Met Phe Val Glu Lys Ile Leu Asn Thr Asn Val Asp
        275                 280                 285

Leu Thr Val Glu Asp Ile Val Asp Phe Ile Val Lys Glu Leu Lys Phe
    290                 295                 300

Trp Asn Ile Thr Lys Arg Ile Glu Lys Val Lys Lys Phe Asn Asn Glu
305                 310                 315                 320

Phe Leu Glu Asn Arg Arg Asn Arg Thr Tyr Ile Lys Ser Tyr Val Leu
                325                 330                 335

Leu Asp Lys His Glu Lys Phe Lys Ile Glu Arg Glu Asn Lys Lys Asp
            340                 345                 350

Lys Ile Val Lys Phe Phe Val Glu Asn Ile Lys Asn Asn Ser Ile Lys
        355                 360                 365

Glu Lys Ile Glu Lys Ile Leu Ala Glu Phe Lys Ile Asn Glu Leu Ile
    370                 375                 380

Lys Lys Leu Glu Lys Glu Leu Lys Lys Gly Asn Cys Asp Thr Glu Ile
385                 390                 395                 400

Phe Gly Ile Phe Lys Lys His Tyr Lys Val Asn Phe Asp Ser Lys Lys
                405                 410                 415

Phe Ser Asn Lys Ser Asp Glu Glu Lys Glu Leu Tyr Lys Ile Ile Tyr
            420                 425                 430

Arg Tyr Leu Lys Gly Arg Ile Glu Lys Ile Leu Val Asn Glu Gln Lys
        435                 440                 445

Val Arg Leu Lys Lys Met Glu Lys Ile Glu Ile Glu Lys Ile Leu Asn
    450                 455                 460

Glu Ser Ile Leu Ser Glu Lys Ile Leu Lys Arg Val Lys Gln Tyr Thr
465                 470                 475                 480

Leu Glu His Ile Met Tyr Leu Gly Lys Leu Arg His Asn Asp Ile Val
                485                 490                 495

Lys Met Thr Val Asn Thr Asp Asp Phe Ser Arg Leu His Ala Lys Glu
            500                 505                 510

Glu Leu Asp Leu Glu Leu Ile Thr Phe Phe Ala Ser Thr Asn Met Glu
        515                 520                 525

Leu Asn Lys Ile Phe Asn Gly Lys Glu Lys Val Thr Asp Phe Phe Gly
    530                 535                 540

Phe Asn Leu Asn Gly Gln Lys Ile Thr Leu Lys Glu Lys Val Pro Ser
545                 550                 555                 560

Phe Lys Leu Asn Ile Leu Lys Lys Leu Asn Phe Ile Asn Asn Glu Asn
                565                 570                 575

Asn Ile Asp Glu Lys Leu Ser His Phe Tyr Ser Phe Gln Lys Glu Gly
            580                 585                 590

Tyr Leu Leu Arg Asn Lys Ile Leu His Asn Ser Tyr Gly Asn Ile Gln
        595                 600                 605

Glu Thr Lys Asn Leu Lys Gly Glu Tyr Glu Asn Val Glu Lys Leu Ile
    610                 615                 620
```

```
Lys Glu Leu Lys Val Ser Asp Glu Glu Ile Ser Lys Ser Leu Ser Leu
625                 630                 635                 640

Asp Val Ile Phe Glu Gly Lys Val Asp Ile Ile Asn Lys Ile Asn Ser
                645                 650                 655

Leu Lys Ile Gly Glu Tyr Lys Asp Lys Lys Tyr Leu Pro Ser Phe Ser
            660                 665                 670

Lys Ile Val Leu Glu Ile Thr Arg Lys Phe Arg Glu Ile Asn Lys Asp
        675                 680                 685

Lys Leu Phe Asp Ile Glu Ser Glu Lys Ile Ile Leu Asn Ala Val Lys
    690                 695                 700

Tyr Val Asn Lys Ile Leu Tyr Glu Lys Ile Thr Ser Asn Glu Glu Asn
705                 710                 715                 720

Glu Phe Leu Lys Thr Leu Pro Asp Lys Leu Val Lys Lys Ser Asn Asn
                725                 730                 735

Lys Lys Glu Asn Lys Asn Leu Leu Ser Ile Glu Glu Tyr Tyr Lys Asn
            740                 745                 750

Ala Gln Val Ser Ser Ser Lys Gly Asp Lys Lys Ala Ile Lys Lys Tyr
        755                 760                 765

Gln Asn Lys Val Thr Asn Ala Tyr Leu Glu Tyr Leu Glu Asn Thr Phe
    770                 775                 780

Thr Glu Ile Ile Asp Phe Ser Lys Phe Asn Leu Asn Tyr Asp Glu Ile
785                 790                 795                 800

Lys Thr Lys Ile Glu Glu Arg Lys Asp Asn Lys Ser Lys Ile Ile Ile
                805                 810                 815

Asp Ser Ile Ser Thr Asn Ile Asn Ile Thr Asn Asp Ile Glu Tyr Ile
            820                 825                 830

Ile Ser Ile Phe Ala Leu Leu Asn Ser Asn Thr Tyr Ile Asn Lys Ile
        835                 840                 845

Arg Asn Arg Phe Phe Ala Thr Ser Val Trp Leu Glu Lys Gln Asn Gly
    850                 855                 860

Thr Lys Glu Tyr Asp Tyr Glu Asn Ile Ile Ser Ile Leu Asp Glu Val
865                 870                 875                 880

Leu Leu Ile Asn Leu Leu Arg Glu Asn Asn Ile Thr Asp Ile Leu Asp
                885                 890                 895

Leu Lys Asn Ala Ile Ile Asp Ala Lys Ile Val Glu Asn Asp Glu Thr
            900                 905                 910

Tyr Ile Lys Asn Tyr Ile Phe Glu Ser Asn Glu Glu Lys Leu Lys Lys
        915                 920                 925

Arg Leu Phe Cys Glu Glu Leu Val Asp Lys Glu Asp Ile Arg Lys Ile
    930                 935                 940

Phe Glu Asp Glu Asn Phe Lys Phe Lys Ser Phe Ile Lys Lys Asn Glu
945                 950                 955                 960

Ile Gly Asn Phe Lys Ile Asn Phe Gly Ile Leu Ser Asn Leu Glu Cys
                965                 970                 975

Asn Ser Glu Val Glu Ala Lys Lys Ile Ile Gly Lys Asn Ser Lys Lys
            980                 985                 990

Leu Glu Ser Phe Ile Gln Asn Ile  Ile Asp Glu Tyr Lys  Ser Asn Ile
        995                 1000                1005

Arg Thr  Leu Phe Ser Ser Glu  Phe Leu Glu Lys Tyr  Lys Glu Glu
    1010                1015                1020

Ile Asp  Asn Leu Val Glu Asp  Thr Glu Ser Glu Asn  Lys Asn Lys
    1025                1030                1035
```

```
Phe Glu  Lys Ile Tyr Tyr Pro  Lys Glu His Lys Asn  Glu Leu Tyr
    1040                 1045                 1050

Ile Tyr  Lys Lys Asn Leu Phe  Leu Asn Ile Gly Asn  Pro Asn Phe
    1055                 1060                 1065

Asp Lys  Ile Tyr Gly Leu Ile  Ser Lys Asp Ile Lys  Asn Val Asp
    1070                 1075                 1080

Thr Lys  Ile Leu Phe Asp Asp  Asp Ile Lys Lys Asn  Lys Ile Ser
    1085                 1090                 1095

Glu Ile  Asp Ala Ile Leu Lys  Asn Leu Asn Asp Lys  Leu Asn Gly
    1100                 1105                 1110

Tyr Ser  Asn Asp Tyr Lys Ala  Lys Tyr Val Asn Lys  Leu Lys Glu
    1115                 1120                 1125

Asn Asp  Asp Phe Phe Ala Lys  Asn Ile Gln Asn Glu  Asn Tyr Ser
    1130                 1135                 1140

Ser Phe  Gly Glu Phe Glu Lys  Asp Tyr Asn Lys Val  Ser Glu Tyr
    1145                 1150                 1155

Lys Lys  Ile Arg Asp Leu Val  Glu Phe Asn Tyr Leu  Asn Lys Ile
    1160                 1165                 1170

Glu Ser  Tyr Leu Ile Asp Ile  Asn Trp Lys Leu Ala  Ile Gln Met
    1175                 1180                 1185

Ala Arg  Phe Glu Arg Asp Met  His Tyr Ile Val Asn  Gly Leu Arg
    1190                 1195                 1200

Glu Leu  Gly Ile Ile Lys Leu  Ser Gly Tyr Asn Thr  Gly Ile Ser
    1205                 1210                 1215

Arg Ala  Tyr Pro Lys Arg Asn  Gly Ser Asp Gly Phe  Tyr Thr Thr
    1220                 1225                 1230

Thr Ala  Tyr Tyr Lys Phe Phe  Asp Glu Glu Ser Tyr  Lys Lys Phe
    1235                 1240                 1245

Glu Lys  Ile Cys Tyr Gly Phe  Gly Ile Asp Leu Ser  Glu Asn Ser
    1250                 1255                 1260

Glu Ile  Asn Lys Pro Glu Asn  Glu Ser Ile Arg Asn  Tyr Ile Ser
    1265                 1270                 1275

His Phe  Tyr Ile Val Arg Asn  Pro Phe Ala Asp Tyr  Ser Ile Ala
    1280                 1285                 1290

Glu Gln  Ile Asp Arg Val Ser  Asn Leu Leu Ser Tyr  Ser Thr Arg
    1295                 1300                 1305

Tyr Asn  Asn Ser Thr Tyr Ala  Ser Val Phe Glu Val  Phe Lys Lys
    1310                 1315                 1320

Asp Val  Asn Leu Asp Tyr Asp  Glu Leu Lys Lys Lys  Phe Arg Leu
    1325                 1330                 1335

Ile Gly  Asn Asn Asp Ile Leu  Glu Arg Leu Met Lys  Pro Lys Lys
    1340                 1345                 1350

Val Ser  Val Leu Glu Leu Glu  Ser Tyr Asn Ser Asp  Tyr Ile Lys
    1355                 1360                 1365

Asn Leu  Ile Ile Glu Leu Leu  Thr Lys Ile Glu Asn  Thr Asn Asp
    1370                 1375                 1380

Thr Leu
    1385
```

<210> SEQ ID NO 29
<211> LENGTH: 1152
<212> TYPE: PRT
<213> ORGANISM: Artificial Sequence
<220> FEATURE:
<223> OTHER INFORMATION: Chemically synthesized

<400> SEQUENCE: 29

Met Lys Val Thr Lys Val Asp Gly Ile Ser His Lys Lys Tyr Ile Glu
1               5                   10                  15

Glu Gly Lys Leu Val Lys Ser Thr Ser Glu Glu Asn Arg Thr Ser Glu
            20                  25                  30

Arg Leu Ser Glu Leu Leu Ser Ile Arg Leu Asp Ile Tyr Ile Lys Asn
        35                  40                  45

Pro Asp Asn Ala Ser Glu Glu Glu Asn Arg Ile Arg Arg Glu Asn Leu
    50                  55                  60

Lys Lys Phe Phe Ser Asn Lys Val Leu His Leu Lys Asp Ser Val Leu
65                  70                  75                  80

Tyr Leu Lys Asn Arg Lys Glu Lys Asn Ala Val Gln Asp Lys Asn Tyr
                85                  90                  95

Ser Glu Glu Asp Ile Ser Glu Tyr Asp Leu Lys Asn Lys Asn Ser Phe
            100                 105                 110

Ser Val Leu Lys Lys Ile Leu Leu Asn Glu Asp Val Asn Ser Glu Glu
        115                 120                 125

Leu Glu Ile Phe Arg Lys Asp Val Glu Ala Lys Leu Asn Lys Ile Asn
    130                 135                 140

Ser Leu Lys Tyr Ser Phe Glu Glu Asn Lys Ala Asn Tyr Gln Lys Ile
145                 150                 155                 160

Asn Glu Asn Asn Val Glu Lys Val Gly Gly Lys Ser Lys Arg Asn Ile
                165                 170                 175

Ile Tyr Asp Tyr Tyr Arg Glu Ser Ala Lys Arg Asn Asp Tyr Ile Asn
            180                 185                 190

Asn Val Gln Glu Ala Phe Asp Lys Leu Tyr Lys Lys Glu Asp Ile Glu
        195                 200                 205

Lys Leu Phe Phe Leu Ile Glu Asn Ser Lys Lys His Glu Lys Tyr Lys
    210                 215                 220

Ile Arg Glu Tyr Tyr His Lys Ile Ile Gly Arg Lys Asn Asp Lys Glu
225                 230                 235                 240

Asn Phe Ala Lys Ile Ile Tyr Glu Glu Ile Gln Asn Val Asn Asn Ile
                245                 250                 255

Lys Glu Leu Ile Glu Lys Ile Pro Asp Met Ser Glu Leu Lys Lys Ser
            260                 265                 270

Gln Val Phe Tyr Lys Tyr Tyr Leu Asp Lys Glu Glu Leu Asn Asp Lys
        275                 280                 285

Asn Ile Lys Tyr Ala Phe Cys His Phe Val Glu Ile Glu Met Ser Gln
    290                 295                 300

Leu Leu Lys Asn Tyr Val Tyr Lys Arg Leu Ser Asn Ile Ser Asn Asp
305                 310                 315                 320

Lys Ile Lys Arg Ile Phe Glu Tyr Gln Asn Leu Lys Lys Leu Ile Glu
                325                 330                 335

Asn Lys Leu Leu Asn Lys Leu Asp Thr Tyr Val Arg Asn Cys Gly Lys
            340                 345                 350

Tyr Asn Tyr Tyr Leu Gln Val Gly Glu Ile Ala Thr Ser Asp Phe Ile
        355                 360                 365

Ala Arg Asn Arg Gln Asn Glu Ala Phe Leu Arg Asn Ile Ile Gly Val
    370                 375                 380

Ser Ser Val Ala Tyr Phe Ser Leu Arg Asn Ile Leu Glu Thr Glu Asn
385                 390                 395                 400

Glu Asn Asp Ile Thr Gly Arg Met Arg Gly Lys Thr Val Lys Asn Asn

```
                405                 410                 415

Lys Gly Glu Glu Lys Tyr Val Ser Gly Glu Val Asp Lys Ile Tyr Asn
            420                 425                 430

Glu Asn Lys Gln Asn Glu Val Lys Glu Asn Leu Lys Met Phe Tyr Ser
        435                 440                 445

Tyr Asp Phe Asn Met Asp Asn Lys Asn Glu Ile Glu Asp Phe Phe Ala
    450                 455                 460

Asn Ile Asp Glu Ala Ile Ser Ser Ile Arg His Gly Ile Val His Phe
465                 470                 475                 480

Asn Leu Glu Leu Glu Gly Lys Asp Ile Phe Ala Phe Lys Asn Ile Ala
                485                 490                 495

Pro Ser Glu Ile Ser Lys Lys Met Phe Gln Asn Glu Ile Asn Glu Lys
            500                 505                 510

Lys Leu Lys Leu Lys Ile Phe Lys Gln Leu Asn Ser Ala Asn Val Phe
        515                 520                 525

Asn Tyr Tyr Glu Lys Asp Val Ile Ile Lys Tyr Leu Lys Asn Thr Lys
    530                 535                 540

Phe Asn Phe Val Asn Lys Asn Ile Pro Phe Val Pro Ser Phe Thr Lys
545                 550                 555                 560

Leu Tyr Asn Lys Ile Glu Asp Leu Arg Asn Thr Leu Lys Phe Phe Trp
                565                 570                 575

Ser Val Pro Lys Asp Lys Glu Glu Lys Asp Ala Gln Ile Tyr Leu Leu
            580                 585                 590

Lys Asn Ile Tyr Tyr Gly Glu Phe Leu Asn Lys Phe Val Lys Asn Ser
        595                 600                 605

Lys Val Phe Phe Lys Ile Thr Asn Glu Val Ile Lys Ile Asn Lys Gln
    610                 615                 620

Arg Asn Gln Lys Thr Gly His Tyr Lys Tyr Gln Lys Phe Glu Asn Ile
625                 630                 635                 640

Glu Lys Thr Val Pro Val Glu Tyr Leu Ala Ile Ile Gln Ser Arg Glu
                645                 650                 655

Met Ile Asn Asn Gln Asp Lys Glu Glu Lys Asn Thr Tyr Ile Asp Phe
            660                 665                 670

Ile Gln Gln Ile Phe Leu Lys Gly Phe Ile Asp Tyr Leu Asn Lys Asn
        675                 680                 685

Asn Leu Lys Tyr Ile Glu Ser Asn Asn Asn Asn Asp Asn Asn Asp Ile
    690                 695                 700

Phe Ser Lys Ile Lys Ile Lys Lys Asp Asn Lys Glu Lys Tyr Asp Lys
705                 710                 715                 720

Ile Leu Lys Asn Tyr Glu Lys His Asn Arg Asn Lys Glu Ile Pro His
                725                 730                 735

Glu Ile Asn Glu Phe Val Arg Glu Ile Lys Leu Gly Lys Ile Leu Lys
            740                 745                 750

Tyr Thr Glu Asn Leu Asn Met Phe Tyr Leu Ile Leu Lys Leu Leu Asn
        755                 760                 765

His Lys Glu Leu Thr Asn Leu Lys Gly Ser Leu Glu Lys Tyr Gln Ser
    770                 775                 780

Ala Asn Lys Glu Glu Thr Phe Ser Asp Glu Leu Glu Leu Ile Asn Leu
785                 790                 795                 800

Leu Asn Leu Asp Asn Asn Arg Val Thr Glu Asp Phe Glu Leu Glu Ala
                805                 810                 815

Asn Glu Ile Gly Lys Phe Leu Asp Phe Asn Glu Asn Lys Ile Lys Asp
            820                 825                 830
```

```
Arg Lys Glu Leu Lys Lys Phe Asp Thr Asn Lys Ile Tyr Phe Asp Gly
        835                 840                 845

Glu Asn Ile Ile Lys His Arg Ala Phe Tyr Asn Ile Lys Lys Tyr Gly
    850                 855                 860

Met Leu Asn Leu Leu Glu Lys Ile Ala Asp Lys Ala Lys Tyr Lys Ile
865                 870                 875                 880

Ser Leu Lys Glu Leu Lys Glu Tyr Ser Asn Lys Lys Asn Glu Ile Glu
                885                 890                 895

Lys Asn Tyr Thr Met Gln Gln Asn Leu His Arg Lys Tyr Ala Arg Pro
            900                 905                 910

Lys Lys Asp Glu Lys Phe Asn Asp Glu Asp Tyr Lys Glu Tyr Glu Lys
        915                 920                 925

Ala Ile Gly Asn Ile Gln Lys Tyr Thr His Leu Lys Asn Lys Val Glu
    930                 935                 940

Phe Asn Glu Leu Asn Leu Leu Gln Gly Leu Leu Leu Lys Ile Leu His
945                 950                 955                 960

Arg Leu Val Gly Tyr Thr Ser Ile Trp Glu Arg Asp Leu Arg Phe Arg
                965                 970                 975

Leu Lys Gly Glu Phe Pro Glu Asn His Tyr Ile Glu Glu Ile Phe Asn
            980                 985                 990

Phe Asp Asn Ser Lys Asn Val Lys  Tyr Lys Ser Gly Gln  Ile Val Glu
        995                 1000                 1005

Lys Tyr  Ile Asn Phe Tyr Lys  Glu Leu Tyr Lys Asp  Asn Val Glu
    1010                 1015                 1020

Lys Arg  Ser Ile Tyr Ser Asp  Lys Lys Val Lys Lys  Leu Lys Gln
    1025                 1030                 1035

Glu Lys  Lys Asp Leu Tyr Ile  Arg Asn Tyr Ile Ala  His Phe Asn
    1040                 1045                 1050

Tyr Ile  Pro His Ala Glu Ile  Ser Leu Leu Glu Val  Leu Glu Asn
    1055                 1060                 1065

Leu Arg  Lys Leu Leu Ser Tyr  Asp Arg Lys Leu Lys  Asn Ala Ile
    1070                 1075                 1080

Met Lys  Ser Ile Val Asp Ile  Leu Lys Glu Tyr Gly  Phe Val Ala
    1085                 1090                 1095

Thr Phe  Lys Ile Gly Ala Asp  Lys Lys Ile Glu Ile  Gln Thr Leu
    1100                 1105                 1110

Glu Ser  Glu Lys Ile Val His  Leu Lys Asn Leu Lys  Lys Lys Lys
    1115                 1120                 1125

Leu Met  Thr Asp Arg Asn Ser  Glu Glu Leu Cys Glu  Leu Val Lys
    1130                 1135                 1140

Val Met  Phe Glu Tyr Lys Ala  Leu Glu
    1145                 1150
```

<210> SEQ ID NO 30
<211> LENGTH: 1152
<212> TYPE: PRT
<213> ORGANISM: Artificial Sequence
<220> FEATURE:
<223> OTHER INFORMATION: Chemically synthesized

<400> SEQUENCE: 30

```
Met Lys Val Thr Lys Val Asp Gly Ile Ser His Lys Lys Tyr Ile Glu
1               5                   10                  15

Glu Gly Lys Leu Val Lys Ser Thr Ser Glu Glu Asn Arg Thr Ser Glu
            20                  25                  30
```

```
Arg Leu Ser Glu Leu Leu Ser Ile Arg Leu Asp Ile Tyr Ile Lys Asn
        35                  40                  45

Pro Asp Asn Ala Ser Glu Glu Glu Asn Arg Ile Arg Arg Glu Asn Leu
    50                  55                  60

Lys Lys Phe Phe Ser Asn Lys Val Leu His Leu Lys Asp Ser Val Leu
65                  70                  75                  80

Tyr Leu Lys Asn Arg Lys Glu Lys Asn Ala Val Gln Asp Lys Asn Tyr
                85                  90                  95

Ser Glu Glu Asp Ile Ser Glu Tyr Asp Leu Lys Asn Lys Asn Ser Phe
            100                 105                 110

Ser Val Leu Lys Lys Ile Leu Leu Asn Glu Asp Val Asn Ser Glu Glu
        115                 120                 125

Leu Glu Ile Phe Arg Lys Asp Val Glu Ala Lys Leu Asn Lys Ile Asn
    130                 135                 140

Ser Leu Lys Tyr Ser Phe Glu Glu Asn Lys Ala Asn Tyr Gln Lys Ile
145                 150                 155                 160

Asn Glu Asn Asn Val Glu Lys Val Gly Gly Lys Ser Lys Arg Asn Ile
                165                 170                 175

Ile Tyr Asp Tyr Tyr Arg Glu Ser Ala Lys Arg Asn Asp Tyr Ile Asn
            180                 185                 190

Asn Val Gln Glu Ala Phe Asp Lys Leu Tyr Lys Lys Glu Asp Ile Glu
        195                 200                 205

Lys Leu Phe Phe Leu Ile Glu Asn Ser Lys Lys His Glu Lys Tyr Lys
    210                 215                 220

Ile Arg Glu Tyr Tyr His Lys Ile Ile Gly Arg Lys Asn Asp Lys Glu
225                 230                 235                 240

Asn Phe Ala Lys Ile Ile Tyr Glu Glu Ile Gln Asn Val Asn Asn Ile
                245                 250                 255

Lys Glu Leu Ile Glu Lys Ile Pro Asp Met Ser Glu Leu Lys Lys Ser
            260                 265                 270

Gln Val Phe Tyr Lys Tyr Tyr Leu Asp Lys Glu Glu Leu Asn Asp Lys
        275                 280                 285

Asn Ile Lys Tyr Ala Phe Cys His Phe Val Glu Ile Glu Met Ser Gln
    290                 295                 300

Leu Leu Lys Asn Tyr Val Tyr Lys Arg Leu Ser Asn Ile Ser Asn Asp
305                 310                 315                 320

Lys Ile Lys Arg Ile Phe Glu Tyr Gln Asn Leu Lys Lys Leu Ile Glu
                325                 330                 335

Asn Lys Leu Leu Asn Lys Leu Asp Thr Tyr Val Arg Asn Cys Gly Lys
            340                 345                 350

Tyr Asn Tyr Tyr Leu Gln Val Gly Glu Ile Ala Thr Ser Asp Phe Ile
        355                 360                 365

Ala Arg Asn Arg Gln Asn Glu Ala Phe Leu Arg Asn Ile Ile Gly Val
    370                 375                 380

Ser Ser Val Ala Tyr Phe Ser Leu Arg Asn Ile Leu Glu Thr Glu Asn
385                 390                 395                 400

Glu Asn Asp Ile Thr Gly Arg Met Arg Gly Lys Thr Val Lys Asn Asn
                405                 410                 415

Lys Gly Glu Glu Lys Tyr Val Ser Gly Glu Val Asp Lys Ile Tyr Asn
            420                 425                 430

Glu Asn Lys Gln Asn Glu Val Lys Glu Asn Leu Lys Met Phe Tyr Ser
        435                 440                 445
```

```
Tyr Asp Phe Asn Met Asp Asn Lys Asn Glu Ile Glu Asp Phe Phe Ala
    450                 455                 460

Asn Ile Asp Glu Ala Ile Ser Ser Ile Arg His Gly Ile Val His Phe
465                 470                 475                 480

Asn Leu Glu Leu Glu Gly Lys Asp Ile Phe Ala Phe Lys Asn Ile Ala
                485                 490                 495

Pro Ser Glu Ile Ser Lys Lys Met Phe Gln Asn Glu Ile Asn Glu Lys
            500                 505                 510

Lys Leu Lys Leu Lys Ile Phe Lys Gln Leu Asn Ser Ala Asn Val Phe
        515                 520                 525

Asn Tyr Tyr Glu Lys Asp Val Ile Ile Lys Tyr Leu Lys Asn Thr Lys
    530                 535                 540

Phe Asn Phe Val Asn Lys Asn Ile Pro Phe Val Pro Ser Phe Thr Lys
545                 550                 555                 560

Leu Tyr Asn Lys Ile Glu Asp Leu Arg Asn Thr Leu Lys Phe Phe Trp
                565                 570                 575

Ser Val Pro Lys Asp Lys Glu Glu Lys Asp Ala Gln Ile Tyr Leu Leu
            580                 585                 590

Lys Asn Ile Tyr Tyr Gly Glu Phe Leu Asn Lys Phe Val Lys Asn Ser
        595                 600                 605

Lys Val Phe Phe Lys Ile Thr Asn Glu Val Ile Lys Ile Asn Lys Gln
    610                 615                 620

Arg Asn Gln Lys Thr Gly His Tyr Lys Tyr Gln Lys Phe Glu Asn Ile
625                 630                 635                 640

Glu Lys Thr Val Pro Val Glu Tyr Leu Ala Ile Ile Gln Ser Arg Glu
                645                 650                 655

Met Ile Asn Asn Gln Asp Lys Glu Glu Lys Asn Thr Tyr Ile Asp Phe
            660                 665                 670

Ile Gln Gln Ile Phe Leu Lys Gly Phe Ile Asp Tyr Leu Asn Lys Asn
        675                 680                 685

Asn Leu Lys Tyr Ile Glu Ser Asn Asn Asn Asn Asp Asn Asn Asp Ile
    690                 695                 700

Phe Ser Lys Ile Lys Ile Lys Lys Asp Asn Lys Glu Lys Tyr Asp Lys
705                 710                 715                 720

Ile Leu Lys Asn Tyr Glu Lys His Asn Arg Asn Lys Glu Ile Pro His
                725                 730                 735

Glu Ile Asn Glu Phe Val Arg Glu Ile Lys Leu Gly Lys Ile Leu Lys
            740                 745                 750

Tyr Thr Glu Asn Leu Asn Met Phe Tyr Leu Ile Leu Lys Leu Leu Asn
        755                 760                 765

His Lys Glu Leu Thr Asn Leu Lys Gly Ser Leu Glu Lys Tyr Gln Ser
    770                 775                 780

Ala Asn Lys Glu Glu Thr Phe Ser Asp Glu Leu Glu Leu Ile Asn Leu
785                 790                 795                 800

Leu Asn Leu Asp Asn Asn Arg Val Thr Glu Asp Phe Glu Leu Glu Ala
                805                 810                 815

Asn Glu Ile Gly Lys Phe Leu Asp Phe Asn Glu Asn Lys Ile Lys Asp
            820                 825                 830

Arg Lys Glu Leu Lys Lys Phe Asp Thr Asn Lys Ile Tyr Phe Asp Gly
        835                 840                 845

Glu Asn Ile Ile Lys His Arg Ala Phe Tyr Asn Ile Lys Lys Tyr Gly
    850                 855                 860

Met Leu Asn Leu Leu Glu Lys Ile Ala Asp Lys Ala Lys Tyr Lys Ile
```

```
865                 870                 875                 880

Ser Leu Lys Glu Leu Lys Glu Tyr Ser Asn Lys Lys Asn Glu Ile Glu
                885                 890                 895

Lys Asn Tyr Thr Met Gln Gln Asn Leu His Arg Lys Tyr Ala Arg Pro
            900                 905                 910

Lys Lys Asp Glu Lys Phe Asn Asp Glu Asp Tyr Lys Glu Tyr Glu Lys
        915                 920                 925

Ala Ile Gly Asn Ile Gln Lys Tyr Thr His Leu Lys Asn Lys Val Glu
    930                 935                 940

Phe Asn Glu Leu Asn Leu Leu Gln Gly Leu Leu Leu Lys Ile Leu His
945                 950                 955                 960

Arg Leu Val Gly Tyr Thr Ser Ile Trp Glu Arg Asp Leu Arg Phe Arg
                965                 970                 975

Leu Lys Gly Glu Phe Pro Glu Asn His Tyr Ile Glu Glu Ile Phe Asn
            980                 985                 990

Phe Asp Asn Ser Lys Asn Val Lys  Tyr Lys Ser Gly Gln  Ile Val Glu
        995                 1000                1005

Lys Tyr  Ile Asn Phe Tyr Lys  Glu Leu Tyr Lys Asp  Asn Val Glu
    1010                1015                1020

Lys Arg  Ser Ile Tyr Ser Asp  Lys Lys Val Lys Lys  Leu Lys Gln
    1025                1030                1035

Glu Lys  Lys Asp Leu Tyr Ile  Arg Asn Tyr Ile Ala  His Phe Asn
    1040                1045                1050

Tyr Ile  Pro His Ala Glu Ile  Ser Leu Leu Glu Val  Leu Glu Asn
    1055                1060                1065

Leu Arg  Lys Leu Leu Ser Tyr  Asp Arg Lys Leu Lys  Asn Ala Ile
    1070                1075                1080

Met Lys  Ser Ile Val Asp Ile  Leu Lys Glu Tyr Gly  Phe Val Ala
    1085                1090                1095

Thr Phe  Lys Ile Gly Ala Asp  Lys Lys Ile Glu Ile  Gln Thr Leu
    1100                1105                1110

Glu Ser  Glu Lys Ile Val His  Leu Lys Asn Leu Lys  Lys Lys Lys
    1115                1120                1125

Leu Met  Thr Asp Arg Asn Ser  Glu Glu Leu Cys Glu  Leu Val Lys
    1130                1135                1140

Val Met  Phe Glu Tyr Lys Ala  Leu Glu
    1145                1150


<210> SEQ ID NO 31
<211> LENGTH: 970
<212> TYPE: PRT
<213> ORGANISM: Artificial Sequence
<220> FEATURE:
<223> OTHER INFORMATION: Chemically synthesized

<400> SEQUENCE: 31

Met Leu Ala Leu Leu His Gln Glu Val Pro Ser Gln Lys Leu His Asn
1               5                   10                  15

Leu Lys Ser Leu Asn Thr Glu Ser Leu Thr Lys Leu Phe Lys Pro Lys
            20                  25                  30

Phe Gln Asn Met Ile Ser Tyr Pro Pro Ser Lys Gly Ala Glu His Val
        35                  40                  45

Gln Phe Cys Leu Thr Asp Ile Ala Val Pro Ala Ile Arg Asp Leu Asp
    50                  55                  60

Glu Ile Lys Pro Asp Trp Gly Ile Phe Phe Glu Lys Leu Lys Pro Tyr
```

```
65                  70                  75                  80

Thr Asp Trp Ala Glu Ser Tyr Ile His Tyr Lys Gln Thr Thr Ile Gln
                85                  90                  95

Lys Ser Ile Glu Gln Asn Lys Ile Gln Ser Pro Asp Ser Pro Arg Lys
            100                 105                 110

Leu Val Leu Gln Lys Tyr Val Thr Ala Phe Leu Asn Gly Glu Pro Leu
        115                 120                 125

Gly Leu Asp Leu Val Ala Lys Lys Tyr Lys Leu Ala Asp Leu Ala Glu
    130                 135                 140

Ser Phe Lys Val Val Asp Leu Asn Glu Asp Lys Ser Ala Asn Tyr Lys
145                 150                 155                 160

Ile Lys Ala Cys Leu Gln Gln His Gln Arg Asn Ile Leu Asp Glu Leu
                165                 170                 175

Lys Glu Asp Pro Glu Leu Asn Gln Tyr Gly Ile Glu Val Lys Lys Tyr
            180                 185                 190

Ile Gln Arg Tyr Phe Pro Ile Lys Arg Ala Pro Asn Arg Ser Lys His
        195                 200                 205

Ala Arg Ala Asp Phe Leu Lys Lys Glu Leu Ile Glu Ser Thr Val Glu
    210                 215                 220

Gln Gln Phe Lys Asn Ala Val Tyr His Tyr Val Leu Glu Gln Gly Lys
225                 230                 235                 240

Met Glu Ala Tyr Glu Leu Thr Asp Pro Lys Thr Lys Asp Leu Gln Asp
                245                 250                 255

Ile Arg Ser Gly Glu Ala Phe Ser Phe Lys Phe Ile Asn Ala Cys Ala
            260                 265                 270

Phe Ala Ser Asn Asn Leu Lys Met Ile Leu Asn Pro Glu Cys Glu Lys
        275                 280                 285

Asp Ile Leu Gly Lys Gly Asp Phe Lys Lys Asn Leu Pro Asn Ser Thr
    290                 295                 300

Thr Gln Ser Asp Val Val Lys Lys Met Ile Pro Phe Phe Ser Asp Glu
305                 310                 315                 320

Ile Gln Asn Val Asn Phe Asp Glu Ala Ile Trp Ala Ile Arg Gly Ser
                325                 330                 335

Ile Gln Gln Ile Arg Asn Glu Val Tyr His Cys Lys Lys His Ser Trp
            340                 345                 350

Lys Ser Ile Leu Lys Ile Lys Gly Phe Glu Phe Glu Pro Asn Asn Met
        355                 360                 365

Lys Tyr Thr Asp Ser Asp Met Gln Lys Leu Met Asp Lys Asp Ile Ala
    370                 375                 380

Lys Ile Pro Asp Phe Ile Glu Glu Lys Leu Lys Ser Ser Gly Ile Ile
385                 390                 395                 400

Arg Phe Tyr Ser His Asp Lys Leu Gln Ser Ile Trp Glu Met Lys Gln
                405                 410                 415

Gly Phe Ser Leu Leu Thr Thr Asn Ala Pro Phe Val Pro Ser Phe Lys
            420                 425                 430

Arg Val Tyr Ala Lys Gly His Asp Tyr Gln Thr Ser Lys Asn Arg Tyr
        435                 440                 445

Tyr Asp Leu Gly Leu Thr Thr Phe Asp Ile Leu Glu Tyr Gly Glu Glu
    450                 455                 460

Asp Phe Arg Ala Arg Tyr Phe Leu Thr Lys Leu Val Tyr Tyr Gln Gln
465                 470                 475                 480

Phe Met Pro Trp Phe Thr Ala Asp Asn Asn Ala Phe Arg Asp Ala Ala
                485                 490                 495
```

```
Asn Phe Val Leu Arg Leu Asn Lys Asn Arg Gln Gln Asp Ala Lys Ala
            500                 505                 510

Phe Ile Asn Ile Arg Glu Val Glu Glu Gly Glu Met Pro Arg Asp Tyr
        515                 520                 525

Met Gly Tyr Val Gln Gly Gln Ile Ala Ile His Glu Asp Ser Thr Glu
    530                 535                 540

Asp Thr Pro Asn His Phe Glu Lys Phe Ile Ser Gln Val Phe Ile Lys
545                 550                 555                 560

Gly Phe Asp Ser His Met Arg Ser Ala Asp Leu Lys Phe Ile Lys Asn
                565                 570                 575

Pro Arg Asn Gln Gly Leu Glu Gln Ser Glu Ile Glu Glu Met Ser Phe
            580                 585                 590

Asp Ile Lys Val Glu Pro Ser Phe Leu Lys Asn Lys Asp Asp Tyr Ile
        595                 600                 605

Ala Phe Trp Thr Phe Cys Lys Met Leu Asp Ala Arg His Leu Ser Glu
    610                 615                 620

Leu Arg Asn Glu Met Ile Lys Tyr Asp Gly His Leu Thr Gly Glu Gln
625                 630                 635                 640

Glu Ile Ile Gly Leu Ala Leu Leu Gly Val Asp Ser Arg Glu Asn Asp
                645                 650                 655

Trp Lys Gln Phe Phe Ser Ser Glu Arg Glu Tyr Glu Lys Ile Met Lys
            660                 665                 670

Gly Tyr Val Gly Glu Glu Leu Tyr Gln Arg Glu Pro Tyr Arg Gln Ser
        675                 680                 685

Asp Gly Lys Thr Pro Ile Leu Phe Arg Gly Val Glu Gln Ala Arg Lys
    690                 695                 700

Tyr Gly Thr Glu Thr Val Ile Gln Arg Leu Phe Asp Ala Ser Pro Glu
705                 710                 715                 720

Phe Lys Val Ser Lys Cys Asn Ile Thr Glu Trp Glu Arg Gln Lys Glu
                725                 730                 735

Thr Ile Glu Glu Thr Ile Glu Arg Arg Lys Glu Leu His Asn Glu Trp
            740                 745                 750

Glu Lys Asn Pro Lys Lys Pro Gln Asn Asn Ala Phe Phe Lys Glu Tyr
        755                 760                 765

Lys Glu Cys Cys Asp Ala Ile Asp Ala Tyr Asn Trp His Lys Asn Lys
    770                 775                 780

Thr Thr Leu Val Tyr Val Asn Glu Leu His His Leu Leu Ile Glu Ile
785                 790                 795                 800

Leu Gly Arg Tyr Val Gly Tyr Val Ala Ile Ala Asp Arg Asp Phe Gln
                805                 810                 815

Cys Met Ala Asn Gln Tyr Phe Lys His Ser Gly Ile Thr Glu Arg Val
            820                 825                 830

Glu Tyr Trp Gly Asp Asn Arg Leu Lys Ser Ile Lys Lys Leu Asp Thr
        835                 840                 845

Phe Leu Lys Lys Glu Gly Leu Phe Val Ser Glu Lys Asn Ala Arg Asn
    850                 855                 860

His Ile Ala His Leu Asn Tyr Leu Ser Leu Lys Ser Glu Cys Thr Leu
865                 870                 875                 880

Leu Tyr Leu Ser Glu Arg Leu Arg Glu Ile Phe Lys Tyr Asp Arg Lys
                885                 890                 895

Leu Lys Asn Ala Val Ser Lys Ser Leu Ile Asp Ile Leu Asp Arg His
            900                 905                 910
```

Gly Met Ser Val Val Phe Ala Asn Leu Lys Glu Asn Lys His Arg Leu
915 920 925

Val Ile Lys Ser Leu Glu Pro Lys Lys Leu Arg His Leu Gly Glu Lys
930 935 940

Lys Ile Asp Asn Gly Tyr Ile Glu Thr Asn Gln Val Ser Glu Glu Tyr
945 950 955 960

Cys Gly Ile Val Lys Arg Leu Leu Glu Ile
965 970

<210> SEQ ID NO 32
<211> LENGTH: 1124
<212> TYPE: PRT
<213> ORGANISM: Artificial Sequence
<220> FEATURE:
<223> OTHER INFORMATION: Chemically synthesized

<400> SEQUENCE: 32

Met Glu Asp Asp Lys Lys Thr Thr Gly Ser Ile Ser Tyr Glu Leu Lys
1 5 10 15

Asp Lys His Phe Trp Ala Ala Phe Leu Asn Leu Ala Arg His Asn Val
20 25 30

Tyr Ile Thr Ile Asn His Ile Asn Lys Leu Leu Glu Ile Arg Glu Ile
35 40 45

Asp Asn Asp Glu Lys Val Leu Asp Ile Lys Thr Leu Trp Gln Lys Gly
50 55 60

Asn Lys Asp Leu Asn Gln Lys Ala Arg Leu Arg Glu Leu Met Thr Lys
65 70 75 80

His Phe Pro Phe Leu Glu Thr Ala Ile Tyr Thr Lys Asn Lys Glu Asp
85 90 95

Lys Lys Glu Val Lys Gln Glu Lys Gln Ala Glu Ala Gln Ser Leu Glu
100 105 110

Ser Leu Lys Asp Cys Leu Phe Leu Phe Leu Asp Lys Leu Gln Glu Ala
115 120 125

Arg Asn Tyr Tyr Ser His Tyr Lys Tyr Ser Glu Phe Ser Lys Glu Pro
130 135 140

Glu Phe Glu Glu Gly Leu Leu Glu Lys Met Tyr Asn Ile Phe Gly Asn
145 150 155 160

Asn Ile Gln Leu Val Ile Asn Asp Tyr Gln His Asn Lys Asp Ile Asn
165 170 175

Pro Asp Glu Asp Phe Lys His Leu Asp Arg Lys Gly Gln Phe Lys Tyr
180 185 190

Ser Phe Ala Asp Asn Glu Gly Asn Ile Thr Glu Ser Gly Leu Leu Phe
195 200 205

Phe Val Ser Leu Phe Leu Glu Lys Lys Asp Ala Ile Trp Met Gln Gln
210 215 220

Lys Leu Asn Gly Phe Lys Asp Asn Leu Glu Asn Lys Lys Lys Met Thr
225 230 235 240

His Glu Val Phe Cys Arg Ser Arg Ile Leu Met Pro Lys Leu Arg Leu
245 250 255

Glu Ser Thr Gln Thr Gln Asp Trp Ile Leu Leu Asp Met Leu Asn Glu
260 265 270

Leu Ile Arg Cys Pro Lys Ser Leu Tyr Glu Arg Leu Gln Gly Asp Asp
275 280 285

Arg Glu Lys Phe Lys Val Pro Phe Asp Pro Ala Asp Glu Asp Tyr Asn
290 295 300

```
Ala Glu Gln Glu Pro Phe Lys Asn Thr Leu Ile Arg His Gln Asp Arg
305                 310                 315                 320

Phe Pro Tyr Phe Val Leu Arg Tyr Phe Asp Tyr Asn Glu Ile Phe Lys
                325                 330                 335

Asn Leu Arg Phe Gln Ile Asp Leu Gly Thr Tyr His Phe Ser Ile Tyr
            340                 345                 350

Lys Lys Leu Ile Gly Gly Gln Lys Glu Asp Arg His Leu Thr His Lys
        355                 360                 365

Leu Tyr Gly Phe Glu Arg Ile Gln Glu Phe Ala Lys Gln Asn Arg Pro
    370                 375                 380

Asp Glu Trp Lys Ala Ile Val Lys Asp Leu Asp Thr Tyr Glu Thr Ser
385                 390                 395                 400

Asn Lys Arg Tyr Ile Ser Glu Thr Thr Pro His Tyr His Leu Glu Asn
                405                 410                 415

Gln Lys Ile Gly Ile Arg Phe Arg Asn Gly Asn Lys Glu Ile Trp Pro
            420                 425                 430

Ser Leu Lys Thr Asn Asp Glu Asn Asn Glu Lys Ser Lys Tyr Lys Leu
        435                 440                 445

Asp Lys Gln Tyr Gln Ala Glu Ala Phe Leu Ser Val His Glu Leu Leu
    450                 455                 460

Pro Met Met Phe Tyr Tyr Leu Leu Leu Lys Lys Glu Lys Pro Asn Asn
465                 470                 475                 480

Asp Glu Ile Asn Ala Ser Ile Val Glu Gly Phe Ile Lys Arg Glu Ile
                485                 490                 495

Arg Asn Ile Phe Lys Leu Tyr Asp Ala Phe Ala Asn Gly Glu Ile Asn
            500                 505                 510

Asn Ile Asp Asp Leu Glu Lys Tyr Cys Ala Asp Lys Gly Ile Pro Lys
        515                 520                 525

Arg His Leu Pro Lys Gln Met Val Ala Ile Leu Tyr Asp Glu His Lys
    530                 535                 540

Asp Met Val Lys Glu Ala Lys Arg Lys Gln Lys Glu Met Val Lys Asp
545                 550                 555                 560

Thr Lys Lys Leu Leu Ala Thr Leu Glu Lys Gln Thr Gln Lys Glu Lys
                565                 570                 575

Glu Asp Asp Gly Arg Asn Val Lys Leu Leu Lys Ser Gly Glu Ile Ala
            580                 585                 590

Arg Trp Leu Val Asn Asp Met Met Arg Phe Gln Pro Val Gln Lys Asp
        595                 600                 605

Asn Glu Gly Lys Pro Leu Asn Asn Ser Lys Ala Asn Ser Thr Glu Tyr
    610                 615                 620

Gln Met Leu Gln Arg Ser Leu Ala Leu Tyr Asn Asn Glu Glu Lys Pro
625                 630                 635                 640

Thr Arg Tyr Phe Arg Gln Val Asn Leu Ile Glu Ser Asn Asn Pro His
                645                 650                 655

Pro Phe Leu Lys Trp Thr Lys Trp Glu Glu Cys Asn Asn Ile Leu Thr
            660                 665                 670

Phe Tyr Tyr Ser Tyr Leu Thr Lys Lys Ile Glu Phe Leu Asn Lys Leu
        675                 680                 685

Lys Pro Glu Asp Trp Lys Lys Asn Gln Tyr Phe Leu Lys Leu Lys Glu
    690                 695                 700

Pro Lys Thr Asn Arg Glu Thr Leu Val Gln Gly Trp Lys Asn Gly Phe
705                 710                 715                 720

Asn Leu Pro Arg Gly Ile Phe Thr Glu Pro Ile Arg Glu Trp Phe Lys
```

```
            725                 730                 735

Arg His Gln Asn Asn Ser Lys Glu Tyr Glu Lys Val Glu Ala Leu Asp
        740                 745                 750

Arg Val Gly Leu Val Thr Lys Val Ile Pro Leu Phe Phe Lys Glu Glu
    755                 760                 765

Tyr Phe Lys Asp Lys Glu Glu Asn Phe Lys Glu Asp Thr Gln Lys Glu
    770                 775                 780

Ile Asn Asp Cys Val Gln Pro Phe Tyr Asn Phe Pro Tyr Asn Val Gly
785                 790                 795                 800

Asn Ile His Lys Pro Lys Glu Lys Asp Phe Leu His Arg Glu Glu Arg
            805                 810                 815

Ile Glu Leu Trp Asp Lys Lys Lys Asp Lys Phe Lys Gly Tyr Lys Glu
        820                 825                 830

Lys Ile Lys Ser Lys Lys Leu Thr Glu Lys Asp Lys Glu Glu Phe Arg
    835                 840                 845

Ser Tyr Leu Glu Phe Gln Ser Trp Asn Lys Phe Glu Arg Glu Leu Arg
    850                 855                 860

Leu Val Arg Asn Gln Asp Ile Val Thr Trp Leu Leu Cys Lys Glu Leu
865                 870                 875                 880

Ile Asp Lys Leu Lys Ile Asp Glu Leu Asn Ile Glu Glu Leu Lys Lys
            885                 890                 895

Leu Arg Leu Asn Asn Ile Asp Thr Asp Thr Ala Lys Lys Glu Lys Asn
        900                 905                 910

Asn Ile Leu Asn Arg Val Met Pro Met Glu Leu Pro Val Thr Val Tyr
    915                 920                 925

Glu Ile Asp Asp Ser His Lys Ile Val Lys Asp Lys Pro Leu His Thr
    930                 935                 940

Ile Tyr Ile Lys Glu Ala Glu Thr Lys Leu Leu Lys Gln Gly Asn Phe
945                 950                 955                 960

Lys Ala Leu Val Lys Asp Arg Arg Leu Asn Gly Leu Phe Ser Phe Val
            965                 970                 975

Lys Thr Asn Ser Glu Ala Glu Ser Lys Arg Asn Pro Ile Ser Lys Leu
        980                 985                 990

Arg Val Glu Tyr Glu Leu Gly Glu  Tyr Gln Glu Ala Arg  Ile Glu Ile
    995                 1000                 1005

Ile Gln  Asp Met Leu Ala Leu  Glu Glu Lys Leu Ile  Asn Lys Tyr
    1010                 1015                 1020

Lys Asp  Leu Pro Thr Asn Lys  Phe Ser Glu Met Leu  Asn Ser Trp
    1025                 1030                 1035

Leu Glu  Gly Lys Asp Glu Ala  Asp Lys Ala Arg Phe  Gln Asn Asp
    1040                 1045                 1050

Val Asp  Phe Leu Ile Ala Val  Arg Asn Ala Phe Ser  His Asn Gln
    1055                 1060                 1065

Tyr Pro  Met His Asn Lys Ile  Glu Phe Ala Asn Ile  Lys Pro Phe
    1070                 1075                 1080

Ser Leu  Tyr Thr Ala Asn Asn  Ser Glu Glu Lys Gly  Leu Gly Ile
    1085                 1090                 1095

Ala Asn  Gln Leu Lys Asp Lys  Thr Lys Glu Thr Thr  Asp Lys Ile
    1100                 1105                 1110

Lys Lys  Ile Glu Lys Pro Ile  Glu Thr Lys Glu
    1115                 1120
```

<210> SEQ ID NO 33

<211> LENGTH: 1127
<212> TYPE: PRT
<213> ORGANISM: Artificial Sequence
<220> FEATURE:
<223> OTHER INFORMATION: Chemically synthesized

<400> SEQUENCE: 33

Met Gln Lys Gln Asp Lys Leu Phe Val Asp Arg Lys Lys Asn Ala Ile
1 5 10 15

Phe Ala Phe Pro Lys Tyr Ile Thr Ile Met Glu Asn Lys Glu Lys Pro
20 25 30

Glu Pro Ile Tyr Tyr Glu Leu Thr Asp Lys His Phe Trp Ala Ala Phe
35 40 45

Leu Asn Leu Ala Arg His Asn Val Tyr Thr Thr Ile Asn His Ile Asn
50 55 60

Arg Arg Leu Glu Ile Ala Glu Leu Lys Asp Asp Gly Tyr Met Met Gly
65 70 75 80

Ile Lys Gly Ser Trp Asn Glu Gln Ala Lys Lys Leu Asp Lys Lys Val
85 90 95

Arg Leu Arg Asp Leu Ile Met Lys His Phe Pro Phe Leu Glu Ala Ala
100 105 110

Ala Tyr Glu Met Thr Asn Ser Lys Ser Pro Asn Asn Lys Glu Gln Arg
115 120 125

Glu Lys Glu Gln Ser Glu Ala Leu Ser Leu Asn Asn Leu Lys Asn Val
130 135 140

Leu Phe Ile Phe Leu Glu Lys Leu Gln Val Leu Arg Asn Tyr Tyr Ser
145 150 155 160

His Tyr Lys Tyr Ser Glu Glu Ser Pro Lys Pro Ile Phe Glu Thr Ser
165 170 175

Leu Leu Lys Asn Met Tyr Lys Val Phe Asp Ala Asn Val Arg Leu Val
180 185 190

Lys Arg Asp Tyr Met His His Glu Asn Ile Asp Met Gln Arg Asp Phe
195 200 205

Thr His Leu Asn Arg Lys Lys Gln Val Gly Arg Thr Lys Asn Ile Ile
210 215 220

Asp Ser Pro Asn Phe His Tyr His Phe Ala Asp Lys Glu Gly Asn Met
225 230 235 240

Thr Ile Ala Gly Leu Leu Phe Phe Val Ser Leu Phe Leu Asp Lys Lys
245 250 255

Asp Ala Ile Trp Met Gln Lys Lys Leu Lys Gly Phe Lys Asp Gly Arg
260 265 270

Asn Leu Arg Glu Gln Met Thr Asn Glu Val Phe Cys Arg Ser Arg Ile
275 280 285

Ser Leu Pro Lys Leu Lys Leu Glu Asn Val Gln Thr Lys Asp Trp Met
290 295 300

Gln Leu Asp Met Leu Asn Glu Leu Val Arg Cys Pro Lys Ser Leu Tyr
305 310 315 320

Glu Arg Leu Arg Glu Lys Asp Arg Glu Ser Phe Lys Val Pro Phe Asp
325 330 335

Ile Phe Ser Asp Asp Tyr Asn Ala Glu Glu Glu Pro Phe Lys Asn Thr
340 345 350

Leu Val Arg His Gln Asp Arg Phe Pro Tyr Phe Val Leu Arg Tyr Phe
355 360 365

Asp Leu Asn Glu Ile Phe Glu Gln Leu Arg Phe Gln Ile Asp Leu Gly
370 375 380

```
Thr Tyr His Phe Ser Ile Tyr Asn Lys Arg Ile Gly Asp Glu Asp Glu
385                 390                 395                 400

Val Arg His Leu Thr His His Leu Tyr Gly Phe Ala Arg Ile Gln Asp
                405                 410                 415

Phe Ala Pro Gln Asn Gln Pro Glu Glu Trp Arg Lys Leu Val Lys Asp
            420                 425                 430

Leu Asp His Phe Glu Thr Ser Gln Glu Pro Tyr Ile Ser Lys Thr Ala
        435                 440                 445

Pro His Tyr His Leu Glu Asn Glu Lys Ile Gly Ile Lys Phe Cys Ser
    450                 455                 460

Ala His Asn Asn Leu Phe Pro Ser Leu Gln Thr Asp Lys Thr Cys Asn
465                 470                 475                 480

Gly Arg Ser Lys Phe Asn Leu Gly Thr Gln Phe Thr Ala Glu Ala Phe
                485                 490                 495

Leu Ser Val His Glu Leu Leu Pro Met Met Phe Tyr Tyr Leu Leu Leu
            500                 505                 510

Thr Lys Asp Tyr Ser Arg Lys Glu Ser Ala Asp Lys Val Glu Gly Ile
        515                 520                 525

Ile Arg Lys Glu Ile Ser Asn Ile Tyr Ala Ile Tyr Asp Ala Phe Ala
    530                 535                 540

Asn Asn Glu Ile Asn Ser Ile Ala Asp Leu Thr Arg Arg Leu Gln Asn
545                 550                 555                 560

Thr Asn Ile Leu Gln Gly His Leu Pro Lys Gln Met Ile Ser Ile Leu
                565                 570                 575

Lys Gly Arg Gln Lys Asp Met Gly Lys Glu Ala Glu Arg Lys Ile Gly
            580                 585                 590

Glu Met Ile Asp Asp Thr Gln Arg Arg Leu Asp Leu Leu Cys Lys Gln
        595                 600                 605

Thr Asn Gln Lys Ile Arg Ile Gly Lys Arg Asn Ala Gly Leu Leu Lys
    610                 615                 620

Ser Gly Lys Ile Ala Asp Trp Leu Val Asn Asp Met Met Arg Phe Gln
625                 630                 635                 640

Pro Val Gln Lys Asp Gln Asn Asn Ile Pro Ile Asn Asn Ser Lys Ala
                645                 650                 655

Asn Ser Thr Glu Tyr Arg Met Leu Gln Arg Ala Leu Ala Leu Phe Gly
            660                 665                 670

Ser Glu Asn Phe Arg Leu Lys Ala Tyr Phe Asn Gln Met Asn Leu Val
        675                 680                 685

Gly Asn Asp Asn Pro His Pro Phe Leu Ala Glu Thr Gln Trp Glu His
    690                 695                 700

Gln Thr Asn Ile Leu Ser Phe Tyr Arg Asn Tyr Leu Glu Ala Arg Lys
705                 710                 715                 720

Lys Tyr Leu Lys Gly Leu Lys Pro Gln Asn Trp Lys Gln Tyr Gln His
                725                 730                 735

Phe Leu Ile Leu Lys Val Gln Lys Thr Asn Arg Asn Thr Leu Val Thr
            740                 745                 750

Gly Trp Lys Asn Ser Phe Asn Leu Pro Arg Gly Ile Phe Thr Gln Pro
        755                 760                 765

Ile Arg Glu Trp Phe Glu Lys His Asn Asn Ser Lys Arg Ile Tyr Asp
    770                 775                 780

Gln Ile Leu Ser Phe Asp Arg Val Gly Phe Val Ala Lys Ala Ile Pro
785                 790                 795                 800
```

```
Leu Tyr Phe Ala Glu Glu Tyr Lys Asp Asn Val Gln Pro Phe Tyr Asp
                805                 810                 815

Tyr Pro Phe Asn Ile Gly Asn Arg Leu Lys Pro Lys Lys Arg Gln Phe
            820                 825                 830

Leu Asp Lys Lys Glu Arg Val Glu Leu Trp Gln Lys Asn Lys Glu Leu
        835                 840                 845

Phe Lys Asn Tyr Pro Ser Glu Lys Lys Lys Thr Asp Leu Ala Tyr Leu
    850                 855                 860

Asp Phe Leu Ser Trp Lys Lys Phe Glu Arg Glu Leu Arg Leu Ile Lys
865                 870                 875                 880

Asn Gln Asp Ile Val Thr Trp Leu Met Phe Lys Glu Leu Phe Asn Met
                885                 890                 895

Ala Thr Val Glu Gly Leu Lys Ile Gly Glu Ile His Leu Arg Asp Ile
            900                 905                 910

Asp Thr Asn Thr Ala Asn Glu Glu Ser Asn Asn Ile Leu Asn Arg Ile
        915                 920                 925

Met Pro Met Lys Leu Pro Val Lys Thr Tyr Glu Thr Asp Asn Lys Gly
    930                 935                 940

Asn Ile Leu Lys Glu Arg Pro Leu Ala Thr Phe Tyr Ile Glu Glu Thr
945                 950                 955                 960

Glu Thr Lys Val Leu Lys Gln Gly Asn Phe Lys Ala Leu Val Lys Asp
                965                 970                 975

Arg Arg Leu Asn Gly Leu Phe Ser Phe Ala Glu Thr Thr Asp Leu Asn
            980                 985                 990

Leu Glu Glu His Pro Ile Ser Lys  Leu Ser Val Asp Leu  Glu Leu Ile
        995                 1000                1005

Lys Tyr  Gln Thr Thr Arg Ile  Ser Ile Phe Glu Met  Thr Leu Gly
    1010                1015                1020

Leu Glu  Lys Lys Leu Ile Asp  Lys Tyr Ser Thr Leu  Pro Thr Asp
    1025                1030                1035

Ser Phe  Arg Asn Met Leu Glu  Arg Trp Leu Gln Cys  Lys Ala Asn
    1040                1045                1050

Arg Pro  Glu Leu Lys Asn Tyr  Val Asn Ser Leu Ile  Ala Val Arg
    1055                1060                1065

Asn Ala  Phe Ser His Asn Gln  Tyr Pro Met Tyr Asp  Ala Thr Leu
    1070                1075                1080

Phe Ala  Glu Val Lys Lys Phe  Thr Leu Phe Pro Ser  Val Asp Thr
    1085                1090                1095

Lys Lys  Ile Glu Leu Asn Ile  Ala Pro Gln Leu Leu  Glu Ile Val
    1100                1105                1110

Gly Lys  Ala Ile Lys Glu Ile  Glu Lys Ser Glu Asn  Lys Asn
    1115                1120                1125
```

<210> SEQ ID NO 34
<211> LENGTH: 1119
<212> TYPE: PRT
<213> ORGANISM: Artificial Sequence
<220> FEATURE:
<223> OTHER INFORMATION: Chemically synthesized

<400> SEQUENCE: 34

```
Met Thr Glu Gln Asn Glu Lys Pro Tyr Asn Gly Thr Tyr Tyr Thr Leu
1               5                   10                  15

Glu Asp Lys His Phe Trp Ala Ala Phe Leu Asn Leu Ala Arg His Asn
            20                  25                  30
```

```
Ala Tyr Ile Thr Leu Ala His Ile Asp Arg Gln Leu Ala Tyr Ser Lys
        35                  40                  45

Ala Asp Ile Thr Asn Asp Glu Asp Ile Leu Phe Phe Lys Gly Gln Trp
    50                  55                  60

Lys Asn Leu Asp Asn Asp Leu Glu Arg Lys Ala Arg Leu Arg Ser Leu
65                  70                  75                  80

Ile Leu Lys His Phe Ser Phe Leu Glu Gly Ala Ala Tyr Gly Lys Lys
                85                  90                  95

Leu Phe Glu Ser Gln Ser Ser Gly Asn Lys Ser Ser Lys Lys Lys Glu
            100                 105                 110

Leu Ser Lys Lys Glu Lys Glu Glu Leu Gln Ala Asn Ala Leu Ser Leu
        115                 120                 125

Asp Asn Leu Lys Ser Ile Leu Phe Asp Phe Leu Gln Lys Leu Lys Asp
    130                 135                 140

Phe Arg Asn Tyr Tyr Ser His Tyr Arg His Pro Glu Ser Ser Glu Leu
145                 150                 155                 160

Pro Leu Phe Asp Gly Asn Met Leu Gln Arg Leu Tyr Asn Val Phe Asp
                165                 170                 175

Val Ser Val Gln Arg Val Lys Arg Asp His Glu His Asn Asp Lys Val
            180                 185                 190

Asp Pro His Arg His Phe Asn His Leu Val Arg Lys Gly Lys Lys Asp
        195                 200                 205

Lys Tyr Gly Asn Asn Asp Asn Pro Phe Phe Lys His His Phe Val Asp
    210                 215                 220

Arg Glu Gly Thr Val Thr Glu Ala Gly Leu Leu Phe Phe Val Ser Leu
225                 230                 235                 240

Phe Leu Glu Lys Arg Asp Ala Ile Trp Met Gln Lys Lys Ile Arg Gly
                245                 250                 255

Phe Lys Gly Gly Thr Glu Ala Tyr Gln Gln Met Thr Asn Glu Val Phe
            260                 265                 270

Cys Arg Ser Arg Ile Ser Leu Pro Lys Leu Lys Leu Glu Ser Leu Arg
        275                 280                 285

Thr Asp Asp Trp Met Leu Leu Asp Met Leu Asn Glu Leu Val Arg Cys
    290                 295                 300

Pro Lys Ser Leu Tyr Asp Arg Leu Arg Glu Glu Asp Arg Ala Arg Phe
305                 310                 315                 320

Arg Val Pro Val Asp Ile Leu Ser Asp Glu Asp Asp Thr Asp Gly Thr
                325                 330                 335

Glu Glu Asp Pro Phe Lys Asn Thr Leu Val Arg His Gln Asp Arg Phe
            340                 345                 350

Pro Tyr Phe Ala Leu Arg Tyr Phe Asp Leu Lys Lys Val Phe Thr Ser
        355                 360                 365

Leu Arg Phe His Ile Asp Leu Gly Thr Tyr His Phe Ala Ile Tyr Lys
    370                 375                 380

Lys Asn Ile Gly Glu Gln Pro Glu Asp Arg His Leu Thr Arg Asn Leu
385                 390                 395                 400

Tyr Gly Phe Gly Arg Ile Gln Asp Phe Ala Glu Glu His Arg Pro Glu
                405                 410                 415

Glu Trp Lys Arg Leu Val Arg Asp Leu Asp Tyr Phe Glu Thr Gly Asp
            420                 425                 430

Lys Pro Tyr Ile Thr Gln Thr Thr Pro His Tyr His Ile Glu Lys Gly
        435                 440                 445

Lys Ile Gly Leu Arg Phe Val Pro Glu Gly Gln His Leu Trp Pro Ser
```

```
    450                 455                 460

Pro Glu Val Gly Ala Thr Arg Thr Gly Arg Ser Lys Tyr Ala Gln Asp
465                 470                 475                 480

Lys Arg Leu Thr Ala Glu Ala Phe Leu Ser Val His Glu Leu Met Pro
                485                 490                 495

Met Met Phe Tyr Tyr Phe Leu Leu Arg Glu Lys Tyr Ser Glu Glu Val
            500                 505                 510

Ser Ala Glu Lys Val Gln Gly Arg Ile Lys Arg Val Ile Glu Asp Val
        515                 520                 525

Tyr Ala Val Tyr Asp Ala Phe Ala Arg Asp Glu Ile Asn Thr Arg Asp
    530                 535                 540

Glu Leu Asp Ala Cys Leu Ala Asp Lys Gly Ile Arg Arg Gly His Leu
545                 550                 555                 560

Pro Arg Gln Met Ile Ala Ile Leu Ser Gln Glu His Lys Asp Met Glu
                565                 570                 575

Glu Lys Val Arg Lys Lys Leu Gln Glu Met Ile Ala Asp Thr Asp His
            580                 585                 590

Arg Leu Asp Met Leu Asp Arg Gln Thr Asp Arg Lys Ile Arg Ile Gly
        595                 600                 605

Arg Lys Asn Ala Gly Leu Pro Lys Ser Gly Val Val Ala Asp Trp Leu
    610                 615                 620

Val Arg Asp Met Met Arg Phe Gln Pro Val Ala Lys Asp Thr Ser Gly
625                 630                 635                 640

Lys Pro Leu Asn Asn Ser Lys Ala Asn Ser Thr Glu Tyr Arg Met Leu
                645                 650                 655

Gln Arg Ala Leu Ala Leu Phe Gly Gly Glu Lys Glu Arg Leu Thr Pro
            660                 665                 670

Tyr Phe Arg Gln Met Asn Leu Thr Gly Gly Asn Asn Pro His Pro Phe
        675                 680                 685

Leu His Glu Thr Arg Trp Glu Ser His Thr Asn Ile Leu Ser Phe Tyr
    690                 695                 700

Arg Ser Tyr Leu Glu Ala Arg Lys Ala Phe Leu Gln Ser Ile Gly Arg
705                 710                 715                 720

Ser Asp Arg Val Glu Asn His Arg Phe Leu Leu Leu Lys Glu Pro Lys
                725                 730                 735

Thr Asp Arg Gln Thr Leu Val Ala Gly Trp Lys Gly Glu Phe His Leu
            740                 745                 750

Pro Arg Gly Ile Phe Thr Glu Ala Val Arg Asp Cys Leu Ile Glu Met
        755                 760                 765

Gly Tyr Asp Glu Val Gly Ser Tyr Lys Glu Val Gly Phe Met Ala Lys
    770                 775                 780

Ala Val Pro Leu Tyr Phe Glu Arg Ala Ser Lys Asp Arg Val Gln Pro
785                 790                 795                 800

Phe Tyr Asp Tyr Pro Phe Asn Val Gly Asn Ser Leu Lys Pro Lys Lys
                805                 810                 815

Gly Arg Phe Leu Ser Lys Glu Lys Arg Ala Glu Glu Trp Glu Ser Gly
            820                 825                 830

Lys Glu Arg Phe Arg Leu Ala Lys Leu Lys Lys Glu Ile Leu Glu Ala
        835                 840                 845

Lys Glu His Pro Tyr His Asp Phe Lys Ser Trp Gln Lys Phe Glu Arg
    850                 855                 860

Glu Leu Arg Leu Val Lys Asn Gln Asp Ile Ile Thr Trp Met Met Cys
865                 870                 875                 880
```

```
Arg Asp Leu Met Glu Glu Asn Lys Val Glu Gly Leu Asp Thr Gly Thr
                885                 890                 895

Leu Tyr Leu Lys Asp Ile Arg Thr Asp Val Gln Glu Gln Gly Ser Leu
            900                 905                 910

Asn Val Leu Asn Arg Val Lys Pro Met Arg Leu Pro Val Val Val Tyr
        915                 920                 925

Arg Ala Asp Ser Arg Gly His Val His Lys Glu Gln Ala Pro Leu Ala
    930                 935                 940

Thr Val Tyr Ile Glu Glu Arg Asp Thr Lys Leu Leu Lys Gln Gly Asn
945                 950                 955                 960

Phe Lys Ser Phe Val Lys Asp Arg Arg Leu Asn Gly Leu Phe Ser Phe
                965                 970                 975

Val Asp Thr Gly Ala Leu Ala Met Glu Gln Tyr Pro Ile Ser Lys Leu
            980                 985                 990

Arg Val Glu Tyr Glu Leu Ala Lys  Tyr Gln Thr Ala Arg  Val Cys Ala
        995                 1000                1005

Phe Glu  Gln Thr Leu Glu Leu  Glu Glu Ser Leu Leu  Thr Arg Tyr
    1010                1015                1020

Pro His  Leu Pro Asp Lys Asn  Phe Arg Lys Met Leu  Glu Ser Trp
    1025                1030                1035

Ser Asp  Pro Leu Leu Asp Lys  Trp Pro Asp Leu His  Gly Asn Val
    1040                1045                1050

Arg Leu  Leu Ile Ala Val Arg  Asn Ala Phe Ser His  Asn Gln Tyr
    1055                1060                1065

Pro Met  Tyr Asp Glu Thr Leu  Phe Ser Ser Ile Arg  Lys Tyr Asp
    1070                1075                1080

Pro Ser  Ser Pro Asp Ala Ile  Glu Glu Arg Met Gly  Leu Asn Ile
    1085                1090                1095

Ala His  Arg Leu Ser Glu Glu  Val Lys Gln Ala Lys  Glu Met Val
    1100                1105                1110

Glu Arg  Ile Ile Gln Ala
    1115
```

<210> SEQ ID NO 35
<211> LENGTH: 1175
<212> TYPE: PRT
<213> ORGANISM: Artificial Sequence
<220> FEATURE:
<223> OTHER INFORMATION: Chemically synthesized

<400> SEQUENCE: 35

```
Met Thr Glu Gln Ser Glu Arg Pro Tyr Asn Gly Thr Tyr Tyr Thr Leu
1               5                   10                  15

Glu Asp Lys His Phe Trp Ala Ala Phe Leu Asn Leu Ala Arg His Asn
            20                  25                  30

Ala Tyr Ile Thr Leu Thr His Ile Asp Arg Gln Leu Ala Tyr Ser Lys
        35                  40                  45

Ala Asp Ile Thr Asn Asp Gln Asp Val Leu Ser Phe Lys Ala Leu Trp
    50                  55                  60

Lys Asn Phe Asp Asn Asp Leu Glu Arg Lys Ser Arg Leu Arg Ser Leu
65                  70                  75                  80

Ile Leu Lys His Phe Ser Phe Leu Glu Gly Ala Ala Tyr Gly Lys Lys
                85                  90                  95

Leu Phe Glu Ser Lys Ser Ser Gly Asn Lys Ser Ser Lys Asn Lys Glu
            100                 105                 110
```

```
Leu Thr Lys Lys Glu Lys Glu Glu Leu Gln Ala Asn Ala Leu Ser Leu
        115                 120                 125

Asp Asn Leu Lys Ser Ile Leu Phe Asp Phe Leu Gln Lys Leu Lys Asp
    130                 135                 140

Phe Arg Asn Tyr Tyr Ser His Tyr Arg His Ser Gly Ser Ser Glu Leu
145                 150                 155                 160

Pro Leu Phe Asp Gly Asn Met Leu Gln Arg Leu Tyr Asn Val Phe Asp
                165                 170                 175

Val Ser Val Gln Arg Val Lys Ile Asp His Glu His Asn Asp Glu Val
            180                 185                 190

Asp Pro His Tyr His Phe Asn His Leu Val Arg Lys Gly Lys Lys Asp
        195                 200                 205

Arg Tyr Gly His Asn Asp Asn Pro Ser Phe Lys His His Phe Val Asp
    210                 215                 220

Gly Glu Gly Met Val Thr Glu Ala Gly Leu Leu Phe Phe Val Ser Leu
225                 230                 235                 240

Phe Leu Glu Lys Arg Asp Ala Ile Trp Met Gln Lys Lys Ile Arg Gly
                245                 250                 255

Phe Lys Gly Gly Thr Glu Thr Tyr Gln Gln Met Thr Asn Glu Val Phe
            260                 265                 270

Cys Arg Ser Arg Ile Ser Leu Pro Lys Leu Lys Leu Glu Ser Leu Arg
        275                 280                 285

Met Asp Asp Trp Met Leu Leu Asp Met Leu Asn Glu Leu Val Arg Cys
    290                 295                 300

Pro Lys Pro Leu Tyr Asp Arg Leu Arg Glu Asp Asp Arg Ala Cys Phe
305                 310                 315                 320

Arg Val Pro Val Asp Ile Leu Pro Asp Glu Asp Asp Thr Asp Gly Gly
                325                 330                 335

Gly Glu Asp Pro Phe Lys Asn Thr Leu Val Arg His Gln Asp Arg Phe
            340                 345                 350

Pro Tyr Phe Ala Leu Arg Tyr Phe Asp Leu Lys Lys Val Phe Thr Ser
        355                 360                 365

Leu Arg Phe His Ile Asp Leu Gly Thr Tyr His Phe Ala Ile Tyr Lys
    370                 375                 380

Lys Met Ile Gly Glu Gln Pro Glu Asp Arg His Leu Thr Arg Asn Leu
385                 390                 395                 400

Tyr Gly Phe Gly Arg Ile Gln Asp Phe Ala Glu Glu His Arg Pro Glu
                405                 410                 415

Glu Trp Lys Arg Leu Val Arg Asp Leu Asp Tyr Phe Glu Thr Gly Asp
            420                 425                 430

Lys Pro Tyr Ile Ser Gln Thr Ser Pro His Tyr His Ile Glu Lys Gly
        435                 440                 445

Lys Ile Gly Leu Arg Phe Met Pro Glu Gly Gln His Leu Trp Pro Ser
    450                 455                 460

Pro Glu Val Gly Thr Thr Arg Thr Gly Arg Ser Lys Tyr Ala Gln Asp
465                 470                 475                 480

Lys Arg Leu Thr Ala Glu Ala Phe Leu Ser Val His Glu Leu Met Pro
                485                 490                 495

Met Met Phe Tyr Tyr Phe Leu Leu Arg Glu Lys Tyr Ser Glu Glu Val
            500                 505                 510

Ser Ala Glu Arg Val Gln Gly Arg Ile Lys Arg Val Ile Glu Asp Val
        515                 520                 525
```

```
Tyr Ala Val Tyr Asp Ala Phe Ala Arg Asp Glu Ile Asn Thr Arg Asp
    530                 535                 540

Glu Leu Asp Ala Cys Leu Ala Asp Lys Gly Ile Arg Arg Gly His Leu
545                 550                 555                 560

Pro Arg Gln Met Ile Ala Ile Leu Ser Gln Glu His Lys Asp Met Glu
                565                 570                 575

Glu Lys Ile Arg Lys Lys Leu Gln Glu Met Met Ala Asp Thr Asp His
            580                 585                 590

Arg Leu Asp Met Leu Asp Arg Gln Thr Asp Arg Lys Ile Arg Ile Gly
        595                 600                 605

Arg Lys Asn Ala Gly Leu Pro Lys Ser Gly Val Ile Ala Asp Trp Leu
    610                 615                 620

Val Arg Asp Met Met Arg Phe Gln Pro Val Ala Lys Asp Ala Ser Gly
625                 630                 635                 640

Lys Pro Leu Asn Asn Ser Lys Ala Asn Ser Thr Glu Tyr Arg Met Leu
                645                 650                 655

Gln Arg Ala Leu Ala Leu Phe Gly Gly Glu Lys Glu Arg Leu Thr Pro
            660                 665                 670

Tyr Phe Arg Gln Met Asn Leu Thr Gly Gly Asn Asn Pro His Pro Phe
        675                 680                 685

Leu His Glu Thr Arg Trp Glu Ser His Thr Asn Ile Leu Ser Phe Tyr
    690                 695                 700

Arg Ser Tyr Leu Arg Ala Arg Lys Ala Phe Leu Glu Arg Ile Gly Arg
705                 710                 715                 720

Ser Asp Arg Val Glu Asn Arg Pro Phe Leu Leu Leu Lys Glu Pro Lys
                725                 730                 735

Thr Asp Arg Gln Thr Leu Val Ala Gly Trp Lys Gly Glu Phe His Leu
            740                 745                 750

Pro Arg Gly Ile Phe Thr Glu Ala Val Arg Asp Cys Leu Ile Glu Met
        755                 760                 765

Gly His Asp Glu Val Ala Ser Tyr Lys Glu Val Gly Phe Met Ala Lys
    770                 775                 780

Ala Val Pro Leu Tyr Phe Glu Arg Ala Cys Glu Asp Arg Val Gln Pro
785                 790                 795                 800

Phe Tyr Asp Ser Pro Phe Asn Val Gly Asn Ser Leu Lys Pro Lys Lys
                805                 810                 815

Gly Arg Phe Leu Ser Lys Glu Glu Arg Ala Glu Glu Trp Glu Arg Gly
            820                 825                 830

Lys Glu Arg Phe Arg Asp Leu Glu Ala Trp Ser Tyr Ser Ala Ala Arg
        835                 840                 845

Arg Ile Glu Asp Ala Phe Ala Gly Ile Glu Tyr Ala Ser Pro Gly Asn
    850                 855                 860

Lys Lys Lys Ile Glu Gln Leu Leu Arg Asp Leu Ser Leu Trp Glu Ala
865                 870                 875                 880

Phe Glu Ser Lys Leu Lys Val Arg Ala Asp Arg Ile Asn Leu Ala Lys
                885                 890                 895

Leu Lys Lys Glu Ile Leu Glu Ala Gln Glu His Pro Tyr His Asp Phe
            900                 905                 910

Lys Ser Trp Gln Lys Phe Glu Arg Glu Leu Arg Leu Val Lys Asn Gln
        915                 920                 925

Asp Ile Ile Thr Trp Met Met Cys Arg Asp Leu Met Glu Glu Asn Lys
    930                 935                 940

Val Glu Gly Leu Asp Thr Gly Thr Leu Tyr Leu Lys Asp Ile Arg Pro
```

945 950 955 960

Asn Val Gln Glu Gln Gly Ser Leu Asn Val Leu Asn Arg Val Lys Pro
965 970 975

Met Arg Leu Pro Val Val Val Tyr Arg Ala Asp Ser Arg Gly His Val
980 985 990

His Lys Glu Glu Ala Pro Leu Ala Thr Val Tyr Ile Glu Glu Arg Asp
995 1000 1005

Thr Lys Leu Leu Lys Gln Gly Asn Phe Lys Ser Phe Val Lys Asp
1010 1015 1020

Arg Arg Leu Asn Gly Leu Phe Ser Phe Val Asp Thr Gly Gly Leu
1025 1030 1035

Ala Met Glu Gln Tyr Pro Ile Ser Lys Leu Arg Val Glu Tyr Glu
1040 1045 1050

Leu Ala Lys Tyr Gln Thr Ala Arg Val Cys Val Phe Glu Leu Thr
1055 1060 1065

Leu Arg Leu Glu Glu Ser Leu Leu Thr Arg Tyr Pro His Leu Pro
1070 1075 1080

Asp Glu Ser Phe Arg Glu Met Leu Glu Ser Trp Ser Asp Pro Leu
1085 1090 1095

Leu Ala Lys Trp Pro Glu Leu His Gly Lys Val Arg Leu Leu Ile
1100 1105 1110

Ala Val Arg Asn Ala Phe Ser His Asn Gln Tyr Pro Met Tyr Asp
1115 1120 1125

Glu Ala Val Phe Ser Ser Ile Arg Lys Tyr Asp Pro Ser Ser Pro
1130 1135 1140

Asp Ala Ile Glu Glu Arg Met Gly Leu Asn Ile Ala His Arg Leu
1145 1150 1155

Ser Glu Glu Val Lys Gln Ala Lys Glu Thr Val Glu Arg Ile Ile
1160 1165 1170

Gln Ala
1175

<210> SEQ ID NO 36
<211> LENGTH: 1120
<212> TYPE: PRT
<213> ORGANISM: Artificial Sequence
<220> FEATURE:
<223> OTHER INFORMATION: Chemically synthesized

<400> SEQUENCE: 36

Met Glu Asp Asp Lys Lys Thr Thr Asp Ser Ile Arg Tyr Glu Leu Lys
1 5 10 15

Asp Lys His Phe Trp Ala Ala Phe Leu Asn Leu Ala Arg His Asn Val
20 25 30

Tyr Ile Thr Val Asn His Ile Asn Lys Ile Leu Glu Glu Asp Glu Ile
35 40 45

Asn Arg Asp Gly Tyr Glu Asn Thr Leu Glu Asn Ser Trp Asn Glu Ile
50 55 60

Lys Asp Ile Asn Lys Lys Asp Arg Leu Ser Lys Leu Ile Ile Lys His
65 70 75 80

Phe Pro Phe Leu Glu Ala Thr Thr Tyr Arg Gln Asn Pro Thr Asp Thr
85 90 95

Thr Lys Gln Lys Glu Glu Lys Gln Ala Glu Ala Gln Ser Leu Glu Ser
100 105 110

Leu Lys Lys Ser Phe Phe Val Phe Ile Tyr Lys Leu Arg Asp Leu Arg

```
        115                 120                 125

Asn His Tyr Ser His Tyr Lys His Ser Lys Ser Leu Glu Arg Pro Lys
    130                 135                 140

Phe Glu Glu Asp Leu Gln Asn Lys Met Tyr Asn Ile Phe Asp Val Ser
145                 150                 155                 160

Ile Gln Phe Val Lys Glu Asp Tyr Lys His Asn Thr Asp Ile Asn Pro
                165                 170                 175

Lys Lys Asp Phe Lys His Leu Asp Arg Lys Arg Lys Gly Lys Phe His
            180                 185                 190

Tyr Ser Phe Ala Asp Asn Glu Gly Asn Ile Thr Glu Ser Gly Leu Leu
        195                 200                 205

Phe Phe Val Ser Leu Phe Leu Glu Lys Lys Asp Ala Ile Trp Val Gln
    210                 215                 220

Lys Lys Leu Glu Gly Phe Lys Cys Ser Asn Lys Ser Tyr Gln Lys Met
225                 230                 235                 240

Thr Asn Glu Val Phe Cys Arg Ser Arg Met Leu Leu Pro Lys Leu Arg
                245                 250                 255

Leu Glu Ser Thr Gln Thr Gln Asp Trp Ile Leu Leu Asp Met Leu Asn
            260                 265                 270

Glu Leu Ile Arg Cys Pro Lys Ser Leu Tyr Glu Arg Leu Gln Gly Val
        275                 280                 285

Asn Arg Lys Lys Phe Tyr Val Ser Phe Asp Pro Ala Asp Glu Asp Tyr
    290                 295                 300

Asp Ala Glu Gln Glu Pro Phe Lys Asn Thr Leu Val Arg His Gln Asp
305                 310                 315                 320

Arg Phe Pro Tyr Phe Ala Leu Arg Tyr Phe Asp Tyr Asn Glu Val Phe
                325                 330                 335

Ala Asn Leu Arg Phe Gln Ile Asp Leu Gly Thr Tyr His Phe Ser Ile
            340                 345                 350

Tyr Lys Lys Leu Ile Gly Gly Gln Lys Glu Asp Arg His Leu Thr His
        355                 360                 365

Lys Leu Tyr Gly Phe Glu Arg Ile Gln Glu Phe Asp Lys Gln Asn Arg
    370                 375                 380

Pro Asp Glu Trp Lys Ala Ile Val Lys Asp Ser Asp Thr Phe Lys Lys
385                 390                 395                 400

Lys Glu Glu Lys Glu Glu Glu Lys Pro Tyr Ile Ser Glu Thr Thr Pro
                405                 410                 415

His Tyr His Leu Glu Asn Lys Lys Ile Gly Ile Ala Phe Lys Asn His
            420                 425                 430

Asn Ile Trp Pro Ser Thr Gln Thr Glu Leu Thr Asn Asn Lys Arg Lys
        435                 440                 445

Lys Tyr Asn Leu Gly Thr Ser Ile Lys Ala Glu Ala Phe Leu Ser Val
    450                 455                 460

His Glu Leu Leu Pro Met Met Phe Tyr Tyr Leu Leu Leu Lys Thr Glu
465                 470                 475                 480

Asn Thr Lys Asn Asp Asn Lys Val Gly Gly Lys Lys Glu Thr Lys Lys
                485                 490                 495

Gln Gly Lys His Lys Ile Glu Ala Ile Ile Glu Ser Lys Ile Lys Asp
            500                 505                 510

Ile Tyr Ala Leu Tyr Asp Ala Phe Ala Asn Gly Glu Ile Asn Ser Glu
        515                 520                 525

Asp Glu Leu Lys Glu Tyr Leu Lys Gly Lys Asp Ile Lys Ile Val His
    530                 535                 540
```

Leu Pro Lys Gln Met Ile Ala Ile Leu Lys Asn Glu His Lys Asp Met
545 550 555 560

Ala Glu Lys Ala Glu Ala Lys Gln Glu Lys Met Lys Leu Ala Thr Glu
565 570 575

Asn Arg Leu Lys Thr Leu Asp Lys Gln Leu Lys Gly Lys Ile Gln Asn
580 585 590

Gly Lys Arg Tyr Asn Ser Ala Pro Lys Ser Gly Glu Ile Ala Ser Trp
595 600 605

Leu Val Asn Asp Met Met Arg Phe Gln Pro Val Gln Lys Asp Glu Asn
610 615 620

Gly Glu Ser Leu Asn Asn Ser Lys Ala Asn Ser Thr Glu Tyr Gln Leu
625 630 635 640

Leu Gln Arg Thr Leu Ala Phe Phe Gly Ser Glu His Glu Arg Leu Ala
645 650 655

Pro Tyr Phe Lys Gln Thr Lys Leu Ile Glu Ser Ser Asn Pro His Pro
660 665 670

Phe Leu Asn Asp Thr Glu Trp Glu Lys Cys Ser Asn Ile Leu Ser Phe
675 680 685

Tyr Arg Ser Tyr Leu Lys Ala Arg Lys Asn Phe Leu Glu Ser Leu Lys
690 695 700

Pro Glu Asp Trp Glu Lys Asn Gln Tyr Phe Leu Met Leu Lys Glu Pro
705 710 715 720

Lys Thr Asn Arg Glu Thr Leu Val Gln Gly Trp Lys Asn Gly Phe Asn
725 730 735

Leu Pro Arg Gly Phe Phe Thr Glu Pro Ile Arg Lys Trp Phe Met Glu
740 745 750

His Trp Lys Ser Ile Lys Val Asp Asp Leu Lys Arg Val Gly Leu Val
755 760 765

Ala Lys Val Thr Pro Leu Phe Phe Ser Glu Lys Tyr Lys Asp Ser Val
770 775 780

Gln Pro Phe Tyr Asn Tyr Pro Phe Asn Val Gly Asp Val Asn Lys Pro
785 790 795 800

Lys Glu Glu Asp Phe Leu His Arg Glu Glu Arg Ile Glu Leu Trp Asp
805 810 815

Lys Lys Lys Asp Lys Phe Lys Gly Tyr Lys Ala Lys Lys Lys Phe Lys
820 825 830

Glu Met Thr Asp Lys Glu Lys Glu Glu His Arg Ser Tyr Leu Glu Phe
835 840 845

Gln Ser Trp Asn Lys Phe Glu Arg Glu Leu Arg Leu Val Arg Asn Gln
850 855 860

Asp Ile Val Thr Trp Leu Leu Cys Thr Glu Leu Ile Asp Lys Leu Lys
865 870 875 880

Ile Asp Glu Leu Asn Ile Lys Glu Leu Lys Lys Leu Arg Leu Lys Asp
885 890 895

Ile Asn Thr Asp Thr Ala Lys Lys Glu Lys Asn Asn Ile Leu Asn Arg
900 905 910

Val Met Pro Met Glu Leu Pro Val Thr Val Tyr Lys Val Asn Lys Gly
915 920 925

Gly Tyr Ile Ile Lys Asn Lys Pro Leu His Thr Ile Tyr Ile Lys Glu
930 935 940

Ala Glu Thr Lys Leu Leu Lys Gln Gly Asn Phe Lys Ala Leu Val Lys
945 950 955 960

Asp Arg Arg Leu Asn Gly Leu Phe Ser Phe Val Lys Thr Pro Ser Glu
965 970 975

Ala Glu Ser Glu Ser Asn Pro Ile Ser Lys Leu Arg Val Glu Tyr Glu
980 985 990

Leu Gly Lys Tyr Gln Asn Ala Arg Leu Asp Ile Ile Glu Asp Met Leu
995 1000 1005

Ala Leu Glu Lys Lys Leu Ile Asp Lys Tyr Asn Ser Leu Asp Thr
1010 1015 1020

Asp Asn Phe His Asn Met Leu Thr Gly Trp Leu Glu Leu Lys Gly
1025 1030 1035

Glu Ala Lys Lys Ala Arg Phe Gln Asn Asp Val Lys Leu Leu Thr
1040 1045 1050

Ala Val Arg Asn Ala Phe Ser His Asn Gln Tyr Pro Met Tyr Asp
1055 1060 1065

Glu Asn Leu Phe Gly Asn Ile Glu Arg Phe Ser Leu Ser Ser Ser
1070 1075 1080

Asn Ile Ile Glu Ser Lys Gly Leu Asp Ile Ala Ala Lys Leu Lys
1085 1090 1095

Glu Glu Val Ser Lys Ala Ala Lys Lys Ile Gln Asn Glu Glu Asp
1100 1105 1110

Asn Lys Lys Glu Lys Glu Thr
1115 1120

<210> SEQ ID NO 37
<211> LENGTH: 1132
<212> TYPE: PRT
<213> ORGANISM: Artificial Sequence
<220> FEATURE:
<223> OTHER INFORMATION: Chemically synthesized

<400> SEQUENCE: 37

Met Glu Asp Asp Lys Lys Thr Lys Glu Ser Thr Asn Met Leu Asp Asn
1 5 10 15

Lys His Phe Trp Ala Ala Phe Leu Asn Leu Ala Arg His Asn Val Tyr
20 25 30

Ile Thr Val Asn His Ile Asn Lys Val Leu Glu Leu Lys Asn Lys Lys
35 40 45

Asp Gln Asp Ile Ile Ile Asp Asn Asp Gln Asp Ile Leu Ala Ile Lys
50 55 60

Thr His Trp Glu Lys Val Asn Gly Asp Leu Asn Lys Thr Glu Arg Leu
65 70 75 80

Arg Glu Leu Met Thr Lys His Phe Pro Phe Leu Glu Thr Ala Ile Tyr
85 90 95

Thr Lys Asn Lys Glu Asp Lys Glu Glu Val Lys Gln Glu Lys Gln Ala
100 105 110

Lys Ala Gln Ser Phe Asp Ser Leu Lys His Cys Leu Phe Leu Phe Leu
115 120 125

Glu Lys Leu Gln Glu Ala Arg Asn Tyr Tyr Ser His Tyr Lys Tyr Ser
130 135 140

Glu Ser Thr Lys Glu Pro Met Leu Glu Lys Glu Leu Leu Lys Lys Met
145 150 155 160

Tyr Asn Ile Phe Asp Asp Asn Ile Gln Leu Val Ile Lys Asp Tyr Gln
165 170 175

His Asn Lys Asp Ile Asn Pro Asp Glu Asp Phe Lys His Leu Asp Arg
180 185 190

```
Thr Glu Glu Glu Phe Asn Tyr Tyr Phe Thr Thr Asn Lys Lys Gly Asn
        195                 200                 205

Ile Thr Ala Ser Gly Leu Leu Phe Phe Val Ser Leu Phe Leu Glu Lys
    210                 215                 220

Lys Asp Ala Ile Trp Met Gln Gln Lys Leu Arg Gly Phe Lys Asp Asn
225                 230                 235                 240

Arg Glu Ser Lys Lys Lys Met Thr His Glu Val Phe Cys Arg Ser Arg
                245                 250                 255

Met Leu Leu Pro Lys Leu Arg Leu Glu Ser Thr Gln Thr Gln Asp Trp
            260                 265                 270

Ile Leu Leu Asp Met Leu Asn Glu Leu Ile Arg Cys Pro Lys Ser Leu
        275                 280                 285

Tyr Glu Arg Leu Gln Gly Glu Tyr Arg Lys Lys Phe Asn Val Pro Phe
    290                 295                 300

Asp Ser Ala Asp Glu Asp Tyr Asp Ala Glu Gln Glu Pro Phe Lys Asn
305                 310                 315                 320

Thr Leu Val Arg His Gln Asp Arg Phe Pro Tyr Phe Ala Leu Arg Tyr
                325                 330                 335

Phe Asp Tyr Asn Glu Ile Phe Thr Asn Leu Arg Phe Gln Ile Asp Leu
            340                 345                 350

Gly Thr Tyr His Phe Ser Ile Tyr Lys Lys Leu Ile Gly Gly Gln Lys
        355                 360                 365

Glu Asp Arg His Leu Thr His Lys Leu Tyr Gly Phe Glu Arg Ile Gln
    370                 375                 380

Glu Phe Ala Lys Gln Asn Arg Thr Asp Glu Trp Lys Ala Ile Val Lys
385                 390                 395                 400

Asp Phe Asp Thr Tyr Glu Thr Ser Glu Glu Pro Tyr Ile Ser Glu Thr
                405                 410                 415

Ala Pro His Tyr His Leu Glu Asn Gln Lys Ile Gly Ile Arg Phe Arg
            420                 425                 430

Asn Asp Asn Asp Glu Ile Trp Pro Ser Leu Lys Thr Asn Gly Glu Asn
        435                 440                 445

Asn Glu Lys Arg Lys Tyr Lys Leu Asp Lys Gln Tyr Gln Ala Glu Ala
    450                 455                 460

Phe Leu Ser Val His Glu Leu Leu Pro Met Met Phe Tyr Tyr Leu Leu
465                 470                 475                 480

Leu Lys Lys Glu Glu Pro Asn Asn Asp Lys Lys Asn Ala Ser Ile Val
                485                 490                 495

Glu Gly Phe Ile Lys Arg Glu Ile Arg Asp Ile Tyr Lys Leu Tyr Asp
            500                 505                 510

Ala Phe Ala Asn Gly Glu Ile Asn Asn Ile Asp Asp Leu Glu Lys Tyr
        515                 520                 525

Cys Glu Asp Lys Gly Ile Pro Lys Arg His Leu Pro Lys Gln Met Val
    530                 535                 540

Ala Ile Leu Tyr Asp Glu His Lys Asp Met Ala Glu Glu Ala Lys Arg
545                 550                 555                 560

Lys Gln Lys Glu Met Val Lys Asp Thr Lys Lys Leu Leu Ala Thr Leu
                565                 570                 575

Glu Lys Gln Thr Gln Gly Glu Ile Glu Asp Gly Gly Arg Asn Ile Arg
            580                 585                 590

Leu Leu Lys Ser Gly Glu Ile Ala Arg Trp Leu Val Asn Asp Met Met
        595                 600                 605

Arg Phe Gln Pro Val Gln Lys Asp Asn Glu Gly Asn Pro Leu Asn Asn
```

```
    610                 615                 620

Ser Lys Ala Asn Ser Thr Glu Tyr Gln Met Leu Gln Arg Ser Leu Ala
625                 630                 635                 640

Leu Tyr Asn Lys Glu Glu Lys Pro Thr Arg Tyr Phe Arg Gln Val Asn
                645                 650                 655

Leu Ile Asn Ser Ser Asn Pro His Pro Phe Leu Lys Trp Thr Lys Trp
            660                 665                 670

Glu Glu Cys Asn Asn Ile Leu Ser Phe Tyr Arg Ser Tyr Leu Thr Lys
        675                 680                 685

Lys Ile Glu Phe Leu Asn Lys Leu Lys Pro Glu Asp Trp Glu Lys Asn
    690                 695                 700

Gln Tyr Phe Leu Lys Leu Lys Glu Pro Lys Thr Asn Arg Glu Thr Leu
705                 710                 715                 720

Val Gln Gly Trp Lys Asn Gly Phe Asn Leu Pro Arg Gly Ile Phe Thr
                725                 730                 735

Glu Pro Ile Arg Glu Trp Phe Lys Arg His Gln Asn Asp Ser Glu Glu
            740                 745                 750

Tyr Glu Lys Val Glu Thr Leu Asp Arg Val Gly Leu Val Thr Lys Val
        755                 760                 765

Ile Pro Leu Phe Phe Lys Lys Glu Asp Ser Lys Asp Lys Glu Glu Tyr
    770                 775                 780

Leu Lys Lys Asp Ala Gln Lys Glu Ile Asn Asn Cys Val Gln Pro Phe
785                 790                 795                 800

Tyr Gly Phe Pro Tyr Asn Val Gly Asn Ile His Lys Pro Asp Glu Lys
                805                 810                 815

Asp Phe Leu Pro Ser Glu Glu Arg Lys Lys Leu Trp Gly Asp Lys Lys
            820                 825                 830

Tyr Lys Phe Lys Gly Tyr Lys Ala Lys Val Lys Ser Lys Lys Leu Thr
        835                 840                 845

Asp Lys Glu Lys Glu Glu Tyr Arg Ser Tyr Leu Glu Phe Gln Ser Trp
    850                 855                 860

Asn Lys Phe Glu Arg Glu Leu Arg Leu Val Arg Asn Gln Asp Ile Val
865                 870                 875                 880

Thr Trp Leu Leu Cys Thr Glu Leu Ile Asp Lys Leu Lys Val Glu Gly
                885                 890                 895

Leu Asn Val Glu Glu Leu Lys Lys Leu Arg Leu Lys Asp Ile Asp Thr
            900                 905                 910

Asp Thr Ala Lys Gln Glu Lys Asn Asn Ile Leu Asn Arg Val Met Pro
        915                 920                 925

Met Gln Leu Pro Val Thr Val Tyr Glu Ile Asp Asp Ser His Asn Ile
    930                 935                 940

Val Lys Asp Arg Pro Leu His Thr Val Tyr Ile Glu Glu Thr Lys Thr
945                 950                 955                 960

Lys Leu Leu Lys Gln Gly Asn Phe Lys Ala Leu Val Lys Asp Arg Arg
                965                 970                 975

Leu Asn Gly Leu Phe Ser Phe Val Asp Thr Ser Ser Glu Thr Glu Leu
            980                 985                 990

Lys Ser Asn Pro Ile Ser Lys Ser  Leu Val Glu Tyr Glu  Leu Gly Glu
        995                 1000                1005

Tyr Gln  Asn Ala Arg Ile Glu  Thr Ile Lys Asp Met  Leu Leu Leu
    1010                1015                1020

Glu Glu  Thr Leu Ile Glu Lys  Tyr Lys Thr Leu Pro  Thr Asp Asn
    1025                1030                1035
```

```
Phe Ser  Asp Met Leu Asn Gly  Trp Leu Glu Gly Lys  Asp Glu Ala
    1040                 1045                 1050

Asp Lys  Ala Arg Phe Gln Asn  Asp Val Lys Leu Leu  Val Ala Val
    1055                 1060                 1065

Arg Asn  Ala Phe Ser His Asn  Gln Tyr Pro Met Arg  Asn Arg Ile
    1070                 1075                 1080

Ala Phe  Ala Asn Ile Asn Pro  Phe Ser Leu Ser Ser  Ala Asp Thr
    1085                 1090                 1095

Ser Glu  Glu Lys Lys Leu Asp  Ile Ala Asn Gln Leu  Lys Asp Lys
    1100                 1105                 1110

Thr His  Lys Ile Ile Lys Arg  Ile Ile Glu Ile Glu  Lys Pro Ile
    1115                 1120                 1125

Glu Thr  Lys Glu
    1130


<210> SEQ ID NO 38
<211> LENGTH: 1126
<212> TYPE: PRT
<213> ORGANISM: Artificial Sequence
<220> FEATURE:
<223> OTHER INFORMATION: Chemically synthesized

<400> SEQUENCE: 38

Met Glu Asp Asp Lys Lys Thr Thr Asp Ser Ile Arg Tyr Glu Leu Lys
1               5                   10                  15

Asp Lys His Phe Trp Ala Ala Phe Leu Asn Leu Ala Arg His Asn Val
            20                  25                  30

Tyr Ile Thr Val Asn His Ile Asn Lys Ile Leu Glu Glu Gly Glu Ile
        35                  40                  45

Asn Arg Asp Gly Tyr Glu Thr Thr Leu Lys Asn Thr Trp Asn Glu Ile
    50                  55                  60

Lys Asp Ile Asn Lys Lys Asp Arg Leu Ser Lys Leu Ile Ile Lys His
65                  70                  75                  80

Phe Pro Phe Leu Glu Ala Ala Thr Tyr Arg Leu Asn Pro Thr Asp Thr
                85                  90                  95

Thr Lys Gln Lys Glu Glu Lys Gln Ala Glu Ala Gln Ser Leu Glu Ser
            100                 105                 110

Leu Arg Lys Ser Phe Phe Val Phe Ile Tyr Lys Leu Arg Asp Leu Arg
        115                 120                 125

Asn His Tyr Ser His Tyr Lys His Ser Lys Ser Leu Glu Arg Pro Lys
    130                 135                 140

Phe Glu Glu Gly Leu Leu Glu Lys Met Tyr Asn Ile Phe Asn Ala Ser
145                 150                 155                 160

Ile Arg Leu Val Lys Glu Asp Tyr Gln Tyr Asn Lys Asp Ile Asn Pro
                165                 170                 175

Asp Glu Asp Phe Lys His Leu Asp Arg Thr Glu Glu Glu Phe Asn Tyr
            180                 185                 190

Tyr Phe Thr Lys Asp Asn Glu Gly Asn Ile Thr Glu Ser Gly Leu Leu
        195                 200                 205

Phe Phe Val Ser Leu Phe Leu Glu Lys Lys Asp Ala Ile Trp Met Gln
    210                 215                 220

Gln Lys Leu Arg Gly Phe Lys Asp Asn Arg Glu Asn Lys Lys Lys Met
225                 230                 235                 240

Thr Asn Glu Val Phe Cys Arg Ser Arg Met Leu Leu Pro Lys Leu Arg
                245                 250                 255
```

```
Leu Gln Ser Thr Gln Thr Gln Asp Trp Ile Leu Leu Asp Met Leu Asn
            260                 265                 270

Glu Leu Ile Arg Cys Pro Lys Ser Leu Tyr Glu Arg Leu Arg Glu Glu
        275                 280                 285

Asp Arg Glu Lys Phe Arg Val Pro Ile Glu Ile Ala Asp Glu Asp Tyr
    290                 295                 300

Asp Ala Glu Gln Glu Pro Phe Lys Asn Thr Leu Val Arg His Gln Asp
305                 310                 315                 320

Arg Phe Pro Tyr Phe Ala Leu Arg Tyr Phe Asp Tyr Asn Glu Ile Phe
                325                 330                 335

Thr Asn Leu Arg Phe Gln Ile Asp Leu Gly Thr Tyr His Phe Ser Ile
            340                 345                 350

Tyr Lys Lys Gln Ile Gly Asp Tyr Lys Glu Ser His His Leu Thr His
        355                 360                 365

Lys Leu Tyr Gly Phe Glu Arg Ile Gln Glu Phe Thr Lys Gln Asn Arg
    370                 375                 380

Pro Asp Glu Trp Arg Lys Phe Val Lys Thr Phe Asn Ser Phe Glu Thr
385                 390                 395                 400

Ser Lys Glu Pro Tyr Ile Pro Glu Thr Thr Pro His Tyr His Leu Glu
                405                 410                 415

Asn Gln Lys Ile Gly Ile Arg Phe Arg Asn Asp Asn Asp Lys Ile Trp
            420                 425                 430

Pro Ser Leu Lys Thr Asn Ser Glu Lys Asn Glu Lys Ser Lys Tyr Lys
        435                 440                 445

Leu Asp Lys Ser Phe Gln Ala Glu Ala Phe Leu Ser Val His Glu Leu
    450                 455                 460

Leu Pro Met Met Phe Tyr Tyr Leu Leu Leu Lys Thr Glu Asn Thr Asp
465                 470                 475                 480

Asn Asp Asn Glu Ile Glu Thr Lys Lys Lys Glu Asn Lys Asn Asp Lys
                485                 490                 495

Gln Glu Lys His Lys Ile Glu Glu Ile Ile Glu Asn Lys Ile Thr Glu
            500                 505                 510

Ile Tyr Ala Leu Tyr Asp Thr Phe Ala Asn Gly Glu Ile Lys Ser Ile
        515                 520                 525

Asp Glu Leu Glu Glu Tyr Cys Lys Gly Lys Asp Ile Glu Ile Gly His
    530                 535                 540

Leu Pro Lys Gln Met Ile Ala Ile Leu Lys Asp Glu His Lys Val Met
545                 550                 555                 560

Ala Thr Glu Ala Glu Arg Lys Gln Glu Glu Met Leu Val Asp Val Gln
                565                 570                 575

Lys Ser Leu Glu Ser Leu Asp Asn Gln Ile Asn Glu Glu Ile Glu Asn
            580                 585                 590

Val Glu Arg Lys Asn Ser Ser Leu Lys Ser Gly Lys Ile Ala Ser Trp
        595                 600                 605

Leu Val Asn Asp Met Met Arg Phe Gln Pro Val Gln Lys Asp Asn Glu
    610                 615                 620

Gly Lys Pro Leu Asn Asn Ser Lys Ala Asn Ser Thr Glu Tyr Gln Leu
625                 630                 635                 640

Leu Gln Arg Thr Leu Ala Phe Phe Gly Ser Glu His Glu Arg Leu Ala
                645                 650                 655

Pro Tyr Phe Lys Gln Thr Lys Leu Ile Glu Ser Ser Asn Pro His Pro
            660                 665                 670
```

```
Phe Leu Lys Asp Thr Glu Trp Glu Lys Cys Asn Asn Ile Leu Ser Phe
        675                 680                 685

Tyr Arg Ser Tyr Leu Glu Ala Lys Lys Asn Phe Leu Glu Ser Leu Lys
    690                 695                 700

Pro Glu Asp Trp Glu Lys Asn Gln Tyr Phe Leu Lys Leu Lys Glu Pro
705                 710                 715                 720

Lys Thr Lys Pro Lys Thr Leu Val Gln Gly Trp Lys Asn Gly Phe Asn
                725                 730                 735

Leu Pro Arg Gly Ile Phe Thr Glu Pro Ile Arg Lys Trp Phe Met Lys
            740                 745                 750

His Arg Glu Asn Ile Thr Val Ala Glu Leu Lys Arg Val Gly Leu Val
        755                 760                 765

Ala Lys Val Ile Pro Leu Phe Phe Ser Glu Glu Tyr Lys Asp Ser Val
    770                 775                 780

Gln Pro Phe Tyr Asn Tyr His Phe Asn Val Gly Asn Ile Asn Lys Pro
785                 790                 795                 800

Asp Glu Lys Asn Phe Leu Asn Cys Glu Glu Arg Arg Glu Leu Leu Arg
                805                 810                 815

Lys Lys Lys Asp Glu Phe Lys Lys Met Thr Asp Lys Glu Lys Glu Glu
            820                 825                 830

Asn Pro Ser Tyr Leu Glu Phe Lys Ser Trp Asn Lys Phe Glu Arg Glu
        835                 840                 845

Leu Arg Leu Val Arg Asn Gln Asp Ile Val Thr Trp Leu Leu Cys Met
    850                 855                 860

Glu Leu Phe Asn Lys Lys Lys Ile Lys Glu Leu Asn Val Glu Lys Ile
865                 870                 875                 880

Tyr Leu Lys Asn Ile Asn Thr Asn Thr Thr Lys Lys Glu Lys Asn Thr
                885                 890                 895

Glu Glu Lys Asn Gly Glu Glu Lys Asn Ile Lys Glu Lys Asn Asn Ile
            900                 905                 910

Leu Asn Arg Ile Met Pro Met Arg Leu Pro Ile Lys Val Tyr Gly Arg
        915                 920                 925

Glu Asn Phe Ser Lys Asn Lys Lys Lys Lys Ile Arg Arg Asn Thr Phe
    930                 935                 940

Phe Thr Val Tyr Ile Glu Glu Lys Gly Thr Lys Leu Leu Lys Gln Gly
945                 950                 955                 960

Asn Phe Lys Ala Leu Glu Arg Asp Arg Arg Leu Gly Gly Leu Phe Ser
                965                 970                 975

Phe Val Lys Thr Pro Ser Lys Ala Glu Ser Lys Ser Asn Thr Ile Ser
            980                 985                 990

Lys Leu Arg Val Glu Tyr Glu Leu  Gly Glu Tyr Gln Lys  Ala Arg Ile
        995                 1000                 1005

Glu Ile  Ile Lys Asp Met Leu  Ala Leu Glu Lys Thr  Leu Ile Asp
    1010                 1015                 1020

Lys Tyr  Asn Ser Leu Asp Thr  Asp Asn Phe Asn Lys  Met Leu Thr
    1025                 1030                 1035

Asp Trp  Leu Glu Leu Lys Gly  Glu Pro Asp Lys Ala  Ser Phe Gln
    1040                 1045                 1050

Asn Asp  Val Asp Leu Leu Ile  Ala Val Arg Asn Ala  Phe Ser His
    1055                 1060                 1065

Asn Gln  Tyr Pro Met Arg Asn  Arg Ile Ala Phe Ala  Asn Ile Asn
    1070                 1075                 1080

Pro Phe  Ser Leu Ser Ser Ala  Asn Thr Ser Glu Glu  Lys Gly Leu
```

```
    1085                1090                1095

Gly Ile  Ala Asn Gln Leu Lys  Asp Lys Thr His Lys  Thr Ile Glu
    1100                1105                1110

Lys Ile  Ile Glu Ile Glu Lys  Pro Ile Glu Thr Lys  Glu
    1115                1120                1125


<210> SEQ ID NO 39
<211> LENGTH: 1154
<212> TYPE: PRT
<213> ORGANISM: Artificial Sequence
<220> FEATURE:
<223> OTHER INFORMATION: Chemically synthesized

<400> SEQUENCE: 39

Met Arg Val Ser Lys Val Lys Val Lys Asp Gly Gly Lys Asp Lys Met
1               5                   10                  15

Val Leu Val His Arg Lys Thr Thr Gly Ala Gln Leu Val Tyr Ser Gly
            20                  25                  30

Gln Pro Val Ser Asn Glu Thr Ser Asn Ile Leu Pro Glu Lys Lys Arg
        35                  40                  45

Gln Ser Phe Asp Leu Ser Thr Leu Asn Lys Thr Ile Ile Lys Phe Asp
    50                  55                  60

Thr Ala Lys Lys Gln Lys Leu Asn Val Asp Gln Tyr Lys Ile Val Glu
65                  70                  75                  80

Lys Ile Phe Lys Tyr Pro Lys Gln Glu Leu Pro Lys Gln Ile Lys Ala
                85                  90                  95

Glu Glu Ile Leu Pro Phe Leu Asn His Lys Phe Gln Glu Pro Val Lys
            100                 105                 110

Tyr Trp Lys Asn Gly Lys Glu Glu Ser Phe Asn Leu Thr Leu Leu Ile
        115                 120                 125

Val Glu Ala Val Gln Ala Gln Asp Lys Arg Lys Leu Gln Pro Tyr Tyr
    130                 135                 140

Asp Trp Lys Thr Trp Tyr Ile Gln Thr Lys Ser Asp Leu Leu Lys Lys
145                 150                 155                 160

Ser Ile Glu Asn Asn Arg Ile Asp Leu Thr Glu Asn Leu Ser Lys Arg
                165                 170                 175

Lys Lys Ala Leu Leu Ala Trp Glu Thr Glu Phe Thr Ala Ser Gly Ser
            180                 185                 190

Ile Asp Leu Thr His Tyr His Lys Val Tyr Met Thr Asp Val Leu Cys
        195                 200                 205

Lys Met Leu Gln Asp Val Lys Pro Leu Thr Asp Asp Lys Gly Lys Ile
    210                 215                 220

Asn Thr Asn Ala Tyr His Arg Gly Leu Lys Lys Ala Leu Gln Asn His
225                 230                 235                 240

Gln Pro Ala Ile Phe Gly Thr Arg Glu Val Pro Asn Glu Ala Asn Arg
                245                 250                 255

Ala Asp Asn Gln Leu Ser Ile Tyr His Leu Glu Val Val Lys Tyr Leu
            260                 265                 270

Glu His Tyr Phe Pro Ile Lys Thr Ser Lys Arg Arg Asn Thr Ala Asp
        275                 280                 285

Asp Ile Ala His Tyr Leu Lys Ala Gln Thr Leu Lys Thr Thr Ile Glu
    290                 295                 300

Lys Gln Leu Val Asn Ala Ile Arg Ala Asn Ile Ile Gln Gln Gly Lys
305                 310                 315                 320

Thr Asn His His Glu Leu Lys Ala Asp Thr Thr Ser Asn Asp Leu Ile
```

```
                325                 330                 335

Arg Ile Lys Thr Asn Glu Ala Phe Val Leu Asn Leu Thr Gly Thr Cys
            340                 345                 350

Ala Phe Ala Ala Asn Asn Ile Arg Asn Met Val Asp Asn Glu Gln Thr
        355                 360                 365

Asn Asp Ile Leu Gly Lys Gly Asp Phe Ile Lys Ser Leu Leu Lys Asp
    370                 375                 380

Asn Thr Asn Ser Gln Leu Tyr Ser Phe Phe Phe Gly Glu Gly Leu Ser
385                 390                 395                 400

Thr Asn Lys Ala Glu Lys Glu Thr Gln Leu Trp Gly Ile Arg Gly Ala
                405                 410                 415

Val Gln Gln Ile Arg Asn Asn Val Asn His Tyr Lys Lys Asp Ala Leu
            420                 425                 430

Lys Thr Val Phe Asn Ile Ser Asn Phe Glu Asn Pro Thr Ile Thr Asp
        435                 440                 445

Pro Lys Gln Gln Thr Asn Tyr Ala Asp Thr Ile Tyr Lys Ala Arg Phe
    450                 455                 460

Ile Asn Glu Leu Glu Lys Ile Pro Glu Ala Phe Ala Gln Gln Leu Lys
465                 470                 475                 480

Thr Gly Gly Ala Val Ser Tyr Tyr Thr Ile Glu Asn Leu Lys Ser Leu
                485                 490                 495

Leu Thr Thr Phe Gln Phe Ser Leu Cys Arg Ser Thr Ile Pro Phe Ala
            500                 505                 510

Pro Gly Phe Lys Lys Val Phe Asn Gly Gly Ile Asn Tyr Gln Asn Ala
        515                 520                 525

Lys Gln Asp Glu Ser Phe Tyr Glu Leu Met Leu Glu Gln Tyr Leu Arg
    530                 535                 540

Lys Glu Asn Phe Ala Glu Glu Ser Tyr Asn Ala Arg Tyr Phe Met Leu
545                 550                 555                 560

Lys Leu Ile Tyr Asn Asn Leu Phe Leu Pro Gly Phe Thr Thr Asp Arg
                565                 570                 575

Lys Ala Phe Ala Asp Ser Val Gly Phe Val Gln Met Gln Asn Lys Lys
            580                 585                 590

Gln Ala Glu Lys Val Asn Pro Arg Lys Lys Glu Ala Tyr Ala Phe Glu
        595                 600                 605

Ala Val Arg Pro Met Thr Ala Ala Asp Ser Ile Ala Asp Tyr Met Ala
    610                 615                 620

Tyr Val Gln Ser Glu Leu Met Gln Glu Gln Asn Lys Lys Glu Glu Lys
625                 630                 635                 640

Val Ala Glu Glu Thr Arg Ile Asn Phe Glu Lys Phe Val Leu Gln Val
                645                 650                 655

Phe Ile Lys Gly Phe Asp Ser Phe Leu Arg Ala Lys Glu Phe Asp Phe
            660                 665                 670

Val Gln Met Pro Gln Pro Gln Leu Thr Ala Thr Ala Ser Asn Gln Gln
        675                 680                 685

Lys Ala Asp Lys Leu Asn Gln Leu Glu Ala Ser Ile Thr Ala Asp Cys
    690                 695                 700

Lys Leu Thr Pro Gln Tyr Ala Lys Ala Asp Asp Ala Thr His Ile Ala
705                 710                 715                 720

Phe Tyr Val Phe Cys Lys Leu Leu Asp Ala Ala His Leu Ser Asn Leu
                725                 730                 735

Arg Asn Glu Leu Ile Lys Phe Arg Glu Ser Val Asn Glu Phe Lys Phe
            740                 745                 750
```

```
His His Leu Leu Glu Ile Ile Glu Ile Cys Leu Leu Ser Ala Asp Val
        755                 760                 765

Val Pro Thr Asp Tyr Arg Asp Leu Tyr Ser Ser Glu Ala Asp Cys Leu
    770                 775                 780

Ala Arg Leu Arg Pro Phe Ile Glu Gln Gly Ala Asp Ile Thr Asn Trp
785                 790                 795                 800

Ser Asp Leu Phe Val Gln Ser Asp Lys His Ser Pro Val Ile His Ala
                805                 810                 815

Asn Ile Glu Leu Ser Val Lys Tyr Gly Thr Thr Lys Leu Leu Glu Gln
            820                 825                 830

Ile Ile Asn Lys Asp Thr Gln Phe Lys Thr Thr Glu Ala Asn Phe Thr
        835                 840                 845

Ala Trp Asn Thr Ala Gln Lys Ser Ile Glu Gln Leu Ile Lys Gln Arg
    850                 855                 860

Glu Asp His His Glu Gln Trp Val Lys Ala Lys Asn Ala Asp Asp Lys
865                 870                 875                 880

Glu Lys Gln Glu Arg Lys Arg Glu Lys Ser Asn Phe Ala Gln Lys Phe
                885                 890                 895

Ile Glu Lys His Gly Asp Asp Tyr Leu Asp Ile Cys Asp Tyr Ile Asn
            900                 905                 910

Thr Tyr Asn Trp Leu Asp Asn Lys Met His Phe Val His Leu Asn Arg
        915                 920                 925

Leu His Gly Leu Thr Ile Glu Leu Leu Gly Arg Met Ala Gly Phe Val
    930                 935                 940

Ala Leu Phe Asp Arg Asp Phe Gln Phe Phe Asp Glu Gln Gln Ile Ala
945                 950                 955                 960

Asp Glu Phe Lys Leu His Gly Phe Val Asn Leu His Ser Ile Asp Lys
                965                 970                 975

Lys Leu Asn Glu Val Pro Thr Lys Lys Ile Lys Glu Ile Tyr Asp Ile
            980                 985                 990

Arg Asn Lys Ile Ile Gln Ile Asn  Gly Asn Lys Ile Asn  Glu Ser Val
        995                 1000                1005

Arg Ala  Asn Leu Ile Gln Phe  Ile Ser Ser Lys Arg  Asn Tyr Tyr
    1010                 1015                 1020

Asn Asn  Ala Phe Leu His Val  Ser Asn Asp Glu Ile  Lys Glu Lys
    1025                 1030                 1035

Gln Met  Tyr Asp Ile Arg Asn  His Ile Ala His Phe  Asn Tyr Leu
    1040                 1045                 1050

Thr Lys  Asp Ala Ala Asp Phe  Ser Leu Ile Asp Leu  Ile Asn Glu
    1055                 1060                 1065

Leu Arg  Glu Leu Leu His Tyr  Asp Arg Lys Leu Lys  Asn Ala Val
    1070                 1075                 1080

Ser Lys  Ala Phe Ile Asp Leu  Phe Asp Lys His Gly  Met Ile Leu
    1085                 1090                 1095

Lys Leu  Lys Leu Asn Ala Asp  His Lys Leu Lys Val  Glu Ser Leu
    1100                 1105                 1110

Glu Pro  Lys Lys Ile Tyr His  Leu Gly Ser Ser Ala  Lys Asp Lys
    1115                 1120                 1125

Pro Glu  Tyr Gln Tyr Cys Thr  Asn Gln Val Met Met  Ala Tyr Cys
    1130                 1135                 1140

Asn Met  Cys Arg Ser Leu Leu  Glu Met Lys Lys
    1145                 1150
```

<210> SEQ ID NO 40
<211> LENGTH: 1151
<212> TYPE: PRT
<213> ORGANISM: Artificial Sequence
<220> FEATURE:
<223> OTHER INFORMATION: Chemically synthesized

<400> SEQUENCE: 40

Met Glu Asp Lys Pro Phe Trp Ala Ala Phe Phe Asn Leu Ala Arg His
1 5 10 15

Asn Val Tyr Leu Thr Val Asn His Ile Asn Lys Leu Leu Asp Leu Glu
20 25 30

Lys Leu Tyr Asp Glu Gly Lys His Lys Glu Ile Phe Glu Arg Glu Asp
35 40 45

Ile Phe Asn Ile Ser Asp Asp Val Met Asn Asp Ala Asn Ser Asn Gly
50 55 60

Lys Lys Arg Lys Leu Asp Ile Lys Lys Ile Trp Asp Asp Leu Asp Thr
65 70 75 80

Asp Leu Thr Arg Lys Tyr Gln Leu Arg Glu Leu Ile Leu Lys His Phe
85 90 95

Pro Phe Ile Gln Pro Ala Ile Ile Gly Ala Gln Thr Lys Glu Arg Thr
100 105 110

Thr Ile Asp Lys Asp Lys Arg Ser Thr Ser Thr Ser Asn Asp Ser Leu
115 120 125

Lys Gln Thr Gly Glu Gly Asp Ile Asn Asp Leu Leu Ser Leu Ser Asn
130 135 140

Val Lys Ser Met Phe Phe Arg Leu Leu Gln Ile Leu Glu Gln Leu Arg
145 150 155 160

Asn Tyr Tyr Ser His Val Lys His Ser Lys Ser Ala Thr Met Pro Asn
165 170 175

Phe Asp Glu Asp Leu Leu Asn Trp Met Arg Tyr Ile Phe Ile Asp Ser
180 185 190

Val Asn Lys Val Lys Glu Asp Tyr Ser Ser Asn Ser Val Ile Asp Pro
195 200 205

Asn Thr Ser Phe Ser His Leu Ile Tyr Lys Asp Glu Gln Gly Lys Ile
210 215 220

Lys Pro Cys Arg Tyr Pro Phe Thr Ser Lys Asp Gly Ser Ile Asn Ala
225 230 235 240

Phe Gly Leu Leu Phe Phe Val Ser Leu Phe Leu Glu Lys Gln Asp Ser
245 250 255

Ile Trp Met Gln Lys Lys Ile Pro Gly Phe Lys Lys Ala Ser Glu Asn
260 265 270

Tyr Met Lys Met Thr Asn Glu Val Phe Cys Arg Asn His Ile Leu Leu
275 280 285

Pro Lys Ile Arg Leu Glu Thr Val Tyr Asp Lys Asp Trp Met Leu Leu
290 295 300

Asp Met Leu Asn Glu Val Val Arg Cys Pro Leu Ser Leu Tyr Lys Arg
305 310 315 320

Leu Thr Pro Ala Ala Gln Asn Lys Phe Lys Val Pro Glu Lys Ser Ser
325 330 335

Asp Asn Ala Asn Arg Gln Glu Asp Asp Asn Pro Phe Ser Arg Ile Leu
340 345 350

Val Arg His Gln Asn Arg Phe Pro Tyr Phe Val Leu Arg Phe Phe Asp
355 360 365

```
Leu Asn Glu Val Phe Thr Thr Leu Arg Phe Gln Ile Asn Leu Gly Cys
    370                 375                 380

Tyr His Phe Ala Ile Cys Lys Lys Gln Ile Gly Asp Lys Lys Glu Val
385                 390                 395                 400

His His Leu Ile Arg Thr Leu Tyr Gly Phe Ser Arg Leu Gln Asn Phe
                405                 410                 415

Thr Gln Asn Thr Arg Pro Glu Glu Trp Asn Thr Leu Val Lys Thr Thr
            420                 425                 430

Glu Pro Ser Ser Gly Asn Asp Gly Lys Thr Val Gln Gly Val Pro Leu
        435                 440                 445

Pro Tyr Ile Ser Tyr Thr Ile Pro His Tyr Gln Ile Glu Asn Glu Lys
    450                 455                 460

Ile Gly Ile Lys Ile Phe Asp Gly Asp Thr Ala Val Asp Thr Asp Ile
465                 470                 475                 480

Trp Pro Ser Val Ser Thr Glu Lys Gln Leu Asn Lys Pro Asp Lys Tyr
                485                 490                 495

Thr Leu Thr Pro Gly Phe Lys Ala Asp Val Phe Leu Ser Val His Glu
            500                 505                 510

Leu Leu Pro Met Met Phe Tyr Tyr Gln Leu Leu Leu Cys Glu Gly Met
        515                 520                 525

Leu Lys Thr Asp Ala Gly Asn Ala Val Glu Lys Val Leu Ile Asp Thr
    530                 535                 540

Arg Asn Ala Ile Phe Asn Leu Tyr Asp Ala Phe Val Gln Glu Lys Ile
545                 550                 555                 560

Asn Thr Ile Thr Asp Leu Glu Asn Tyr Leu Gln Asp Lys Pro Ile Leu
                565                 570                 575

Ile Gly His Leu Pro Lys Gln Met Ile Asp Leu Leu Lys Gly His Gln
            580                 585                 590

Arg Asp Met Leu Lys Ala Val Glu Gln Lys Lys Ala Met Leu Ile Lys
        595                 600                 605

Asp Thr Glu Arg Arg Leu Lys Leu Leu Asp Lys Gln Leu Lys Gln Glu
    610                 615                 620

Thr Asp Val Ala Ala Lys Asn Thr Gly Thr Leu Leu Lys Asn Gly Gln
625                 630                 635                 640

Ile Ala Asp Trp Leu Val Asn Asp Met Met Arg Phe Gln Pro Val Lys
                645                 650                 655

Arg Asp Lys Glu Gly Asn Pro Ile Asn Cys Ser Lys Ala Asn Ser Thr
            660                 665                 670

Glu Tyr Gln Met Leu Gln Arg Ala Phe Ala Phe Tyr Ala Thr Asp Ser
        675                 680                 685

Cys Arg Leu Ser Arg Tyr Phe Thr Gln Leu His Leu Ile His Ser Asp
    690                 695                 700

Asn Ser His Leu Phe Leu Ser Arg Phe Glu Tyr Asp Lys Gln Pro Asn
705                 710                 715                 720

Leu Ile Ala Phe Tyr Ala Ala Tyr Leu Lys Ala Lys Leu Glu Phe Leu
                725                 730                 735

Asn Glu Leu Gln Pro Gln Asn Trp Ala Ser Asp Asn Tyr Phe Leu Leu
            740                 745                 750

Leu Arg Ala Pro Lys Asn Asp Arg Gln Lys Leu Ala Glu Gly Trp Lys
        755                 760                 765

Asn Gly Phe Asn Leu Pro Arg Gly Leu Phe Thr Glu Lys Ile Lys Thr
    770                 775                 780

Trp Phe Asn Glu His Lys Thr Ile Val Asp Ile Ser Asp Cys Asp Ile
```

```
785                 790                 795                 800

Phe Lys Asn Arg Val Gly Gln Val Ala Arg Leu Ile Pro Val Phe Phe
                805                 810                 815

Asp Lys Lys Phe Lys Asp His Ser Gln Pro Phe Tyr Arg Tyr Asp Phe
            820                 825                 830

Asn Val Gly Asn Val Ser Lys Pro Thr Glu Ala Asn Tyr Leu Ser Lys
        835                 840                 845

Gly Lys Arg Glu Glu Leu Phe Lys Ser Tyr Gln Asn Lys Phe Lys Asn
    850                 855                 860

Asn Ile Pro Ala Glu Lys Thr Lys Glu Tyr Arg Glu Tyr Lys Asn Phe
865                 870                 875                 880

Ser Leu Trp Lys Lys Phe Glu Arg Glu Leu Arg Leu Ile Lys Asn Gln
                885                 890                 895

Asp Ile Leu Ile Trp Leu Met Cys Lys Asn Leu Phe Asp Glu Lys Ile
            900                 905                 910

Lys Pro Lys Lys Asp Ile Leu Glu Pro Arg Ile Ala Val Ser Tyr Ile
        915                 920                 925

Lys Leu Asp Ser Leu Gln Thr Asn Thr Ser Thr Ala Gly Ser Leu Asn
    930                 935                 940

Ala Leu Ala Lys Val Val Pro Met Thr Leu Ala Ile His Ile Asp Ser
945                 950                 955                 960

Pro Lys Pro Lys Gly Lys Ala Gly Asn Asn Glu Lys Glu Asn Lys Glu
                965                 970                 975

Phe Thr Val Tyr Ile Lys Glu Glu Gly Thr Lys Leu Leu Lys Trp Gly
            980                 985                 990

Asn Phe Lys Thr Leu Leu Ala Asp  Arg Arg Ile Lys Gly  Leu Phe Ser
        995                 1000                1005

Tyr Ile  Glu His Asp Asp Ile  Asp Leu Lys Gln His  Pro Leu Thr
    1010                1015                1020

Lys Arg  Arg Val Asp Leu Glu  Leu Asp Leu Tyr Gln  Thr Cys Arg
    1025                1030                1035

Ile Asp  Ile Phe Gln Gln Thr  Leu Gly Leu Glu Ala  Gln Leu Leu
    1040                1045                1050

Asp Lys  Tyr Ser Asp Leu Asn  Thr Asp Asn Phe Tyr  Gln Met Leu
    1055                1060                1065

Ile Gly  Trp Arg Lys Lys Glu  Gly Ile Pro Arg Asn  Ile Lys Glu
    1070                1075                1080

Asp Thr  Asp Phe Leu Lys Asp  Val Arg Asn Ala Phe  Ser His Asn
    1085                1090                1095

Gln Tyr  Pro Asp Ser Lys Lys  Ile Ala Phe Arg Arg  Ile Arg Lys
    1100                1105                1110

Phe Asn  Pro Lys Glu Leu Ile  Leu Glu Glu Glu Glu  Gly Leu Gly
    1115                1120                1125

Ile Ala  Thr Gln Met Tyr Lys  Glu Val Glu Lys Val  Val Asn Arg
    1130                1135                1140

Ile Lys  Arg Ile Glu Leu Phe  Asp
    1145                1150
```

<210> SEQ ID NO 41
<211> LENGTH: 1322
<212> TYPE: PRT
<213> ORGANISM: Artificial Sequence
<220> FEATURE:
<223> OTHER INFORMATION: Chemically synthesized

<400> SEQUENCE: 41

Met Ser Lys Glu Cys Lys Lys Gln Arg Gln Glu Lys Lys Arg Arg Leu
1               5                   10                  15

Gln Lys Ala Asn Phe Ser Ile Ser Leu Thr Gly Lys His Val Phe Gly
            20                  25                  30

Ala Tyr Phe Asn Met Ala Arg Thr Asn Phe Val Lys Thr Ile Asn Tyr
        35                  40                  45

Ile Leu Pro Ile Ala Gly Val Arg Gly Asn Tyr Ser Glu Asn Gln Ile
    50                  55                  60

Asn Lys Met Leu His Ala Leu Phe Leu Ile Gln Ala Gly Arg Asn Glu
65                  70                  75                  80

Glu Leu Thr Thr Glu Gln Lys Gln Trp Glu Lys Lys Leu Arg Leu Asn
                85                  90                  95

Pro Glu Gln Gln Thr Lys Phe Gln Lys Leu Leu Phe Lys His Phe Pro
            100                 105                 110

Val Leu Gly Pro Met Met Ala Asp Val Ala Asp His Lys Ala Tyr Leu
        115                 120                 125

Asn Lys Lys Lys Ser Thr Val Gln Thr Glu Asp Glu Thr Phe Ala Met
    130                 135                 140

Leu Lys Gly Val Ser Leu Ala Asp Cys Leu Asp Ile Ile Cys Leu Met
145                 150                 155                 160

Ala Asp Thr Leu Thr Glu Cys Arg Asn Phe Tyr Thr His Lys Asp Pro
                165                 170                 175

Tyr Asn Lys Pro Ser Gln Leu Ala Asp Gln Tyr Leu His Gln Glu Met
            180                 185                 190

Ile Ala Lys Lys Leu Asp Lys Val Val Val Ala Ser Arg Arg Ile Leu
        195                 200                 205

Lys Asp Arg Glu Gly Leu Ser Val Asn Glu Val Glu Phe Leu Thr Gly
    210                 215                 220

Ile Asp His Leu His Gln Glu Val Leu Lys Asp Glu Phe Gly Asn Ala
225                 230                 235                 240

Lys Val Lys Asp Gly Lys Val Met Lys Thr Phe Val Glu Tyr Asp Asp
                245                 250                 255

Phe Tyr Phe Lys Ile Ser Gly Lys Arg Leu Val Asn Gly Tyr Thr Val
            260                 265                 270

Thr Thr Lys Asp Asp Lys Pro Val Asn Val Asn Thr Met Leu Pro Ala
        275                 280                 285

Leu Ser Asp Phe Gly Leu Leu Tyr Phe Cys Val Leu Phe Leu Ser Lys
    290                 295                 300

Pro Tyr Ala Lys Leu Phe Ile Asp Glu Val Arg Leu Phe Glu Tyr Ser
305                 310                 315                 320

Pro Phe Asp Asp Lys Glu Asn Met Ile Met Ser Glu Met Leu Ser Ile
                325                 330                 335

Tyr Arg Ile Arg Thr Pro Arg Leu His Lys Ile Asp Ser His Asp Ser
            340                 345                 350

Lys Ala Thr Leu Ala Met Asp Ile Phe Gly Glu Leu Arg Arg Cys Pro
        355                 360                 365

Met Glu Leu Tyr Asn Leu Leu Asp Lys Asn Ala Gly Gln Pro Phe Phe
    370                 375                 380

His Asp Glu Val Lys His Pro Asn Ser His Thr Pro Asp Val Ser Lys
385                 390                 395                 400

Arg Leu Arg Tyr Asp Asp Arg Phe Pro Thr Leu Ala Leu Arg Tyr Ile
                405                 410                 415

```
Asp Glu Thr Glu Leu Phe Lys Arg Ile Arg Phe Gln Leu Gln Leu Gly
            420                 425                 430

Ser Phe Arg Tyr Lys Phe Tyr Asp Lys Glu Asn Cys Ile Asp Gly Arg
        435                 440                 445

Val Arg Val Arg Arg Ile Gln Lys Glu Ile Asn Gly Tyr Gly Arg Met
    450                 455                 460

Gln Glu Val Ala Asp Lys Arg Met Asp Lys Trp Gly Asp Leu Ile Gln
465                 470                 475                 480

Lys Arg Glu Glu Arg Ser Val Lys Leu Glu His Glu Glu Leu Tyr Ile
                485                 490                 495

Asn Leu Asp Gln Phe Leu Glu Asp Thr Ala Asp Ser Thr Pro Tyr Val
            500                 505                 510

Thr Asp Arg Arg Pro Ala Tyr Asn Ile His Ala Asn Arg Ile Gly Leu
        515                 520                 525

Tyr Trp Glu Asp Ser Gln Asn Pro Lys Gln Tyr Lys Val Phe Asp Glu
    530                 535                 540

Asn Gly Met Tyr Ile Pro Glu Leu Val Val Thr Glu Asp Lys Lys Ala
545                 550                 555                 560

Pro Ile Lys Met Pro Ala Pro Arg Cys Ala Leu Ser Val Tyr Asp Leu
                565                 570                 575

Pro Ala Met Leu Phe Tyr Glu Tyr Leu Arg Glu Gln Gln Asp Asn Glu
            580                 585                 590

Phe Pro Ser Ala Glu Gln Val Ile Ile Glu Tyr Glu Asp Asp Tyr Arg
        595                 600                 605

Lys Phe Phe Lys Ala Val Ala Glu Gly Lys Leu Lys Pro Phe Lys Arg
    610                 615                 620

Pro Lys Glu Phe Arg Asp Phe Leu Lys Lys Glu Tyr Pro Lys Leu Arg
625                 630                 635                 640

Met Ala Asp Ile Pro Lys Lys Leu Gln Leu Phe Leu Cys Ser His Gly
                645                 650                 655

Leu Cys Tyr Asn Asn Lys Pro Glu Thr Val Tyr Glu Arg Leu Asp Arg
            660                 665                 670

Leu Thr Leu Gln His Leu Glu Glu Arg Glu Leu His Ile Gln Asn Arg
        675                 680                 685

Leu Glu His Tyr Gln Lys Asp Arg Asp Met Ile Gly Asn Lys Asp Asn
    690                 695                 700

Gln Tyr Gly Lys Lys Ser Phe Ser Asp Val Arg His Gly Ala Leu Ala
705                 710                 715                 720

Arg Tyr Leu Ala Gln Ser Met Met Glu Trp Gln Pro Thr Lys Leu Lys
                725                 730                 735

Asp Lys Glu Lys Gly His Asp Lys Leu Thr Gly Leu Asn Tyr Asn Val
            740                 745                 750

Leu Thr Ala Tyr Leu Ala Thr Tyr Gly His Pro Gln Val Pro Glu Glu
        755                 760                 765

Gly Phe Thr Pro Arg Thr Leu Glu Gln Val Leu Ile Asn Ala His Leu
    770                 775                 780

Ile Gly Gly Ser Asn Pro His Pro Phe Ile Asn Lys Val Leu Ala Leu
785                 790                 795                 800

Gly Asn Arg Asn Ile Glu Glu Leu Tyr Leu His Tyr Leu Glu Glu Glu
                805                 810                 815

Leu Lys His Ile Arg Ser Arg Ile Gln Ser Leu Ser Ser Asn Pro Ser
            820                 825                 830
```

```
Asp Lys Ala Leu Ser Ala Leu Pro Phe Ile His His Asp Arg Met Arg
        835                 840                 845

Tyr His Glu Arg Thr Ser Glu Glu Met Met Ala Leu Ala Ala Arg Tyr
    850                 855                 860

Thr Thr Ile Gln Leu Pro Asp Gly Leu Phe Thr Pro Tyr Ile Leu Glu
865                 870                 875                 880

Ile Leu Gln Lys His Tyr Thr Glu Asn Ser Asp Leu Gln Asn Ala Leu
                885                 890                 895

Ser Gln Asp Val Pro Val Lys Leu Asn Pro Thr Cys Asn Ala Ala Tyr
            900                 905                 910

Leu Ile Thr Leu Phe Tyr Gln Thr Val Leu Lys Asp Asn Ala Gln Pro
        915                 920                 925

Phe Tyr Leu Ser Asp Lys Thr Tyr Thr Arg Asn Lys Asp Gly Glu Lys
    930                 935                 940

Ala Glu Ser Phe Ser Phe Lys Arg Ala Tyr Glu Leu Phe Ser Val Leu
945                 950                 955                 960

Asn Asn Asn Lys Lys Asp Thr Phe Pro Phe Glu Met Ile Pro Leu Phe
                965                 970                 975

Leu Thr Ser Asp Glu Ile Gln Glu Arg Leu Ser Ala Lys Leu Leu Asp
            980                 985                 990

Gly Asp Gly Asn Pro Val Pro Glu  Val Gly Glu Lys Gly  Lys Pro Ala
        995                 1000                1005

Thr Asp  Ser Gln Gly Asn Thr  Ile Trp Lys Arg Arg  Ile Tyr Ser
    1010                1015                1020

Glu Val  Asp Asp Tyr Ala Glu  Lys Leu Thr Asp Arg  Asp Met Lys
    1025                1030                1035

Ile Ser  Phe Lys Gly Glu Trp  Glu Lys Leu Pro Arg  Trp Lys Gln
    1040                1045                1050

Asp Lys  Ile Ile Lys Arg Arg  Asp Glu Thr Arg Arg  Gln Met Arg
    1055                1060                1065

Asp Glu  Leu Leu Gln Arg Met  Pro Arg Tyr Ile Arg  Asp Ile Lys
    1070                1075                1080

Asp Asn  Glu Arg Thr Leu Arg  Arg Tyr Lys Thr Gln  Asp Met Val
    1085                1090                1095

Leu Phe  Leu Leu Ala Glu Lys  Met Phe Thr Asn Ile  Ile Ser Glu
    1100                1105                1110

Gln Ser  Ser Glu Phe Asn Trp  Lys Gln Met Arg Leu  Ser Lys Val
    1115                1120                1125

Cys Asn  Glu Ala Phe Leu Arg  Gln Thr Leu Thr Phe  Arg Val Pro
    1130                1135                1140

Val Thr  Val Gly Glu Thr Thr  Ile Tyr Val Glu Gln  Glu Asn Met
    1145                1150                1155

Ser Leu  Lys Asn Tyr Gly Glu  Phe Tyr Arg Phe Leu  Thr Asp Asp
    1160                1165                1170

Arg Leu  Met Ser Leu Leu Asn  Asn Ile Val Glu Thr  Leu Lys Pro
    1175                1180                1185

Asn Glu  Asn Gly Asp Leu Val  Ile Arg His Thr Asp  Leu Met Ser
    1190                1195                1200

Glu Leu  Ala Ala Tyr Asp Gln  Tyr Arg Ser Thr Ile  Phe Met Leu
    1205                1210                1215

Ile Gln  Ser Ile Glu Asn Leu  Ile Ile Thr Asn Asn  Ala Val Leu
    1220                1225                1230

Asp Asp  Pro Asp Ala Asp Gly  Phe Trp Val Arg Glu  Asp Leu Pro
```

```
    1235                1240                1245

Lys Arg  Asn Asn Phe Ala Ser  Leu Leu Glu Leu Ile  Asn Gln Leu
    1250                1255                1260

Asn Asn  Val Glu Leu Thr Asp  Asp Glu Arg Lys Leu  Leu Val Ala
    1265                1270                1275

Ile Arg  Asn Ala Phe Ser His  Asn Ser Tyr Asn Ile  Asp Phe Ser
    1280                1285                1290

Leu Ile  Lys Asp Val Lys His  Leu Pro Glu Val Ala  Lys Gly Ile
    1295                1300                1305

Leu Gln  His Leu Gln Ser Met  Leu Gly Val Glu Ile  Thr Lys
    1310                1315                1320


<210> SEQ ID NO 42
<211> LENGTH: 1095
<212> TYPE: PRT
<213> ORGANISM: Artificial Sequence
<220> FEATURE:
<223> OTHER INFORMATION: Chemically synthesized

<400> SEQUENCE: 42

Met Glu Lys Pro Leu Leu Pro Asn Val Tyr Thr Leu Lys His Lys Phe
1               5                   10                  15

Phe Trp Gly Ala Phe Leu Asn Ile Ala Arg His Asn Ala Phe Ile Thr
            20                  25                  30

Ile Cys His Ile Asn Glu Gln Leu Gly Leu Lys Thr Pro Ser Asn Asp
        35                  40                  45

Asp Lys Ile Val Asp Val Val Cys Glu Thr Trp Asn Asn Ile Leu Asn
    50                  55                  60

Asn Asp His Asp Leu Leu Lys Lys Ser Gln Leu Thr Glu Leu Ile Leu
65                  70                  75                  80

Lys His Phe Pro Phe Leu Thr Ala Met Cys Tyr His Pro Pro Lys Lys
                85                  90                  95

Glu Gly Lys Lys Lys Gly His Gln Lys Glu Gln Gln Lys Glu Lys Glu
            100                 105                 110

Ser Glu Ala Gln Ser Gln Ala Glu Ala Leu Asn Pro Ser Lys Leu Ile
        115                 120                 125

Glu Ala Leu Glu Ile Leu Val Asn Gln Leu His Ser Leu Arg Asn Tyr
    130                 135                 140

Tyr Ser His Tyr Lys His Lys Lys Pro Asp Ala Glu Lys Asp Ile Phe
145                 150                 155                 160

Lys His Leu Tyr Lys Ala Phe Asp Ala Ser Leu Arg Met Val Lys Glu
                165                 170                 175

Asp Tyr Lys Ala His Phe Thr Val Asn Leu Thr Arg Asp Phe Ala His
            180                 185                 190

Leu Asn Arg Lys Gly Lys Asn Lys Gln Asp Asn Pro Asp Phe Asn Arg
        195                 200                 205

Tyr Arg Phe Glu Lys Asp Gly Phe Phe Thr Glu Ser Gly Leu Leu Phe
    210                 215                 220

Phe Thr Asn Leu Phe Leu Asp Lys Arg Asp Ala Tyr Trp Met Leu Lys
225                 230                 235                 240

Lys Val Ser Gly Phe Lys Ala Ser His Lys Gln Arg Glu Lys Met Thr
                245                 250                 255

Thr Glu Val Phe Cys Arg Ser Arg Ile Leu Leu Pro Lys Leu Arg Leu
            260                 265                 270

Glu Ser Arg Tyr Asp His Asn Gln Met Leu Leu Asp Met Leu Ser Glu
```

```
        275                 280                 285

Leu Ser Arg Cys Pro Lys Leu Leu Tyr Glu Lys Leu Ser Glu Glu Asn
    290                 295                 300

Lys Lys His Phe Gln Val Glu Ala Asp Gly Phe Leu Asp Glu Ile Glu
305                 310                 315                 320

Glu Glu Gln Asn Pro Phe Lys Asp Thr Leu Ile Arg His Gln Asp Arg
                325                 330                 335

Phe Pro Tyr Phe Ala Leu Arg Tyr Leu Asp Leu Asn Glu Ser Phe Lys
            340                 345                 350

Ser Ile Arg Phe Gln Val Asp Leu Gly Thr Tyr His Tyr Cys Ile Tyr
        355                 360                 365

Asp Lys Lys Ile Gly Asp Glu Gln Glu Lys Arg His Leu Thr Arg Thr
    370                 375                 380

Leu Leu Ser Phe Gly Arg Leu Gln Asp Phe Thr Glu Ile Asn Arg Pro
385                 390                 395                 400

Gln Glu Trp Lys Ala Leu Thr Lys Asp Leu Asp Tyr Lys Glu Thr Ser
                405                 410                 415

Asn Gln Pro Phe Ile Ser Lys Thr Thr Pro His Tyr His Ile Thr Asp
            420                 425                 430

Asn Lys Ile Gly Phe Arg Leu Gly Thr Ser Lys Glu Leu Tyr Pro Ser
        435                 440                 445

Leu Glu Ile Lys Asp Gly Ala Asn Arg Ile Ala Lys Tyr Pro Tyr Asn
    450                 455                 460

Ser Gly Phe Val Ala His Ala Phe Ile Ser Val His Glu Leu Leu Pro
465                 470                 475                 480

Leu Met Phe Tyr Gln His Leu Thr Gly Lys Ser Glu Asp Leu Leu Lys
                485                 490                 495

Glu Thr Val Arg His Ile Gln Arg Ile Tyr Lys Asp Phe Glu Glu Glu
            500                 505                 510

Arg Ile Asn Thr Ile Glu Asp Leu Glu Lys Ala Asn Gln Gly Arg Leu
        515                 520                 525

Pro Leu Gly Ala Phe Pro Lys Gln Met Leu Gly Leu Leu Gln Asn Lys
    530                 535                 540

Gln Pro Asp Leu Ser Glu Lys Ala Lys Ile Lys Ile Glu Lys Leu Ile
545                 550                 555                 560

Ala Glu Thr Lys Leu Leu Ser His Arg Leu Asn Thr Lys Leu Lys Ser
                565                 570                 575

Ser Pro Lys Leu Gly Lys Arg Arg Glu Lys Leu Ile Lys Thr Gly Val
            580                 585                 590

Leu Ala Asp Trp Leu Val Lys Asp Phe Met Arg Phe Gln Pro Val Ala
        595                 600                 605

Tyr Asp Ala Gln Asn Gln Pro Ile Lys Ser Ser Lys Ala Asn Ser Thr
    610                 615                 620

Glu Phe Trp Phe Ile Arg Arg Ala Leu Ala Leu Tyr Gly Gly Glu Lys
625                 630                 635                 640

Asn Arg Leu Glu Gly Tyr Phe Lys Gln Thr Asn Leu Ile Gly Asn Thr
                645                 650                 655

Asn Pro His Pro Phe Leu Asn Lys Phe Asn Trp Lys Ala Cys Arg Asn
            660                 665                 670

Leu Val Asp Phe Tyr Gln Gln Tyr Leu Glu Gln Arg Glu Lys Phe Leu
        675                 680                 685

Glu Ala Ile Lys Asn Gln Pro Trp Glu Pro Tyr Gln Tyr Cys Leu Leu
    690                 695                 700
```

```
Leu Lys Ile Pro Lys Glu Asn Arg Lys Asn Leu Val Lys Gly Trp Glu
705                 710                 715                 720

Gln Gly Gly Ile Ser Leu Pro Arg Gly Leu Phe Thr Glu Ala Ile Arg
                725                 730                 735

Glu Thr Leu Ser Glu Asp Leu Met Leu Ser Lys Pro Ile Arg Lys Glu
            740                 745                 750

Ile Lys Lys His Gly Arg Val Gly Phe Ile Ser Arg Ala Ile Thr Leu
        755                 760                 765

Tyr Phe Lys Glu Lys Tyr Gln Asp Lys His Gln Ser Phe Tyr Asn Leu
    770                 775                 780

Ser Tyr Lys Leu Glu Ala Lys Ala Pro Leu Leu Lys Arg Glu Glu His
785                 790                 795                 800

Tyr Glu Tyr Trp Gln Gln Asn Lys Pro Gln Ser Pro Thr Glu Ser Gln
                805                 810                 815

Arg Leu Glu Leu His Thr Ser Asp Arg Trp Lys Asp Tyr Leu Leu Tyr
            820                 825                 830

Lys Arg Trp Gln His Leu Glu Lys Lys Leu Arg Leu Tyr Arg Asn Gln
        835                 840                 845

Asp Val Met Leu Trp Leu Met Thr Leu Glu Leu Thr Lys Asn His Phe
    850                 855                 860

Lys Glu Leu Asn Leu Asn Tyr His Gln Leu Lys Leu Glu Asn Leu Ala
865                 870                 875                 880

Val Asn Val Gln Glu Ala Asp Ala Lys Leu Asn Pro Leu Asn Gln Thr
                885                 890                 895

Leu Pro Met Val Leu Pro Val Lys Val Tyr Pro Ala Thr Ala Phe Gly
            900                 905                 910

Glu Val Gln Tyr His Lys Thr Pro Ile Arg Thr Val Tyr Ile Arg Glu
        915                 920                 925

Glu His Thr Lys Ala Leu Lys Met Gly Asn Phe Lys Ala Leu Val Lys
    930                 935                 940

Asp Arg Arg Leu Asn Gly Leu Phe Ser Phe Ile Lys Glu Glu Asn Asp
945                 950                 955                 960

Thr Gln Lys His Pro Ile Ser Gln Leu Arg Leu Arg Arg Glu Leu Glu
                965                 970                 975

Ile Tyr Gln Ser Leu Arg Val Asp Ala Phe Lys Glu Thr Leu Ser Leu
            980                 985                 990

Glu Glu Lys Leu Leu Asn Lys His  Thr Ser Leu Ser Ser  Leu Glu Asn
        995                 1000                1005

Glu Phe  Arg Ala Leu Leu Glu  Glu Trp Lys Lys Glu  Tyr Ala Ala
    1010                 1015                 1020

Ser Ser  Met Val Thr Asp Glu  His Ile Ala Phe Ile  Ala Ser Val
    1025                 1030                 1035

Arg Asn  Ala Phe Cys His Asn  Gln Tyr Pro Phe Tyr  Lys Glu Ala
    1040                 1045                 1050

Leu His  Ala Pro Ile Pro Leu  Phe Thr Val Ala Gln  Pro Thr Thr
    1055                 1060                 1065

Glu Glu  Lys Asp Gly Leu Gly  Ile Ala Glu Ala Leu  Leu Lys Val
    1070                 1075                 1080

Leu Arg  Glu Tyr Cys Glu Ile  Val Lys Ser Gln Ile
    1085                 1090                 1095
```

<210> SEQ ID NO 43
<211> LENGTH: 1285

<212> TYPE: PRT
<213> ORGANISM: Artificial Sequence
<220> FEATURE:
<223> OTHER INFORMATION: Chemically synthesized

<400> SEQUENCE: 43

```
Met Gln Ile Gly Lys Val Gln Gly Arg Thr Ile Ser Glu Phe Gly Asp
1               5                   10                  15

Pro Ala Gly Gly Leu Lys Arg Lys Ile Ser Thr Asp Gly Lys Asn Arg
            20                  25                  30

Lys Glu Leu Pro Ala His Leu Ser Ser Asp Pro Lys Ala Leu Ile Gly
        35                  40                  45

Gln Trp Ile Ser Gly Ile Asp Lys Ile Tyr Arg Lys Pro Asp Ser Arg
    50                  55                  60

Lys Ser Asp Gly Lys Ala Ile His Ser Pro Thr Pro Ser Lys Met Gln
65                  70                  75                  80

Phe Asp Ala Arg Asp Asp Leu Gly Glu Ala Phe Trp Lys Leu Val Ser
                85                  90                  95

Glu Ala Gly Leu Ala Gln Asp Ser Asp Tyr Asp Gln Phe Lys Arg Arg
            100                 105                 110

Leu His Pro Tyr Gly Asp Lys Phe Gln Pro Ala Asp Ser Gly Ala Lys
        115                 120                 125

Leu Lys Phe Glu Ala Asp Pro Pro Glu Pro Gln Ala Phe His Gly Arg
    130                 135                 140

Trp Tyr Gly Ala Met Ser Lys Arg Gly Asn Asp Ala Lys Glu Leu Ala
145                 150                 155                 160

Ala Ala Leu Tyr Glu His Leu His Val Asp Glu Lys Arg Ile Asp Gly
                165                 170                 175

Gln Pro Lys Arg Asn Pro Lys Thr Asp Lys Phe Ala Pro Gly Leu Val
            180                 185                 190

Val Ala Arg Ala Leu Gly Ile Glu Ser Ser Val Leu Pro Arg Gly Met
        195                 200                 205

Ala Arg Leu Ala Arg Asn Trp Gly Glu Glu Glu Ile Gln Thr Tyr Phe
    210                 215                 220

Val Val Asp Val Ala Ala Ser Val Lys Glu Val Ala Lys Ala Ala Val
225                 230                 235                 240

Ser Ala Ala Gln Ala Phe Asp Pro Pro Arg Gln Val Ser Gly Arg Ser
                245                 250                 255

Leu Ser Pro Lys Val Gly Phe Ala Leu Ala Glu His Leu Glu Arg Val
            260                 265                 270

Thr Gly Ser Lys Arg Cys Ser Phe Asp Pro Ala Ala Gly Pro Ser Val
        275                 280                 285

Leu Ala Leu His Asp Glu Val Lys Lys Thr Tyr Lys Arg Leu Cys Ala
    290                 295                 300

Arg Gly Lys Asn Ala Ala Arg Ala Phe Pro Ala Asp Lys Thr Glu Leu
305                 310                 315                 320

Leu Ala Leu Met Arg His Thr His Glu Asn Arg Val Arg Asn Gln Met
                325                 330                 335

Val Arg Met Gly Arg Val Ser Glu Tyr Arg Gly Gln Gln Ala Gly Asp
            340                 345                 350

Leu Ala Gln Ser His Tyr Trp Thr Ser Ala Gly Gln Thr Glu Ile Lys
        355                 360                 365

Glu Ser Glu Ile Phe Val Arg Leu Trp Val Gly Ala Phe Ala Leu Ala
    370                 375                 380
```

Gly Arg Ser Met Lys Ala Trp Ile Asp Pro Met Gly Lys Ile Val Asn
385 390 395 400

Thr Glu Lys Asn Asp Arg Asp Leu Thr Ala Ala Val Asn Ile Arg Gln
405 410 415

Val Ile Ser Asn Lys Glu Met Val Ala Glu Ala Met Ala Arg Arg Gly
420 425 430

Ile Tyr Phe Gly Glu Thr Pro Glu Leu Asp Arg Leu Gly Ala Glu Gly
435 440 445

Asn Glu Gly Phe Val Phe Ala Leu Leu Arg Tyr Leu Arg Gly Cys Arg
450 455 460

Asn Gln Thr Phe His Leu Gly Ala Arg Ala Gly Phe Leu Lys Glu Ile
465 470 475 480

Arg Lys Glu Leu Glu Lys Thr Arg Trp Gly Lys Ala Lys Glu Ala Glu
485 490 495

His Val Val Leu Thr Asp Lys Thr Val Ala Ala Ile Arg Ala Ile Ile
500 505 510

Asp Asn Asp Ala Lys Ala Leu Gly Ala Arg Leu Leu Ala Asp Leu Ser
515 520 525

Gly Ala Phe Val Ala His Tyr Ala Ser Lys Glu His Phe Ser Thr Leu
530 535 540

Tyr Ser Glu Ile Val Lys Ala Val Lys Asp Ala Pro Glu Val Ser Ser
545 550 555 560

Gly Leu Pro Arg Leu Lys Leu Leu Leu Lys Arg Ala Asp Gly Val Arg
565 570 575

Gly Tyr Val His Gly Leu Arg Asp Thr Arg Lys His Ala Phe Ala Thr
580 585 590

Lys Leu Pro Pro Pro Pro Ala Pro Arg Glu Leu Asp Asp Pro Ala Thr
595 600 605

Lys Ala Arg Tyr Ile Ala Leu Leu Arg Leu Tyr Asp Gly Pro Phe Arg
610 615 620

Ala Tyr Ala Ser Gly Ile Thr Gly Thr Ala Leu Ala Gly Pro Ala Ala
625 630 635 640

Arg Ala Lys Glu Ala Ala Thr Ala Leu Ala Gln Ser Val Asn Val Thr
645 650 655

Lys Ala Tyr Ser Asp Val Met Glu Gly Arg Ser Ser Arg Leu Arg Pro
660 665 670

Pro Asn Asp Gly Glu Thr Leu Arg Glu Tyr Leu Ser Ala Leu Thr Gly
675 680 685

Glu Thr Ala Thr Glu Phe Arg Val Gln Ile Gly Tyr Glu Ser Asp Ser
690 695 700

Glu Asn Ala Arg Lys Gln Ala Glu Phe Ile Glu Asn Tyr Arg Arg Asp
705 710 715 720

Met Leu Ala Phe Met Phe Glu Asp Tyr Ile Arg Ala Lys Gly Phe Asp
725 730 735

Trp Ile Leu Lys Ile Glu Pro Gly Ala Thr Ala Met Thr Arg Ala Pro
740 745 750

Val Leu Pro Glu Pro Ile Asp Thr Arg Gly Gln Tyr Glu His Trp Gln
755 760 765

Ala Ala Leu Tyr Leu Val Met His Phe Val Pro Ala Ser Asp Val Ser
770 775 780

Asn Leu Leu His Gln Leu Arg Lys Trp Glu Ala Leu Gln Gly Lys Tyr
785 790 795 800

Glu Leu Val Gln Asp Gly Asp Ala Thr Asp Gln Ala Asp Ala Arg Arg

```
                805                 810                 815

Glu Ala Leu Asp Leu Val Lys Arg Phe Arg Asp Val Leu Val Leu Phe
            820                 825                 830

Leu Lys Thr Gly Glu Ala Arg Phe Glu Gly Arg Ala Ala Pro Phe Asp
        835                 840                 845

Leu Lys Pro Phe Arg Ala Leu Phe Ala Asn Pro Ala Thr Phe Asp Arg
    850                 855                 860

Leu Phe Met Ala Thr Pro Thr Thr Ala Arg Pro Ala Glu Asp Asp Pro
865                 870                 875                 880

Glu Gly Asp Gly Ala Ser Glu Pro Glu Leu Arg Val Ala Arg Thr Leu
                885                 890                 895

Arg Gly Leu Arg Gln Ile Ala Arg Tyr Asn His Met Ala Val Leu Ser
            900                 905                 910

Asp Leu Phe Ala Lys His Lys Val Arg Asp Glu Glu Val Ala Arg Leu
        915                 920                 925

Ala Glu Ile Glu Asp Glu Thr Gln Glu Lys Ser Gln Ile Val Ala Ala
    930                 935                 940

Gln Glu Leu Arg Thr Asp Leu His Asp Lys Val Met Lys Cys His Pro
945                 950                 955                 960

Lys Thr Ile Ser Pro Glu Glu Arg Gln Ser Tyr Ala Ala Ala Ile Lys
                965                 970                 975

Thr Ile Glu Glu His Arg Phe Leu Val Gly Arg Val Tyr Leu Gly Asp
            980                 985                 990

His Leu Arg Leu His Arg Leu Met  Met Asp Val Ile Gly  Arg Leu Ile
        995                 1000                1005

Asp Tyr  Ala Gly Ala Tyr Glu  Arg Asp Thr Gly Thr  Phe Leu Ile
    1010                1015                1020

Asn Ala  Ser Lys Gln Leu Gly  Ala Gly Ala Asp Trp  Ala Val Thr
    1025                1030                1035

Ile Ala  Gly Ala Ala Asn Thr  Asp Ala Arg Thr Gln  Thr Arg Lys
    1040                1045                1050

Asp Leu  Ala His Phe Asn Val  Leu Asp Arg Ala Asp  Gly Thr Pro
    1055                1060                1065

Asp Leu  Thr Ala Leu Val Asn  Arg Ala Arg Glu Met  Met Ala Tyr
    1070                1075                1080

Asp Arg  Lys Arg Lys Asn Ala  Val Pro Arg Ser Ile  Leu Asp Met
    1085                1090                1095

Leu Ala  Arg Leu Gly Leu Thr  Leu Lys Trp Gln Met  Lys Asp His
    1100                1105                1110

Leu Leu  Gln Asp Ala Thr Ile  Thr Gln Ala Ala Ile  Lys His Leu
    1115                1120                1125

Asp Lys  Val Arg Leu Thr Val  Gly Gly Pro Ala Ala  Val Thr Glu
    1130                1135                1140

Ala Arg  Phe Ser Gln Asp Tyr  Leu Gln Met Val Ala  Ala Val Phe
    1145                1150                1155

Asn Gly  Ser Val Gln Asn Pro  Lys Pro Arg Arg Arg  Asp Asp Gly
    1160                1165                1170

Asp Ala  Trp His Lys Pro Pro  Lys Pro Ala Thr Ala  Gln Ser Gln
    1175                1180                1185

Pro Asp  Gln Lys Pro Pro Asn  Lys Ala Pro Ser Ala  Gly Ser Arg
    1190                1195                1200

Leu Pro  Pro Pro Gln Val Gly  Glu Val Tyr Glu Gly  Val Val Val
    1205                1210                1215
```

```
Lys Val  Ile Asp Thr Gly Ser  Leu Gly Phe Leu Ala  Val Glu Gly
    1220                 1225                 1230

Val Ala  Gly Asn Ile Gly Leu  His Ile Ser Arg Leu  Arg Arg Ile
    1235                 1240                 1245

Arg Glu  Asp Ala Ile Ile Val  Gly Arg Arg Tyr Arg  Phe Arg Val
    1250                 1255                 1260

Glu Ile  Tyr Val Pro Pro Lys  Ser Asn Thr Ser Lys  Leu Asn Ala
    1265                 1270                 1275

Ala Asp  Leu Val Arg Ile Asp
    1280                 1285


<210> SEQ ID NO 44
<211> LENGTH: 1285
<212> TYPE: PRT
<213> ORGANISM: Artificial Sequence
<220> FEATURE:
<223> OTHER INFORMATION: Chemically synthesized

<400> SEQUENCE: 44

Met Gln Ile Gly Lys Val Gln Gly Arg Thr Ile Ser Glu Phe Gly Asp
1               5                   10                  15

Pro Ala Gly Gly Leu Lys Arg Lys Ile Ser Thr Asp Gly Lys Asn Arg
            20                  25                  30

Lys Glu Leu Pro Ala His Leu Ser Ser Asp Pro Lys Ala Leu Ile Gly
        35                  40                  45

Gln Trp Ile Ser Gly Ile Asp Lys Ile Tyr Arg Lys Pro Asp Ser Arg
    50                  55                  60

Lys Ser Asp Gly Lys Ala Ile His Ser Pro Thr Pro Ser Lys Met Gln
65                  70                  75                  80

Phe Asp Ala Arg Asp Asp Leu Gly Glu Ala Phe Trp Lys Leu Val Ser
                85                  90                  95

Glu Ala Gly Leu Ala Gln Asp Ser Asp Tyr Asp Gln Phe Lys Arg Arg
            100                 105                 110

Leu His Pro Tyr Gly Asp Lys Phe Gln Pro Ala Asp Ser Gly Ala Lys
        115                 120                 125

Leu Lys Phe Glu Ala Asp Pro Pro Glu Pro Gln Ala Phe His Gly Arg
    130                 135                 140

Trp Tyr Gly Ala Met Ser Lys Arg Gly Asn Asp Ala Lys Glu Leu Ala
145                 150                 155                 160

Ala Ala Leu Tyr Glu His Leu His Val Asp Glu Lys Arg Ile Asp Gly
                165                 170                 175

Gln Pro Lys Arg Asn Pro Lys Thr Asp Lys Phe Ala Pro Gly Leu Val
            180                 185                 190

Val Ala Arg Ala Leu Gly Ile Glu Ser Ser Val Leu Pro Arg Gly Met
        195                 200                 205

Ala Arg Leu Ala Arg Asn Trp Gly Glu Glu Glu Ile Gln Thr Tyr Phe
    210                 215                 220

Val Val Asp Val Ala Ala Ser Val Lys Glu Val Ala Lys Ala Ala Val
225                 230                 235                 240

Ser Ala Ala Gln Ala Phe Asp Pro Pro Arg Gln Val Ser Gly Arg Ser
                245                 250                 255

Leu Ser Pro Lys Val Gly Phe Ala Leu Ala Glu His Leu Glu Arg Val
            260                 265                 270

Thr Gly Ser Lys Arg Cys Ser Phe Asp Pro Ala Ala Gly Pro Ser Val
        275                 280                 285
```

```
Leu Ala Leu His Asp Glu Val Lys Lys Thr Tyr Lys Arg Leu Cys Ala
    290                 295                 300

Arg Gly Lys Asn Ala Ala Arg Ala Phe Pro Ala Asp Lys Thr Glu Leu
305                 310                 315                 320

Leu Ala Leu Met Arg His Thr His Glu Asn Arg Val Arg Asn Gln Met
                325                 330                 335

Val Arg Met Gly Arg Val Ser Glu Tyr Arg Gly Gln Gln Ala Gly Asp
            340                 345                 350

Leu Ala Gln Ser His Tyr Trp Thr Ser Ala Gly Gln Thr Glu Ile Lys
        355                 360                 365

Glu Ser Glu Ile Phe Val Arg Leu Trp Val Gly Ala Phe Ala Leu Ala
    370                 375                 380

Gly Arg Ser Met Lys Ala Trp Ile Asp Pro Met Gly Lys Ile Val Asn
385                 390                 395                 400

Thr Glu Lys Asn Asp Arg Asp Leu Thr Ala Ala Val Asn Ile Arg Gln
                405                 410                 415

Val Ile Ser Asn Lys Glu Met Val Ala Glu Ala Met Ala Arg Arg Gly
            420                 425                 430

Ile Tyr Phe Gly Glu Thr Pro Glu Leu Asp Arg Leu Gly Ala Glu Gly
        435                 440                 445

Asn Glu Gly Phe Val Phe Ala Leu Leu Arg Tyr Leu Arg Gly Cys Arg
    450                 455                 460

Asn Gln Thr Phe His Leu Gly Ala Arg Ala Gly Phe Leu Lys Glu Ile
465                 470                 475                 480

Arg Lys Glu Leu Glu Lys Thr Arg Trp Gly Lys Ala Lys Glu Ala Glu
                485                 490                 495

His Val Val Leu Thr Asp Lys Thr Val Ala Ala Ile Arg Ala Ile Ile
            500                 505                 510

Asp Asn Asp Ala Lys Ala Leu Gly Ala Arg Leu Leu Ala Asp Leu Ser
        515                 520                 525

Gly Ala Phe Val Ala His Tyr Ala Ser Lys Glu His Phe Ser Thr Leu
    530                 535                 540

Tyr Ser Glu Ile Val Lys Ala Val Lys Asp Ala Pro Glu Val Ser Ser
545                 550                 555                 560

Gly Leu Pro Arg Leu Lys Leu Leu Leu Lys Arg Ala Asp Gly Val Arg
                565                 570                 575

Gly Tyr Val His Gly Leu Arg Asp Thr Arg Lys His Ala Phe Ala Thr
            580                 585                 590

Lys Leu Pro Pro Pro Pro Ala Pro Arg Glu Leu Asp Asp Pro Ala Thr
        595                 600                 605

Lys Ala Arg Tyr Ile Ala Leu Leu Arg Leu Tyr Asp Gly Pro Phe Arg
    610                 615                 620

Ala Tyr Ala Ser Gly Ile Thr Gly Thr Ala Leu Ala Gly Pro Ala Ala
625                 630                 635                 640

Arg Ala Lys Glu Ala Ala Thr Ala Leu Ala Gln Ser Val Asn Val Thr
                645                 650                 655

Lys Ala Tyr Ser Asp Val Met Glu Gly Arg Ser Ser Arg Leu Arg Pro
            660                 665                 670

Pro Asn Asp Gly Glu Thr Leu Arg Glu Tyr Leu Ser Ala Leu Thr Gly
        675                 680                 685

Glu Thr Ala Thr Glu Phe Arg Val Gln Ile Gly Tyr Glu Ser Asp Ser
    690                 695                 700
```

```
Glu Asn Ala Arg Lys Gln Ala Glu Phe Ile Glu Asn Tyr Arg Arg Asp
705                 710                 715                 720

Met Leu Ala Phe Met Phe Glu Asp Tyr Ile Arg Ala Lys Gly Phe Asp
                725                 730                 735

Trp Ile Leu Lys Ile Glu Pro Gly Ala Thr Ala Met Thr Arg Ala Pro
            740                 745                 750

Val Leu Pro Glu Pro Ile Asp Thr Arg Gly Gln Tyr Glu His Trp Gln
        755                 760                 765

Ala Ala Leu Tyr Leu Val Met His Phe Val Pro Ala Ser Asp Val Ser
    770                 775                 780

Asn Leu Leu His Gln Leu Arg Lys Trp Glu Ala Leu Gln Gly Lys Tyr
785                 790                 795                 800

Glu Leu Val Gln Asp Gly Asp Ala Thr Asp Gln Ala Asp Ala Arg Arg
                805                 810                 815

Glu Ala Leu Asp Leu Val Lys Arg Phe Arg Asp Val Leu Val Leu Phe
            820                 825                 830

Leu Lys Thr Gly Glu Ala Arg Phe Glu Gly Arg Ala Ala Pro Phe Asp
        835                 840                 845

Leu Lys Pro Phe Arg Ala Leu Phe Ala Asn Pro Ala Thr Phe Asp Arg
    850                 855                 860

Leu Phe Met Ala Thr Pro Thr Thr Ala Arg Pro Ala Glu Asp Asp Pro
865                 870                 875                 880

Glu Gly Asp Gly Ala Ser Glu Pro Glu Leu Arg Val Ala Arg Thr Leu
                885                 890                 895

Arg Gly Leu Arg Gln Ile Ala Arg Tyr Asn His Met Ala Val Leu Ser
            900                 905                 910

Asp Leu Phe Ala Lys His Lys Val Arg Asp Glu Glu Val Ala Arg Leu
        915                 920                 925

Ala Glu Ile Glu Asp Glu Thr Gln Glu Lys Ser Gln Ile Val Ala Ala
    930                 935                 940

Gln Glu Leu Arg Thr Asp Leu His Asp Lys Val Met Lys Cys His Pro
945                 950                 955                 960

Lys Thr Ile Ser Pro Glu Glu Arg Gln Ser Tyr Ala Ala Ala Ile Lys
                965                 970                 975

Thr Ile Glu Glu His Arg Phe Leu Val Gly Arg Val Tyr Leu Gly Asp
            980                 985                 990

His Leu Arg Leu His Arg Leu Met  Met Asp Val Ile Gly  Arg Leu Ile
        995                 1000                1005

Asp Tyr  Ala Gly Ala Tyr Glu  Arg Asp Thr Gly Thr  Phe Leu Ile
    1010                1015                1020

Asn Ala  Ser Lys Gln Leu Gly  Ala Gly Ala Asp Trp  Ala Val Thr
    1025                1030                1035

Ile Ala  Gly Ala Ala Asn Thr  Asp Ala Arg Thr Gln  Thr Arg Lys
    1040                1045                1050

Asp Leu  Ala His Phe Asn Val  Leu Asp Arg Ala Asp  Gly Thr Pro
    1055                1060                1065

Asp Leu  Thr Ala Leu Val Asn  Arg Ala Arg Glu Met  Met Ala Tyr
    1070                1075                1080

Asp Arg  Lys Arg Lys Asn Ala  Val Pro Arg Ser Ile  Leu Asp Met
    1085                1090                1095

Leu Ala  Arg Leu Gly Leu Thr  Leu Lys Trp Gln Met  Lys Asp His
    1100                1105                1110

Leu Leu  Gln Asp Ala Thr Ile  Thr Gln Ala Ala Ile  Lys His Leu
```

```
    1115                1120                1125

Asp Lys  Val Arg Leu Thr Val  Gly Gly Pro Ala Ala  Val Thr Glu
    1130                1135                1140

Ala Arg  Phe Ser Gln Asp Tyr  Leu Gln Met Val Ala  Ala Val Phe
    1145                1150                1155

Asn Gly  Ser Val Gln Asn Pro  Lys Pro Arg Arg Arg  Asp Asp Gly
    1160                1165                1170

Asp Ala  Trp His Lys Pro Pro  Lys Pro Ala Thr Ala  Gln Ser Gln
    1175                1180                1185

Pro Asp  Gln Lys Pro Pro Asn  Lys Ala Pro Ser Ala  Gly Ser Arg
    1190                1195                1200

Leu Pro  Pro Pro Gln Val Gly  Glu Val Tyr Glu Gly  Val Val Val
    1205                1210                1215

Lys Val  Ile Asp Thr Gly Ser  Leu Gly Phe Leu Ala  Val Glu Gly
    1220                1225                1230

Val Ala  Gly Asn Ile Gly Leu  His Ile Ser Arg Leu  Arg Arg Ile
    1235                1240                1245

Arg Glu  Asp Ala Ile Ile Val  Gly Arg Arg Tyr Arg  Phe Arg Val
    1250                1255                1260

Glu Ile  Tyr Val Pro Pro Lys  Ser Asn Thr Ser Lys  Leu Asn Ala
    1265                1270                1275

Ala Asp  Leu Val Arg Ile Asp
    1280                1285


<210> SEQ ID NO 45
<211> LENGTH: 1285
<212> TYPE: PRT
<213> ORGANISM: Artificial Sequence
<220> FEATURE:
<223> OTHER INFORMATION: Chemically synthesized

<400> SEQUENCE: 45

Met Gln Ile Gly Lys Val Gln Gly Arg Thr Ile Ser Glu Phe Gly Asp
1               5                   10                  15

Pro Ala Gly Gly Leu Lys Arg Lys Ile Ser Thr Asp Gly Lys Asn Arg
            20                  25                  30

Lys Glu Leu Pro Ala His Leu Ser Ser Asp Pro Lys Ala Leu Ile Gly
        35                  40                  45

Gln Trp Ile Ser Gly Ile Asp Lys Ile Tyr Arg Lys Pro Asp Ser Arg
    50                  55                  60

Lys Ser Asp Gly Lys Ala Ile His Ser Pro Thr Pro Ser Lys Met Gln
65                  70                  75                  80

Phe Asp Ala Arg Asp Asp Leu Gly Glu Ala Phe Trp Lys Leu Val Ser
                85                  90                  95

Glu Ala Gly Leu Ala Gln Asp Ser Asp Tyr Asp Gln Phe Lys Arg Arg
            100                 105                 110

Leu His Pro Tyr Gly Asp Lys Phe Gln Pro Ala Asp Ser Gly Ala Lys
        115                 120                 125

Leu Lys Phe Glu Ala Asp Pro Pro Glu Pro Gln Ala Phe His Gly Arg
    130                 135                 140

Trp Tyr Gly Ala Met Ser Lys Arg Gly Asn Asp Ala Lys Glu Leu Ala
145                 150                 155                 160

Ala Ala Leu Tyr Glu His Leu His Val Asp Glu Lys Arg Ile Asp Gly
                165                 170                 175

Gln Pro Lys Arg Asn Pro Lys Thr Asp Lys Phe Ala Pro Gly Leu Val
```

```
            180                 185                 190

Val Ala Arg Ala Leu Gly Ile Glu Ser Ser Val Leu Pro Arg Gly Met
        195                 200                 205

Ala Arg Leu Ala Arg Asn Trp Gly Glu Glu Glu Ile Gln Thr Tyr Phe
    210                 215                 220

Val Val Asp Val Ala Ala Ser Val Lys Glu Val Ala Lys Ala Ala Val
225                 230                 235                 240

Ser Ala Ala Gln Ala Phe Asp Pro Pro Arg Gln Val Ser Gly Arg Ser
                245                 250                 255

Leu Ser Pro Lys Val Gly Phe Ala Leu Ala Glu His Leu Glu Arg Val
            260                 265                 270

Thr Gly Ser Lys Arg Cys Ser Phe Asp Pro Ala Ala Gly Pro Ser Val
        275                 280                 285

Leu Ala Leu His Asp Glu Val Lys Lys Thr Tyr Lys Arg Leu Cys Ala
    290                 295                 300

Arg Gly Lys Asn Ala Ala Arg Ala Phe Pro Ala Asp Lys Thr Glu Leu
305                 310                 315                 320

Leu Ala Leu Met Arg His Thr His Glu Asn Arg Val Arg Asn Gln Met
                325                 330                 335

Val Arg Met Gly Arg Val Ser Glu Tyr Arg Gly Gln Gln Ala Gly Asp
            340                 345                 350

Leu Ala Gln Ser His Tyr Trp Thr Ser Ala Gly Gln Thr Glu Ile Lys
        355                 360                 365

Glu Ser Glu Ile Phe Val Arg Leu Trp Val Gly Ala Phe Ala Leu Ala
    370                 375                 380

Gly Arg Ser Met Lys Ala Trp Ile Asp Pro Met Gly Lys Ile Val Asn
385                 390                 395                 400

Thr Glu Lys Asn Asp Arg Asp Leu Thr Ala Ala Val Asn Ile Arg Gln
                405                 410                 415

Val Ile Ser Asn Lys Glu Met Val Ala Glu Ala Met Ala Arg Arg Gly
            420                 425                 430

Ile Tyr Phe Gly Glu Thr Pro Glu Leu Asp Arg Leu Gly Ala Glu Gly
        435                 440                 445

Asn Glu Gly Phe Val Phe Ala Leu Leu Arg Tyr Leu Arg Gly Cys Arg
    450                 455                 460

Asn Gln Thr Phe His Leu Gly Ala Arg Ala Gly Phe Leu Lys Glu Ile
465                 470                 475                 480

Arg Lys Glu Leu Glu Lys Thr Arg Trp Gly Lys Ala Lys Glu Ala Glu
                485                 490                 495

His Val Val Leu Thr Asp Lys Thr Val Ala Ala Ile Arg Ala Ile Ile
            500                 505                 510

Asp Asn Asp Ala Lys Ala Leu Gly Ala Arg Leu Leu Ala Asp Leu Ser
        515                 520                 525

Gly Ala Phe Val Ala His Tyr Ala Ser Lys Glu His Phe Ser Thr Leu
    530                 535                 540

Tyr Ser Glu Ile Val Lys Ala Val Lys Asp Ala Pro Glu Val Ser Ser
545                 550                 555                 560

Gly Leu Pro Arg Leu Lys Leu Leu Leu Lys Arg Ala Asp Gly Val Arg
                565                 570                 575

Gly Tyr Val His Gly Leu Arg Asp Thr Arg Lys His Ala Phe Ala Thr
            580                 585                 590

Lys Leu Pro Pro Pro Pro Ala Pro Arg Glu Leu Asp Asp Pro Ala Thr
        595                 600                 605
```

```
Lys Ala Arg Tyr Ile Ala Leu Leu Arg Leu Tyr Asp Gly Pro Phe Arg
    610                 615                 620

Ala Tyr Ala Ser Gly Ile Thr Gly Thr Ala Leu Ala Gly Pro Ala Ala
625                 630                 635                 640

Arg Ala Lys Glu Ala Ala Thr Ala Leu Ala Gln Ser Val Asn Val Thr
                645                 650                 655

Lys Ala Tyr Ser Asp Val Met Glu Gly Arg Thr Ser Arg Leu Arg Pro
            660                 665                 670

Pro Asn Asp Gly Glu Thr Leu Arg Glu Tyr Leu Ser Ala Leu Thr Gly
        675                 680                 685

Glu Thr Ala Thr Glu Phe Arg Val Gln Ile Gly Tyr Glu Ser Asp Ser
    690                 695                 700

Glu Asn Ala Arg Lys Gln Ala Glu Phe Ile Glu Asn Tyr Arg Arg Asp
705                 710                 715                 720

Met Leu Ala Phe Met Phe Glu Asp Tyr Ile Arg Ala Lys Gly Phe Asp
                725                 730                 735

Trp Ile Leu Lys Ile Glu Pro Gly Ala Thr Ala Met Thr Arg Ala Pro
            740                 745                 750

Val Leu Pro Glu Pro Ile Asp Thr Arg Gly Gln Tyr Glu His Trp Gln
        755                 760                 765

Ala Ala Leu Tyr Leu Val Met His Phe Val Pro Ala Ser Asp Val Ser
    770                 775                 780

Asn Leu Leu His Gln Leu Arg Lys Trp Glu Ala Leu Gln Gly Lys Tyr
785                 790                 795                 800

Glu Leu Val Gln Asp Gly Asp Ala Thr Asp Gln Ala Asp Ala Arg Arg
                805                 810                 815

Glu Ala Leu Asp Leu Val Lys Arg Phe Arg Asp Val Leu Val Leu Phe
            820                 825                 830

Leu Lys Thr Gly Glu Ala Arg Phe Glu Gly Arg Ala Ala Pro Phe Asp
        835                 840                 845

Leu Lys Pro Phe Arg Ala Leu Phe Ala Asn Pro Ala Thr Phe Asp Arg
    850                 855                 860

Leu Phe Met Ala Thr Pro Thr Thr Ala Arg Pro Ala Glu Asp Asp Pro
865                 870                 875                 880

Glu Gly Asp Gly Ala Ser Glu Pro Glu Leu Arg Val Ala Arg Thr Leu
                885                 890                 895

Arg Gly Leu Arg Gln Ile Ala Arg Tyr Asn His Met Ala Val Leu Ser
            900                 905                 910

Asp Leu Phe Ala Lys His Lys Val Arg Asp Glu Glu Val Ala Arg Leu
        915                 920                 925

Ala Glu Ile Glu Asp Glu Thr Gln Glu Lys Ser Gln Ile Val Ala Ala
    930                 935                 940

Gln Glu Leu Arg Thr Asp Leu His Asp Lys Val Met Lys Cys His Pro
945                 950                 955                 960

Lys Thr Ile Ser Pro Glu Glu Arg Gln Ser Tyr Ala Ala Ala Ile Lys
                965                 970                 975

Thr Ile Glu Glu His Arg Phe Leu Val Gly Arg Val Tyr Leu Gly Asp
            980                 985                 990

His Leu Arg Leu His Arg Leu Met  Met Asp Val Ile Gly  Arg Leu Ile
        995                  1000                 1005

Asp Tyr  Ala Gly Ala Tyr Glu  Arg Asp Thr Gly Thr  Phe Leu Ile
    1010                 1015                 1020
```

Asn Ala Ser Lys Gln Leu Gly Ala Gly Ala Asp Trp Ala Val Thr
1025 1030 1035

Ile Ala Gly Ala Ala Asn Thr Asp Ala Arg Thr Gln Thr Arg Lys
1040 1045 1050

Asp Leu Ala His Phe Asn Val Leu Asp Arg Ala Asp Gly Thr Pro
1055 1060 1065

Asp Leu Thr Ala Leu Val Asn Arg Ala Arg Glu Met Met Ala Tyr
1070 1075 1080

Asp Arg Lys Arg Lys Asn Ala Val Pro Arg Ser Ile Leu Asp Met
1085 1090 1095

Leu Ala Arg Leu Gly Leu Thr Leu Lys Trp Gln Met Lys Asp His
1100 1105 1110

Leu Leu Gln Asp Ala Thr Ile Thr Gln Ala Ala Ile Lys His Leu
1115 1120 1125

Asp Lys Val Arg Leu Thr Val Gly Gly Pro Ala Ala Val Thr Glu
1130 1135 1140

Ala Arg Phe Ser Gln Asp Tyr Leu Gln Met Val Ala Ala Val Phe
1145 1150 1155

Asn Gly Ser Val Gln Asn Pro Lys Pro Arg Arg Arg Asp Asp Gly
1160 1165 1170

Asp Ala Trp His Lys Pro Pro Lys Pro Ala Thr Ala Gln Ser Gln
1175 1180 1185

Pro Asp Gln Lys Pro Pro Asn Lys Ala Pro Ser Ala Gly Ser Arg
1190 1195 1200

Leu Pro Pro Pro Gln Val Gly Glu Val Tyr Glu Gly Val Val Val
1205 1210 1215

Lys Val Ile Asp Thr Gly Ser Leu Gly Phe Leu Ala Val Glu Gly
1220 1225 1230

Val Ala Gly Asn Ile Gly Leu His Ile Ser Arg Leu Arg Arg Ile
1235 1240 1245

Arg Glu Asp Ala Ile Ile Val Gly Arg Arg Tyr Arg Phe Arg Val
1250 1255 1260

Glu Ile Tyr Val Pro Pro Lys Ser Asn Thr Ser Lys Leu Asn Ala
1265 1270 1275

Ala Asp Leu Val Arg Ile Asp
1280 1285

<210> SEQ ID NO 46
<211> LENGTH: 922
<212> TYPE: PRT
<213> ORGANISM: Artificial Sequence
<220> FEATURE:
<223> OTHER INFORMATION: Chemically synthesized

<400> SEQUENCE: 46

Met Ala Lys Lys Asn Lys Met Lys Pro Arg Glu Leu Arg Glu Ala Gln
1 5 10 15

Lys Lys Ala Arg Gln Leu Lys Ala Ala Glu Ile Asn Asn Asn Ala Ala
20 25 30

Pro Ala Ile Ala Ala Met Pro Ala Ala Glu Val Ile Ala Pro Val Ala
35 40 45

Glu Lys Lys Lys Ser Ser Val Lys Ala Ala Gly Met Lys Ser Ile Leu
50 55 60

Val Ser Glu Asn Lys Met Tyr Ile Thr Ser Phe Gly Lys Gly Asn Ser
65 70 75 80

```
Ala Val Leu Glu Tyr Glu Val Asp Asn Asn Asp Tyr Asn Lys Thr Gln
                85                  90                  95

Leu Ser Ser Lys Asp Asn Ser Asn Ile Glu Leu Gly Asp Val Asn Glu
            100                 105                 110

Val Asn Ile Thr Phe Ser Ser Lys His Gly Phe Gly Ser Gly Val Glu
        115                 120                 125

Ile Asn Thr Ser Asn Pro Thr His Arg Ser Gly Glu Ser Ser Pro Val
    130                 135                 140

Arg Gly Asp Met Leu Gly Leu Lys Ser Glu Leu Glu Lys Arg Phe Phe
145                 150                 155                 160

Gly Lys Thr Phe Asp Asp Asn Ile His Ile Gln Leu Ile Tyr Asn Ile
                165                 170                 175

Leu Asp Ile Glu Lys Ile Leu Ala Val Tyr Val Thr Asn Ile Val Tyr
            180                 185                 190

Ala Leu Asn Asn Met Leu Gly Ile Lys Asp Ser Glu Ser Tyr Asp Asp
        195                 200                 205

Phe Met Gly Tyr Leu Ser Ala Arg Asn Thr Tyr Glu Val Phe Thr His
    210                 215                 220

Pro Asp Lys Ser Asn Leu Ser Asp Lys Val Lys Gly Asn Ile Lys Lys
225                 230                 235                 240

Ser Leu Ser Lys Phe Asn Asp Leu Leu Lys Thr Lys Arg Leu Gly Tyr
                245                 250                 255

Phe Gly Leu Glu Glu Pro Lys Thr Lys Asp Thr Arg Ala Ser Glu Ala
            260                 265                 270

Tyr Lys Lys Arg Val Tyr His Met Leu Ala Ile Val Gly Gln Ile Arg
        275                 280                 285

Gln Cys Val Phe His Asp Lys Ser Gly Ala Lys Arg Phe Asp Leu Tyr
    290                 295                 300

Ser Phe Ile Asn Asn Ile Asp Pro Glu Tyr Arg Asp Thr Leu Asp Tyr
305                 310                 315                 320

Leu Val Glu Glu Arg Leu Lys Ser Ile Asn Lys Asp Phe Ile Glu Gly
                325                 330                 335

Asn Lys Val Asn Ile Ser Leu Leu Ile Asp Met Met Lys Gly Tyr Glu
            340                 345                 350

Ala Asp Asp Ile Ile Arg Leu Tyr Tyr Asp Phe Ile Val Leu Lys Ser
        355                 360                 365

Gln Lys Asn Leu Gly Phe Ser Ile Lys Lys Leu Arg Glu Lys Met Leu
    370                 375                 380

Glu Glu Tyr Gly Phe Arg Phe Lys Asp Lys Gln Tyr Asp Ser Val Arg
385                 390                 395                 400

Ser Lys Met Tyr Lys Leu Met Asp Phe Leu Leu Phe Cys Asn Tyr Tyr
                405                 410                 415

Arg Asn Asp Val Ala Ala Gly Glu Ala Leu Val Arg Lys Leu Arg Phe
            420                 425                 430

Ser Met Thr Asp Asp Glu Lys Glu Gly Ile Tyr Ala Asp Glu Ala Ala
        435                 440                 445

Lys Leu Trp Gly Lys Phe Arg Asn Asp Phe Glu Asn Ile Ala Asp His
    450                 455                 460

Met Asn Gly Asp Val Ile Lys Glu Leu Gly Lys Ala Asp Met Asp Phe
465                 470                 475                 480

Asp Glu Lys Ile Leu Asp Ser Glu Lys Lys Asn Ala Ser Asp Leu Leu
                485                 490                 495

Tyr Phe Ser Lys Met Ile Tyr Met Leu Thr Tyr Phe Leu Asp Gly Lys
```

```
            500                 505                 510

Glu Ile Asn Asp Leu Leu Thr Thr Leu Ile Ser Lys Phe Asp Asn Ile
        515                 520                 525

Lys Glu Phe Leu Lys Ile Met Lys Ser Ser Ala Val Asp Val Glu Cys
    530                 535                 540

Glu Leu Thr Ala Gly Tyr Lys Leu Phe Asn Asp Ser Gln Arg Ile Thr
545                 550                 555                 560

Asn Glu Leu Phe Ile Val Lys Asn Ile Ala Ser Met Arg Lys Pro Ala
                565                 570                 575

Ala Ser Ala Lys Leu Thr Met Phe Arg Asp Ala Leu Thr Ile Leu Gly
            580                 585                 590

Ile Asp Asp Asn Ile Thr Asp Asp Arg Ile Ser Glu Ile Leu Lys Leu
        595                 600                 605

Lys Glu Lys Gly Lys Gly Ile His Gly Leu Arg Asn Phe Ile Thr Asn
    610                 615                 620

Asn Val Ile Glu Ser Ser Arg Phe Val Tyr Leu Ile Lys Tyr Ala Asn
625                 630                 635                 640

Ala Gln Lys Ile Arg Glu Val Ala Lys Asn Glu Lys Val Val Met Phe
                645                 650                 655

Val Leu Gly Gly Ile Pro Asp Thr Gln Ile Glu Arg Tyr Tyr Lys Ser
            660                 665                 670

Cys Val Glu Phe Pro Asp Met Asn Ser Ser Leu Glu Ala Lys Arg Ser
        675                 680                 685

Glu Leu Ala Arg Met Ile Lys Asn Ile Ser Phe Asp Asp Phe Lys Asn
    690                 695                 700

Val Lys Gln Gln Ala Lys Gly Arg Glu Asn Val Ala Lys Glu Arg Ala
705                 710                 715                 720

Lys Ala Val Ile Gly Leu Tyr Leu Thr Val Met Tyr Leu Leu Val Lys
                725                 730                 735

Asn Leu Val Asn Val Asn Ala Arg Tyr Val Ile Ala Ile His Cys Leu
            740                 745                 750

Glu Arg Asp Phe Gly Leu Tyr Lys Glu Ile Ile Pro Glu Leu Ala Ser
        755                 760                 765

Lys Asn Leu Lys Asn Asp Tyr Arg Ile Leu Ser Gln Thr Leu Cys Glu
    770                 775                 780

Leu Cys Asp Asp Arg Asn Glu Ser Ser Asn Leu Phe Leu Lys Lys Asn
785                 790                 795                 800

Lys Arg Leu Arg Lys Cys Val Glu Val Asp Ile Asn Asn Ala Asp Ser
                805                 810                 815

Ser Met Thr Arg Lys Tyr Arg Asn Cys Ile Ala His Leu Thr Val Val
            820                 825                 830

Arg Glu Leu Lys Glu Tyr Ile Gly Asp Ile Arg Thr Val Asp Ser Tyr
        835                 840                 845

Phe Ser Ile Tyr His Tyr Val Met Gln Arg Cys Ile Thr Lys Arg Gly
    850                 855                 860

Asp Asp Thr Lys Gln Glu Glu Lys Ile Lys Tyr Glu Asp Asp Leu Leu
865                 870                 875                 880

Lys Asn His Gly Tyr Thr Lys Asp Phe Val Lys Ala Leu Asn Ser Pro
                885                 890                 895

Phe Gly Tyr Asn Ile Pro Arg Phe Lys Asn Leu Ser Ile Glu Gln Leu
            900                 905                 910

Phe Asp Arg Asn Glu Tyr Leu Thr Glu Lys
        915                 920
```

<210> SEQ ID NO 47
<211> LENGTH: 1089
<212> TYPE: PRT
<213> ORGANISM: Artificial Sequence
<220> FEATURE:
<223> OTHER INFORMATION: Chemically synthesized

<400> SEQUENCE: 47

Asn Ile Pro Ala Leu Val Glu Asn Gln Lys Lys Tyr Phe Gly Thr Tyr
1               5                   10                  15

Ser Val Met Ala Met Leu Asn Ala Gln Thr Val Leu Asp His Ile Gln
            20                  25                  30

Lys Val Ala Asp Ile Glu Gly Glu Gln Asn Glu Asn Asn Glu Asn Leu
        35                  40                  45

Trp Phe His Pro Val Met Ser His Leu Tyr Asn Ala Lys Asn Gly Tyr
    50                  55                  60

Asp Lys Gln Pro Glu Lys Thr Met Phe Ile Ile Glu Arg Leu Gln Ser
65                  70                  75                  80

Tyr Phe Pro Phe Leu Lys Ile Met Ala Glu Asn Gln Arg Glu Tyr Ser
                85                  90                  95

Asn Gly Lys Tyr Lys Gln Asn Arg Val Glu Val Asn Ser Asn Asp Ile
            100                 105                 110

Phe Glu Val Leu Lys Arg Ala Phe Gly Val Leu Lys Met Tyr Arg Asp
        115                 120                 125

Leu Thr Asn Ala Tyr Lys Thr Tyr Glu Glu Lys Leu Asn Asp Gly Cys
    130                 135                 140

Glu Phe Leu Thr Ser Thr Glu Gln Pro Leu Ser Gly Met Ile Asn Asn
145                 150                 155                 160

Tyr Tyr Thr Val Ala Leu Arg Asn Met Asn Glu Arg Tyr Gly Tyr Lys
                165                 170                 175

Thr Glu Asp Leu Ala Phe Ile Gln Asp Lys Arg Phe Lys Phe Val Lys
            180                 185                 190

Asp Ala Tyr Gly Lys Lys Lys Ser Gln Val Asn Thr Gly Phe Phe Leu
        195                 200                 205

Ser Leu Gln Asp Tyr Asn Gly Asp Thr Gln Lys Lys Leu His Leu Ser
    210                 215                 220

Gly Val Gly Ile Ala Leu Leu Ile Cys Leu Phe Leu Asp Lys Gln Tyr
225                 230                 235                 240

Ile Asn Ile Phe Leu Ser Arg Leu Pro Ile Phe Ser Ser Tyr Asn Ala
                245                 250                 255

Gln Ser Glu Glu Arg Arg Ile Ile Ile Arg Ser Phe Gly Ile Asn Ser
            260                 265                 270

Ile Lys Leu Pro Lys Asp Arg Ile His Ser Glu Lys Ser Asn Lys Ser
        275                 280                 285

Val Ala Met Asp Met Leu Asn Glu Val Lys Arg Cys Pro Asp Glu Leu
    290                 295                 300

Phe Thr Thr Leu Ser Ala Glu Lys Gln Ser Arg Phe Arg Ile Ile Ser
305                 310                 315                 320

Asp Asp His Asn Glu Val Leu Met Lys Arg Ser Ser Asp Arg Phe Val
                325                 330                 335

Pro Leu Leu Leu Gln Tyr Ile Asp Tyr Gly Lys Leu Phe Asp His Ile
            340                 345                 350

Arg Phe His Val Asn Met Gly Lys Leu Arg Tyr Leu Leu Lys Ala Asp
        355                 360                 365

```
Lys Thr Cys Ile Asp Gly Gln Thr Arg Val Arg Val Ile Glu Gln Pro
    370                 375                 380

Leu Asn Gly Phe Gly Arg Leu Glu Glu Ala Glu Thr Met Arg Lys Gln
385                 390                 395                 400

Glu Asn Gly Thr Phe Gly Asn Ser Gly Ile Arg Ile Arg Asp Phe Glu
                405                 410                 415

Asn Met Lys Arg Asp Asp Ala Asn Pro Ala Asn Tyr Pro Tyr Ile Val
            420                 425                 430

Asp Thr Tyr Thr His Tyr Ile Leu Glu Asn Asn Lys Val Glu Met Phe
        435                 440                 445

Ile Asn Asp Lys Glu Asp Ser Ala Pro Leu Leu Pro Val Ile Glu Asp
    450                 455                 460

Asp Arg Tyr Val Val Lys Thr Ile Pro Ser Cys Arg Met Ser Thr Leu
465                 470                 475                 480

Glu Ile Pro Ala Met Ala Phe His Met Phe Leu Phe Gly Ser Lys Lys
                485                 490                 495

Thr Glu Lys Leu Ile Val Asp Val His Asn Arg Tyr Lys Arg Leu Phe
            500                 505                 510

Gln Ala Met Gln Lys Glu Glu Val Thr Ala Glu Asn Ile Ala Ser Phe
        515                 520                 525

Gly Ile Ala Glu Ser Asp Leu Pro Gln Lys Ile Leu Asp Leu Ile Ser
    530                 535                 540

Gly Asn Ala His Gly Lys Asp Val Asp Ala Phe Ile Arg Leu Thr Val
545                 550                 555                 560

Asp Asp Met Leu Thr Asp Thr Glu Arg Arg Ile Lys Arg Phe Lys Asp
                565                 570                 575

Asp Arg Lys Ser Ile Arg Ser Ala Asp Asn Lys Met Gly Lys Arg Gly
            580                 585                 590

Phe Lys Gln Ile Ser Thr Gly Lys Leu Ala Asp Phe Leu Ala Lys Asp
        595                 600                 605

Ile Val Leu Phe Gln Pro Ser Val Asn Asp Gly Glu Asn Lys Ile Thr
    610                 615                 620

Gly Leu Asn Tyr Arg Ile Met Gln Ser Ala Ile Ala Val Tyr Asp Ser
625                 630                 635                 640

Gly Asp Asp Tyr Glu Ala Lys Gln Gln Phe Lys Leu Met Phe Glu Lys
                645                 650                 655

Ala Arg Leu Ile Gly Lys Gly Thr Thr Glu Pro His Pro Phe Leu Tyr
            660                 665                 670

Lys Val Phe Ala Arg Ser Ile Pro Ala Asn Ala Val Glu Phe Tyr Glu
        675                 680                 685

Arg Tyr Leu Ile Glu Arg Lys Phe Tyr Leu Thr Gly Leu Ser Asn Glu
    690                 695                 700

Ile Lys Lys Gly Asn Arg Val Asp Val Pro Phe Ile Arg Arg Asp Gln
705                 710                 715                 720

Asn Lys Trp Lys Thr Pro Ala Met Lys Thr Leu Gly Arg Ile Tyr Ser
                725                 730                 735

Glu Asp Leu Pro Val Glu Leu Pro Arg Gln Met Phe Asp Asn Glu Ile
            740                 745                 750

Lys Ser His Leu Lys Ser Leu Pro Gln Met Glu Gly Ile Asp Phe Asn
        755                 760                 765

Asn Ala Asn Val Thr Tyr Leu Ile Ala Glu Tyr Met Lys Arg Val Leu
    770                 775                 780
```

Asp Asp Asp Phe Gln Thr Phe Tyr Gln Trp Asn Arg Asn Tyr Arg Tyr
785 790 795 800

Met Asp Met Leu Lys Gly Glu Tyr Asp Arg Lys Gly Ser Leu Gln His
805 810 815

Cys Phe Thr Ser Val Glu Glu Arg Glu Gly Leu Trp Lys Glu Arg Ala
820 825 830

Ser Arg Thr Glu Arg Tyr Arg Lys Gln Ala Ser Asn Lys Ile Arg Ser
835 840 845

Asn Arg Gln Met Arg Asn Ala Ser Ser Glu Glu Ile Glu Thr Ile Leu
850 855 860

Asp Lys Arg Leu Ser Asn Ser Arg Asn Glu Tyr Gln Lys Ser Glu Lys
865 870 875 880

Val Ile Arg Arg Tyr Arg Val Gln Asp Ala Leu Leu Phe Leu Leu Ala
885 890 895

Lys Lys Thr Leu Thr Glu Leu Ala Asp Phe Asp Gly Glu Arg Phe Lys
900 905 910

Leu Lys Glu Ile Met Pro Asp Ala Glu Lys Gly Ile Leu Ser Glu Ile
915 920 925

Met Pro Met Ser Phe Thr Phe Glu Lys Gly Gly Lys Lys Tyr Thr Ile
930 935 940

Thr Ser Glu Gly Met Lys Leu Lys Asn Tyr Gly Asp Phe Phe Val Leu
945 950 955 960

Ala Ser Asp Lys Arg Ile Gly Asn Leu Leu Glu Leu Val Gly Ser Asp
965 970 975

Ile Val Ser Lys Glu Asp Ile Met Glu Glu Phe Asn Lys Tyr Asp Gln
980 985 990

Cys Arg Pro Glu Ile Ser Ser Ile Val Phe Asn Leu Glu Lys Trp Ala
995 1000 1005

Phe Asp Thr Tyr Pro Glu Leu Ser Ala Arg Val Asp Arg Glu Glu
1010 1015 1020

Lys Val Asp Phe Lys Ser Ile Leu Lys Ile Leu Leu Asn Asn Lys
1025 1030 1035

Asn Ile Asn Lys Glu Gln Ser Asp Ile Leu Arg Lys Ile Arg Asn
1040 1045 1050

Ala Phe Asp Ala Asn Asn Tyr Pro Asp Lys Gly Val Val Glu Ile
1055 1060 1065

Lys Ala Leu Pro Glu Ile Ala Met Ser Ile Lys Lys Ala Phe Gly
1070 1075 1080

Glu Tyr Ala Ile Met Lys
1085

<210> SEQ ID NO 48
<211> LENGTH: 982
<212> TYPE: PRT
<213> ORGANISM: Artificial Sequence
<220> FEATURE:
<223> OTHER INFORMATION: Chemically synthesized

<400> SEQUENCE: 48

Asn Ile Pro Ala Leu Val Glu Asn Gln Lys Lys Tyr Phe Gly Thr Tyr
1 5 10 15

Ser Val Met Ala Met Leu Asn Ala Gln Thr Val Leu Asp His Ile Gln
20 25 30

Lys Val Ala Asp Ile Glu Gly Glu Gln Asn Glu Asn Asn Glu Asn Leu
35 40 45

```
Trp Phe His Pro Val Met Ser His Leu Tyr Asn Ala Lys Asn Gly Tyr
    50                  55                  60

Asp Lys Gln Pro Glu Lys Thr Met Phe Ile Ile Glu Arg Leu Gln Ser
65                  70                  75                  80

Tyr Phe Pro Phe Leu Lys Ile Met Ala Glu Asn Gln Arg Glu Tyr Ser
                85                  90                  95

Asn Gly Lys Tyr Lys Gln Asn Arg Val Glu Val Asn Ser Asn Asp Ile
            100                 105                 110

Phe Glu Val Leu Lys Arg Ala Phe Gly Val Leu Lys Met Tyr Arg Asp
        115                 120                 125

Leu Thr Asn Ala Tyr Lys Thr Tyr Glu Glu Lys Leu Asn Asp Gly Cys
    130                 135                 140

Glu Phe Leu Thr Ser Thr Glu Gln Pro Leu Ser Gly Met Ile Asn Asn
145                 150                 155                 160

Tyr Tyr Thr Val Ala Leu Arg Asn Met Asn Glu Arg Tyr Gly Tyr Lys
                165                 170                 175

Thr Glu Asp Leu Ala Phe Ile Gln Asp Lys Arg Phe Lys Phe Val Lys
            180                 185                 190

Asp Ala Tyr Gly Lys Lys Lys Ser Gln Val Asn Thr Gly Phe Phe Leu
        195                 200                 205

Ser Leu Gln Asp Tyr Asn Gly Asp Thr Gln Lys Lys Leu His Leu Ser
    210                 215                 220

Gly Val Gly Ile Ala Leu Leu Ile Cys Leu Phe Leu Asp Lys Gln Tyr
225                 230                 235                 240

Ile Asn Ile Phe Leu Ser Arg Leu Pro Ile Phe Ser Ser Tyr Asn Ala
                245                 250                 255

Gln Ser Glu Glu Arg Arg Ile Ile Ile Arg Ser Phe Gly Ile Asn Ser
            260                 265                 270

Ile Lys Leu Pro Lys Asp Arg Ile His Ser Glu Lys Ser Asn Lys Ser
        275                 280                 285

Val Ala Met Asp Met Leu Asn Glu Val Lys Arg Cys Pro Asp Glu Leu
    290                 295                 300

Phe Thr Thr Leu Ser Ala Glu Lys Gln Ser Arg Phe Arg Ile Ile Ser
305                 310                 315                 320

Asp Asp His Asn Glu Val Leu Met Lys Arg Ser Ser Asp Arg Phe Val
                325                 330                 335

Pro Leu Leu Leu Gln Tyr Ile Asp Tyr Gly Lys Leu Phe Asp His Ile
            340                 345                 350

Arg Phe His Val Asn Met Gly Lys Leu Arg Tyr Leu Leu Lys Ala Asp
        355                 360                 365

Lys Thr Cys Ile Asp Gly Gln Thr Arg Val Arg Val Ile Glu Gln Pro
    370                 375                 380

Leu Asn Gly Phe Gly Arg Leu Glu Glu Ala Glu Thr Met Arg Lys Gln
385                 390                 395                 400

Glu Asn Gly Thr Phe Gly Asn Ser Gly Ile Arg Ile Arg Asp Phe Glu
                405                 410                 415

Asn Met Lys Arg Asp Asp Ala Asn Pro Ala Asn Tyr Pro Tyr Ile Val
            420                 425                 430

Asp Thr Tyr Thr His Tyr Ile Leu Glu Asn Asn Lys Val Glu Met Phe
        435                 440                 445

Ile Asn Asp Lys Glu Asp Ser Ala Pro Leu Leu Pro Val Ile Glu Asp
    450                 455                 460

Asp Arg Tyr Val Val Lys Thr Ile Pro Ser Cys Arg Met Ser Thr Leu
```

```
465                 470                 475                 480

Glu Ile Pro Ala Met Ala Phe His Met Phe Leu Phe Gly Ser Lys Lys
                485                 490                 495

Thr Glu Lys Leu Ile Val Asp Val His Asn Arg Tyr Lys Arg Leu Phe
            500                 505                 510

Gln Ala Met Gln Lys Glu Glu Val Thr Ala Glu Asn Ile Ala Ser Phe
        515                 520                 525

Gly Ile Ala Glu Ser Asp Leu Pro Gln Lys Ile Leu Asp Leu Ile Ser
    530                 535                 540

Gly Asn Ala His Gly Lys Asp Val Asp Ala Phe Ile Arg Leu Thr Val
545                 550                 555                 560

Asp Asp Met Leu Thr Asp Thr Glu Arg Arg Ile Lys Arg Phe Lys Asp
                565                 570                 575

Asp Arg Lys Ser Ile Arg Ser Ala Asp Asn Lys Met Gly Lys Arg Gly
            580                 585                 590

Phe Lys Gln Ile Ser Thr Gly Lys Leu Ala Asp Phe Leu Ala Lys Asp
        595                 600                 605

Ile Val Leu Phe Gln Pro Ser Val Asn Asp Gly Glu Asn Lys Ile Thr
    610                 615                 620

Gly Leu Asn Tyr Arg Ile Met Gln Ser Ala Ile Ala Val Tyr Asp Ser
625                 630                 635                 640

Gly Asp Asp Tyr Glu Ala Lys Gln Gln Phe Lys Leu Met Phe Glu Lys
                645                 650                 655

Ala Arg Leu Ile Gly Lys Gly Thr Thr Glu Pro His Pro Phe Leu Tyr
            660                 665                 670

Lys Val Phe Ala Arg Ser Ile Pro Ala Asn Ala Val Glu Phe Tyr Glu
        675                 680                 685

Arg Tyr Leu Ile Glu Arg Lys Phe Tyr Leu Thr Gly Leu Ser Asn Glu
    690                 695                 700

Ile Lys Lys Gly Asn Arg Val Asp Val Pro Phe Ile Arg Arg Asp Gln
705                 710                 715                 720

Asn Lys Trp Lys Thr Pro Ala Met Lys Thr Leu Gly Arg Ile Tyr Ser
                725                 730                 735

Glu Asp Leu Pro Val Glu Leu Pro Arg Gln Met Phe Asp Asn Glu Ile
            740                 745                 750

Lys Ser His Leu Lys Ser Leu Pro Gln Met Glu Gly Ile Asp Phe Asn
        755                 760                 765

Asn Ala Asn Val Thr Tyr Leu Ile Ala Glu Tyr Met Lys Arg Val Leu
    770                 775                 780

Asp Asp Asp Phe Gln Thr Phe Tyr Gln Trp Asn Arg Asn Tyr Arg Tyr
785                 790                 795                 800

Met Asp Met Leu Lys Gly Glu Tyr Asp Arg Lys Gly Ser Leu Gln His
                805                 810                 815

Cys Phe Thr Ser Val Glu Glu Arg Glu Gly Leu Trp Lys Glu Arg Ala
            820                 825                 830

Ser Arg Thr Glu Arg Tyr Arg Lys Gln Ala Ser Asn Lys Ile Arg Ser
        835                 840                 845

Asn Arg Gln Met Arg Asn Ala Ser Ser Glu Glu Ile Glu Thr Ile Leu
    850                 855                 860

Asp Lys Arg Leu Ser Asn Ser Arg Asn Glu Tyr Gln Lys Ser Glu Lys
865                 870                 875                 880

Val Ile Arg Arg Tyr Arg Val Gln Asp Ala Leu Leu Phe Leu Leu Ala
                885                 890                 895
```

Lys Lys Thr Leu Thr Glu Leu Ala Asp Phe Asp Gly Glu Arg Phe Lys
900 905 910

Leu Lys Glu Ile Met Pro Asp Ala Glu Lys Gly Ile Leu Ser Glu Ile
915 920 925

Met Pro Met Ser Phe Thr Phe Glu Lys Gly Gly Lys Lys Tyr Thr Ile
930 935 940

Thr Ser Glu Gly Met Lys Leu Lys Asn Tyr Gly Asp Phe Phe Val Leu
945 950 955 960

Ala Ser Asp Lys Arg Ile Gly Asn Leu Leu Glu Leu Val Gly Ser Asp
965 970 975

Ile Val Ser Lys Glu Asp
980

<210> SEQ ID NO 49
<211> LENGTH: 14
<212> TYPE: PRT
<213> ORGANISM: Artificial Sequence
<220> FEATURE:
<223> OTHER INFORMATION: Chemically synthesized

<400> SEQUENCE: 49

Ser Arg Gly Gly Gly Gly Ser Gly Gly Gly Gly Ser Thr Arg
1 5 10

<210> SEQ ID NO 50
<211> LENGTH: 4
<212> TYPE: PRT
<213> ORGANISM: Artificial Sequence
<220> FEATURE:
<223> OTHER INFORMATION: Chemically synthesized

<400> SEQUENCE: 50

Gly Gly Gly Gly
1

<210> SEQ ID NO 51
<211> LENGTH: 10
<212> TYPE: PRT
<213> ORGANISM: Artificial Sequence
<220> FEATURE:
<223> OTHER INFORMATION: Chemically synthesized

<400> SEQUENCE: 51

Gly Gly Gly Gly Ser Gly Gly Gly Gly Ser
1 5 10

<210> SEQ ID NO 52
<211> LENGTH: 5
<212> TYPE: PRT
<213> ORGANISM: Artificial Sequence
<220> FEATURE:
<223> OTHER INFORMATION: Chemically synthesized

<400> SEQUENCE: 52

Glu Ala Ala Ala Lys
1 5

<210> SEQ ID NO 53
<211> LENGTH: 10
<212> TYPE: PRT
<213> ORGANISM: Artificial Sequence
<220> FEATURE:
<223> OTHER INFORMATION: Chemically synthesized

<400> SEQUENCE: 53

Glu Ala Ala Ala Lys Glu Ala Ala Ala Lys
1 5 10

<210> SEQ ID NO 54
<211> LENGTH: 12
<212> TYPE: PRT
<213> ORGANISM: Artificial Sequence
<220> FEATURE:
<223> OTHER INFORMATION: Chemically synthesized

<400> SEQUENCE: 54

Lys Ala Glu Glu Glu Lys Lys Ala Ala Glu Glu Lys
1 5 10

<210> SEQ ID NO 55
<211> LENGTH: 16
<212> TYPE: PRT
<213> ORGANISM: Artificial Sequence
<220> FEATURE:
<223> OTHER INFORMATION: Chemically synthesized

<400> SEQUENCE: 55

Ser Gly Ser Glu Thr Pro Gly Thr Ser Glu Ser Ala Thr Pro Glu Ser
1 5 10 15

<210> SEQ ID NO 56
<211> LENGTH: 22
<212> TYPE: PRT
<213> ORGANISM: Artificial Sequence
<220> FEATURE:
<223> OTHER INFORMATION: Chemically synthesized

<400> SEQUENCE: 56

Asp Tyr Lys Asp His Asp Gly Asp Tyr Lys Asp His Asp Ile Asp Tyr
1 5 10 15

Lys Asp Asp Asp Asp Lys
20

<210> SEQ ID NO 57
<211> LENGTH: 11
<212> TYPE: PRT
<213> ORGANISM: Artificial Sequence
<220> FEATURE:
<223> OTHER INFORMATION: Chemically synthesized

<400> SEQUENCE: 57

Leu Gln Leu Pro Pro Leu Glu Arg Leu Thr Leu
1 5 10

<210> SEQ ID NO 58
<211> LENGTH: 16
<212> TYPE: PRT
<213> ORGANISM: Artificial Sequence
<220> FEATURE:
<223> OTHER INFORMATION: Chemically synthesized

<400> SEQUENCE: 58

Gly Ser Leu Gln Leu Pro Pro Leu Glu Arg Leu Thr Leu Gly Ser Ser
1 5 10 15

<210> SEQ ID NO 59
<211> LENGTH: 259
<212> TYPE: PRT
<213> ORGANISM: Artificial Sequence
<220> FEATURE:

<223> OTHER INFORMATION: Chemically synthesized

<400> SEQUENCE: 59

Pro Arg Lys Ile Ile Ala Thr Val Leu Met Thr Glu Asp Ile Lys Leu
1 5 10 15

Asn Lys Ala Glu Lys Ala Trp Lys Pro Ser Ser Lys Arg Thr Ala Ala
20 25 30

Asp Lys Asp Arg Gly Glu Glu Asp Ala Asp Gly Ser Lys Thr Gln Asp
35 40 45

Leu Phe Arg Arg Val Arg Ser Ile Leu Asn Lys Leu Thr Pro Gln Met
50 55 60

Phe Gln Gln Leu Met Lys Gln Val Thr Gln Leu Ala Ile Asp Thr Glu
65 70 75 80

Glu Arg Leu Lys Gly Val Ile Asp Leu Ile Phe Glu Lys Ala Ile Ser
85 90 95

Glu Pro Asn Phe Ser Val Ala Tyr Ala Asn Met Cys Arg Cys Leu Met
100 105 110

Ala Leu Lys Val Pro Thr Thr Glu Lys Pro Thr Val Thr Val Asn Phe
115 120 125

Arg Lys Leu Leu Leu Asn Arg Cys Gln Lys Glu Phe Glu Lys Asp Lys
130 135 140

Asp Asp Asp Glu Val Phe Glu Lys Lys Gln Lys Glu Met Asp Glu Ala
145 150 155 160

Ala Thr Ala Glu Glu Arg Gly Arg Leu Lys Glu Glu Leu Glu Glu Ala
165 170 175

Arg Asp Ile Ala Arg Arg Arg Ser Leu Gly Asn Ile Lys Phe Ile Gly
180 185 190

Glu Leu Phe Lys Leu Lys Met Leu Thr Glu Ala Ile Met His Asp Cys
195 200 205

Val Val Lys Leu Leu Lys Asn His Asp Glu Glu Ser Leu Glu Cys Leu
210 215 220

Cys Arg Leu Leu Thr Thr Ile Gly Lys Asp Leu Asp Phe Glu Lys Ala
225 230 235 240

Lys Pro Arg Met Asp Gln Tyr Phe Asn Gln Met Glu Lys Ile Ile Lys
245 250 255

Glu Lys Lys

<210> SEQ ID NO 60
<211> LENGTH: 263
<212> TYPE: PRT
<213> ORGANISM: Artificial Sequence
<220> FEATURE:
<223> OTHER INFORMATION: Chemically synthesized

<400> SEQUENCE: 60

Ala Asn Glu Lys Glu Arg His Asp Ala Ile Phe Arg Lys Val Arg Gly
1 5 10 15

Ile Leu Asn Lys Leu Thr Pro Glu Lys Phe Asp Lys Leu Cys Leu Glu
20 25 30

Leu Leu Asn Val Gly Val Glu Ser Lys Leu Ile Leu Lys Gly Val Ile
35 40 45

Leu Leu Ile Val Asp Lys Ala Leu Glu Glu Pro Lys Tyr Ser Ser Leu
50 55 60

Tyr Ala Gln Leu Cys Leu Arg Leu Ala Glu Asp Ala Pro Asn Phe Asp
65 70 75 80

Gly Pro Ala Ala Glu Gly Gln Pro Gly Gln Lys Gln Ser Thr Thr Phe
85 90 95

Arg Arg Leu Leu Ile Ser Lys Leu Gln Asp Glu Phe Glu Asn Arg Thr
100 105 110

Arg Asn Val Asp Val Tyr Asp Lys Arg Glu Asn Pro Leu Leu Pro Glu
115 120 125

Glu Glu Glu Gln Arg Ala Ile Ala Lys Ile Lys Met Leu Gly Asn Ile
130 135 140

Lys Phe Ile Gly Glu Leu Gly Lys Leu Asp Leu Ile His Glu Ser Ile
145 150 155 160

Leu His Lys Cys Ile Lys Thr Leu Leu Glu Lys Lys Lys Arg Val Gln
165 170 175

Leu Lys Asp Met Gly Glu Asp Leu Glu Cys Leu Cys Gln Ile Met Arg
180 185 190

Thr Val Gly Pro Arg Leu Asp His Glu Arg Ala Lys Ser Leu Met Asp
195 200 205

Gln Tyr Phe Ala Arg Met Cys Ser Leu Met Leu Ser Lys Glu Leu Pro
210 215 220

Ala Arg Ile Arg Phe Leu Leu Gln Asp Thr Val Glu Leu Arg Glu His
225 230 235 240

His Trp Val Pro Arg Lys Ala Phe Leu Asp Asn Gly Pro Lys Thr Ile
245 250 255

Asn Gln Ile Arg Gln Asp Ala
260

<210> SEQ ID NO 61
<211> LENGTH: 250
<212> TYPE: PRT
<213> ORGANISM: Artificial Sequence
<220> FEATURE:
<223> OTHER INFORMATION: Chemically synthesized

<400> SEQUENCE: 61

Leu Phe Arg Lys Val Arg Ser Ile Leu Asn Lys Leu Thr Pro Gln Met
1 5 10 15

Phe Asn Gln Leu Met Lys Gln Val Ser Gly Leu Thr Val Asp Thr Glu
20 25 30

Glu Arg Leu Lys Gly Val Ile Asp Leu Val Phe Glu Lys Ala Ile Asp
35 40 45

Glu Pro Ser Phe Ser Val Ala Tyr Ala Asn Met Cys Arg Cys Leu Val
50 55 60

Thr Leu Lys Val Pro Met Ala Asp Lys Pro Gly Asn Thr Val Asn Phe
65 70 75 80

Arg Lys Leu Leu Leu Asn Arg Cys Gln Lys Glu Phe Glu Lys Asp Lys
85 90 95

Ala Asp Asp Asp Val Phe Glu Lys Lys Gln Lys Glu Leu Glu Ala Ala
100 105 110

Ser Ala Pro Glu Glu Arg Thr Arg Leu His Asp Glu Leu Glu Glu Ala
115 120 125

Lys Asp Lys Ala Arg Arg Arg Ser Ile Gly Asn Ile Lys Phe Ile Gly
130 135 140

Glu Leu Phe Lys Leu Lys Met Leu Thr Glu Ala Ile Met His Asp Cys
145 150 155 160

Val Val Lys Leu Leu Lys Asn His Asp Glu Glu Ser Leu Glu Cys Leu
165 170 175

Cys Arg Leu Leu Thr Thr Ile Gly Lys Asp Leu Asp Phe Glu Lys Ala
180 185 190

Lys Pro Arg Met Asp Gln Tyr Phe Asn Gln Met Glu Lys Ile Val Lys
195 200 205

Glu Arg Lys Thr Ser Ser Arg Ile Arg Phe Met Leu Gln Asp Val Ile
210 215 220

Asp Leu Arg Leu Cys Asn Trp Val Ser Arg Arg Ala Asp Gln Gly Pro
225 230 235 240

Lys Thr Ile Glu Gln Ile His Lys Glu Ala
245 250

<210> SEQ ID NO 62
<211> LENGTH: 283
<212> TYPE: PRT
<213> ORGANISM: Artificial Sequence
<220> FEATURE:
<223> OTHER INFORMATION: Chemically synthesized

<400> SEQUENCE: 62

Asp Gly Cys Glu Asp Tyr Pro Thr Leu Ser Glu Tyr Val Gln Asp Phe
1 5 10 15

Leu Asn His Leu Thr Glu Gln Pro Gly Ser Phe Glu Thr Glu Ile Glu
20 25 30

Gln Phe Ala Glu Thr Leu Asn Gly Cys Val Thr Thr Asp Asp Ala Leu
35 40 45

Gln Glu Leu Val Glu Leu Ile Tyr Gln Gln Ala Thr Ser Ile Pro Asn
50 55 60

Phe Ser Tyr Met Gly Ala Arg Leu Cys Asn Tyr Leu Ser His His Leu
65 70 75 80

Thr Ile Ser Pro Gln Ser Gly Asn Phe Arg Gln Leu Leu Leu Gln Arg
85 90 95

Cys Arg Thr Glu Tyr Glu Val Lys Asp Gln Ala Ala Lys Gly Asp Glu
100 105 110

Val Thr Arg Lys Arg Phe His Ala Phe Val Leu Phe Leu Gly Glu Leu
115 120 125

Tyr Leu Asn Leu Glu Ile Lys Gly Thr Asn Gly Gln Val Thr Arg Ala
130 135 140

Asp Ile Leu Gln Val Gly Leu Arg Glu Leu Leu Asn Ala Leu Phe Ser
145 150 155 160

Asn Pro Met Asp Asp Asn Leu Ile Cys Ala Val Lys Leu Leu Lys Leu
165 170 175

Thr Gly Ser Val Leu Glu Asp Ala Trp Lys Glu Lys Gly Lys Met Asp
180 185 190

Met Glu Glu Ile Ile Gln Arg Ile Glu Asn Val Val Leu Asp Ala Asn
195 200 205

Cys Ser Arg Asp Val Lys Gln Met Leu Leu Lys Leu Val Glu Leu Arg
210 215 220

Ser Ser Asn Trp Gly Arg Val His Ala Thr Ser Thr Tyr Arg Glu Ala
225 230 235 240

Thr Pro Glu Asn Asp Pro Asn Tyr Phe Met Asn Glu Pro Thr Phe Tyr
245 250 255

Thr Ser Asp Gly Val Pro Phe Thr Ala Ala Asp Pro Asp Tyr Gln Glu
260 265 270

Lys Tyr Gln Glu Leu Leu Glu Arg Glu Asp Phe
275 280

<210> SEQ ID NO 63
<211> LENGTH: 275
<212> TYPE: PRT
<213> ORGANISM: Artificial Sequence
<220> FEATURE:
<223> OTHER INFORMATION: Chemically synthesized

<400> SEQUENCE: 63

Lys Thr Glu Leu Leu Asp Lys Asp Glu Val Glu Arg Lys Met Lys Ser
1               5                   10                  15

Leu Leu Asn Lys Leu Thr Leu Glu Met Phe Asp Ala Ile Ser Ser Glu
            20                  25                  30

Ile Leu Ala Ile Ala Asn Ile Ser Val Trp Glu Thr Asn Gly Glu Thr
        35                  40                  45

Leu Lys Ala Val Ile Glu Gln Ile Phe Leu Lys Ala Cys Asp Glu Pro
    50                  55                  60

His Trp Ser Ser Met Tyr Ala Gln Leu Cys Gly Lys Val Val Lys Glu
65                  70                  75                  80

Leu Asn Pro Asp Ile Thr Asp Glu Thr Asn Glu Gly Lys Thr Gly Pro
                85                  90                  95

Lys Leu Val Leu His Tyr Leu Val Ala Arg Cys His Ala Glu Phe Asp
            100                 105                 110

Lys Gly Trp Thr Asp Lys Leu Pro Thr Asn Glu Asp Gly Thr Pro Leu
        115                 120                 125

Glu Pro Glu Met Met Ser Glu Glu Tyr Tyr Ala Ala Ala Ser Ala Lys
    130                 135                 140

Arg Arg Gly Leu Gly Leu Val Arg Phe Ile Gly Phe Leu Tyr Arg Leu
145                 150                 155                 160

Asn Leu Leu Thr Gly Lys Met Met Phe Glu Cys Phe Arg Arg Leu Met
                165                 170                 175

Lys Asp Leu Thr Asp Ser Pro Ser Glu Glu Thr Leu Glu Ser Val Val
            180                 185                 190

Glu Leu Leu Asn Thr Val Gly Glu Gln Phe Glu Thr Asp Ser Phe Arg
        195                 200                 205

Thr Gly Gln Ala Thr Leu Glu Gly Ser Gln Leu Leu Asp Ser Leu Phe
    210                 215                 220

Gly Ile Leu Asp Asn Ile Ile Gln Thr Ala Lys Ile Ser Ser Arg Ile
225                 230                 235                 240

Lys Phe Lys Leu Ile Asp Ile Lys Glu Leu Arg His Asp Lys Asn Trp
                245                 250                 255

Asn Ser Asp Lys Lys Asp Asn Gly Pro Lys Thr Ile Gln Gln Ile His
            260                 265                 270

Glu Glu Glu
        275

<210> SEQ ID NO 64
<211> LENGTH: 275
<212> TYPE: PRT
<213> ORGANISM: Artificial Sequence
<220> FEATURE:
<223> OTHER INFORMATION: Chemically synthesized

<400> SEQUENCE: 64

Lys Thr Glu Leu Phe Asp Lys Glu Glu Val Glu Arg Lys Met Lys Ser
1               5                   10                  15

Leu Leu Asn Lys Leu Thr Leu Glu Met Phe Asp Ser Ile Ser Ser Glu
            20                  25                  30

```
Ile Leu Asp Ile Ala Asn Gln Ser Lys Trp Glu Asp Asp Gly Glu Thr
        35                  40                  45

Leu Lys Ile Val Ile Glu Gln Ile Phe His Lys Ala Cys Asp Glu Pro
    50                  55                  60

His Trp Ser Ser Met Tyr Ala Gln Leu Cys Gly Lys Val Val Lys Asp
65                  70                  75                  80

Leu Asp Pro Asn Ile Lys Asp Lys Glu Asn Glu Gly Lys Asn Gly Pro
                85                  90                  95

Lys Leu Val Leu His Tyr Leu Val Ala Arg Cys His Glu Glu Phe Glu
            100                 105                 110

Lys Gly Trp Ala Asp Lys Leu Pro Ala Gly Glu Asp Gly Asn Pro Leu
        115                 120                 125

Glu Pro Glu Met Met Ser Asp Glu Tyr Tyr Ile Ala Ala Ala Ala Lys
    130                 135                 140

Arg Arg Gly Leu Gly Leu Val Arg Phe Ile Gly Tyr Leu Tyr Cys Leu
145                 150                 155                 160

Asn Leu Leu Thr Gly Lys Met Met Phe Glu Cys Phe Arg Arg Leu Met
                165                 170                 175

Lys Asp Leu Asn Asn Asp Pro Ser Glu Glu Thr Leu Glu Ser Val Ile
            180                 185                 190

Glu Leu Leu Asn Thr Val Gly Glu Gln Phe Glu His Asp Lys Phe Val
        195                 200                 205

Thr Pro Gln Ala Thr Leu Glu Gly Ser Val Leu Leu Asp Asn Leu Phe
    210                 215                 220

Met Leu Leu Gln His Ile Ile Asp Gly Gly Thr Ile Ser Asn Arg Ile
225                 230                 235                 240

Lys Phe Lys Leu Ile Asp Val Lys Glu Leu Arg Glu Ile Lys His Trp
                245                 250                 255

Asn Ser Ala Lys Lys Asp Ala Gly Pro Lys Thr Ile Gln Gln Ile His
            260                 265                 270

Gln Glu Glu
        275
```

<210> SEQ ID NO 65
<211> LENGTH: 216
<212> TYPE: PRT
<213> ORGANISM: Artificial Sequence
<220> FEATURE:
<223> OTHER INFORMATION: Chemically synthesized

<400> SEQUENCE: 65

```
Ala Thr Val Glu Pro Glu Thr Thr Pro Thr Pro Asn Pro Pro Thr Thr
1               5                   10                  15

Glu Glu Glu Lys Thr Glu Ser Asn Gln Glu Val Ala Asn Pro Glu His
            20                  25                  30

Tyr Ile Lys His Pro Leu Gln Asn Arg Trp Ala Leu Trp Phe Phe Lys
        35                  40                  45

Asn Asp Lys Ser Lys Thr Trp Gln Ala Asn Leu Arg Leu Ile Ser Lys
    50                  55                  60

Phe Asp Thr Val Glu Asp Phe Trp Ala Leu Tyr Asn His Ile Gln Leu
65                  70                  75                  80

Ser Ser Asn Leu Met Pro Gly Cys Asp Tyr Ser Leu Phe Lys Asp Gly
                85                  90                  95

Ile Glu Pro Met Trp Glu Asp Glu Lys Asn Lys Arg Gly Gly Arg Trp
            100                 105                 110
```

Leu Ile Thr Leu Asn Lys Gln Gln Arg Arg Ser Asp Leu Asp Arg Phe
115 120 125

Trp Leu Glu Thr Leu Leu Cys Leu Ile Gly Glu Ser Phe Asp Asp Tyr
130 135 140

Ser Asp Asp Val Cys Gly Ala Val Val Asn Val Arg Ala Lys Gly Asp
145 150 155 160

Lys Ile Ala Ile Trp Thr Thr Glu Cys Glu Asn Arg Glu Ala Val Thr
165 170 175

His Ile Gly Arg Val Tyr Lys Glu Arg Leu Gly Leu Pro Pro Lys Ile
180 185 190

Val Ile Gly Tyr Gln Ser His Ala Asp Thr Ala Thr Lys Ser Gly Ser
195 200 205

Thr Thr Lys Asn Arg Phe Val Val
210 215

<210> SEQ ID NO 66
<211> LENGTH: 216
<212> TYPE: PRT
<213> ORGANISM: Artificial Sequence
<220> FEATURE:
<223> OTHER INFORMATION: Chemically synthesized

<400> SEQUENCE: 66

Ala Thr Val Glu Pro Glu Thr Thr Pro Thr Pro Asn Pro Pro Thr Thr
1 5 10 15

Glu Glu Glu Lys Thr Glu Ser Asn Gln Glu Val Ala Asn Pro Glu His
20 25 30

Tyr Ile Lys His Pro Leu Gln Asn Arg Trp Ala Leu Trp Phe Phe Lys
35 40 45

Asn Asp Lys Ser Lys Thr Trp Gln Ala Asn Leu Arg Leu Ile Ser Lys
50 55 60

Phe Asp Thr Val Glu Asp Phe Trp Ala Leu Tyr Asn His Ile Gln Leu
65 70 75 80

Ser Ser Asn Leu Met Pro Gly Cys Asp Tyr Ser Leu Phe Lys Asp Gly
85 90 95

Ile Glu Pro Met Leu Glu Asp Glu Lys Asn Lys Arg Gly Gly Arg Trp
100 105 110

Leu Ile Thr Leu Asn Lys Gln Gln Arg Arg Ser Asp Leu Asp Arg Phe
115 120 125

Trp Leu Glu Thr Leu Leu Cys Leu Ile Gly Glu Ser Phe Asp Asp Tyr
130 135 140

Ser Asp Asp Val Cys Gly Ala Val Val Asn Val Arg Ala Lys Gly Asp
145 150 155 160

Lys Ile Ala Ile Trp Thr Thr Glu Cys Glu Asn Arg Glu Ala Val Thr
165 170 175

His Ile Gly Arg Val Tyr Lys Glu Arg Leu Gly Leu Pro Pro Lys Ile
180 185 190

Val Ile Gly Tyr Gln Ser His Ala Asp Thr Ala Thr Lys Ser Gly Ser
195 200 205

Thr Thr Lys Asn Arg Phe Val Val
210 215

<210> SEQ ID NO 67
<211> LENGTH: 521
<212> TYPE: PRT
<213> ORGANISM: Artificial Sequence
<220> FEATURE:
<223> OTHER INFORMATION: Chemically synthesized

<400> SEQUENCE: 67

```
Pro Arg Pro Glu Glu Ala Asp Glu Thr Trp Asp Ser Lys Glu Asp Lys
1               5                   10                  15

Ile His Asn Ala Glu Asn Ile Gln Pro Gly Glu Gln Lys Tyr Glu Tyr
            20                  25                  30

Lys Ser Asp Gln Trp Lys Pro Leu Asn Leu Glu Glu Lys Lys Arg Tyr
        35                  40                  45

Asp Arg Glu Phe Leu Leu Gly Phe Gln Phe Ile Phe Ala Ser Met Gln
    50                  55                  60

Lys Pro Glu Gly Leu Pro His Ile Ser Asp Val Val Leu Asp Lys Ala
65                  70                  75                  80

Asn Lys Thr Pro Leu Arg Pro Leu Asp Pro Thr Arg Leu Gln Gly Ile
                85                  90                  95

Asn Cys Gly Pro Asp Phe Thr Pro Ser Phe Ala Asn Leu Gly Arg Thr
            100                 105                 110

Thr Leu Ser Thr Arg Gly Pro Pro Arg Gly Gly Pro Gly Gly Glu Leu
        115                 120                 125

Pro Arg Gly Pro Ala Gly Leu Gly Pro Arg Arg Ser Gln Gln Gly Pro
    130                 135                 140

Arg Lys Glu Pro Arg Lys Ile Ile Ala Thr Val Leu Met Thr Glu Asp
145                 150                 155                 160

Ile Lys Leu Asn Lys Ala Glu Lys Ala Trp Lys Pro Ser Ser Lys Arg
                165                 170                 175

Thr Ala Ala Asp Lys Asp Arg Gly Glu Glu Asp Ala Asp Gly Ser Lys
            180                 185                 190

Thr Gln Asp Leu Phe Arg Arg Val Arg Ser Ile Leu Asn Lys Leu Thr
        195                 200                 205

Pro Gln Met Phe Gln Gln Leu Met Lys Gln Val Thr Gln Leu Ala Ile
    210                 215                 220

Asp Thr Glu Glu Arg Leu Lys Gly Val Ile Asp Leu Ile Phe Glu Lys
225                 230                 235                 240

Ala Ile Ser Glu Pro Asn Phe Ser Val Ala Tyr Ala Asn Met Cys Arg
                245                 250                 255

Cys Leu Met Ala Leu Lys Val Pro Thr Thr Glu Lys Pro Thr Val Thr
            260                 265                 270

Val Asn Phe Arg Lys Leu Leu Leu Asn Arg Cys Gln Lys Glu Phe Glu
        275                 280                 285

Lys Asp Lys Asp Asp Asp Glu Val Phe Glu Lys Lys Gln Lys Glu Met
    290                 295                 300

Asp Glu Ala Ala Thr Ala Glu Glu Arg Gly Arg Leu Lys Glu Glu Leu
305                 310                 315                 320

Glu Glu Ala Arg Asp Ile Ala Arg Arg Arg Ser Leu Gly Asn Ile Lys
                325                 330                 335

Phe Ile Gly Glu Leu Phe Lys Leu Lys Met Leu Thr Glu Ala Ile Met
            340                 345                 350

His Asp Cys Val Val Lys Leu Leu Lys Asn His Asp Glu Glu Ser Leu
        355                 360                 365

Glu Cys Leu Cys Arg Leu Leu Thr Thr Ile Gly Lys Asp Leu Asp Phe
    370                 375                 380

Glu Lys Ala Lys Pro Arg Met Asp Gln Tyr Phe Asn Gln Met Glu Lys
385                 390                 395                 400
```

```
Ile Ile Lys Glu Lys Lys Thr Ser Ser Arg Ile Arg Phe Met Leu Gln
                405                 410                 415

Asp Val Leu Asp Leu Arg Gly Ser Asn Trp Val Pro Arg Arg Gly Asp
            420                 425                 430

Gln Gly Pro Lys Thr Ile Asp Gln Ile His Lys Glu Ala Glu Met Glu
        435                 440                 445

Glu His Arg Glu His Ile Lys Val Gln Gln Leu Met Ala Lys Gly Ser
    450                 455                 460

Asp Lys Arg Arg Gly Gly Pro Pro Gly Pro Pro Ile Ser Arg Gly Leu
465                 470                 475                 480

Pro Leu Val Asp Asp Gly Gly Trp Asn Thr Val Pro Ile Ser Lys Gly
                485                 490                 495

Ser Arg Pro Ile Asp Thr Ser Arg Leu Thr Lys Ile Thr Lys Pro Gly
            500                 505                 510

Ser Ile Asp Ser Asn Asn Gln Leu Phe
        515                 520
```

<210> SEQ ID NO 68
<211> LENGTH: 1599
<212> TYPE: PRT
<213> ORGANISM: Artificial Sequence
<220> FEATURE:
<223> OTHER INFORMATION: Chemically synthesized

<400> SEQUENCE: 68

```
Met Asn Lys Ala Pro Gln Ser Thr Gly Pro Pro Pro Ala Pro Ser Pro
1               5                   10                  15

Gly Leu Pro Gln Pro Ala Phe Pro Pro Gly Gln Thr Ala Pro Val Val
            20                  25                  30

Phe Ser Thr Pro Gln Ala Thr Gln Met Asn Thr Pro Ser Gln Pro Arg
        35                  40                  45

Gln His Phe Tyr Pro Ser Arg Ala Gln Pro Pro Ser Ser Ala Ala Ser
    50                  55                  60

Arg Val Gln Ser Ala Ala Pro Ala Arg Pro Gly Pro Ala Ala His Val
65                  70                  75                  80

Tyr Pro Ala Gly Ser Gln Val Met Met Ile Pro Ser Gln Ile Ser Tyr
                85                  90                  95

Pro Ala Ser Gln Gly Ala Tyr Tyr Ile Pro Gly Gln Gly Arg Ser Thr
            100                 105                 110

Tyr Val Val Pro Thr Gln Gln Tyr Pro Val Gln Pro Gly Ala Pro Gly
        115                 120                 125

Phe Tyr Pro Gly Ala Ser Pro Thr Glu Phe Gly Thr Tyr Ala Gly Ala
    130                 135                 140

Tyr Tyr Pro Ala Gln Gly Val Gln Gln Phe Pro Thr Gly Val Ala Pro
145                 150                 155                 160

Thr Pro Val Leu Met Asn Gln Pro Pro Gln Ile Ala Pro Lys Arg Glu
                165                 170                 175

Arg Lys Thr Ile Arg Ile Arg Asp Pro Asn Gln Gly Gly Lys Asp Ile
            180                 185                 190

Thr Glu Glu Ile Met Ser Gly Ala Arg Thr Ala Ser Thr Pro Thr Pro
        195                 200                 205

Pro Gln Thr Gly Gly Gly Leu Glu Pro Gln Ala Asn Gly Glu Thr Pro
    210                 215                 220

Gln Val Ala Val Ile Val Arg Pro Asp Asp Arg Ser Gln Gly Ala Ile
225                 230                 235                 240
```

```
Ile Ala Asp Arg Pro Gly Leu Pro Gly Pro Glu His Ser Pro Ser Glu
                245                 250                 255

Ser Gln Pro Ser Ser Pro Ser Pro Thr Pro Ser Pro Ser Pro Val Leu
            260                 265                 270

Glu Pro Gly Ser Glu Pro Asn Leu Ala Val Leu Ser Ile Pro Gly Asp
        275                 280                 285

Thr Met Thr Thr Ile Gln Met Ser Val Glu Glu Ser Thr Pro Ile Ser
    290                 295                 300

Arg Glu Thr Gly Glu Pro Tyr Arg Leu Ser Pro Glu Pro Thr Pro Leu
305                 310                 315                 320

Ala Glu Pro Ile Leu Glu Val Glu Val Thr Leu Ser Lys Pro Val Pro
                325                 330                 335

Glu Ser Glu Phe Ser Ser Ser Pro Leu Gln Ala Pro Thr Pro Leu Ala
            340                 345                 350

Ser His Thr Val Glu Ile His Glu Pro Asn Gly Met Val Pro Ser Glu
        355                 360                 365

Asp Leu Glu Pro Glu Val Glu Ser Ser Pro Glu Leu Ala Pro Pro Pro
    370                 375                 380

Ala Cys Pro Ser Glu Ser Pro Val Pro Ile Ala Pro Thr Ala Gln Pro
385                 390                 395                 400

Glu Glu Leu Leu Asn Gly Ala Pro Ser Pro Pro Ala Val Asp Leu Ser
                405                 410                 415

Pro Val Ser Glu Pro Glu Glu Gln Ala Lys Glu Val Thr Ala Ser Met
            420                 425                 430

Ala Pro Pro Thr Ile Pro Ser Ala Thr Pro Ala Thr Ala Pro Ser Ala
        435                 440                 445

Thr Ser Pro Ala Gln Glu Glu Glu Met Glu Glu Glu Glu Glu Glu Glu
    450                 455                 460

Glu Gly Glu Ala Gly Glu Ala Gly Glu Ala Glu Ser Glu Lys Gly Gly
465                 470                 475                 480

Glu Glu Leu Leu Pro Pro Glu Ser Thr Pro Ile Pro Ala Asn Leu Ser
                485                 490                 495

Gln Asn Leu Glu Ala Ala Ala Ala Thr Gln Val Ala Val Ser Val Pro
            500                 505                 510

Lys Arg Arg Arg Lys Ile Lys Glu Leu Asn Lys Lys Glu Ala Val Gly
        515                 520                 525

Asp Leu Leu Asp Ala Phe Lys Glu Ala Asn Pro Ala Val Pro Glu Val
    530                 535                 540

Glu Asn Gln Pro Pro Ala Gly Ser Asn Pro Gly Pro Glu Ser Glu Gly
545                 550                 555                 560

Ser Gly Val Pro Pro Arg Pro Glu Glu Ala Asp Glu Thr Trp Asp Ser
                565                 570                 575

Lys Glu Asp Lys Ile His Asn Ala Glu Asn Ile Gln Pro Gly Glu Gln
            580                 585                 590

Lys Tyr Glu Tyr Lys Ser Asp Gln Trp Lys Pro Leu Asn Leu Glu Glu
        595                 600                 605

Lys Lys Arg Tyr Asp Arg Glu Phe Leu Leu Gly Phe Gln Phe Ile Phe
    610                 615                 620

Ala Ser Met Gln Lys Pro Glu Gly Leu Pro His Ile Ser Asp Val Val
625                 630                 635                 640

Leu Asp Lys Ala Asn Lys Thr Pro Leu Arg Pro Leu Asp Pro Thr Arg
                645                 650                 655
```

```
Leu Gln Gly Ile Asn Cys Gly Pro Asp Phe Thr Pro Ser Phe Ala Asn
            660                 665                 670

Leu Gly Arg Thr Thr Leu Ser Thr Arg Gly Pro Pro Arg Gly Gly Pro
        675                 680                 685

Gly Gly Glu Leu Pro Arg Gly Pro Ala Gly Leu Gly Pro Arg Arg Ser
    690                 695                 700

Gln Gln Gly Pro Arg Lys Glu Pro Arg Lys Ile Ile Ala Thr Val Leu
705                 710                 715                 720

Met Thr Glu Asp Ile Lys Leu Asn Lys Ala Glu Lys Ala Trp Lys Pro
                725                 730                 735

Ser Ser Lys Arg Thr Ala Ala Asp Lys Asp Arg Gly Glu Glu Asp Ala
            740                 745                 750

Asp Gly Ser Lys Thr Gln Asp Leu Phe Arg Arg Val Arg Ser Ile Leu
        755                 760                 765

Asn Lys Leu Thr Pro Gln Met Phe Gln Gln Leu Met Lys Gln Val Thr
    770                 775                 780

Gln Leu Ala Ile Asp Thr Glu Glu Arg Leu Lys Gly Val Ile Asp Leu
785                 790                 795                 800

Ile Phe Glu Lys Ala Ile Ser Glu Pro Asn Phe Ser Val Ala Tyr Ala
                805                 810                 815

Asn Met Cys Arg Cys Leu Met Ala Leu Lys Val Pro Thr Thr Glu Lys
            820                 825                 830

Pro Thr Val Thr Val Asn Phe Arg Lys Leu Leu Leu Asn Arg Cys Gln
        835                 840                 845

Lys Glu Phe Glu Lys Asp Lys Asp Asp Asp Glu Val Phe Glu Lys Lys
    850                 855                 860

Gln Lys Glu Met Asp Glu Ala Ala Thr Ala Glu Glu Arg Gly Arg Leu
865                 870                 875                 880

Lys Glu Glu Leu Glu Glu Ala Arg Asp Ile Ala Arg Arg Arg Ser Leu
                885                 890                 895

Gly Asn Ile Lys Phe Ile Gly Glu Leu Phe Lys Leu Lys Met Leu Thr
            900                 905                 910

Glu Ala Ile Met His Asp Cys Val Val Lys Leu Leu Lys Asn His Asp
        915                 920                 925

Glu Glu Ser Leu Glu Cys Leu Cys Arg Leu Leu Thr Thr Ile Gly Lys
    930                 935                 940

Asp Leu Asp Phe Glu Lys Ala Lys Pro Arg Met Asp Gln Tyr Phe Asn
945                 950                 955                 960

Gln Met Glu Lys Ile Ile Lys Glu Lys Lys Thr Ser Ser Arg Ile Arg
                965                 970                 975

Phe Met Leu Gln Asp Val Leu Asp Leu Arg Gly Ser Asn Trp Val Pro
            980                 985                 990

Arg Arg Gly Asp Gln Gly Pro Lys  Thr Ile Asp Gln Ile  His Lys Glu
        995                 1000                1005

Ala Glu  Met Glu Glu His Arg  Glu His Ile Lys Val  Gln Gln Leu
    1010                1015                1020

Met Ala  Lys Gly Ser Asp Lys  Arg Arg Gly Gly Pro  Pro Gly Pro
    1025                1030                1035

Pro Ile  Ser Arg Gly Leu Pro  Leu Val Asp Asp Gly  Gly Trp Asn
    1040                1045                1050

Thr Val  Pro Ile Ser Lys Gly  Ser Arg Pro Ile Asp  Thr Ser Arg
    1055                1060                1065

Leu Thr  Lys Ile Thr Lys Pro  Gly Ser Ile Asp Ser  Asn Asn Gln
```

```
    1070                1075                1080

Leu Phe  Ala Pro Gly Gly Arg  Leu Ser Trp Gly Lys  Gly Ser Ser
    1085                1090                1095

Gly Gly  Ser Gly Ala Lys Pro  Ser Asp Ala Ala Ser  Glu Ala Ala
    1100                1105                1110

Arg Pro  Ala Thr Ser Thr Leu  Asn Arg Phe Ser Ala  Leu Gln Gln
    1115                1120                1125

Ala Val  Pro Thr Glu Ser Thr  Asp Asn Arg Arg Val  Val Gln Arg
    1130                1135                1140

Ser Ser  Leu Ser Arg Glu Arg  Gly Glu Lys Ala Gly  Asp Arg Gly
    1145                1150                1155

Asp Arg  Leu Glu Arg Ser Glu  Arg Gly Gly Asp Arg  Gly Asp Arg
    1160                1165                1170

Leu Asp  Arg Ala Arg Thr Pro  Ala Thr Lys Arg Ser  Phe Ser Lys
    1175                1180                1185

Glu Val  Glu Glu Arg Ser Arg  Glu Arg Pro Ser Gln  Pro Glu Gly
    1190                1195                1200

Leu Arg  Lys Ala Ala Ser Leu  Thr Glu Asp Arg Asp  Arg Gly Arg
    1205                1210                1215

Asp Ala  Val Lys Arg Glu Ala  Ala Leu Pro Pro Val  Ser Pro Leu
    1220                1225                1230

Lys Ala  Ala Leu Ser Glu Glu  Glu Leu Glu Lys Lys  Ser Lys Ala
    1235                1240                1245

Ile Ile  Glu Glu Tyr Leu His  Leu Asn Asp Met Lys  Glu Ala Val
    1250                1255                1260

Gln Cys  Val Gln Glu Leu Ala  Ser Pro Ser Leu Leu  Phe Ile Phe
    1265                1270                1275

Val Arg  His Gly Val Glu Ser  Thr Leu Glu Arg Ser  Ala Ile Ala
    1280                1285                1290

Arg Glu  His Met Gly Gln Leu  Leu His Gln Leu Leu  Cys Ala Gly
    1295                1300                1305

His Leu  Ser Thr Ala Gln Tyr  Tyr Gln Gly Leu Tyr  Glu Ile Leu
    1310                1315                1320

Glu Leu  Ala Glu Asp Met Glu  Ile Asp Ile Pro His  Val Trp Leu
    1325                1330                1335

Tyr Leu  Ala Glu Leu Val Thr  Pro Ile Leu Gln Glu  Gly Gly Val
    1340                1345                1350

Pro Met  Gly Glu Leu Phe Arg  Glu Ile Thr Lys Pro  Leu Arg Pro
    1355                1360                1365

Leu Gly  Lys Ala Ala Ser Leu  Leu Leu Glu Ile Leu  Gly Leu Leu
    1370                1375                1380

Cys Lys  Ser Met Gly Pro Lys  Lys Val Gly Thr Leu  Trp Arg Glu
    1385                1390                1395

Ala Gly  Leu Ser Trp Lys Glu  Phe Leu Pro Glu Gly  Gln Asp Ile
    1400                1405                1410

Gly Ala  Phe Val Ala Glu Gln  Lys Val Glu Tyr Thr  Leu Gly Glu
    1415                1420                1425

Glu Ser  Glu Ala Pro Gly Gln  Arg Ala Leu Pro Ser  Glu Glu Leu
    1430                1435                1440

Asn Arg  Gln Leu Glu Lys Leu  Leu Lys Glu Gly Ser  Ser Asn Gln
    1445                1450                1455

Arg Val  Phe Asp Trp Ile Glu  Ala Asn Leu Ser Glu  Gln Gln Ile
    1460                1465                1470
```

Val Ser Asn Thr Leu Val Arg Ala Leu Met Thr Ala Val Cys Tyr
1475 1480 1485

Ser Ala Ile Ile Phe Glu Thr Pro Leu Arg Val Asp Val Ala Val
1490 1495 1500

Leu Lys Ala Arg Ala Lys Leu Leu Gln Lys Tyr Leu Cys Asp Glu
1505 1510 1515

Gln Lys Glu Leu Gln Ala Leu Tyr Ala Leu Gln Ala Leu Val Val
1520 1525 1530

Thr Leu Glu Gln Pro Pro Asn Leu Leu Arg Met Phe Phe Asp Ala
1535 1540 1545

Leu Tyr Asp Glu Asp Val Val Lys Glu Asp Ala Phe Tyr Ser Trp
1550 1555 1560

Glu Ser Ser Lys Asp Pro Ala Glu Gln Gln Gly Lys Gly Val Ala
1565 1570 1575

Leu Lys Ser Val Thr Ala Phe Phe Lys Trp Leu Arg Glu Ala Glu
1580 1585 1590

Glu Glu Ser Asp His Asn
1595

<210> SEQ ID NO 69
<211> LENGTH: 112
<212> TYPE: PRT
<213> ORGANISM: Artificial Sequence
<220> FEATURE:
<223> OTHER INFORMATION: Chemically synthesized

<400> SEQUENCE: 69

Ser Ala Ile Gln Asn Leu His Ser Phe Asp Pro Phe Ala Asp Ala Ser
1 5 10 15

Lys Gly Asp Asp Leu Leu Pro Ala Gly Thr Glu Asp Tyr Ile His Ile
20 25 30

Arg Ile Gln Gln Arg Asn Gly Arg Lys Thr Leu Thr Thr Val Gln Gly
35 40 45

Ile Ala Asp Asp Tyr Asp Lys Lys Lys Leu Val Lys Ala Phe Lys Lys
50 55 60

Lys Phe Ala Cys Asn Gly Thr Val Ile Glu His Pro Glu Tyr Gly Glu
65 70 75 80

Val Ile Gln Leu Gln Gly Asp Gln Arg Lys Asn Ile Cys Gln Phe Leu
85 90 95

Val Glu Ile Gly Leu Ala Lys Asp Asp Gln Leu Lys Val His Gly Phe
100 105 110

<210> SEQ ID NO 70
<211> LENGTH: 143
<212> TYPE: PRT
<213> ORGANISM: Artificial Sequence
<220> FEATURE:
<223> OTHER INFORMATION: Chemically synthesized

<400> SEQUENCE: 70

Pro Lys Asn Lys Gly Lys Gly Gly Lys Asn Arg Arg Arg Gly Lys Asn
1 5 10 15

Glu Asn Glu Ser Glu Lys Arg Glu Leu Val Phe Lys Glu Asp Gly Gln
20 25 30

Glu Tyr Ala Gln Val Ile Lys Met Leu Gly Asn Gly Arg Leu Glu Ala
35 40 45

Met Cys Phe Asp Gly Val Lys Arg Leu Cys His Ile Arg Gly Lys Leu

```
    50                  55                  60

Arg Lys Lys Val Trp Ile Asn Thr Ser Asp Ile Ile Leu Val Gly Leu
65                  70                  75                  80

Arg Asp Tyr Gln Asp Asn Lys Ala Asp Val Ile Leu Lys Tyr Asn Ala
                85                  90                  95

Asp Glu Ala Arg Ser Leu Lys Ala Tyr Gly Glu Leu Pro Glu His Ala
            100                 105                 110

Lys Ile Asn Glu Thr Asp Thr Phe Gly Pro Gly Asp Asp Asp Glu Ile
        115                 120                 125

Gln Phe Asp Asp Ile Gly Asp Asp Asp Glu Asp Ile Asp Asp Ile
    130                 135                 140


<210> SEQ ID NO 71
<211> LENGTH: 111
<212> TYPE: PRT
<213> ORGANISM: Artificial Sequence
<220> FEATURE:
<223> OTHER INFORMATION: Chemically synthesized

<400> SEQUENCE: 71

Ala Lys Gly Lys Thr Lys Ser Lys Val Gly Pro Tyr Arg Gly Arg Gly
1               5                   10                  15

Val Ala Leu Thr Asp Asp Glu Tyr Asp Glu Trp Arg Glu His Asn Ala
            20                  25                  30

Thr Arg Lys Leu Asp Leu Ser Val Glu Asp Phe Leu Met Leu Arg His
        35                  40                  45

Arg Ala Ala Leu Gly Ala Asp Asp Ala Asp Ala Val Lys Phe Arg Ser
    50                  55                  60

Trp Trp Asn Ser Arg Ser Arg Leu Ala Asp Asp Tyr Glu Asp Val Thr
65                  70                  75                  80

Val Ile Gly Lys Gly Gly Val Lys His Glu Lys Ile Arg Thr Asn Thr
                85                  90                  95

Leu Arg Ala Val Asp Arg Gly Tyr Asp Val Ser Phe Ala Glu Glu
            100                 105                 110


<210> SEQ ID NO 72
<211> LENGTH: 124
<212> TYPE: PRT
<213> ORGANISM: Artificial Sequence
<220> FEATURE:
<223> OTHER INFORMATION: Chemically synthesized

<400> SEQUENCE: 72

Gly Lys Lys Gly Lys Asn Lys Lys Gly Arg Gly Arg Pro Gly Val Phe
1               5                   10                  15

Arg Thr Arg Gly Leu Thr Asp Glu Glu Tyr Asp Glu Phe Lys Lys Arg
            20                  25                  30

Arg Glu Ser Arg Gly Gly Lys Tyr Ser Ile Asp Asp Tyr Leu Ala Asp
        35                  40                  45

Arg Glu Arg Glu Glu Glu Leu Leu Glu Arg Asp Glu Glu Glu Ala Ile
    50                  55                  60

Phe Gly Asp Gly Phe Gly Leu Lys Ala Thr Arg Arg Ser Arg Lys Ala
65                  70                  75                  80

Glu Arg Ala Lys Leu Gly Leu Val Ser Gly Gly Asp Ile Arg Ala Arg
                85                  90                  95

Lys Pro Ile Asp Trp Asn Val Val Gly Pro Ser Trp Ala Asp Asp Asp
            100                 105                 110
```

```
Arg Gln Val Asp Tyr Gly Glu Lys Ile Asn Phe Glu
        115                 120


<210> SEQ ID NO 73
<211> LENGTH: 193
<212> TYPE: PRT
<213> ORGANISM: Artificial Sequence
<220> FEATURE:
<223> OTHER INFORMATION: Chemically synthesized

<400> SEQUENCE: 73

Gly Phe Asn Arg Arg Gln Arg Gln Lys Leu Lys Phe Arg Gln Ala Arg
1               5                   10                  15

Asp Asn Arg Met Ala Arg Glu Val Tyr Gly Asp Asp Ser Thr Met Glu
            20                  25                  30

Asp Tyr Phe Gly Ser Ala Tyr Ser Lys Lys Gly Lys Ser Lys Gly Arg
        35                  40                  45

Thr Arg Gly Met Gly Thr Lys Thr Arg Lys Phe Val Asn Met Tyr Gly
    50                  55                  60

Tyr Asp Pro Thr Asp Tyr Asn Phe Val Arg Phe Val Asp Pro Leu Thr
65                  70                  75                  80

Gly His Thr Leu Asp Glu Asn Pro Leu Met Asp Ile Asn Leu Val Gln
                85                  90                  95

Glu His Phe Ser Gln Val Arg Asn Asp Tyr Leu Gly Asp Asp Lys Ile
            100                 105                 110

Thr Met Gln His Ile Met Ser Asn Pro Gly Ile Val Ala Tyr Tyr Ile
        115                 120                 125

Lys Asp Ala Thr Gln Lys Ala Leu Lys Val Asp Leu Thr Pro His Asn
    130                 135                 140

Pro Leu Arg Val Cys Asp Lys Thr Ala Thr Ile Ala Gly Phe Pro Glu
145                 150                 155                 160

Arg Glu Phe Glu Leu Arg Gln Thr Gly Gln Pro Val Leu Val Glu Pro
                165                 170                 175

Asn Ala Ile Pro Gln Ile Asn Glu Glu Gly Asp Glu Glu Val Gly His
            180                 185                 190

Glu


<210> SEQ ID NO 74
<211> LENGTH: 427
<212> TYPE: PRT
<213> ORGANISM: Artificial Sequence
<220> FEATURE:
<223> OTHER INFORMATION: Chemically synthesized

<400> SEQUENCE: 74

Ser Thr Leu Lys Glu Val Gln Asp Asn Ile Thr Leu His Glu Gln Gln
1               5                   10                  15

Leu Val Thr Ala Arg Gln Lys Leu Lys Asp Ala Glu Arg Ala Val Glu
            20                  25                  30

Leu Asp Pro Asp Asp Val Asn Lys Ser Thr Leu Gln Ser Arg Arg Ala
        35                  40                  45

Ala Val Ser Ala Leu Glu Thr Lys Leu Gly Glu Leu Lys Arg Glu Leu
    50                  55                  60

Ala Asp Leu Ile Ala Ala Gln Lys Leu Ala Ser Lys Pro Val Asp Pro
65                  70                  75                  80

Thr Gly Ile Glu Pro Asp Asp His Leu Lys Glu Lys Ser Ser Leu Arg
                85                  90                  95
```

Tyr Gly Asn Val Leu Asp Val Asn Ser Ile Asp Leu Glu Glu Pro Ser
100 105 110

Gly Gln Thr Ala Asp Trp Lys Ser Ile Gly Leu Tyr Ile Leu Ser Phe
115 120 125

Ala Leu Pro Ile Ile Leu Lys Ala Leu Tyr Met Leu Ser Thr Arg Gly
130 135 140

Arg Gln Thr Ile Lys Glu Asn Lys Gly Thr Arg Ile Arg Phe Lys Asp
145 150 155 160

Asp Ser Ser Tyr Glu Glu Val Asn Gly Ile Arg Lys Pro Arg His Leu
165 170 175

Tyr Val Ser Met Pro Thr Ala Gln Ser Thr Met Lys Ala Asp Glu Ile
180 185 190

Thr Pro Gly Arg Phe Arg Thr Ile Ala Cys Gly Leu Phe Pro Ala Gln
195 200 205

Val Lys Ala Arg Asn Ile Ile Ser Pro Val Met Gly Val Ile Gly Phe
210 215 220

Ser Phe Phe Val Lys Asp Trp Met Glu Arg Ile Asp Asp Phe Leu Ala
225 230 235 240

Ala Arg Cys Pro Phe Leu Pro Glu Gln Lys Asp Pro Arg Asp Ala Ala
245 250 255

Leu Ala Thr Asn Arg Ala Tyr Phe Ile Thr Arg Gln Leu Gln Val Asp
260 265 270

Glu Ser Lys Val Ser Asp Ile Glu Asp Leu Ile Ala Asp Ala Arg Ala
275 280 285

Glu Ser Ala Thr Ile Phe Ala Asp Ile Ala Thr Pro His Ser Val Trp
290 295 300

Val Phe Ala Cys Ala Pro Asp Arg Cys Pro Pro Thr Ala Leu Tyr Val
305 310 315 320

Ala Gly Met Pro Glu Leu Gly Ala Phe Phe Ala Ile Leu Gln Asp Met
325 330 335

Arg Asn Thr Ile Met Ala Ser Lys Ser Val Gly Thr Ser Glu Glu Lys
340 345 350

Leu Lys Lys Lys Ser Ala Phe Tyr Gln Ser Tyr Leu Arg Arg Thr Gln
355 360 365

Ser Met Gly Ile Gln Leu Asp Gln Lys Ile Ile Ile Leu Tyr Met Ser
370 375 380

His Trp Gly Arg Glu Ala Val Asn His Phe His Leu Gly Asp Asp Met
385 390 395 400

Asp Pro Glu Leu Arg Glu Leu Ala Gln Thr Leu Val Asp Ile Lys Val
405 410 415

Arg Glu Ile Ser Asn Gln Glu Pro Leu Lys Leu
420 425

<210> SEQ ID NO 75
<211> LENGTH: 186
<212> TYPE: PRT
<213> ORGANISM: Artificial Sequence
<220> FEATURE:
<223> OTHER INFORMATION: Chemically synthesized

<400> SEQUENCE: 75

Ser Thr Leu Lys Glu Val Gln Asp Asn Ile Thr Leu His Glu Gln Gln
1 5 10 15

Leu Val Thr Ala Arg Gln Lys Leu Lys Asp Ala Glu Arg Ala Val Glu
20 25 30

```
Leu Asp Pro Asp Asp Val Asn Lys Ser Thr Leu Gln Ser Arg Arg Ala
        35                  40                  45

Ala Val Ser Ala Leu Glu Thr Lys Leu Gly Glu Leu Lys Arg Glu Leu
    50                  55                  60

Ala Asp Leu Ile Ala Ala Gln Lys Leu Ala Ser Lys Pro Val Asp Pro
65                  70                  75                  80

Thr Gly Ile Glu Pro Asp Asp His Leu Lys Glu Lys Ser Ser Leu Arg
                85                  90                  95

Tyr Gly Asn Val Leu Asp Val Asn Ser Ile Asp Leu Glu Glu Pro Ser
            100                 105                 110

Gly Gln Thr Ala Asp Trp Lys Ser Ile Gly Leu Tyr Ile Leu Ser Phe
        115                 120                 125

Ala Leu Pro Ile Ile Leu Lys Ala Leu Tyr Met Leu Ser Thr Arg Gly
    130                 135                 140

Arg Gln Thr Ile Lys Glu Asn Lys Gly Thr Arg Ile Arg Phe Lys Asp
145                 150                 155                 160

Asp Ser Ser Tyr Glu Glu Val Asn Gly Ile Arg Lys Pro Arg His Leu
                165                 170                 175

Tyr Val Ser Met Pro Thr Ala Gln Ser Thr
            180                 185


<210> SEQ ID NO 76
<211> LENGTH: 71
<212> TYPE: PRT
<213> ORGANISM: Artificial Sequence
<220> FEATURE:
<223> OTHER INFORMATION: Chemically synthesized

<400> SEQUENCE: 76

Ala Lys Glu Asp Asn Ile Glu Met Gln Gly Thr Val Leu Glu Thr Leu
1               5                   10                  15

Pro Asn Thr Met Phe Arg Val Glu Leu Glu Asn Gly His Val Val Thr
            20                  25                  30

Ala His Ile Ser Gly Lys Met Arg Lys Asn Tyr Ile Arg Ile Leu Thr
        35                  40                  45

Gly Asp Lys Val Thr Val Glu Leu Thr Pro Tyr Asp Leu Ser Lys Gly
    50                  55                  60

Arg Ile Val Phe Arg Ser Arg
65                  70


<210> SEQ ID NO 77
<211> LENGTH: 180
<212> TYPE: PRT
<213> ORGANISM: Artificial Sequence
<220> FEATURE:
<223> OTHER INFORMATION: Chemically synthesized

<400> SEQUENCE: 77

Met Lys Gly Gly Lys Arg Val Gln Thr Ala Arg Pro Asn Arg Ile Asn
1               5                   10                  15

Gly Glu Ile Arg Ala Gln Glu Val Arg Leu Thr Gly Leu Glu Gly Glu
            20                  25                  30

Gln Leu Gly Ile Val Ser Leu Arg Glu Ala Leu Glu Lys Ala Glu Glu
        35                  40                  45

Ala Gly Val Asp Leu Val Glu Ile Ser Pro Asn Ala Glu Pro Pro Val
    50                  55                  60

Cys Arg Ile Met Asp Tyr Gly Lys Phe Leu Tyr Glu Lys Ser Lys Ser
65                  70                  75                  80
```

Ser Lys Glu Gln Lys Lys Lys Gln Lys Val Ile Gln Val Lys Glu Ile
85 90 95

Lys Phe Arg Pro Gly Thr Asp Glu Gly Asp Tyr Gln Val Lys Leu Arg
100 105 110

Ser Leu Ile Arg Phe Leu Glu Glu Gly Asp Lys Ala Lys Ile Thr Leu
115 120 125

Arg Phe Arg Gly Arg Glu Met Ala His Gln Gln Ile Gly Met Glu Val
130 135 140

Leu Asn Arg Val Lys Asp Asp Leu Gln Glu Leu Ala Val Val Glu Ser
145 150 155 160

Phe Pro Thr Lys Ile Glu Gly Arg Gln Met Ile Met Val Leu Ala Pro
165 170 175

Lys Lys Lys Gln
180

<210> SEQ ID NO 78
<211> LENGTH: 1663
<212> TYPE: PRT
<213> ORGANISM: Artificial Sequence
<220> FEATURE:
<223> OTHER INFORMATION: Chemically synthesized

<400> SEQUENCE: 78

Met Asp Tyr Lys Asp His Asp Gly Asp Tyr Lys Asp His Asp Ile Asp
1 5 10 15

Tyr Lys Asp Asp Asp Asp Lys Gly Ser Leu Gln Leu Pro Pro Leu Glu
20 25 30

Arg Leu Thr Leu Gly Ser Ser Asn Ile Pro Ala Leu Val Glu Asn Gln
35 40 45

Lys Lys Tyr Phe Gly Thr Tyr Ser Val Met Ala Met Leu Asn Ala Gln
50 55 60

Thr Val Leu Asp His Ile Gln Lys Val Ala Asp Ile Glu Gly Glu Gln
65 70 75 80

Asn Glu Asn Asn Glu Asn Leu Trp Phe His Pro Val Met Ser His Leu
85 90 95

Tyr Asn Ala Lys Asn Gly Tyr Asp Lys Gln Pro Glu Lys Thr Met Phe
100 105 110

Ile Ile Glu Arg Leu Gln Ser Tyr Phe Pro Phe Leu Lys Ile Met Ala
115 120 125

Glu Asn Gln Arg Glu Tyr Ser Asn Gly Lys Tyr Lys Gln Asn Arg Val
130 135 140

Glu Val Asn Ser Asn Asp Ile Phe Glu Val Leu Lys Arg Ala Phe Gly
145 150 155 160

Val Leu Lys Met Tyr Arg Asp Leu Thr Asn Ala Tyr Lys Thr Tyr Glu
165 170 175

Glu Lys Leu Asn Asp Gly Cys Glu Phe Leu Thr Ser Thr Glu Gln Pro
180 185 190

Leu Ser Gly Met Ile Asn Asn Tyr Tyr Thr Val Ala Leu Arg Asn Met
195 200 205

Asn Glu Arg Tyr Gly Tyr Lys Thr Glu Asp Leu Ala Phe Ile Gln Asp
210 215 220

Lys Arg Phe Lys Phe Val Lys Asp Ala Tyr Gly Lys Lys Lys Ser Gln
225 230 235 240

Val Asn Thr Gly Phe Phe Leu Ser Leu Gln Asp Tyr Asn Gly Asp Thr
245 250 255

```
Gln Lys Lys Leu His Leu Ser Gly Val Gly Ile Ala Leu Leu Ile Cys
            260                 265                 270

Leu Phe Leu Asp Lys Gln Tyr Ile Asn Ile Phe Leu Ser Arg Leu Pro
        275                 280                 285

Ile Phe Ser Ser Tyr Asn Ala Gln Ser Glu Glu Arg Arg Ile Ile Ile
    290                 295                 300

Arg Ser Phe Gly Ile Asn Ser Ile Lys Leu Pro Lys Asp Arg Ile His
305                 310                 315                 320

Ser Glu Lys Ser Asn Lys Ser Val Ala Met Asp Met Leu Asn Glu Val
                325                 330                 335

Lys Arg Cys Pro Asp Glu Leu Phe Thr Thr Leu Ser Ala Glu Lys Gln
            340                 345                 350

Ser Arg Phe Arg Ile Ile Ser Asp Asp His Asn Glu Val Leu Met Lys
        355                 360                 365

Arg Ser Ser Asp Arg Phe Val Pro Leu Leu Leu Gln Tyr Ile Asp Tyr
    370                 375                 380

Gly Lys Leu Phe Asp His Ile Arg Phe His Val Asn Met Gly Lys Leu
385                 390                 395                 400

Arg Tyr Leu Leu Lys Ala Asp Lys Thr Cys Ile Asp Gly Gln Thr Arg
                405                 410                 415

Val Arg Val Ile Glu Gln Pro Leu Asn Gly Phe Gly Arg Leu Glu Glu
            420                 425                 430

Ala Glu Thr Met Arg Lys Gln Glu Asn Gly Thr Phe Gly Asn Ser Gly
        435                 440                 445

Ile Arg Ile Arg Asp Phe Glu Asn Met Lys Arg Asp Asp Ala Asn Pro
    450                 455                 460

Ala Asn Tyr Pro Tyr Ile Val Asp Thr Tyr Thr His Tyr Ile Leu Glu
465                 470                 475                 480

Asn Asn Lys Val Glu Met Phe Ile Asn Asp Lys Glu Asp Ser Ala Pro
                485                 490                 495

Leu Leu Pro Val Ile Glu Asp Asp Arg Tyr Val Val Lys Thr Ile Pro
            500                 505                 510

Ser Cys Arg Met Ser Thr Leu Glu Ile Pro Ala Met Ala Phe His Met
        515                 520                 525

Phe Leu Phe Gly Ser Lys Lys Thr Glu Lys Leu Ile Val Asp Val His
    530                 535                 540

Asn Arg Tyr Lys Arg Leu Phe Gln Ala Met Gln Lys Glu Glu Val Thr
545                 550                 555                 560

Ala Glu Asn Ile Ala Ser Phe Gly Ile Ala Glu Ser Asp Leu Pro Gln
                565                 570                 575

Lys Ile Leu Asp Leu Ile Ser Gly Asn Ala His Gly Lys Asp Val Asp
            580                 585                 590

Ala Phe Ile Arg Leu Thr Val Asp Asp Met Leu Thr Asp Thr Glu Arg
        595                 600                 605

Arg Ile Lys Arg Phe Lys Asp Asp Arg Lys Ser Ile Arg Ser Ala Asp
    610                 615                 620

Asn Lys Met Gly Lys Arg Gly Phe Lys Gln Ile Ser Thr Gly Lys Leu
625                 630                 635                 640

Ala Asp Phe Leu Ala Lys Asp Ile Val Leu Phe Gln Pro Ser Val Asn
                645                 650                 655

Asp Gly Glu Asn Lys Ile Thr Gly Leu Asn Tyr Arg Ile Met Gln Ser
            660                 665                 670
```

```
Ala Ile Ala Val Tyr Asp Ser Gly Asp Asp Tyr Glu Ala Lys Gln Gln
        675                 680                 685

Phe Lys Leu Met Phe Glu Lys Ala Arg Leu Ile Gly Lys Gly Thr Thr
    690                 695                 700

Glu Pro His Pro Phe Leu Tyr Lys Val Phe Ala Arg Ser Ile Pro Ala
705                 710                 715                 720

Asn Ala Val Glu Phe Tyr Glu Arg Tyr Leu Ile Glu Arg Lys Phe Tyr
                725                 730                 735

Leu Thr Gly Leu Ser Asn Glu Ile Lys Lys Gly Asn Arg Val Asp Val
            740                 745                 750

Pro Phe Ile Arg Arg Asp Gln Asn Lys Trp Lys Thr Pro Ala Met Lys
        755                 760                 765

Thr Leu Gly Arg Ile Tyr Ser Glu Asp Leu Pro Val Glu Leu Pro Arg
    770                 775                 780

Gln Met Phe Asp Asn Glu Ile Lys Ser His Leu Lys Ser Leu Pro Gln
785                 790                 795                 800

Met Glu Gly Ile Asp Phe Asn Asn Ala Asn Val Thr Tyr Leu Ile Ala
                805                 810                 815

Glu Tyr Met Lys Arg Val Leu Asp Asp Asp Phe Gln Thr Phe Tyr Gln
            820                 825                 830

Trp Asn Arg Asn Tyr Arg Tyr Met Asp Met Leu Lys Gly Glu Tyr Asp
        835                 840                 845

Arg Lys Gly Ser Leu Gln His Cys Phe Thr Ser Val Glu Glu Arg Glu
    850                 855                 860

Gly Leu Trp Lys Glu Arg Ala Ser Arg Thr Glu Arg Tyr Arg Lys Gln
865                 870                 875                 880

Ala Ser Asn Lys Ile Arg Ser Asn Arg Gln Met Arg Asn Ala Ser Ser
                885                 890                 895

Glu Glu Ile Glu Thr Ile Leu Asp Lys Arg Leu Ser Asn Ser Arg Asn
            900                 905                 910

Glu Tyr Gln Lys Ser Glu Lys Val Ile Arg Arg Tyr Arg Val Gln Asp
        915                 920                 925

Ala Leu Leu Phe Leu Leu Ala Lys Lys Thr Leu Thr Glu Leu Ala Asp
    930                 935                 940

Phe Asp Gly Glu Arg Phe Lys Leu Lys Glu Ile Met Pro Asp Ala Glu
945                 950                 955                 960

Lys Gly Ile Leu Ser Glu Ile Met Pro Met Ser Phe Thr Phe Glu Lys
                965                 970                 975

Gly Gly Lys Lys Tyr Thr Ile Thr Ser Glu Gly Met Lys Leu Lys Asn
            980                 985                 990

Tyr Gly Asp Phe Phe Val Leu Ala  Ser Asp Lys Arg Ile  Gly Asn Leu
        995                 1000                 1005

Leu Glu  Leu Val Gly Ser Asp  Ile Val Ser Lys Glu  Asp Ile Met
    1010                 1015                 1020

Glu Glu  Phe Asn Lys Tyr Asp  Gln Cys Arg Pro Glu  Ile Ser Ser
    1025                 1030                 1035

Ile Val  Phe Asn Leu Glu Lys  Trp Ala Phe Asp Thr  Tyr Pro Glu
    1040                 1045                 1050

Leu Ser  Ala Arg Val Asp Arg  Glu Glu Lys Val Asp  Phe Lys Ser
    1055                 1060                 1065

Ile Leu  Lys Ile Leu Leu Asn  Asn Lys Asn Ile Asn  Lys Glu Gln
    1070                 1075                 1080

Ser Asp  Ile Leu Arg Lys Ile  Arg Asn Ala Phe Asp  Ala Asn Asn
```

```
    1085                1090                1095

Tyr Pro  Asp Lys Gly Val Val  Glu Ile Lys Ala Leu  Pro Glu Ile
    1100                1105                1110

Ala Met  Ser Ile Lys Lys Ala  Phe Gly Glu Tyr Ala  Ile Met Lys
    1115                1120                1125

Ser Arg  Gly Gly Gly Gly Ser  Gly Gly Gly Gly Ser  Thr Arg Pro
    1130                1135                1140

Arg Pro  Glu Glu Ala Asp Glu  Thr Trp Asp Ser Lys  Glu Asp Lys
    1145                1150                1155

Ile His  Asn Ala Glu Asn Ile  Gln Pro Gly Glu Gln  Lys Tyr Glu
    1160                1165                1170

Tyr Lys  Ser Asp Gln Trp Lys  Pro Leu Asn Leu Glu  Glu Lys Lys
    1175                1180                1185

Arg Tyr  Asp Arg Glu Phe Leu  Leu Gly Phe Gln Phe  Ile Phe Ala
    1190                1195                1200

Ser Met  Gln Lys Pro Glu Gly  Leu Pro His Ile Ser  Asp Val Val
    1205                1210                1215

Leu Asp  Lys Ala Asn Lys Thr  Pro Leu Arg Pro Leu  Asp Pro Thr
    1220                1225                1230

Arg Leu  Gln Gly Ile Asn Cys  Gly Pro Asp Phe Thr  Pro Ser Phe
    1235                1240                1245

Ala Asn  Leu Gly Arg Thr Thr  Leu Ser Thr Arg Gly  Pro Pro Arg
    1250                1255                1260

Gly Gly  Pro Gly Gly Glu Leu  Pro Arg Gly Pro Ala  Gly Leu Gly
    1265                1270                1275

Pro Arg  Arg Ser Gln Gln Gly  Pro Arg Lys Glu Pro  Arg Lys Ile
    1280                1285                1290

Ile Ala  Thr Val Leu Met Thr  Glu Asp Ile Lys Leu  Asn Lys Ala
    1295                1300                1305

Glu Lys  Ala Trp Lys Pro Ser  Ser Lys Arg Thr Ala  Ala Asp Lys
    1310                1315                1320

Asp Arg  Gly Glu Glu Asp Ala  Asp Gly Ser Lys Thr  Gln Asp Leu
    1325                1330                1335

Phe Arg  Arg Val Arg Ser Ile  Leu Asn Lys Leu Thr  Pro Gln Met
    1340                1345                1350

Phe Gln  Gln Leu Met Lys Gln  Val Thr Gln Leu Ala  Ile Asp Thr
    1355                1360                1365

Glu Glu  Arg Leu Lys Gly Val  Ile Asp Leu Ile Phe  Glu Lys Ala
    1370                1375                1380

Ile Ser  Glu Pro Asn Phe Ser  Val Ala Tyr Ala Asn  Met Cys Arg
    1385                1390                1395

Cys Leu  Met Ala Leu Lys Val  Pro Thr Thr Glu Lys  Pro Thr Val
    1400                1405                1410

Thr Val  Asn Phe Arg Lys Leu  Leu Leu Asn Arg Cys  Gln Lys Glu
    1415                1420                1425

Phe Glu  Lys Asp Lys Asp Asp  Asp Glu Val Phe Glu  Lys Lys Gln
    1430                1435                1440

Lys Glu  Met Asp Glu Ala Ala  Thr Ala Glu Glu Arg  Gly Arg Leu
    1445                1450                1455

Lys Glu  Glu Leu Glu Glu Ala  Arg Asp Ile Ala Arg  Arg Arg Ser
    1460                1465                1470

Leu Gly  Asn Ile Lys Phe Ile  Gly Glu Leu Phe Lys  Leu Lys Met
    1475                1480                1485
```

```
Leu Thr  Glu Ala Ile Met His  Asp Cys Val Val Lys  Leu Leu Lys
    1490                 1495                 1500

Asn His  Asp Glu Glu Ser Leu  Glu Cys Leu Cys Arg  Leu Leu Thr
    1505                 1510                 1515

Thr Ile  Gly Lys Asp Leu Asp  Phe Glu Lys Ala Lys  Pro Arg Met
    1520                 1525                 1530

Asp Gln  Tyr Phe Asn Gln Met  Glu Lys Ile Ile Lys  Glu Lys Lys
    1535                 1540                 1545

Thr Ser  Ser Arg Ile Arg Phe  Met Leu Gln Asp Val  Leu Asp Leu
    1550                 1555                 1560

Arg Gly  Ser Asn Trp Val Pro  Arg Arg Gly Asp Gln  Gly Pro Lys
    1565                 1570                 1575

Thr Ile  Asp Gln Ile His Lys  Glu Ala Glu Met Glu  Glu His Arg
    1580                 1585                 1590

Glu His  Ile Lys Val Gln Gln  Leu Met Ala Lys Gly  Ser Asp Lys
    1595                 1600                 1605

Arg Arg  Gly Gly Pro Pro Gly  Pro Pro Ile Ser Arg  Gly Leu Pro
    1610                 1615                 1620

Leu Val  Asp Asp Gly Gly Trp  Asn Thr Val Pro Ile  Ser Lys Gly
    1625                 1630                 1635

Ser Arg  Pro Ile Asp Thr Ser  Arg Leu Thr Lys Ile  Thr Lys Pro
    1640                 1645                 1650

Gly Ser  Ile Asp Ser Asn Asn  Gln Leu Phe
    1655                 1660
```

<210> SEQ ID NO 79
<211> LENGTH: 3267
<212> TYPE: DNA
<213> ORGANISM: Artificial Sequence
<220> FEATURE:
<223> OTHER INFORMATION: Chemically synthesized

<400> SEQUENCE: 79

```
aacatccccg ctctggtgga aaaccagaag aagtactttg gcacctacag cgtgatggcc     60

atgctgaacg ctcagaccgt gctggaccac atccagaagg tggccgatat tgagggcgag    120

cagaacgaga acaacgagaa tctgtggttt caccccgtga tgagccacct gtacaacgcc    180

aagaacggct acgacaagca gcccgagaaa accatgttca tcatcgagcg gctgcagagc    240

tacttcccat tcctgaagat catggccgag aaccagagag agtacagcaa cggcaagtac    300

aagcagaacc gcgtggaagt gaacagcaac gacatcttcg aggtgctgaa gcgcgccttc    360

ggcgtgctga agatgtacag ggacctgacc aaccactaca agacctacga ggaaaagctg    420

aacgacggct gcgagttcct gaccagcaca gagcaacctc tgagcggcat gatcaacaac    480

tactacacag tggccctgcg gaacatgaac gagagatacg gctacaagac agaggacctg    540

gccttcatcc aggacaagcg gttcaagttc gtgaaggacg cctacggcaa gaaaaagtcc    600

caagtgaata ccggattctt cctgagcctg caggactaca acggcgacac acagaagaag    660

ctgcacctga gcggagtggg aatcgccctg ctgatctgcc tgttcctgga caagcagtac    720

atcaacatct ttctgagcag gctgcccatc ttctccagct acaatgccca gagcgaggaa    780

cggcggatca tcatcagatc cttcggcatc aacagcatca agctgcccaa ggaccggatc    840

cacagcgaga agtccaacaa gagcgtggcc atggatatgc tcaacgaagt gaagcggtgc    900

cccgacgagc tgttcacaac actgtctgcc gagaagcagt cccggttcag aatcatcagc    960
```

```
gacgaccaca atgaagtgct gatgaagcgg agcagcgaca gattcgtgcc tctgctgctg   1020
cagtatatcg attacggcaa gctgttcgac cacatcaggt tccacgtgaa catgggcaag   1080
ctgagatacc tgctgaaggc cgacaagacc tgcatcgacg gccagaccag agtcagagtg   1140
atcgagcagc ccctgaacgg cttcggcaga ctggaagagg ccgagacaat gcggaagcaa   1200
gagaacggca ccttcggcaa cagcggcatc cggatcagag acttcgagaa catgaagcgg   1260
gacgacgcca atcctgccaa ctatccctac atcgtggaca cctacacaca ctacatcctg   1320
gaaaacaaca aggtcgagat gtttatcaac gacaaagagg acagcgcccc actgctgccc   1380
gtgatcgagg atgatagata cgtggtcaag acaatcccca gctgccggat gagcaccctg   1440
gaaattccag ccatggcctt ccacatgttt ctgttcggca gcaagaaaac cgagaagctg   1500
atcgtggacg tgcacaaccg gtacaagaga ctgttccagg ccatgcagaa agaagaagtg   1560
accgccgaga atatcgccag cttcggaatc gccgagagcg acctgcctca gaagatcctg   1620
gatctgatca gcggcaatgc ccacggcaag gatgtggacg ccttcatcag actgaccgtg   1680
gacgacatgc tgaccgacac cgagcggaga atcaagagat tcaaggacga ccggaagtcc   1740
attcggagcg ccgacaacaa gatgggaaag agaggcttca agcagatctc cacaggcaag   1800
ctggccgact tcctggccaa ggacatcgtg ctgtttcagc ccagcgtgaa cgatggcgag   1860
aacaagatca ccggcctgaa ctaccggatc atgcagagcg ccattgccgt gtacgatagc   1920
ggcgacgatt acgaggccaa gcagcagttc aagctgatgt tcgagaaggc ccggctgatc   1980
ggcaagggca caacagagcc tcatccattt ctgtacaagg tgttcgcccg cagcatcccc   2040
gccaatgccg tcgagttcta cgagcgctac ctgatcgagc ggaagttcta cctgaccggc   2100
ctgtccaacg agatcaagaa aggcaacaga gtggatgtgc ccttcatccg gcgggaccag   2160
aacaagtgga aaacacccgc catgaagacc ctgggcagaa tctacagcga ggatctgccc   2220
gtggaactgc ccagacagat gttcgacaat gagatcaagt cccacctgaa gtccctgcca   2280
cagatggaag gcatcgactt caacaatgcc aacgtgacct atctgatcgc cgagtacatg   2340
aagagagtgc tggacgacga cttccagacc ttctaccagt ggaaccgcaa ctaccggtac   2400
atggacatgc ttaagggcga gtacgacaga aagggctccc tgcagcactg cttcaccagc   2460
gtggaagaga gagaaggcct ctggaaagag cgggcctcca gaacagagcg gtacagaaag   2520
caggccagca acaagatccg cagcaaccgg cagatgagaa acgccagcag cgaagagatc   2580
gagacaatcc tggataagcg gctgagcaac agccggaacg agtaccagaa aagcgagaaa   2640
gtgatccggc gctacagagt gcaggatgcc ctgctgtttc tgctggccaa aaagaccctg   2700
accgaactgg ccgatttcga cggcgagagg ttcaaactga aagaaatcat gcccgacgcc   2760
gagaagggaa tcctgagcga gatcatgccc atgagcttca ccttcgagaa aggcggcaag   2820
aagtacacca tcaccagcga gggcatgaag ctgaagaact acggcgactt ctttgtgctg   2880
gctagcgaca agaggatcgg caacctgctg gaactcgtgg gcagcgacat cgtgtccaaa   2940
gaggatatca tggaagagtt caacaaatac gaccagtgca ggcccgagat cagctccatc   3000
gtgttcaacc tggaaaagtg ggccttcgac acataccccg agctgtctgc cagagtggac   3060
cgggaagaga aggtggactt caagagcatc ctgaaaatcc tgctgaacaa caagaacatc   3120
aacaaagagc agagcgacat cctgcggaag atccggaacg ccttcgatca caacaattac   3180
cccgacaaag gcgtggtgga aatcaaggcc ctgcctgaga tcgccatgag catcaagaag   3240
gcctttgggg agtacgccat catgaag                                       3267
```

<210> SEQ ID NO 80
<211> LENGTH: 2946
<212> TYPE: DNA
<213> ORGANISM: Artificial Sequence
<220> FEATURE:
<223> OTHER INFORMATION: Chemically synthesized

<400> SEQUENCE: 80
aacatccccg ctctggtgga aaaccagaag aagtactttg gcacctacag cgtgatggcc 60
atgctgaacg ctcagaccgt gctggaccac atccagaagg tggccgatat tgagggcgag 120
cagaacgaga acaacgagaa tctgtggttt caccccgtga tgagccacct gtacaacgcc 180
aagaacggct acgacaagca gcccgagaaa accatgttca tcatcgagcg gctgcagagc 240
tacttcccat tcctgaagat catggccgag aaccagagag agtacagcaa cggcaagtac 300
aagcagaacc gcgtggaagt gaacagcaac gacatcttcg aggtgctgaa gcgcgccttc 360
ggcgtgctga agatgtacag ggacctgacc aaccactaca agacctacga ggaaaagctg 420
aacgacggct gcgagttcct gaccagcaca gagcaacctc tgagcggcat gatcaacaac 480
tactacacag tggccctgcg gaacatgaac gagagatacg gctacaagac agaggacctg 540
gccttcatcc aggacaagcg gttcaagttc gtgaaggacg cctacggcaa gaaaaagtcc 600
caagtgaata ccggattctt cctgagcctg caggactaca acggcgacac acagaagaag 660
ctgcacctga gcggagtggg aatcgccctg ctgatctgcc tgttcctgga caagcagtac 720
atcaacatct ttctgagcag gctgcccatc ttctccagct acaatgccca gagcgaggaa 780
cggcggatca tcatcagatc cttcggcatc aacagcatca agctgcccaa ggaccggatc 840
cacagcgaga agtccaacaa gagcgtggcc atggatatgc tcaacgaagt gaagcggtgc 900
cccgacgagc tgttcacaac actgtctgcc gagaagcagt cccggttcag aatcatcagc 960
gacgaccaca atgaagtgct gatgaagcgg agcagcgaca gattcgtgcc tctgctgctg 1020
cagtatatcg attacggcaa gctgttcgac cacatcaggt tccacgtgaa catgggcaag 1080
ctgagatacc tgctgaaggc cgacaagacc tgcatcgacg gccagaccag agtcagagtg 1140
atcgagcagc ccctgaacgg cttcggcaga ctggaagagg ccgagacaat gcggaagcaa 1200
gagaacggca ccttcggcaa cagcggcatc cggatcagag acttcgagaa catgaagcgg 1260
gacgacgcca atcctgccaa ctatccctac atcgtggaca cctacacaca ctacatcctg 1320
gaaaacaaca aggtcgagat gtttatcaac gacaaagagg acagcgcccc actgctgccc 1380
gtgatcgagg atgatagata cgtggtcaag acaatcccca gctgccggat gagcaccctg 1440
gaaattccag ccatggcctt ccacatgttt ctgttcggca gcaagaaaac cgagaagctg 1500
atcgtggacg tgcacaaccg gtacaagaga ctgttccagg ccatgcagaa agaagaagtg 1560
accgccgaga atatcgccag cttcggaatc gccgagagcg acctgcctca gaagatcctg 1620
gatctgatca gcggcaatgc ccacggcaag gatgtggacg ccttcatcag actgaccgtg 1680
gacgacatgc tgaccgacac cgagcggaga atcaagagat tcaaggacga ccggaagtcc 1740
attcggagcg ccgacaacaa gatgggaaag agaggcttca agcagatctc cacaggcaag 1800
ctggccgact tcctggccaa ggacatcgtg ctgtttcagc ccagcgtgaa cgatggcgag 1860
aacaagatca ccggcctgaa ctaccggatc atgcagagcg ccattgccgt gtacgatagc 1920
ggcgacgatt acgaggccaa gcagcagttc aagctgatgt tcgagaaggc ccggctgatc 1980
ggcaagggca caacagagcc tcatccattt ctgtacaagg tgttcgcccg cagcatcccc 2040
gccaatgccg tcgagttcta cgagcgctac ctgatcgagc ggaagttcta cctgaccggc 2100
ctgtccaacg agatcaagaa aggcaacaga gtggatgtgc ccttcatccg gcgggaccag 2160
aacaagtgga aaacacccgc catgaagacc ctgggcagaa tctacagcga ggatctgccc 2220
gtggaactgc ccagacagat gttcgacaat gagatcaagt cccacctgaa gtccctgcca 2280
cagatggaag gcatcgactt caacaatgcc aacgtgacct atctgatcgc cgagtacatg 2340
aagagagtgc tggacgacga cttccagacc ttctaccagt ggaaccgcaa ctaccggtac 2400
atggacatgc ttaagggcga gtacgacaga aagggctccc tgcagcactg cttcaccagc 2460
gtggaagaga gagaaggcct ctggaaagag cgggcctcca gaacagagcg gtacagaaag 2520
caggccagca acaagatccg cagcaaccgg cagatgagaa acgccagcag cgaagagatc 2580
gagacaatcc tggataagcg gctgagcaac agccggaacg agtaccagaa aagcgagaaa 2640
gtgatccggc gctacagagt gcaggatgcc ctgctgtttc tgctggccaa aaagaccctg 2700
accgaactgg ccgatttcga cggcgagagg ttcaaactga aagaaatcat gcccgacgcc 2760
gagaagggaa tcctgagcga gatcatgccc atgagcttca ccttcgagaa aggcggcaag 2820
aagtacacca tcaccagcga gggcatgaag ctgaagaact acggcgactt ctttgtgctg 2880
gctagcgaca agaggatcgg caacctgctg gaactcgtgg gcagcgacat cgtgtccaaa 2940
gaggat 2946

<210> SEQ ID NO 81
<211> LENGTH: 3267
<212> TYPE: DNA
<213> ORGANISM: Artificial Sequence
<220> FEATURE:
<223> OTHER INFORMATION: Chemically synthesized

<400> SEQUENCE: 81
aacatccccg ctctggtgga aaaccagaag aagtactttg gcacctacag cgtgatggcc 60
atgctgaacg ctcagaccgt gctggaccac atccagaagg tggccgatat tgagggcgag 120
cagaacgaga acaacgagaa tctgtggttt caccccgtga tgagccacct gtacaacgcc 180
aagaacggct acgacaagca gcccgagaaa accatgttca tcatcgagcg gctgcagagc 240
tacttcccat tcctgaagat catggccgag aaccagagag agtacagcaa cggcaagtac 300
aagcagaacc gcgtggaagt gaacagcaac gacatcttcg aggtgctgaa gcgcgccttc 360
ggcgtgctga agatgtacag ggacctgacc aacgcataca agacctacga ggaaaagctg 420
aacgacggct gcgagttcct gaccagcaca gagcaacctc tgagcggcat gatcaacaac 480
tactacacag tggccctgcg gaacatgaac gagagatacg gctacaagac agaggacctg 540
gccttcatcc aggacaagcg gttcaagttc gtgaaggacg cctacggcaa gaaaaagtcc 600
caagtgaata ccggattctt cctgagcctg caggactaca acggcgacac acagaagaag 660
ctgcacctga gcggagtggg aatcgccctg ctgatctgcc tgttcctgga caagcagtac 720
atcaacatct ttctgagcag gctgcccatc ttctccagct acaatgccca gagcgaggaa 780
cggcggatca tcatcagatc cttcggcatc aacagcatca agctgcccaa ggaccggatc 840
cacagcgaga agtccaacaa gagcgtggcc atggatatgc tcaacgaagt gaagcggtgc 900
cccgacgagc tgttcacaac actgtctgcc gagaagcagt cccggttcag aatcatcagc 960
gacgaccaca atgaagtgct gatgaagcgg agcagcgaca gattcgtgcc tctgctgctg 1020
cagtatatcg attacggcaa gctgttcgac cacatcaggt tccacgtgaa catgggcaag 1080
ctgagatacc tgctgaaggc cgacaagacc tgcatcgacg gccagaccag agtcagagtg 1140
atcgagcagc ccctgaacgg cttcggcaga ctggaagagg ccgagacaat gcggaagcaa 1200
gagaacggca ccttcggcaa cagcggcatc cggatcagag acttcgagaa catgaagcgg 1260
gacgacgcca atcctgccaa ctatccctac atcgtggaca cctacacaca ctacatcctg 1320
gaaaacaaca aggtcgagat gtttatcaac gacaaagagg acagcgcccc actgctgccc 1380
gtgatcgagg atgatagata cgtggtcaag acaatcccca gctgccggat gagcaccctg 1440
gaaattccag ccatggcctt ccacatgttt ctgttcggca gcaagaaaac cgagaagctg 1500
atcgtggacg tgcacaaccg gtacaagaga ctgttccagg ccatgcagaa agaagaagtg 1560
accgccgaga atatcgccag cttcggaatc gccgagagcg acctgcctca gaagatcctg 1620
gatctgatca gcggcaatgc ccacggcaag gatgtggacg ccttcatcag actgaccgtg 1680
gacgacatgc tgaccgacac cgagcggaga atcaagagat tcaaggacga ccggaagtcc 1740
attcggagcg ccgacaacaa gatgggaaag agaggcttca agcagatctc cacaggcaag 1800
ctggccgact tcctggccaa ggacatcgtg ctgtttcagc ccagcgtgaa cgatggcgag 1860
aacaagatca ccggcctgaa ctaccggatc atgcagagcg ccattgccgt gtacgatagc 1920
ggcgacgatt acgaggccaa gcagcagttc aagctgatgt tcgagaaggc ccggctgatc 1980
ggcaagggca caacagagcc tcatccattt ctgtacaagg tgttcgcccg cagcatcccc 2040
gccaatgccg tcgagttcta cgagcgctac ctgatcgagc ggaagttcta cctgaccggc 2100
ctgtccaacg agatcaagaa aggcaacaga gtggatgtgc ccttcatccg gcgggaccag 2160
aacaagtgga aaacacccgc catgaagacc ctgggcagaa tctacagcga ggatctgccc 2220
gtggaactgc ccagacagat gttcgacaat gagatcaagt cccacctgaa gtccctgcca 2280
cagatggaag gcatcgactt caacaatgcc aacgtgacct atctgatcgc cgagtacatg 2340
aagagagtgc tggacgacga cttccagacc ttctaccagt ggaaccgcaa ctaccggtac 2400
atggacatgc ttaagggcga gtacgacaga aagggctccc tgcagcactg cttcaccagc 2460
gtggaagaga gagaaggcct ctggaaagag cgggcctcca gaacagagcg gtacagaaag 2520
caggccagca acaagatccg cagcaaccgg cagatgagaa acgccagcag cgaagagatc 2580
gagacaatcc tggataagcg gctgagcaac agccggaacg agtaccagaa aagcgagaaa 2640
gtgatccggc gctacagagt gcaggatgcc ctgctgtttc tgctggccaa aaagaccctg 2700
accgaactgg ccgatttcga cggcgagagg ttcaaactga aagaaatcat gcccgacgcc 2760
gagaagggaa tcctgagcga gatcatgccc atgagcttca ccttcgagaa aggcggcaag 2820
aagtacacca tcaccagcga gggcatgaag ctgaagaact acggcgactt ctttgtgctg 2880
gctagcgaca agaggatcgg caacctgctg gaactcgtgg gcagcgacat cgtgtccaaa 2940
gaggatatca tggaagagtt caacaaatac gaccagtgca ggcccgagat cagctccatc 3000
gtgttcaacc tggaaaagtg ggccttcgac acataccccg agctgtctgc cagagtggac 3060
cgggaagaga aggtggactt caagagcatc ctgaaaatcc tgctgaacaa caagaacatc 3120
aacaaagagc agagcgacat cctgcggaag atccggaacg ccttcgatgc aaacaattac 3180
cccgacaaag gcgtggtgga aatcaaggcc ctgcctgaga tcgccatgag catcaagaag 3240
gcctttgggg agtacgccat catgaag 3267

<210> SEQ ID NO 82
<211> LENGTH: 3867
<212> TYPE: DNA
<213> ORGANISM: Artificial Sequence
<220> FEATURE:
<223> OTHER INFORMATION: Chemically synthesized

<400> SEQUENCE: 82

```
atggactaca aagaccatga cggtgattat aaagatcatg acatcgatta caaggatgac     60
gatgacaagg gcggaaactc aaagaaaagg tcactggagg acaacgaaac ggaaatcaaa    120
gtctccagag acacctggaa cactaagaac atgcggtccc tggaaccgcc acgaagcaag    180
aaacggatac atggaggcaa catccccgct ctggtggaaa accagaagaa gtactttggc    240
acctacagcg tgatggccat gctgaacgct cagaccgtgc tggaccacat ccagaaggtg    300
gccgatattg agggcgagca gaacgagaac aacgagaatc tgtggtttca ccccgtgatg    360
agccacctgt acaacgccaa gaacggctac gacaagcagc ccgagaaaac catgttcatc    420
atcgagcggc tgcagagcta cttcccattc ctgaagatca tggccgagaa ccagagagag    480
tacagcaacg gcaagtacaa gcagaaccgc gtggaagtga acagcaacga catcttcgag    540
gtgctgaagc gcgccttcgg cgtgctgaag atgtacaggg acctgaccaa cgcatacaag    600
acctacgagg aaaagctgaa cgacggctgc gagttcctga ccagcacaga gcaacctctg    660
agcggcatga tcaacaacta ctacacagtg gccctgcgga acatgaacga gagatacggc    720
tacaagacag aggacctggc cttcatccag gacaagcggt tcaagttcgt gaaggacgcc    780
tacggcaaga aaaagtccca agtgaatacc ggattcttcc tgagcctgca ggactacaac    840
ggcgacacac agaagaagct gcacctgagc ggagtgggaa tcgccctgct gatctgcctg    900
ttcctggaca agcagtacat caacatcttt ctgagcaggc tgcccatctt ctccagctac    960
aatgcccaga gcgaggaacg gcggatcatc atcagatcct tcggcatcaa cagcatcaag   1020
ctgcccaagg accggatcca cagcgagaag tccaacaaga gcgtggccat ggatatgctc   1080
aacgaagtga agcggtgccc cgacgagctg ttcacaacac tgtctgccga gaagcagtcc   1140
cggttcagaa tcatcagcga cgaccacaat gaagtgctga tgaagcggag cagcgacaga   1200
ttcgtgcctc tgctgctgca gtatatcgat tacggcaagc tgttcgacca catcaggttc   1260
cacgtgaaca tgggcaagct gagatacctg ctgaaggccg acaagacctg catcgacggc   1320
cagaccagag tcagagtgat cgagcagccc ctgaacggct tcggcagact ggaagaggcc   1380
gagacaatgc ggaagcaaga gaacggcacc ttcggcaaca gcggcatccg gatcagagac   1440
ttcgagaaca tgaagcggga cgacgccaat cctgccaact atccctacat cgtggacacc   1500
tacacacact acatcctgga aaacaacaag gtcgagatgt ttatcaacga caaagaggac   1560
agcgccccac tgctgcccgt gatcgaggat gatagatacg tggtcaagac aatccccagc   1620
tgccggatga gcaccctgga aattccagcc atggccttcc acatgtttct gttcggcagc   1680
aagaaaaccg agaagctgat cgtggacgtg cacaaccggt acaagagact gttccaggcc   1740
atgcagaaag aagaagtgac cgccgagaat atcgccagct tcggaatcgc cgagagcgac   1800
ctgcctcaga agatcctgga tctgatcagc ggcaatgccc acggcaagga tgtggacgcc   1860
ttcatcagac tgaccgtgga cgacatgctg accgacaccg agcggagaat caagagattc   1920
aaggacgacc ggaagtccat tcggagcgcc gacaacaaga tgggaaagag aggcttcaag   1980
cagatctcca caggcaagct ggccgacttc ctggccaagg acatcgtgct gtttcagccc   2040
agcgtgaacg atggcgagaa caagatcacc ggcctgaact accggatcat gcagagcgcc   2100
attgccgtgt acgatagcgg cgacgattac gaggccaagc agcagttcaa gctgatgttc   2160
gagaaggccc ggctgatcgg caagggcaca acagagcctc atccatttct gtacaaggtg   2220
ttcgcccgca gcatccccgc caatgccgtc gagttctacg agcgctacct gatcgagcgg   2280
aagttctacc tgaccggcct gtccaacgag atcaagaaag gcaacagagt ggatgtgccc   2340
```

```
ttcatccggc gggaccagaa caagtggaaa acacccgcca tgaagaccct gggcagaatc   2400

tacagcgagg atctgcccgt ggaactgccc agacagatgt tcgacaatga gatcaagtcc   2460

cacctgaagt ccctgccaca gatggaaggc atcgacttca acaatgccaa cgtgacctat   2520

ctgatcgccg agtacatgaa gagagtgctg gacgacgact tccagacctt ctaccagtgg   2580

aaccgcaact accggtacat ggacatgctt aagggcgagt acgacagaaa gggctccctg   2640

cagcactgct tcaccagcgt ggaagagaga gaaggcctct ggaaagagcg ggcctccaga   2700

acagagcggt acagaaagca ggccagcaac aagatccgca gcaaccggca gatgagaaac   2760

gccagcagcg aagagatcga gacaatcctg gataagcggc tgagcaacag ccggaacgag   2820

taccagaaaa gcgagaaagt gatccggcgc tacagagtgc aggatgccct gctgtttctg   2880

ctggccaaaa agaccctgac cgaactggcc gatttcgacg gcgagaggtt caaactgaaa   2940

gaaatcatgc ccgacgccga gaagggaatc ctgagcgaga tcatgcccat gagcttcacc   3000

ttcgagaaag gcggcaagaa gtacaccatc accagcgagg gcatgaagct gaagaactac   3060

ggcgacttct ttgtgctggc tagcgacaag aggatcggca acctgctgga actcgtgggc   3120

agcgacatcg tgtccaaaga ggatcgaggc ggtggaggta gtggaggggg aggatcaacg   3180

cgttctgtgg taccgcccaa tcgctcgcag accggctggc cccggggggt cactcagttc   3240

ggcaacaagt acatccagca gacgaagccc ctcaccctgg agcgcaccat caacctgtac   3300

cctcttacca attatacttt tggtacaaaa gagcccctct acgagaagga cagctctgtt   3360

gcagccagat ttcagcgcat gagggaagaa tttgataaaa ttggaatgag gaggactgta   3420

gaaggggttc tgattgtaca tgagcaccgg ctaccccatg tgttactgct gcagctggga   3480

acaactttct tcaaactacc tggtggtgaa cttaacccag gagaagatga agttgaagga   3540

ctaaaacgct taatgacaga gatactgggt cgtcaggatg gagttttgca agactgggtc   3600

attgacgatt gcattggtaa ctggtggaga ccaaattttg aacctcctca gtatccatat   3660

attcctgcac atattacaaa gcctaaggaa cataagaagt tgtttctggt tcagcttcaa   3720

gaaaaagcct tgtttgcagt ccctaaaaat tacaagctgg tagctgcacc attgtttgaa   3780

ttgtatgaca atgcaccagg atatggaccc atcatttcta gtctccctca gctgttgagc   3840

aggttcaatt ttatttacaa ctagtaa                                      3867
```

<210> SEQ ID NO 83
<211> LENGTH: 42
<212> TYPE: DNA
<213> ORGANISM: Artificial Sequence
<220> FEATURE:
<223> OTHER INFORMATION: Chemically synthesized

<400> SEQUENCE: 83

```
tcgcgaggcg gtggaggtag tggaggggga ggatcaacgc gt                        42
```

<210> SEQ ID NO 84
<211> LENGTH: 66
<212> TYPE: DNA
<213> ORGANISM: Artificial Sequence
<220> FEATURE:
<223> OTHER INFORMATION: Chemically synthesized

<400> SEQUENCE: 84

```
gactacaaag accatgacgg tgattataaa gatcatgaca tcgattacaa ggatgacgat     60

gacaag                                                                66
```

<210> SEQ ID NO 85
<211> LENGTH: 33
<212> TYPE: DNA
<213> ORGANISM: Artificial Sequence
<220> FEATURE:
<223> OTHER INFORMATION: Chemically synthesized

<400> SEQUENCE: 85
cttcaactgc ctccacttga aagactgaca ctg 33

<210> SEQ ID NO 86
<211> LENGTH: 48
<212> TYPE: DNA
<213> ORGANISM: Artificial Sequence
<220> FEATURE:
<223> OTHER INFORMATION: Chemically synthesized

<400> SEQUENCE: 86
ggatcccttc aactgcctcc acttgaaaga ctgacactgg gtagttcc 48

<210> SEQ ID NO 87
<211> LENGTH: 1569
<212> TYPE: DNA
<213> ORGANISM: Artificial Sequence
<220> FEATURE:
<223> OTHER INFORMATION: Chemically synthesized

<400> SEQUENCE: 87
ccacgtcctg aggaagcaga tgagacctgg gactcaaagg aagacaaaat tcacaatgct 60
gagaacatcc agcccgggga acagaagtat gaatataagt cagatcagtg gaagcctcta 120
aacctagagg agaaaaaacg ttacgaccgt gagttcctgc ttggttttca gttcatcttt 180
gccagtatgc agaagccaga gggattgcca catatcagtg acgtggtgct ggacaaggcc 240
aataaaacac cactgcggcc actggatccc actagactac aaggcataaa ttgtggccca 300
gacttcactc catcctttgc caaccttggc cggacaaccc ttagcacccg tgggccccca 360
aggggtgggc caggtgggga gctgccccgt gggccggctg gcctgggacc ccggcgctct 420
cagcagggac cccgaaaaga accacgcaag atcattgcca cagtgttaat gaccgaagat 480
ataaaactga acaaagcaga gaaagcctgg aaacccagca gcaagcggac ggcggctgat 540
aaggatcgag ggggaagaaga tgctgatggc agcaaaaccc aggacctatt ccgcagggtg 600
cgctccatcc tgaataaact gacaccccag atgttccagc agctgatgaa gcaagtgacg 660
cagctggcca tcgacaccga ggaacgcctc aaaggggtca ttgacctcat ttttgagaag 720
gccatttcag agcccaactt ctctgtggcc tatgccaaca tgtgccgctg cctcatggcg 780
ctgaaagtgc ccactacgga aaagccaaca gtgactgtga acttccgaaa gctgttgttg 840
aatcgatgtc agaaggagtt tgagaaagac aaagatgatg atgaggtttt tgagaagaag 900
caaaaagaga tggatgaagc tgctacggca gaggaacgag gacgcctgaa ggaagagctg 960
gaagaggctc gggacatagc ccggcggcgc tctttaggga atatcaagtt tattggagag 1020
ttgttcaaac tgaagatgtt aacagaggca ataatgcatg actgtgtggt caaactgctt 1080
aagaaccatg atgaagagtc ccttgagtgc ctttgtcgtc tgctcaccac cattggcaaa 1140
gacctggact ttgaaaaagc caagccccga atggatcagt atttcaacca gatggaaaaa 1200
atcattaaag aaaagaagac gtcatcccgc atccgcttta tgctgcagga cgtgctggat 1260
ctgcgaggga gcaattgggt gccacgccga ggggatcagg gtcccaagac cattgaccag 1320
atccataagg aggctgagat ggaagaacat cgagagcaca tcaaagtgca gcagctcatg 1380
gccaagggca gtgacaagcg tcggggcggt cctccaggcc ctcccatcag ccgtggactt 1440
ccccttgtgg atgatggtgg ctggaacaca gttcccatca gcaaaggtag ccgccccatt 1500
gacacctcac gactcaccaa gatcaccaag cctggctcca tcgattctaa caaccagctc 1560
ttttagtaa 1569

<210> SEQ ID NO 88
<211> LENGTH: 339
<212> TYPE: DNA
<213> ORGANISM: Artificial Sequence
<220> FEATURE:
<223> OTHER INFORMATION: Chemically synthesized

<400> SEQUENCE: 88
tctgcgatac agaacttgca tagcttcgac ccgtttgctg atgctagcaa gggcgacgat 60
ttgctcccgg ctgggacaga ggactacata cacatacgaa tccaacagcg caatggaagg 120
aagacgctta ctaccgttca gggaatcgcg gacgattatg acaagaagaa gctcgttaaa 180
gcctttaaga agaaattcgc atgcaacggt acagtaatag aacacccaga gtacggagag 240
gtcatacaac tccaaggaga ccaacgaaag aacatttgtc aattcctcgt agaaattggc 300
cttgcgaagg acgaccagct taaagtacat ggtttctag 339

<210> SEQ ID NO 89
<211> LENGTH: 432
<212> TYPE: DNA
<213> ORGANISM: Artificial Sequence
<220> FEATURE:
<223> OTHER INFORMATION: Chemically synthesized

<400> SEQUENCE: 89
ccgaagaata aagggaaggg aggaaagaat agaaggaggg gaaagaatga aaacgaatca 60
gaaaagcgcg aattggtatt caaggaggat gggcaggagt atgcccaagt gattaaaatg 120
ctcggcaacg gtcggctcga agccatgtgc tttgatggag taaagagact ctgtcacata 180
aggggaaagc tcagaaagaa agtttggata aatacatctg acatcatttt ggtaggactc 240
agagactatc aggataataa ggctgacgtg attctcaagt acaacgcgga tgaggcgcga 300
tccctgaaag cctacgggga gcttcctgag cacgcaaaga taaatgagac tgacacattc 360
gggccaggag atgatgatga aattcagttc gacgatatag gggacgacga tgaagatatt 420
gacgacatat ag 432

<210> SEQ ID NO 90
<211> LENGTH: 336
<212> TYPE: DNA
<213> ORGANISM: Artificial Sequence
<220> FEATURE:
<223> OTHER INFORMATION: Chemically synthesized

<400> SEQUENCE: 90
gcaaaaggca agactaaaag taaggtaggc ccttatcggg gtagaggtgt agctcttacc 60
gatgacgaat atgatgaatg gagggaacat aatgcgactc gcaaactcga ccttagtgtg 120
gaggatttcc ttatgctcag gcaccgggcg gcactgggag ccgacgacgc ggatgctgtg 180
aaatttcgca gctggtggaa cagtaggagt cggctggctg atgattacga ggatgttacc 240
gtgataggta aaggcggggt taaacacgag aagattcgga cgaacacgct gagagctgtt 300
gaccggggct atgacgtttc attcgctgag gagtag 336

<210> SEQ ID NO 91
<211> LENGTH: 375
<212> TYPE: DNA
<213> ORGANISM: Artificial Sequence
<220> FEATURE:
<223> OTHER INFORMATION: Chemically synthesized

<400> SEQUENCE: 91
ggaaagaaag ggaagaataa gaaaggacga gggagaccgg gtgtgttccg gacacgcggt 60
cttacagatg aagagtacga cgagttcaaa aagcgccgcg aatcacgcgg cgggaagtac 120
tccatagatg actatttggc agacagggag cgggaagaag aacttcttga aagggacgag 180
gaagaggcaa tttttggcga cggctttgga ctgaaagcta cacggcgaag tcggaaagca 240
gaacgagcga aactcgggct tgtaagtggt ggtgatatta gagcgaggaa gcctattgat 300
tggaatgtgg taggaccatc ctgggctgat gacgaccgcc aagtcgatta cggtgaaaaa 360
atcaacttcg agtag 375

<210> SEQ ID NO 92
<211> LENGTH: 582
<212> TYPE: DNA
<213> ORGANISM: Artificial Sequence
<220> FEATURE:
<223> OTHER INFORMATION: Chemically synthesized

<400> SEQUENCE: 92
ggcttcaacc gccgacagcg ccagaaattg aaatttaggc aggccagaga caatcgcatg 60
gcgagagagg tttatgggga tgatagtacg atggaagact atttcggcag cgcatactcc 120
aagaagggga aaagcaaagg caggacgcgg gggatgggta ctaagacccg caaattcgtc 180
aatatgtacg gttatgaccc cactgactat aactttgttc ggttcgtaga tccactcacg 240
ggacacactc tcgacgaaaa tccgctcatg gacattaact tggtccagga acattttagc 300
caagttagga atgattatct gggcgacgat aaaatcacaa tgcaacatat tatgtctaat 360
cctggcatcg tggcatatta cataaaagac gcgactcaaa aggctttgaa agtagatttg 420
acgcctcata atccactcag agtctgtgat aaaacggcta ccatagctgg gttccctgaa 480
cgggagttcg agcttcgaca gacggggcag ccagttctgg tagagcccaa tgcaattcct 540
caaataaacg aggagggtga cgaagaagtg ggccatgagt ag 582

<210> SEQ ID NO 93
<211> LENGTH: 1284
<212> TYPE: DNA
<213> ORGANISM: Artificial Sequence
<220> FEATURE:
<223> OTHER INFORMATION: Chemically synthesized

<400> SEQUENCE: 93
agcacgctta aggaggtcca agacaacata acactgcacg aacagcagct cgtgacggca 60
cggcagaagc tgaaggatgc agagcgagcc gttgagcttg atccagatga tgtaaataag 120
tcaacgcttc agtcacggag ggccgccgta tccgctctgg aaacaaaatt gggtgaactg 180
aaaagagagc tggccgatct catagccgct caaaaattgg ctagcaaacc agttgacccg 240
actgggatcg aaccggacga ccatctcaaa gagaaaagtt cccttcggta tggtaacgtt 300
ctggatgtaa attctattga tttggaagaa cccagtggac agactgccga ttggaagagc 360
ataggactct acattttgag tttcgcattg ccgataattt tgaaagcgtt gtatatgctc 420
tccactagag gacgccagac tataaaagaa aataaggga cccgaattag gtttaaggat 480

```
gattccagtt acgaggaagt caatggaata cggaagccgc gacatctgta cgtatcaatg    540

cccaccgcac aaagcactat gaaggcagac gagataacac cagggcgatt tcgaacaatc    600

gcatgtggac tgttccccgc tcaagtcaaa gctcggaaca tcatatcacc cgtgatggga    660

gtcatcggtt tctccttttt cgtgaaggat tggatggaac ggattgacga tttcttggcg    720

gccaggtgtc cgtttctgcc ggagcaaaaa gacccacggg acgcagcact ggctacgaat    780

agagcctact ttattacgcg acaattgcaa gtagacgaga gcaaggtgag cgacatcgag    840

gatcttatcg ctgatgcgcg cgcagaaagt gccacaattt tcgcggatat agctaccccc    900

cactccgttt gggtatttgc ctgtgcgcca gaccgatgcc caccgaccgc gctttatgta    960

gccggaatgc cagagttggg ggctttcttc gccatacttc aggacatgag gaatactata   1020

atggcgtcaa agtctgtggg cacgagcgaa gagaagttga agaaaaaatc agccttttac   1080

cagtcatatt tgaggcgcac ccaatcaatg ggtatccagc ttgaccagaa aatcatcatc   1140

ttgtatatgt cccactgggg ccgggaggct gttaaccatt tccatcttgg ggacgacatg   1200

gaccccgagc ttcgagagct tgcacagacg cttgtcgata taaaagtgcg ggagatttcc   1260

aaccaagaac ccttgaaact gtag                                          1284
```

<210> SEQ ID NO 94
<211> LENGTH: 561
<212> TYPE: DNA
<213> ORGANISM: Artificial Sequence
<220> FEATURE:
<223> OTHER INFORMATION: Chemically synthesized

<400> SEQUENCE: 94

```
agcacgctta aggaggtcca agacaacata acactgcacg aacagcagct cgtgacggca     60

cggcagaagc tgaaggatgc agagcgagcc gttgagcttg atccagatga tgtaaataag    120

tcaacgcttc agtcacggag ggccgccgta tccgctctgg aaacaaaatt gggtgaactg    180

aaaagagagc tggccgatct catagccgct caaaaattgg ctagcaaacc agttgacccg    240

actgggatcg aaccggacga ccatctcaaa gagaaaagtt cccttcggta tggtaacgtt    300

ctggatgtaa attctattga tttggaagaa cccagtggac agactgccga ttggaagagc    360

ataggactct acattttgag tttcgcattg ccgataattt tgaaagcgtt gtatatgctc    420

tccactagag gacgccagac tataaaagaa aataagggga cccgaattag gtttaaggat    480

gattccagtt acgaggaagt caatggaata cggaagccgc gacatctgta cgtatcaatg    540

cccaccgcac aaagcactta g                                              561
```

<210> SEQ ID NO 95
<211> LENGTH: 4995
<212> TYPE: DNA
<213> ORGANISM: Artificial Sequence
<220> FEATURE:
<223> OTHER INFORMATION: Chemically synthesized

<400> SEQUENCE: 95

```
atggactaca aagaccatga cggtgattat aaagatcatg acatcgatta caaggatgac     60

gatgacaagg gatcccttca actgcctcca cttgaaagac tgacactggg tagttccaac    120

atccccgctc tggtggaaaa ccagaagaag tactttggca cctacagcgt gatggccatg    180

ctgaacgctc agaccgtgct ggaccacatc cagaaggtgg ccgatattga gggcgagcag    240

aacgagaaca acgagaatct gtggtttcac cccgtgatga gccacctgta caacgccaag    300
```

```
aacggctacg acaagcagcc cgagaaaacc atgttcatca tcgagcggct gcagagctac    360
ttcccattcc tgaagatcat ggccgagaac cagagagagt acagcaacgg caagtacaag    420
cagaaccgcg tggaagtgaa cagcaacgac atcttcgagg tgctgaagcg cgccttcggc    480
gtgctgaaga tgtacaggga cctgaccaac gcatacaaga cctacgagga aaagctgaac    540
gacggctgcg agttcctgac cagcacagag caacctctga gcggcatgat caacaactac    600
tacacagtgg ccctgcggaa catgaacgag agatacggct acaagacaga ggacctggcc    660
ttcatccagg acaagcggtt caagttcgtg aaggacgcct acggcaagaa aaagtcccaa    720
gtgaataccg gattcttcct gagcctgcag gactacaacg gcgacacaca gaagaagctg    780
cacctgagcg gagtgggaat cgccctgctg atctgcctgt tcctggacaa gcagtacatc    840
aacatctttc tgagcaggct gcccatcttc tccagctaca atgcccagag cgaggaacgg    900
cggatcatca tcagatcctt cggcatcaac agcatcaagc tgcccaagga ccggatccac    960
agcgagaagt ccaacaagag cgtggccatg gatatgctca acgaagtgaa gcggtgcccc   1020
gacgagctgt tcacaacact gtctgccgag aagcagtccc ggttcagaat catcagcgac   1080
gaccacaatg aagtgctgat gaagcggagc agcgacagat tcgtgcctct gctgctgcag   1140
tatatcgatt acggcaagct gttcgaccac atcaggttcc acgtgaacat gggcaagctg   1200
agatacctgc tgaaggccga caagacctgc atcgacggcc agaccagagt cagagtgatc   1260
gagcagcccc tgaacggctt cggcagactg gaagaggccg agacaatgcg gaagcaagag   1320
aacggcacct tcggcaacag cggcatccgg atcagagact tcgagaacat gaagcgggac   1380
gacgccaatc ctgccaacta tccctacatc gtggacacct acacacacta catcctggaa   1440
aacaacaagg tcgagatgtt tatcaacgac aaagaggaca gcgcccccact gctgcccgtg   1500
atcgaggatg atagatacgt ggtcaagaca atccccagct gccggatgag caccctggaa   1560
attccagcca tggccttcca catgtttctg ttcggcagca agaaaaccga gaagctgatc   1620
gtggacgtgc acaaccggta caagagactg ttccaggcca tgcagaaaga agaagtgacc   1680
gccgagaata tcgccagctt cggaatcgcc gagagcgacc tgcctcagaa gatcctggat   1740
ctgatcagcg gcaatgccca cggcaaggat gtggacgcct tcatcagact gaccgtggac   1800
gacatgctga ccgacaccga gcggagaatc aagagattca aggacgaccg gaagtccatt   1860
cggagcgccg acaacaagat gggaaagaga ggcttcaagc agatctccac aggcaagctg   1920
gccgacttcc tggccaagga catcgtgctg tttcagccca gcgtgaacga tggcgagaac   1980
aagatcaccg gcctgaacta ccggatcatg cagagcgcca ttgccgtgta cgatagcggc   2040
gacgattacg aggccaagca gcagttcaag ctgatgttcg agaaggcccg gctgatcggc   2100
aagggcacaa cagagcctca tccatttctg tacaaggtgt tcgcccgcag catccccgcc   2160
aatgccgtcg agttctacga gcgctacctg atcgagcgga agttctacct gaccggcctg   2220
tccaacgaga tcaagaaagg caacagagtg gatgtgccct tcatccggcg ggaccagaac   2280
aagtggaaaa cacccgccat gaagaccctg ggcagaatct acagcgagga tctgcccgtg   2340
gaactgccca gacagatgtt cgacaatgag atcaagtccc acctgaagtc cctgccacag   2400
atggaaggca tcgacttcaa caatgccaac gtgacctatc tgatcgccga gtacatgaag   2460
agagtgctgg acgacgactt ccagaccttc taccagtgga accgcaacta ccggtacatg   2520
gacatgctta agggcgagta cgacagaaag ggctccctgc agcactgctt caccagcgtg   2580
gaagagagag aaggcctctg gaaagagcgg gcctccagaa cagagcggta cagaaagcag   2640
gccagcaaca agatccgcag caaccggcag atgagaaacg ccagcagcga agagatcgag   2700
```

```
acaatcctgg ataagcggct gagcaacagc cggaacgagt accagaaaag cgagaaagtg   2760
atccggcgct acagagtgca ggatgccctg ctgtttctgc tggccaaaaa gaccctgacc   2820
gaactggccg atttcgacgg cgagaggttc aaactgaaag aaatcatgcc cgacgccgag   2880
aagggaatcc tgagcgagat catgcccatg agcttcacct tcgagaaagg cggcaagaag   2940
tacaccatca ccagcgaggg catgaagctg aagaactacg gcgacttctt tgtgctggct   3000
agcgacaaga ggatcggcaa cctgctggaa ctcgtgggca gcgacatcgt gtccaaagag   3060
gatatcatgg aagagttcaa caaatacgac cagtgcaggc ccgagatcag ctccatcgtg   3120
ttcaacctgg aaaagtgggc cttcgacaca taccccgagc tgtctgccag agtggaccgg   3180
gaagagaagg tggacttcaa gagcatcctg aaaatcctgc tgaacaacaa gaacatcaac   3240
aaagagcaga gcgacatcct gcggaagatc cggaacgcct tcgatgcaaa caattacccc   3300
gacaaaggcg tggtggaaat caaggccctg cctgagatcg ccatgagcat caagaaggcc   3360
tttggggagt acgccatcat gaagtcgcga ggcggtggag gtagtggagg gggaggatca   3420
acgcgtccac gtcctgagga agcagatgag acctgggact caaaggaaga caaaattcac   3480
aatgctgaga acatccagcc cggggaacag aagtatgaat ataagtcaga tcagtggaag   3540
cctctaaacc tagaggagaa aaaacgttac gaccgtgagt tcctgcttgg ttttcagttc   3600
atctttgcca gtatgcagaa gccagaggga ttgccacata tcagtgacgt ggtgctggac   3660
aaggccaata aaacaccact gcggccactg gatcccacta gactacaagg cataaattgt   3720
ggcccagact tcactccatc ctttgccaac cttggccgga caacccttag cacccgtggg   3780
cccccaaggg gtgggccagg tggggagctg ccccgtgggc cggctggcct gggaccccgg   3840
cgctctcagc agggaccccg aaaagaacca cgcaagatca ttgccacagt gttaatgacc   3900
gaagatataa aactgaacaa agcagagaaa gcctggaaac ccagcagcaa gcggacggcg   3960
gctgataagg atcgaggggga agaagatgct gatggcagca aaacccagga cctattccgc   4020
agggtgcgct ccatcctgaa taaactgaca ccccagatgt tccagcagct gatgaagcaa   4080
gtgacgcagc tggccatcga caccgaggaa cgcctcaaag ggtcattga cctcattttt   4140
gagaaggcca tttcagagcc caacttctct gtggcctatg ccaacatgtg ccgctgcctc   4200
atggcgctga aagtgcccac tacggaaaag ccaacagtga ctgtgaactt ccgaaagctg   4260
ttgttgaatc gatgtcagaa ggagtttgag aaagacaaag atgatgatga ggtttttgag   4320
aagaagcaaa aagagatgga tgaagctgct acggcagagg aacgaggacg cctgaaggaa   4380
gagctggaag aggctcggga catagcccgg cggcgctctt tagggaatat caagtttatt   4440
ggagagttgt tcaaactgaa gatgttaaca gaggcaataa tgcatgactg tgtggtcaaa   4500
ctgcttaaga accatgatga agagtccctt gagtgccttt gtcgtctgct caccaccatt   4560
ggcaaagacc tggactttga aaaagccaag ccccgaatgg atcagtattt caaccagatg   4620
gaaaaaatca ttaaagaaaa gaagacgtca tcccgcatcc gctttatgct gcaggacgtg   4680
ctggatctgc gagggagcaa ttgggtgcca cgccgagggg atcagggtcc caagaccatt   4740
gaccagatcc ataaggaggc tgagatggaa gaacatcgag agcacatcaa agtgcagcag   4800
ctcatggcca agggcagtga caagcgtcgg ggcggtcctc caggccctcc catcagccgt   4860
ggacttcccc ttgtggatga tggtggctgg aacacagttc ccatcagcaa aggtagccgc   4920
cccattgaca cctcacgact caccaagatc accaagcctg gctccatcga ttctaacaac   4980
cagctctttt agtaa                                                    4995
```

TARGETED TRANSLATION OF RNA WITH CRISPR-Cas13 TO ENHANCE PROTEIN SYNTHESIS

CROSS-REFERENCE TO RELATED APPLICATIONS

This application is the U.S. national phase application filed under 35 U.S.C. § 371 claiming benefit to International Patent Application No. PCT/US2021/016907, filed on Feb. 5, 2021, which is entitled to priority to U.S. Provisional Application Ser. No. 62/971,353 filed on Feb. 7, 2020, each of which is incorporated by reference herein in its entirety.

REFERENCE TO A "SEQUENCE LISTING," A TABLE, OR A COMPUTER PROGRAM LISTING APPENDIX SUBMITTED AS AN ASCII TEXT FILE

The Sequence Listing written in the ASCII text file: "204606-0122-00US_SequenceListing"; created on Aug. 5, 2022, and 581,900 bytes in size, is hereby incorporated by reference.

BACKGROUND

The translation of messenger RNA (mRNA) into protein is orchestrated by a large family of highly conserved eukaryotic initiation factors (eIFs) which serve to recruit and stabilize the translational preinitiation complex to the start codon. The recruitment of this complex is the rate limiting step in protein translation, and thus is a major target for regulation of protein synthesis, viral enzymes and is commonly dysregulated in disease. Thus, there is a need in the art to enhance protein synthesis.

SUMMARY OF THE INVENTION

In one aspect, the disclosure provides a fusion protein comprising a CRISPR-associated (Cas) protein, and a translation initiation factor (TIF) protein. In one embodiment, the Cas protein is catalytically dead Cas13 (dCas13). In one embodiment, dCas13 comprises a sequence selected from SEQ ID NOs: 47-48, or a variant thereof.

In one embodiment, the TIF protein is a eukaryotic initiation factor (EIF), a viral protein, or a bacterial translation initiation factor (BTIF). In one embodiment, the TIF protein is an EIF protein. In one embodiment, the EIF protein is selected from the group consisting of EIF4G, EIF4E, EIF1, EIF1AX, and a fragment or variant thereof. In one embodiment, the EIF protein is a ribosome recruitment core fragment of EIF4G. In one embodiment, the EIF protein comprises an amino acid sequence selected from SEQ ID NOs:59-70, or a variant or fragment thereof.

In one embodiment, the TIF protein is a viral protein selected from the group consisting of VPg and Nucleocapsid. In one embodiment, the viral protein comprises an amino acid sequence selected from SEQ ID NOs: 71-75, or a variant or fragment thereof. In one embodiment, the TIF protein is a BTIF protein selected from the group consisting of bacterial IF1 and bacterial IF3. In one embodiment, the BTIF comprises an amino acid sequence selected from SEQ ID NOs: 76-77, or a variant or fragment thereof.

In one embodiment, the fusion protein further comprises a nuclear export signal (NES). In one embodiment, the NES comprises an amino acid sequence selected from SEQ ID NOs: 57-58, or a variant thereof. In one embodiment, the fusion protein comprises an amino acid sequence of SEQ ID NO: 78, or a variant thereof.

In one embodiment, the disclosure provides a nucleic acid molecule encoding a fusion protein of the disclosure. In one embodiment, the nucleic acid molecule comprises a nucleic acid sequence of SEQ ID NO: 95, or a variant thereof.

In one embodiment, the disclosure provides a method of enhancing the synthesis of a protein in a subject. In one embodiment, the method comprises administering to the subject a fusion protein of the disclosure or a nucleic acid molecule of the disclosure. In one embodiment, the method comprises administering a CRISPR guide RNA (crRNA) comprising a sequence complimentary to a target RNA sequence in a mRNA transcript, wherein the mRNA transcript is translated into the protein. In one embodiment, the method is an in vitro or an in vivo method.

In one embodiment, the disclosure provides a method of treating a disease or disorder associated with reduced or low protein expression or synthesis in a subject. In one embodiment, the method comprises administering to the subject a fusion protein of the disclosure or a nucleic acid molecule of the disclosure. In one embodiment, the method comprises administering a CRISPR guide RNA (crRNA) comprising a sequence complimentary to a target RNA sequence in a mRNA transcript, wherein the mRNA transcript is translated into the protein. In one embodiment, the disease or disorder is heart failure and the crRNA comprises a sequence complimentary to SERCA2 mRNA.

BRIEF DESCRIPTION OF THE DRAWINGS

The following detailed description of various embodiments of the disclosure will be better understood when read in conjunction with the appended drawings. For the purpose of illustrating the disclosure, there are shown in the drawing's illustrative embodiments. It should be understood, however, that the invention is not limited to the precise arrangements and instrumentalities of the embodiments shown in the drawings.

FIG. 1A through FIG. 1F, depicts experimental results. FIG. 1A is a diagram of scaffolding EIF4G protein and domains mediating interaction with other eiFs. A central core of EIF4G has been characterized as a ribosome recruitment core (RRC), which is sufficient to mediate recruitment of 40 S to mRNA in tethering experiments. 4E-eiF4E, 3-eiF3, 4A-eiF4A. FIG. 1B is a schematic of the Translation Initiation Complex composed of EIF4G, EIF4E, EIF4A, which recruits 40S ribosome and EIF3. FIG. 1C is a diagram depicting dPspCas13b fusion to EIF4G'rrc' to target mRNAs for translation. FIG. 1D is a diagram of the dPspCas13b-EIF4Grrc expression vector containing an N-terminal 3×FLAG and Nuclear Export Signal (NES). F-3× FLAG. FIG. 1E is a diagram of the sfGFP-Luc reporter, which contains an sfGFP open reading frame and an open reading frame for luciferase in the 3 UTR. FIG. 1F depicts experimental results demonstrating that transfection of the sfGFP-Luc reporter results in weak sfGFP expression. Targeting of synthescriptR (dPspCas13b fusion to EIF4Grrc) to the reporter mRNA resulted in significantly enhanced sfGFP fluorescence, compared to a non-targeting crRNA.

DETAILED DESCRIPTION

Figure 1:
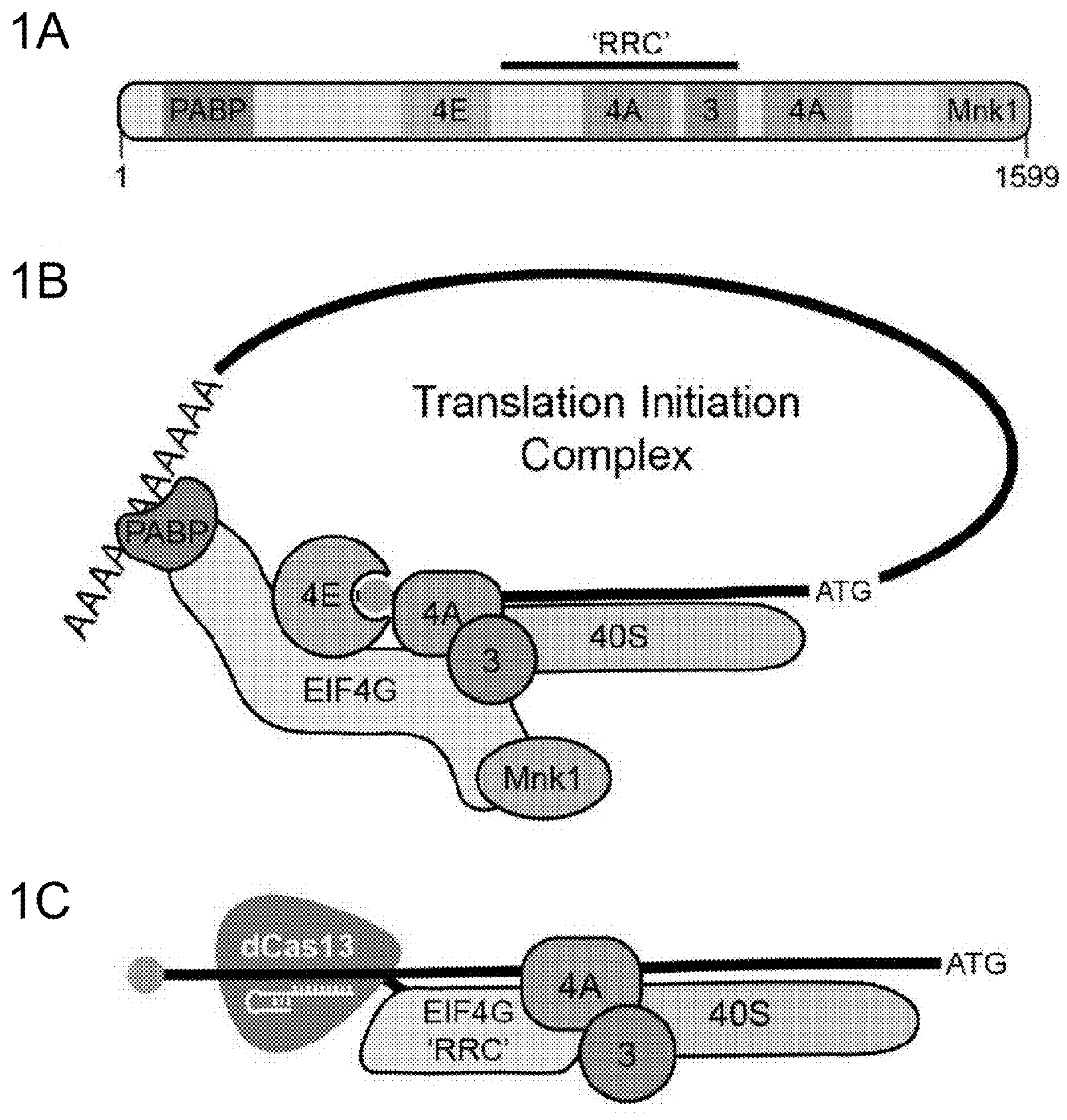
FIG. 1, comprising
Figure 1:
Figure 1:
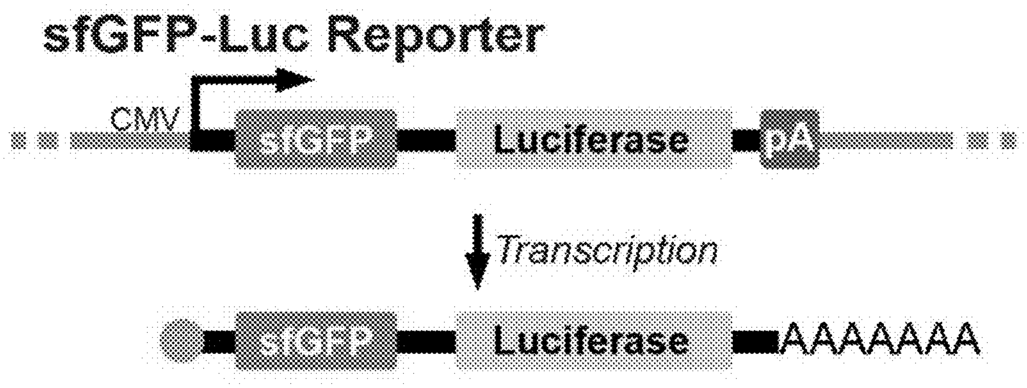
Figure 1:
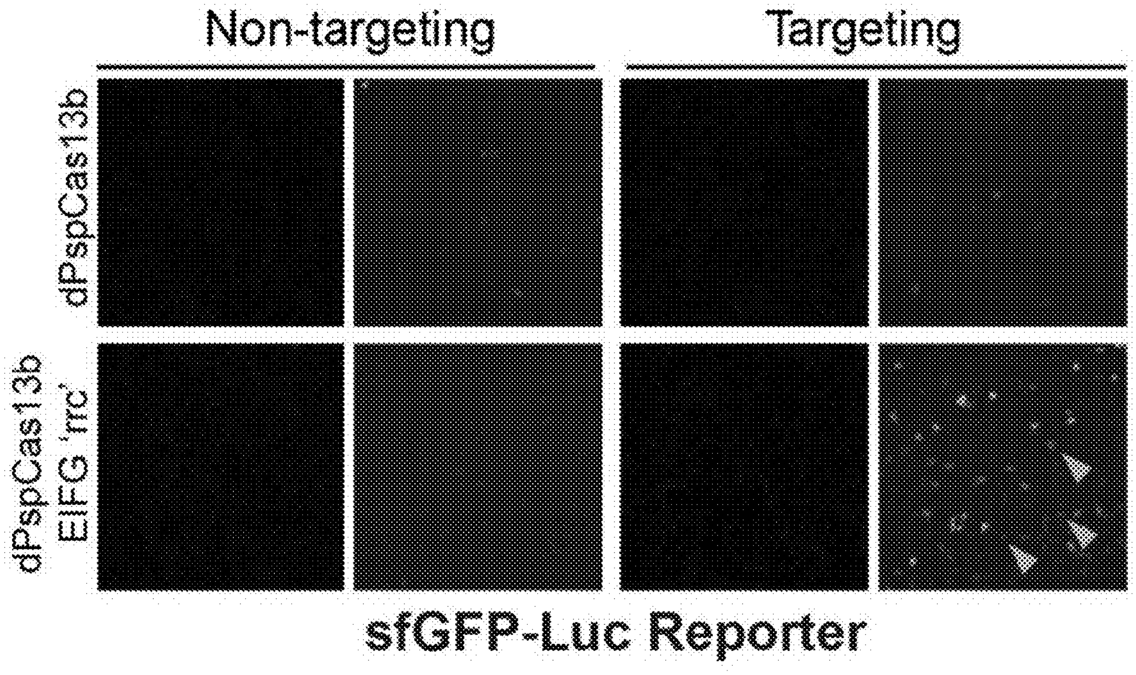

In one aspect, the disclosure is based on the development of novel fusion proteins which allow for enhanced protein synthesis. This fusion protein, termed synthescriptR herein, comprises a Cas protein and a Translation Initiation factor (TIF). For example, in one embodiment, the fusion protein comprises a Cas protein and a eukaryotic initiation factor (EIF). The fusion protein optionally further includes one or more of a nuclear export signal (NES), a protein expression tag or a linker sequence. Mutations in Cas13 generates a catalytically dead enzyme (dCas) but retains RNA binding affinity. Thus, a fusion of dCas13 and an EIF protein allows for targeted enhanced protein synthesis of an mRNA. SynthescriptR allows for non-genomic manipulation of gene expression, useful for both basic research and therapeutic applications.

Therefore, in one embodiment, the disclosure provides compositions and methods for enhancing the synthesis of a protein in a subject. In one embodiment, the disclosure provides a fusion protein comprising a CRISPR-associated (Cas) protein and a eukaryotic initiation factor (EIF) protein. In one embodiment, the fusion protein further comprises a nuclear localization signal. In one embodiment, the fusion protein further comprises a linker. In one embodiment, the linker links the Cas protein and EIF protein. In one embodiment, the fusion protein comprises a tag.

Definitions

Unless defined otherwise, all technical and scientific terms used herein have the same meaning as commonly understood by one of ordinary skill in the art to which this disclosure belongs.

Generally, the nomenclature used herein and the laboratory procedures in cell culture, molecular genetics, organic chemistry, and nucleic acid chemistry and hybridization are those well-known and commonly employed in the art.

Standard techniques are used for nucleic acid and peptide synthesis. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, NY, and Ausubel et al., 2012, Current Protocols in Molecular Biology, John Wiley & Sons, NY), which are provided throughout this document.

The nomenclature used herein and the laboratory procedures used in analytical chemistry and organic syntheses described below are those well-known and commonly employed in the art. Standard techniques or modifications thereof are used for chemical syntheses and chemical analyses.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The terms "patient," "subject," "individual," and the like are used interchangeably herein, and refer to any animal or cell whether in vitro or in vivo, amenable to the methods described herein. In one embodiment, the subjects include vertebrates and invertebrates. Invertebrates include, but are not limited to, *Drosophila melanogaster* and *Caenorhabditis elegans*. Vertebrates include, but are not limited to, primates, rodents, domestic animals or game animals. Primates include, but are not limited to, chimpanzees, cynomolgous monkeys, spider monkeys, and macaques (e.g., Rhesus). Rodents include, but are not limited to, mice, rats, woodchucks, ferrets, rabbits and hamsters. Domestic and game animals include, but are not limited to, cows, horses, pigs, deer, bison, buffalo, feline species (e.g., domestic cat), canine species (e.g., dog, fox, wolf), avian species (e.g., chicken, emu, ostrich), and fish (e.g., zebrafish, trout, catfish and salmon). In some embodiments, the subject is a mammal, e.g., a primate, e.g., a human. In certain non-limiting embodiments, the patient, subject or individual is a human.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule also consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In one embodiment, the first region comprises a first portion and the second region comprises a second portion, whereby, when the first and second portions are arranged in an antiparallel fashion, at least about 50%, at least about 75%, at least about 90%, or at least about 95% of the nucleotide residues of the first portion are capable of base pairing with nucleotide residues in the second portion. In one embodiment, all nucleotide residues of the first portion are capable of base pairing with nucleotide residues in the second portion.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

The term "homology" refers to a degree of complementarity. There may be partial homology or complete homology (i.e., identity). Homology is often measured using sequence analysis software (e.g., Sequence Analysis Software Package of the Genetics Computer Group. University of Wisconsin Biotechnology Center. 1710 University Avenue. Madison, Wis. 53705). Such software matches similar sequences by assigning degrees of homology to various substitutions, deletions, insertions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

"Isolated" means altered or removed from the natural state. For example, a nucleic acid or a peptide naturally present in its normal context in a living animal is not "isolated," but the same nucleic acid or peptide partially or completely separated from the coexisting materials of its natural context is "isolated." An isolated nucleic acid or protein can exist in substantially purified form, or can exist in a non-native environment such as, for example, a host cell.

The term "isolated" when used in relation to a nucleic acid, as in "isolated oligonucleotide" or "isolated polynucleotide" refers to a nucleic acid sequence that is identified and separated from at least one contaminant with which it is ordinarily associated in its source. Thus, an isolated nucleic acid is present in a form or setting that is different from that in which it is found in nature. In contrast, non-isolated nucleic acids (e.g., DNA and RNA) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. However, isolated nucleic acid includes, by way of example, such nucleic acid in cells ordinarily expressing that nucleic acid where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide contains at a minimum, the sense or coding strand (i.e., the oligonucleotide may be single-stranded), but may contain both the sense and anti-sense strands (i.e., the oligonucleotide may be double-stranded).

The term "isolated" when used in relation to a polypeptide, as in "isolated protein" or "isolated polypeptide" refers to a polypeptide that is identified and separated from at least one contaminant with which it is ordinarily associated in its source. Thus, an isolated polypeptide is present in a form or setting that is different from that in which it is found in nature. In contrast, non-isolated polypeptides (e.g., proteins and enzymes) are found in the state they exist in nature.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

By "expression cassette" is meant a nucleic acid molecule comprising a coding sequence operably linked to promoter/regulatory sequences necessary for transcription and, optionally, translation of the coding sequence.

The term "operably linked" as used herein refer to the linkage of nucleic acid sequences in such a manner that a nucleic acid molecule capable of directing the transcription of a given gene and/or the synthesis of a desired protein molecule is produced. The term also refers to the linkage of sequences encoding amino acids in such a manner that a functional (e.g., enzymatically active, capable of binding to a binding partner, capable of inhibiting, etc.) protein or polypeptide is produced.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a n inducible manner.

An "inducible" promoter is a nucleotide sequence which, when operably linked with a polynucleotide which encodes or specifies a gene product, causes the gene product to be produced substantially only when an inducer which corresponds to the promoter is present.

A "constitutive" promoter is a nucleotide sequence which, when operably linked with a polynucleotide which encodes or specifies a gene product, causes the gene product to be produced in a cell under most or all physiological conditions of the cell.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "RNA" as used herein is defined as ribonucleic acid.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

The term "recombinant polypeptide" as used herein is defined as a polypeptide produced by using recombinant DNA methods.

"Variant" as the term is used herein, is a nucleic acid sequence or a peptide sequence that differs in sequence from a reference nucleic acid sequence or peptide sequence respectively, but retains essential biological properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the disclosure can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Fusion Proteins

In one aspect, the present disclosure is based on the development of novel fusions of an editing protein and a Translation Initiation factor (TIF) protein. In one embodiment, the fusion protein is capable of cleaving binding mRNAs and recruit 40S ribosome to the mRNAs. In one embodiment, the fusion protein optionally further includes one or more of a nuclear export signal (NES), a protein detection and/or purification tag or a linker sequence.

In one embodiment, the editing protein includes, but is not limited to, a CRISPR-associated (Cas) protein, a zinc finger nuclease (ZFN) protein, and a protein having an RNA binding domain. In one embodiment, the editing protein is a Cas protein.

Non-limiting examples of Cas proteins include Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2. Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, SpCas9, StCas9, NmCas9, SaCas9, CjCas9, CjCas9, AsCpf1, LbCpf1, FnCpf1, VRER SpCas9, VQR SpCas9, xCas9 3.7, homologs thereof, orthologs thereof, or modified versions thereof. In some embodiments, the Cas protein has DNA or RNA cleavage activity. In some embodiments, the Cas protein directs cleavage of one or both strands of a nucleic acid molecule at the location of a target sequence, such as within the target sequence and/or within the complement of the target sequence. In some embodiments, the Cas protein directs cleavage of one or both strands within about 1, 2, 3, 4, 5, 6, 7, 8, 9, 10, 15, 20, 25, 50, 100, 200, 500, or more base pairs from the first or last nucleotide of a target sequence. In one embodiment, the Cas protein is Cas9, Cas13, or Cpf1. In one embodiment, Cas protein is catalytically deficient (dCas).

In one embodiment, Cas protein is Cas13. In one embodiment, the Cas protein is PspCas13b, PspCas13b Truncation, AdmCas13d, AspCas13b, AspCas13c, BmaCas13a, BzoCas13b, CamCas13a, CcaCas13b, Cga2Cas13a, CgaCas13a, EbaCas13a, EreCas13a, EsCas13d, FbrCas13b, FnbCas13c, FndCas13c, FnfCas13c, FnsCas13c, FpeCas13c, FulCas13c, HheCas13a, LbfCas13a, LbmCas13a, LbnCas13a, LbuCas13a, LseCas13a, LshCas13a, LspCas13a, Lwa2 cas13a, LwaCas13a, LweCas13a, PauCas13b, PbuCas13b, PgiCas13b, PguCas13b, Pin2Cas13b, Pin3Cas13b, PinCas13b, Pprcas13a, PsaCas13b, PsmCas13b, RaCas13d, RanCas13b, RcdCas13a, RcrCas13a, RcsCas13a, RfxCas13d, UrCas13d, dPspCas13b, PspCas13b_A133H, PspCas13b_A1058H, dPspCas13b truncation, dAdmCas13d, dAspCas13b, dAspCas13c, dBmaCas13a, dBzoCas13b, dCamCas13a, dCcaCas13b, dCga2Cas13a, dCgaCas13a, dEbaCas13a, dEreCas13a, dEsCas13d, dFbrCas13b, dFnbCas13c, dFndCas13c, dFnfCas13c, dFnsCas13c, dFpeCas13c, dFulCas13c, dHheCas13a, dLbfCas13a, dLbmCas13a, dLbnCas13a, dLbuCas13a, dLseCas13a, dLshCas13a, dLspCas13a, dLwa2 cas13a, dLwaCas13a, dLweCas13a, dPauCas13b, dPbuCas13b, dPgiCas13b, dPguCas13b, dPin2Cas13b, dPin3Cas13b, dPinCas13b, dPprCas13a, dPsaCas13b, dPsmCas13b, dRaCas13d, dRanCas13b, dRcdCas13a, dRcrCas13a, dRcsCas13a, dRfxCas13d, dUrCas13d, or a variant thereof. Additional Cas proteins are known in the art (e.g., Konermann et al., Cell, 2018, 173:665-676 e14, Yan et al., Mol Cell, 2018, 7:327-339 e5; Cox, D. B. T., et al., Science, 2017, 358: 1019-1027; Abudayyeh et al., Nature, 2017, 550: 280-284, Gootenberg et al., Science, 2017, 356: 438-442; and East-Seletsky et al., Mol Cell, 2017, 66: 373-383 e3, which are herein incorporated by reference).

In one embodiment, the Cas protein comprises a sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs:1-48. In one embodiment, the Cas protein comprises a sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs:1-48. In one embodiment, the Cas protein comprises a sequence of a variant of one of SEQ ID NOs:1-46, wherein the variant renders the Cas protein catalytically inactive. In one embodiment, the Cas protein comprises a sequence of one of SEQ ID NOs:1-46 having one or more insertions, deletions or substitutions, wherein the one or more insertions, deletions or substitutions renders the Cas protein catalytically inactive. In one embodiment, the Cas protein comprises a sequence of one of SEQ ID NOs:1-48. In one embodiment, the Cas protein comprises a sequence of one of SEQ ID NOs:47-48.

In one embodiment, the Cas protein is PspCas13b. In one embodiment, the Cas protein is catalytically dead PspCas13b (dPspCas13b). In one embodiment, the Cas protein comprises an amino acid sequence at least 95% identical to SEQ ID NOs:1, 47 or 48. In one embodiment, the Cas protein comprises an amino acid sequence of SEQ ID NOs:1, 47 or 48.

In one embodiment, the TIF protein is a eukaryotic initiation factor (EIF), a Translational Regulatory Protein of Viral Origin, or a Bacterial Translation Initiation Factor (BTIF). In one embodiment, the TIF comprises a sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs:59-77.

In one embodiment the TIF is an EIF. In one embodiment, the EIF protein is an eIF2, eIF3, eIF1, eIF1A, eIF1AX, eIF4E, eIF4A, eIF4G, eIF4G1, eIF4F, eIF4B, eIF4H, eIF5, eIF5B, eIF2B, DHX29, Ded1p, eIF6, p97, or PABP protein, or a fragment thereof. In one embodiment, the EIF protein is an EIF4F protein, or a fragment thereof. In one embodiment, the EIF4 protein is EIF4A, EIF4E, or EIF4G, or a fragment thereof. In one embodiment, the EIF4 protein is EIF4G, or a fragment thereof. In one embodiment, the EIF4 protein is a EIF4G fragment. In one embodiment, the EIF4G fragment is sufficient to act as a ribosome recruitment core.

In one embodiment, the EIF protein comprises a sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs:59-77. In one embodiment, the EIF protein comprises a sequence of one of SEQ ID NOs: 59-77.

In one embodiment, the EIF protein comprises a fragment of a sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs:65-77. In one embodiment, the EIF protein comprises a fragment of one of SEQ ID NOs: 65-77. In one embodiment, the fragment comprises at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, or at least 50% of the length of the full length EIF protein. In one embodiment, the fragment comprises about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50% of the length of the full length EIF protein.

In one embodiment, the fragment of the EIF protein comprises a sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs:59-63. In one embodiment, the fragment of the EIF protein comprises a sequence of one of SEQ ID NOs:59-63.

In one embodiment the TIF is a viral protein. In one embodiment, the viral protein is a translational regulatory protein of viral origin. In one embodiment, the viral protein increases viral protein synthesis. In one embodiment, the viral protein is a VPg protein or a Nucleocapsid protein.

In one embodiment, the viral protein comprises a sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs:71-75. In one embodiment, the viral protein comprises a sequence of one of SEQ ID NOs: 71-75.

In one embodiment the TIF is a Bacterial Translation Initiation Factor (BTIF). In one embodiment, the BTIF is a Bacterial IF1 or bacterial IF3 protein. In one embodiment, the BTIF is an *E. Coli* BTIF. In one embodiment, the BTIF comprises a sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs:76-77. In one embodiment, the BTIF comprises a sequence of one of SEQ ID NOs: 76-77.

In one embodiment, the fusion protein comprises a Nuclear Export Signal (NES). In one embodiment, the NES is attached to the N-terminal end of the Cas protein. In one embodiment, the NES comprises an amino acid sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to SEQ ID NOs:57 or 58. In one embodiment, the NES comprises an amino acid sequence of SEQ ID NOs: 57 or 58.

In one embodiment, the fusion protein comprises a purification and/or detection tag. In one embodiment, the tag is on the N-terminal end of the fusion protein. In one embodiment, the purification and/or detection tag comprises an amino acid sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to SEQ ID NO:56. In one embodiment, the purification and/or detection tag comprises an amino acid sequence of SEQ ID NO: 56.

In one embodiment, the fusion protein comprises a linker. In one embodiment, the linker links the Cas protein and TIF protein. In one embodiment, the linker is connected to the C-terminal end of the Cas protein and to the N-terminal end of the TIF protein. In one embodiment, the linker comprises a sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs:49-55. In one embodiment, the linker comprises a sequence at of one of SEQ ID NOs: 49-55.

In one embodiment, the fusion protein comprises an amino acid sequence 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to SEQ ID NO:78. In one embodiment, the fusion protein comprises an amino acid sequence of SEQ ID NOs: 78.

The fusion protein of the present disclosure may be made using chemical methods. For example, fusion protein can be synthesized by solid phase techniques (Roberge J Y et al (1995) Science 269: 202-204), cleaved from the resin, and purified by preparative high-performance liquid chromatography. Automated synthesis may be achieved, for example, using the ABI 431 A Peptide Synthesizer (Perkin Elmer) in accordance with the instructions provided by the manufacturer.

The disclosure should also be construed to include any form of a fusion protein having substantial homology to a fusion-protein disclosed herein. In one embodiment, a fusion protein which is "substantially homologous" is about 50% homologous, about 70% homologous, about 80% homologous, about 90% homologous, about 95% homologous, or about 99% homologous to amino acid sequence of a fusion-protein disclosed herein.

The fusion protein may alternatively be made by recombinant means or by cleavage from a longer polypeptide. The composition of a fusion protein may be confirmed by amino acid analysis or sequencing.

The variants of the fusion protein according to the present disclosure may be (i) one in which one or more of the amino acid residues are substituted with a conserved or non-conserved amino acid residue and such substituted amino acid residue may or may not be one encoded by the genetic code, (ii) one in which there are one or more modified amino acid residues, e.g., residues that are modified by the attachment of substituent groups, (iii) one in which the peptide is an alternative splice variant of the fusion protein of the present disclosure, (iv) fragments of the peptides and/or (v) one in which the fusion protein is fused with another peptide, such as a leader or secretory sequence or a sequence which is employed for purification (for example, His-tag) or for detection (for example, Sv5 epitope tag). The fragments include peptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two fusion proteins is determined by comparing the amino acid sequence and its conserved amino acid substitutes of one polypeptide to a sequence of a second polypeptide. Variants are defined to include peptide sequences different from the original sequence. In one embodiment, variants are different from the original sequence in less than 40% of residues per segment of interest different from the original sequence in less than 25% of residues per segment of interest, different by less than 10% of residues per segment of interest, or different from the original protein sequence in just a few residues per segment of interest and at the same time sufficiently homologous to the original sequence to preserve the functionality of the original sequence and/or the ability to stimulate the differentiation of a stem cell into the osteoblast lineage. The present disclosure includes amino acid sequences that are at least 60%, 65%, 70%, 72%, 74%, 76%, 78%, 80%, 90%, or 95% similar or identical to the original amino acid sequence. The degree of identity between two peptides is determined using computer algorithms and methods that are widely known for the persons skilled in the art. The identity between two amino acid sequences may be determined by using the BLASTP algorithm [BLAST Manual, Altschul, S., et al., NCBI NLM NIH Bethesda, Md. 20894, Altschul, S., et al., J. Mol. Biol. 215: 403-410 (1990)].

The fusion protein of the disclosure can be post-translationally modified. For example, post-translational modifications that fall within the scope of the present disclosure include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts (U.S. Pat. No. 6,103,489) to a standard translation reaction.

The fusion protein of the disclosure may include unnatural amino acids formed by post-translational modification or by introducing unnatural amino acids during translation. A variety of approaches are available for introducing unnatural amino acids during protein translation.

A fusion protein of the disclosure may be phosphorylated using conventional methods such as the method described in Reedijk et al. (The EMBO Journal 11(4):1365, 1992).

Cyclic derivatives of the fusion proteins of the disclosure are also part of the present disclosure. Cyclization may allow the fusion protein to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the disclosure, cyclic peptides may comprise a beta-turn in the right position. Beta-turns may be introduced into the peptides of the disclosure by adding the amino acids Pro-Gly at the right position.

It may be desirable to produce a cyclic fusion protein which is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

The disclosure also relates to proteins comprising a fusion protein comprising Cas13 and a TIF protein, wherein the fusion protein is itself fused to, or integrated into, a target protein, and/or a targeting domain capable of directing the chimeric protein to a desired cellular component or cell type or tissue. The chimeric proteins may also contain additional amino acid sequences or domains. The chimeric proteins are recombinant in the sense that the various components are from different sources, and as such are not found together in nature (i.e., are heterologous).

In one embodiment, the targeting domain can be a membrane spanning domain, a membrane binding domain, or a sequence directing the protein to associate with for example vesicles or with the nucleus. In one embodiment, the targeting domain can target a peptide to a particular cell type or tissue. For example, the targeting domain can be a cell surface ligand or an antibody against cell surface antigens of a target tissue. A targeting domain may target the peptide of the disclosure to a cellular component.

A peptide of the disclosure may be synthesized by conventional techniques. For example, the peptides or chimeric proteins may be synthesized by chemical synthesis using solid phase peptide synthesis. These methods employ either solid or solution phase synthesis methods (see for example, J. M. Stewart, and J. D. Young, Solid Phase Peptide Synthesis, 2$^{nd}$ Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis). By way of example, a peptide of the disclosure may be synthesized using 9-fluorenyl methoxycarbonyl (Fmoc) solid phase chemistry with direct incorporation of phosphothreonine as the N-fluorenylmethoxy-carbonyl-O-benzyl-L-phosphothreonine derivative.

N-terminal or C-terminal fusion proteins comprising a peptide or chimeric protein of the disclosure conjugated with other molecules may be prepared by fusing, through recombinant techniques, the N-terminal or C-terminal of the peptide or chimeric protein, and the sequence of a selected protein or selectable marker with a desired biological function. The resultant fusion proteins contain the fusion protein fused to the selected protein or marker protein as described herein. Examples of proteins which may be used to prepare fusion proteins include immunoglobulins, glutathione-S-transferase (GST), hemagglutinin (HA), and truncated myc.

Peptides of the disclosure may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors (see Christian et al 1992, J. Mol. Biol. 227:711; Devlin et al, 1990 Science 249:404; Cwirla et al 1990, Proc. Natl. Acad, Sci. USA, 87:6378). Libraries may also be constructed by concurrent synthesis of overlapping peptides (see U.S. Pat. No. 4,708,871).

The peptides and chimeric proteins of the disclosure may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

Nucleic Acids

In one aspect, the present disclosure is based on the development of novel nucleic acids encoding fusion proteins comprising an editing protein and an TIF protein. In one embodiment, the nucleic acid encodes a fusion protein which is capable of cleaving binding mRNAs and recruiting 40S ribosome to the mRNAs.

In one embodiment, the nucleic acid molecule comprises a nucleic acid sequence encoding an editing protein; and a nucleic acid sequence encoding a TIF protein. In one embodiment, the nucleic acid molecule comprises a nucleic acid sequence encoding a nuclear export signal (NES). In one embodiment, the nucleic acid molecule comprises a nucleic acid sequence encoding a linker. In one embodiment, the nucleic acid molecule comprises a nucleic acid sequence encoding a detection and/or purification tag.

In one embodiment, the editing protein includes, but is not limited to, a CRISPR-associated (Cas) protein, a zinc finger nuclease (ZFN) protein, and a protein having an RNA binding domain. In one embodiment, the editing protein is a Cas protein.

In one embodiment, the nucleic acid molecule encodes comprises a nucleotide sequence encoding a Cas protein described herein. Non-limiting examples of Cas proteins include Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2. Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, SpCas9, StCas9, NmCas9, SaCas9, CjCas9, CjCas9, AsCpf1, LbCpf1, FnCpf1, VRER SpCas9, VQR SpCas9, xCas9 3.7, homologs thereof, orthologs thereof, or modified versions thereof. In some embodiments, the Cas protein has DNA or RNA cleavage activity. In some embodiments, the Cas protein directs cleavage of one or both strands of a nucleic acid molecule at the location of a target sequence, such as within the target sequence and/or within the complement of the target sequence. In some embodiments, the Cas protein directs cleavage of one or both strands within about 1, 2, 3, 4, 5, 6, 7, 8, 9, 10, 15, 20, 25, 50, 100, 200, 500, or more base pairs from the first or last nucleotide of a target sequence. In one embodiment, the Cas protein is Cas9, Cas13, or Cpf1. In one embodiment, Cas protein is catalytically deficient (dCas).

In one embodiment, Cas protein is Cas13. In one embodiment, the Cas protein is PspCas13b, PspCas13b Truncation, AdmCas13d, AspCas13b, AspCas13c, BmaCas13a, BzoCas13b, CamCas13a, CcaCas13b, Cga2Cas13a, CgaCas13a, EbaCas13a, EreCas13a, EsCas13d, FbrCas13b, FnbCas13c, FndCas13c, FnfCas13c, FnsCas13c, FpeCas13c, FulCas13c, HheCas13a, LbfCas13a, LbmCas13a, LbnCas13a, LbuCas13a, LseCas13a, LshCas13a, LspCas13a, Lwa2 cas13a, LwaCas13a, LweCas13a, PauCas13b, PbuCas13b, PgiCas13b, PguCas13b, Pin2Cas13b, Pin3Cas13b, PinCas13b, Pprcas13a, PsaCas13b, PsmCas13b, RaCas13d, RanCas13b, RcdCas13a, RcrCas13a, RcsCas13a, RfxCas13d, UrCas13d, dPspCas13b, PspCas13b_A133H, PspCas13b_A1058H, dPspCas13b truncation, dAdmCas13d, dAspCas13b, dAspCas13c, dBmaCas13a, dBzoCas13b, dCamCas13a, dCcaCas13b, dCga2Cas13a, dCgaCas13a, dEbaCas13a, dEreCas13a, dEsCas13d, dFbrCas13b, dFnbCas13c, dFndCas13c, dFnfCas13c, dFnsCas13c, dFpeCas13c, dFulCas13c, dHheCas13a, dLbfCas13a, dLbmCas13a, dLbnCas13a, dLbuCas13a, dLseCas13a, dLshCas13a, dLspCas13a, dLwa2 cas13a, dLwaCas13a, dLweCas13a, dPauCas13b, dPbuCas13b, dPgiCas13b, dPguCas13b, dPin2Cas13b, dPin3Cas13b, dPinCas13b, dPprCas13a, dPsaCas13b, dPsmCas13b, dRaCas13d, dRanCas13b, dRcdCas13a, dRcrCas13a, dRcsCas13a, dRfxCas13d, dUrCas13d, or a variant thereof. Additional Cas proteins are known in the art (e.g., Konermann et al., Cell, 2018, 173:665-676 e14, Yan et al., Mol Cell, 2018, 7:327-339 e5; Cox, D. B. T., et al., Science, 2017, 358: 1019-1027; Abudayyeh et al., Nature, 2017, 550: 280-284, Gootenberg et al., Science, 2017, 356: 438-442; and East-Seletsky et al., Mol Cell, 2017, 66: 373-383 e3, which are herein incorporated by reference).

In one embodiment, the nucleic acid molecule comprises a nucleotide sequence encoding a Cas protein that comprises an amino acid sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs:1-48. In one embodiment, the nucleic acid molecule comprises a nucleotide sequence encoding a Cas protein that comprises an amino acid sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs:1-48. In one embodiment, the nucleic acid molecule comprises a nucleotide sequence encoding a Cas protein that comprises an amino acid sequence of a variant of one of SEQ ID NOs:1-46, wherein the variant renders the Cas protein catalytically inactive. In one embodiment, the nucleic acid molecule comprises a nucleotide sequence encoding a Cas protein that comprises an amino acid sequence of one of SEQ ID NOs:1-46 having one or more insertions, deletions or substitutions, wherein the one or more insertions, deletions or substitutions renders the Cas protein catalytically inactive. In one embodiment the nucleic acid molecule comprises a nucleotide sequence encoding a Cas protein that comprises an amino acid sequence of one of SEQ ID NOs:1-48. In one embodiment, the nucleic acid molecule comprises a nucleotide sequence encoding a Cas protein that comprises an amino acid sequence of one of SEQ ID NOs:47-48.

In one embodiment, the nucleic acid molecule comprises a nucleotide sequence encoding a PspCas13b protein. In one embodiment, the nucleic acid molecule comprises a nucleotide sequence encoding catalytically dead PspCas13b (dPspCas13b). In one embodiment, the nucleic acid molecule comprises a nucleotide sequence encoding a PspCas13b protein that comprises an amino acid sequence at least 95% identical to SEQ ID NOs:1, 47 or 48. In one embodiment, the nucleic acid molecule comprises a nucleotide sequence encoding a PspCas13b protein that comprises an amino acid sequence of SEQ ID NOs:1, 47 or 48.

In one embodiment, the nucleic acid sequence encoding a Cas protein comprises a nucleic acid sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs: 79-82. In one embodiment, the nucleic acid sequence encoding a Cas protein comprises a nucleic acid sequence of one of SEQ ID NOs:79-82.

In one embodiment, the nucleic acid sequence encoding a dCas protein comprises a nucleic acid sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs: 81-82. In one embodiment, the nucleic acid sequence encoding a Cas protein comprises a nucleic acid sequence of one of SEQ ID NOs:81-82.

In one embodiment, the nucleic acid molecule comprises a nucleotide sequence encoding an TIF protein described herein. In one embodiment, the TIF protein is an eukaryotic initiation factor (EIF), a Translational Regulatory Protein of Viral Origin, or a Bacterial Translation Initiation Factor (BTIF). In one embodiment, the nucleic acid molecule comprises a nucleotide sequence encoding an TIF protein that comprises a sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs:59-77. In one embodiment, the nucleic acid molecule comprises a nucleotide sequence encoding an TIF protein that comprises a sequence of one of SEQ ID NOs:59-77.

In one embodiment, the nucleic acid molecule comprises a nucleotide sequence encoding an EIF protein. In one embodiment, the nucleic acid molecule comprises a nucleotide sequence encoding an EIF protein that comprises an amino acid sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs: 59-70. In one embodiment, the nucleic acid molecule comprises a nucleotide sequence encoding an EIF protein that comprises an amino acid sequence of one of SEQ ID NOs: 59-70.

In one embodiment, the nucleic acid molecule comprises a nucleotide sequence encoding a fragment of a EIF protein, wherein the fragment is a fragment of a sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs: 65-77. In one embodiment, the nucleic acid molecule comprises a nucleotide sequence encoding a fragment of a EIF protein, wherein the fragment is a fragment of one of SEQ ID NOs: 65-77.

In one embodiment, the nucleic acid molecule comprises a nucleotide sequence encoding a fragment of an EIF protein, wherein the fragment comprises a sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs: 59-63. In one embodiment, the nucleic acid molecule comprises a nucleotide sequence encoding a fragment of an EIF protein, wherein the fragment comprises a sequence of one of SEQ ID NOs:59-63.

In one embodiment, the nucleic acid sequence encoding a EIF protein comprises a nucleic acid sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs: 87-89. In one embodiment, the nucleic acid sequence encoding a EIF protein comprises a nucleic acid sequence of one of SEQ ID NOs:87-89.

In one embodiment, the nucleic acid molecule comprises a nucleotide sequence encoding a viral protein. In one embodiment, the nucleic acid molecule comprises a nucleotide sequence encoding a viral protein that comprises an amino acid sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs: 71-75. In one embodiment, the nucleic acid molecule comprises a nucleotide sequence encoding a viral protein that comprises an amino acid sequence of one of SEQ ID NOs: 71-75.

In one embodiment, the nucleic acid sequence encoding a viral protein comprises a nucleic acid sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs: 90-94. In one embodiment, the nucleic acid sequence encoding a viral protein comprises a nucleic acid sequence of one of SEQ ID NOs:90-94.

In one embodiment, the nucleic acid molecule comprises a nucleotide sequence encoding a BTIF protein. In one embodiment, the nucleic acid molecule comprises a nucleotide sequence encoding a viral protein that comprises an amino acid sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs: 76-77. In one embodiment, the nucleic acid molecule comprises a nucleotide sequence encoding a BTIF protein that comprises an amino acid sequence of one of SEQ ID NOs: 76-77.

In one embodiment, the nucleic acid molecule comprises a nucleotide sequence encoding a Nuclear Export Signal (NES). In one embodiment, the nucleic acid molecule comprises a nucleotide sequence encoding a NES that comprises an amino acid sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs: 57-58. In one embodiment, the nucleic acid molecule comprises a nucleotide sequence encoding a NES protein that comprises an amino acid sequence of one of SEQ ID NOs: 57-58.

In one embodiment, the nucleotide sequence encoding NES comprises a sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs: 85-86. In one embodiment, the nucleotide sequence encoding NES comprises a sequence of one of SEQ ID NOs: 85-86.

In one embodiment, the nucleic acid molecule comprises a nucleotide sequence encoding a purification and/or detection tag. In one embodiment, the nucleic acid molecule comprises a nucleotide sequence encoding a purification and/or detection tag that comprises an amino acid sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to SEQ ID NOs: 56. In one embodiment, the nucleic acid molecule comprises a nucleotide sequence encoding a purification and/or detection tag that comprises an amino acid sequence of SEQ ID NOs: 56.

In one embodiment, the nucleotide sequence encoding a tag comprises a sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to SEQ ID NO:84. In one embodiment, the nucleotide sequence encoding tag comprises a sequence of SEQ ID NO: 84.

In one embodiment, the nucleic acid molecule comprises a nucleotide sequence encoding a linker. In one embodiment, the nucleic acid molecule comprises a nucleotide sequence encoding a linker that comprises an amino acid sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs: 49-55. In one embodiment, the nucleic acid molecule comprises a nucleotide sequence encoding a linker that comprises an amino acid sequence of one of SEQ ID NOs: 49-55.

In one embodiment, the nucleotide sequence encoding linker comprises a sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to one of SEQ ID NOs:83. In one embodiment, the nucleotide sequence encoding linker comprises a sequence at of one of SEQ ID NOs: 83.

In one embodiment, the nucleic acid molecule comprises a nucleic acid sequence that encodes a fusion protein comprising an amino acid sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to SEQ ID NO: 78. In one embodiment, the nucleic acid molecule comprises a nucleic acid sequence that encodes a fusion protein comprising an amino acid sequence of SEQ ID NO:78.

In one embodiment, the nucleic acid molecules comprises a nucleic acid sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identical to SEQ ID NO:95. In one embodiment, nucleic acid molecule comprises a nucleic acid sequence of SEQ ID NO: 95.

The isolated nucleic acid sequence encoding a fusion protein can be obtained using any of the many recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The isolated nucleic acid may comprise any type of nucleic acid, including, but not limited to DNA and RNA. For example, in one embodiment, the composition comprises an isolated DNA molecule, including for example, an isolated cDNA molecule, encoding a fusion protein of the disclosure. In one embodiment, the composition comprises an isolated RNA molecule encoding a fusion protein of the disclosure, or a functional fragment thereof.

The nucleic acid molecules of the present disclosure can be modified to improve stability in serum or in growth medium for cell cultures. Modifications can be added to enhance stability, functionality, and/or specificity and to minimize immunostimulatory properties of the nucleic acid molecule of the disclosure. For example, in order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect function of the molecule.

In one embodiment of the present disclosure the nucleic acid molecule may contain at least one modified nucleotide analogue. For example, the ends may be stabilized by incorporating modified nucleotide analogues.

Non-limiting examples of nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides the phosphoester group connecting to adjacent ribonucleotides is replaced by a modified group, e.g., of phosphothioate group. In exemplary sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Other examples of modifications are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In some instances, the nucleic acid molecule comprises at least one of the following chemical modifications: 2'-H, 2'-O-methyl, or 2'-OH modification of one or more nucleotides. In certain embodiments, a nucleic acid molecule of the disclosure can have enhanced resistance to nucleases. For increased nuclease resistance, a nucleic acid molecule, can include, for example, 2'-modified ribose units and/or phosphorothioate linkages. For example, the 2' hydroxyl group (OH) can be modified or replaced with a number of different "oxy" or "deoxy" substituents. For increased nuclease resistance the nucleic acid molecules of the disclosure can include 2'-O-methyl, 2'-fluorine, 2'-O-methoxyethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleobase modifications such as 2-amino-A, 2-thio (e.g., 2-thio-U), G-clamp modifications, can also increase binding affinity to a target.

In one embodiment, the nucleic acid molecule includes a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In one embodiment, the nucleic acid molecule includes at least one 2'-O-methyl-modified nucleotide, and in some embodiments, all of the nucleotides of the nucleic acid molecule include a 2'-O-methyl modification.

In certain embodiments, the nucleic acid molecule of the disclosure has one or more of the following properties:

Nucleic acid agents discussed herein include otherwise unmodified RNA and DNA as well as RNA and DNA that have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, or as occur naturally in the human body. The art has referred to rare or unusual, but naturally occurring, RNAs as modified RNAs, see, e.g., Limbach et al. (Nucleic Acids Res., 1994, 22:2183-2196). Such rare or unusual RNAs, often termed modified RNAs, are typically the result of a post-transcriptional modification and are within the term unmodified RNA as used herein. Modified RNA, as used herein, refers to a molecule in which one or more of the components of the nucleic acid, namely sugars, bases, and phosphate moieties, are different from that which occur in nature, or different from that which occurs in the human body. While they are referred to as "modified RNAs" they will of course, because of the modification, include molecules that are not, strictly speaking, RNAs. Nucleoside surrogates are molecules in which the ribophosphate backbone is replaced with a non-ribophosphate construct that allows the bases to be presented in the correct spatial relationship such that hybridization is substantially similar to what is seen with a ribophosphate backbone, e.g., non-charged mimics of the ribophosphate backbone.

Modifications of the nucleic acid of the disclosure may be present at one or more of, a phosphate group, a sugar group, backbone, N-terminus, C-terminus, or nucleobase.

The present disclosure also includes a vector in which the isolated nucleic acid of the present disclosure is inserted. The art is replete with suitable vectors that are useful in the present disclosure.

In brief summary, the expression of natural or synthetic nucleic acids encoding a fusion protein of the disclosure is typically achieved by operably linking a nucleic acid encoding the fusion protein of the disclosure or portions thereof to a promoter, and incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence.

The vectors of the present disclosure may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the disclosure provides a gene therapy vector.

The isolated nucleic acid of the disclosure can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the vector may be provided to a cell in the form of a viral vector. Viral vector technology is well known in the art and is described, for example, in Sambrook et al.

(2012, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Delivery Systems

In one aspect, the disclosure relates to the development of lentiviral packaging and delivery systems. The lentiviral particle delivers the viral enzymes as proteins. In this fashion, lentiviral enzymes are short lived, thus limiting the potential for off-target editing due to long term expression though the entire life of the cell. The incorporation of editing components, or traditional CRISPR-Cas editing components as proteins in lentiviral particles is advantageous, given that their required activity is only required for a short period of time. Thus, in one embodiment, the disclosure provides a lentiviral delivery system and methods of delivering the compositions of the disclosure, editing genetic material, and nucleic acid delivery using lentiviral delivery systems.

In one embodiment, the delivery system comprises (1) a packaging plasmid (2) a transfer plasmid, and (3) an envelope plasmid. In one embodiment, the delivery system comprises (1) a packaging plasmid (2) an envelope plasmid, and (3) a VPR plasmid.

In one embodiment, the packaging plasmid comprises a nucleic acid sequence encoding a gag-pol polyprotein. In one embodiment, the gag-pol polyprotein comprises catalytically dead integrase. In one embodiment, the gag-pol polyprotein comprises a mutation selected from D116N and D64V. In one embodiment, the transfer plasmid comprises a nucleic acid sequence encoding a CRISPR guide RNA (crRNA) sequence and a fusion protein of the disclosure.

In one embodiment, the envelope plasmid comprises a nucleic acid sequence encoding an envelope protein. In one embodiment, the envelope plasmid comprises a nucleic acid sequence encoding an HIV envelope protein. In one embodiment, the envelope plasmid comprises a nucleic acid sequence encoding a vesicular stomatitis virus g-protein (VSV-g) envelope protein. In one embodiment, the envelope protein can be selected based on the desired cell type.

In one embodiment, the VPR plasmid comprises a nucleic acid sequence encoding a fusion protein comprising VPR and a fusion protein of the disclosure. In one embodiment, the VPR plasmid comprises a nucleic acid sequence encoding a fusion protein comprising VPR, and fusion protein of the disclosure. In one embodiment, the VPR fusion protein comprises a protease cleavage site between VPR and the fusion protein of the disclosure. In one embodiment, the VPR plasmid further comprises a sequence encoding a crRNA sequence.

In one embodiment, the packaging plasmid, transfer plasmid, envelope plasmid, and VPR plasmid are introduced into a cell. In one embodiment, the cell transcribes and translates the nucleic acid sequence encoding the gag-pol protein to produce the gag-pol polyprotein. In one embodiment, the cell transcribes and translates the nucleic acid sequence encoding the envelope protein to produce the envelope protein. In one embodiment, the cell transcribes and translates the fusion protein to produce the VPR-fusion protein. In one embodiment, the cell transcribes and translates the fusion protein to produce the VPR-fusion protein. In one embodiment, the cell transcribes the nucleic acid sequence encoding the guide RNA. In one embodiment, the transcribed transfer plasmid and gag-pol proteins are packaged into a lentiviral vector. In one embodiment, the lentiviral vectors are collected from the cell media. In one embodiment, the viral particles transduce a target cell, wherein the transcribed the crRNA and fusion protein are cleaved and the translated thereby generating the fusion protein and crRNA, wherein the crRNA binds to the Cas protein and directs it to an RNA having a sequence substantially complementary to the crRNA sequence.

In one embodiment, the gag-pol protein, envelope polyprotein, and VPR-fusion protein, which is bound to the crRNA, are packaged into a viral particle. In one embodiment, the viral particles are collected from the cell media. In one embodiment, VPR is cleaved from the fusion protein in the viral particle via the protease site to provide the Cas-TIF fusion protein of the disclosure. In one embodiment, the viral particles transduce a target cell, wherein the guide RNA binds a target region of an RNA thereby targeting the Cas-TIF fusion protein.

Further, a number of additional viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In one embodiment, the composition includes a vector derived from an adeno-associated virus (AAV). The term "AAV vector" means a vector derived from an adeno-associated virus serotype, including without limitation, AAV-1, AAV-2, AAV-3, AAV-4, AAV-5, AAV-6, AAV-7, AAV-8, and AAV-9. AAV vectors have become powerful gene delivery tools for the treatment of various disorders. AAV vectors possess a number of features that render them ideally suited for gene therapy, including a lack of pathogenicity, minimal immunogenicity, and the ability to transduce postmitotic cells in a stable and efficient manner. Expression of a particular gene contained within an AAV vector can be specifically targeted to one or more types of cells by choosing the appropriate combination of AAV serotype, promoter, and delivery method.

AAV vectors can have one or more of the AAV wild-type genes deleted in whole or part, preferably the rep and/or cap genes, but retain functional flanking ITR sequences. Despite the high degree of homology, the different serotypes have tropisms for different tissues. The receptor for AAV1 is unknown; however, AAV1 is known to transduce skeletal and cardiac muscle more efficiently than AAV2. Since most of the studies have been done with pseudotyped vectors in which the vector DNA flanked with AAV2 ITR is packaged into capsids of alternate serotypes, it is clear that the biological differences are related to the capsid rather than to the genomes. Recent evidence indicates that DNA expression cassettes packaged in AAV1 capsids are at least 1 log 10 more efficient at transducing cardiomyocytes than those packaged in AAV2 capsids. In one embodiment, the viral delivery system is an adeno-associated viral delivery system. The adeno-associated virus can be of serotype 1 (AAV1), serotype 2 (AAV2), serotype 3 (AAV3), serotype 4 (AAV4), serotype 5 (AAV5), serotype 6 (AAV6), serotype 7 (AAV7), serotype 8 (AAV8), or serotype 9 (AAV9).

Desirable AAV fragments for assembly into vectors include the cap proteins, including the vp1, vp2, vp3 and hypervariable regions, the rep proteins, including rep 78, rep 68, rep 52, and rep 40, and the sequences encoding these proteins. These fragments may be readily utilized in a variety of vector systems and host cells. Such fragments may be used alone, in combination with other AAV serotype sequences or fragments, or in combination with elements from other AAV or non-AAV viral sequences. As used herein, artificial AAV serotypes include, without limitation, AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid. Thus exemplary AAVs, or artificial AAVs, suitable for expression of one or more proteins, include AAV2/8 (see U.S. Pat. No. 7,282,199), AAV2/5 (available from the National Institutes of Health), AAV2/9 (International Patent Publication No. WO2005/033321), AAV2/6 (U.S. Pat. No. 6,156,303), and AAVrh8 (International Patent Publication No. WO2003/042397), among others.

In certain embodiments, the vector also includes conventional control elements which are operably linked to the transgene in a manner which permits its transcription, translation and/or expression in a cell transfected with the plasmid vector or infected with the virus produced by the disclosure. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the disclosure should not be limited to the use of constitutive promoters. Inducible promoters are also contemplated as part of the disclosure. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Enhancer sequences found on a vector also regulates expression of the gene contained therein. Typically, enhancers are bound with protein factors to enhance the transcription of a gene. Enhancers may be located upstream or downstream of the gene it regulates. Enhancers may also be tissue-specific to enhance transcription in a specific cell or tissue type. In one embodiment, the vector of the present disclosure comprises one or more enhancers to boost transcription of the gene present within the vector.

In order to assess the expression of a fusion protein of the disclosure, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter.

Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). An exemplary method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the disclosure.

Systems

In one aspect, the present disclosure provides a system for enhancing the synthesis of a protein in a subject. In one embodiment the system comprises, in one or more vectors, a nucleic acid sequence encoding a fusion protein, wherein the fusion protein comprises a CRISPR-associated (Cas) protein and a Translation Initiation factor (TIF); and a nucleic acid sequence encoding a CRISPR-Cas system CRISPR guide RNA (crRNA). In one embodiment, the CRISPR-Cas system crRNA substantially hybridizes to a target mRNA sequence in the protein mRNA transcript. In one embodiment, the nucleic acid sequence encoding the fusion protein and the nucleic acid sequence encoding a CRISPR-Cas system crRNA are in the same vector. In one embodiment, the nucleic acid sequence encoding the fusion protein and the nucleic acid sequence encoding a CRISPR-Cas system crRNA are in different vectors.

In one embodiment, the nucleic acid sequence encoding a fusion protein comprises (1) a nucleic acid sequence encoding an amino acid sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to one of SEQ ID NOs: 47-48; and (2) a nucleic acid sequence encoding an amino acid sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to one of SEQ ID NOs: 59-77. In one embodiment, the nucleic acid sequence encoding a fusion protein comprises (1) a nucleic acid sequence encoding an amino acid of one of SEQ ID NOs: 47-48; (2) a nucleic acid sequence encoding an amino acid of one of SEQ ID NOs: 59-77. In one embodiment, the nucleic acid sequence encoding a fusion protein comprises a nucleic acid sequence encoding an amino acid of SEQ ID NO:78.

In one embodiment, the nucleic acid sequence encoding a fusion protein comprises (1) a nucleic acid sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to one of SEQ ID NOs: 79-82; and (2) a nucleic acid sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to one of SEQ ID NOs: 87-94. In one embodiment, the nucleic acid sequence encoding a fusion protein comprises (1) a nucleic acid sequence of one of SEQ ID NOs: 79-82; (2) a nucleic acid sequence of one of SEQ ID NOs: 87-94. In one embodiment, the nucleic acid sequence encoding a fusion protein comprises a nucleic acid sequence of SEQ ID NO:95.

Compositions and Formulations

In one aspect, the present disclosure provides compositions for enhancing the synthesis of a protein in a subject. In one embodiment, the composition comprises a fusion protein, wherein the fusion protein comprises a CRISPR-associated (Cas) protein and a Translation Initiation factor (TIF). For example, in one embodiment, the composition comprises a fusion protein, wherein the fusion protein comprises a Cas protein and a eukaryotic initiation factor (EIF) protein, a Cas protein and viral protein, or a Cas protein and a Bacterial Translation Initiation Factor (BTIF). In one embodiment, the composition comprises a CRISPR-Cas system CRISPR guide RNA (crRNA). In one embodiment, the CRISPR-Cas system crRNA substantially hybridizes to a target mRNA sequence in the mRNA transcript.

In one embodiment, the composition comprises a fusion protein comprising (1) an amino acid sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to one of SEQ ID NOs: 47-48; and (2) an amino acid sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to one of SEQ ID NOs: 59-77. In one embodiment, composition comprises a fusion protein comprising (1) an amino acid of one of SEQ ID NOs: 47-48; and (2) amino acid of one of SEQ ID NOs: 59-77. In one embodiment, composition comprises a fusion protein an amino acid sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to SEQ ID NO:78. In one embodiment, composition comprises a fusion protein an amino acid sequence of SEQ ID NO:78.

The disclosure also encompasses the use of pharmaceutical compositions of the disclosure to practice the methods of the disclosure. Such a pharmaceutical composition may consist of at least one modulator (e.g., inhibitor or activator) composition of the disclosure or a salt thereof in a form suitable for administration to a subject, or the pharmaceutical composition may comprise at least one modulator (e.g., inhibitor or activator) composition of the disclosure or a salt thereof, and one or more pharmaceutically acceptable carriers, one or more additional ingredients, or some combination of these. The compound of the disclosure may be present in the pharmaceutical composition in the form of a physiologically acceptable salt, such as in combination with a physiologically acceptable cation or anion, as is well known in the art.

In an embodiment, the pharmaceutical compositions useful for practicing the methods of the disclosure may be administered to deliver a dose of between 1 ng/kg/day and 100 mg/kg/day. In another embodiment, the pharmaceutical compositions useful for practicing the disclosure may be administered to deliver a dose of between 1 ng/kg/day and 500 mg/kg/day.

The relative amounts of the active ingredient, the pharmaceutically acceptable carrier, and any additional ingredients in a pharmaceutical composition of the disclosure will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the disclosure may be suitably developed for oral, rectal, vaginal, parenteral, topical, pulmonary, intranasal, buccal, ophthalmic, or another route of administration. A composition useful within the methods of the disclosure may be directly administered to the skin, or any other tissue of a mammal. Other contemplated formulations include liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human subject being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

In one embodiment, the compositions of the disclosure are formulated using one or more pharmaceutically acceptable excipients or carriers. In one embodiment, the pharmaceutical compositions of the disclosure comprise a therapeutically effective amount of a compound or conjugate of the disclosure and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, isotonic agents, for example, sugars, sodium chloride, or polyalcohols such as mannitol and sorbitol are included in the composition. Prolonged absorption of the injectable compositions may be brought about by including in the composition an agent that delays absorption, for example, aluminum monostearate or gelatin. In one embodiment, the pharmaceutically acceptable carrier is not DMSO alone.

Formulations may be employed in admixtures with conventional excipients, i.e., pharmaceutically acceptable organic or inorganic carrier substances suitable for oral, vaginal, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the disclosure are known in the art and described, for example in Genaro, ed. (1985, Remington's Pharmaceutical Sciences, Mack Publishing Co., Easton, PA), which is incorporated herein by reference.

The composition of the disclosure may comprise a preservative from about 0.005% to 2.0% by total weight of the composition. The preservative is used to prevent spoilage in the case of exposure to contaminants in the environment. Examples of preservatives useful in accordance with the disclosure included but are not limited to those selected from the group consisting of benzyl alcohol, sorbic acid, parabens, imidurea and combinations thereof. An exemplary preservative is a combination of about 0.5% to 2.0% benzyl alcohol and 0.05% to 0.5% sorbic acid.

In one embodiment, the composition includes an antioxidant and a chelating agent that inhibits the degradation of the compound. Exemplary antioxidants for some compounds are BHT, BHA, alpha-tocopherol and ascorbic acid in the range of about 0.01% to 0.3% and BHT in the range of 0.03% to 0.1% by weight by total weight of the composition. In one embodiment, the chelating agent is present in an amount of from 0.01% to 0.5% by weight by total weight of the composition. Exemplary chelating agents include edetate salts (e.g. disodium edetate) and citric acid in the weight range of about 0.01% to 0.20%. In some embodiments, the chelating agent is in the range of 0.02% to 0.10% by weight by total weight of the composition. The chelating agent is useful for chelating metal ions in the composition that may be detrimental to the shelf life of the formulation. While BHT and disodium edetate are exemplary antioxidants and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the disclosure may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the disclosure may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the disclosure may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

The regimen of administration may affect what constitutes an effective amount. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present disclosure to a subject, include a mammal, for example a human, may be carried out using known procedures, at dosages and for periods of time effective to prevent or treat disease. An effective amount of the therapeutic composition necessary to achieve a therapeutic effect may vary according to factors such as the activity of the particular composition employed; the time of administration; the rate of excretion of the composition; the duration of the treatment; other drugs, compositions or materials used in combination with the composition; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic composition of the disclosure is from about 1 and 5,000 mg/kg of body weight/per day. One of ordinary skill in the art would be able to study the relevant factors and make the determination regarding the effective amount of the therapeutic composition without undue experimentation.

The composition may be administered to a subject as frequently as several times daily, or it may be administered less frequently, such as once a day, once a week, once every two weeks, once a month, or even less frequently, such as once every several months or even once a year or less. It is understood that the amount of composition dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this disclosure may be varied so as to obtain an amount of the active ingredient that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compositions of the disclosure employed in the pharmaceutical composition at levels lower than that required in order to achieve the desired therapeutic effect and gradually increase the dosage until the desired effect is achieved.

In particular embodiments, it is especially advantageous to formulate the composition in dosage unit form for ease of administration and uniformity of dosage. Dosage unit form as used herein refers to physically discrete units suited as unitary dosages for the subjects to be treated; each unit containing a predetermined quantity of therapeutic composition calculated to produce the desired therapeutic effect in association with the required pharmaceutical vehicle. The dosage unit forms of the disclosure are dictated by and directly dependent on (a) the unique characteristics of the therapeutic composition and the particular therapeutic effect to be achieved, and (b) the limitations inherent in the art of compounding/formulating such a therapeutic composition for the treatment of a disease in a subject.

In one embodiment, the compositions of the disclosure are administered to the subject in dosages that range from one to five times per day or more. In another embodiment, the compositions of the disclosure are administered to the subject in range of dosages that include, but are not limited to, once every day, every two, days, every three days to once a week, and once every two weeks. It will be readily apparent to one skilled in the art that the frequency of administration of the various combination compositions of the disclosure will vary from subject to subject depending on many factors including, but not limited to, age, disease or disorder to be treated, gender, overall health, and other factors. Thus, the disclosure should not be construed to be limited to any particular dosage regime and the precise dosage and composition to be administered to any subject will be determined by the attending physical taking all other factors about the subject into account.

Compositions of the disclosure for administration may be in the range of from about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 3050 mg to about 6,000 mg, about 500 mg to about 5,000 mg, about 750 mg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments there between.

In one embodiment, the present disclosure is directed to a packaged pharmaceutical composition comprising a container holding a therapeutically effective amount of a composition of the disclosure, alone or in combination with a second pharmaceutical agent; and instructions for using the composition to treat, prevent, or reduce one or more symptoms of a disease in a subject.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the composition's ability to perform its intended function, e.g., treating or preventing a disease in a subject, or delivering an imaging or diagnostic agent to a subject.

Routes of administration of any of the compositions of the disclosure include oral, nasal, parenteral, sublingual, transdermal, transmucosal (e.g., sublingual, lingual, (trans)buccal, and (intra)nasal), intravesical, intraduodenal, intragastrical, rectal, intra-peritoneal, subcutaneous, intramuscular, intradermal, intra-arterial, intravenous, or administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present disclosure are not limited to the particular formulations and compositions that are described herein.

Methods of Enhancing Synthesis of a Protein

In one aspect, the disclosure provides methods of enhancing the synthesis of a protein in a subject. In one embodiment, the method comprises administering to the subject (1) a nucleic acid molecule encoding a fusion protein of the disclosure comprising a Cas protein and TIF protein or a fusion protein of the disclosure comprising a Cas protein a TIF protein, and (2) a nucleic acid molecule encoding a CRISPR guide RNA (crRNA) comprising a targeting nucleotide sequence complimentary to a target mRNA sequence in the mRNA transcript which is translated into the protein or a guide nucleic acid molecule comprising a targeting nucleotide sequence complimentary to a target mRNA sequence in the mRNA transcript which is translated into the protein.

In one embodiment, the subject is a cell. In one embodiment, the subject is a mammal. For example, in one embodiment, the subject is a human, non-human primate, dog, cat, horse, cow, goat, sheep, rabbit, pig, rat, or mouse. In one embodiment, the subject is a non-mammalian subject. For example, in one embodiment, the subject is a zebrafish, fruit fly, or roundworm.

In one embodiment, the protein synthesis is enhanced in vitro. In one embodiment, the protein synthesis is enhanced in vivo.

In one embodiment, the method regulates the translation of two or more protein coding mRNAs. For example, in one embodiment, the method comprises administering to the subject (1) a nucleic acid molecule encoding a fusion protein of the disclosure comprising a Cas protein and TIF protein or a fusion protein of the disclosure comprising a Cas protein a TIF protein, and (2) a crRNA comprising a targeting nucleotide sequence complimentary to a target mRNA sequence in the mRNA transcript which is translated into the protein. In one embodiment, the target mRNA encodes a protein in an enzymatic pathway, signaling pathway, transcriptional network, thereby regulating the translation of other proteins in the pathway or network.

In one embodiment, the disclosure provides a method of increasing the synthesis of a recombinant protein in a eukaryotic cell. In one embodiment, the method allow for increased protein synthesis in eukaryote cells for drug manufacturing. In one embodiment, the method comprises administering to the cell (1) a nucleic acid molecule encoding a fusion protein of the disclosure comprising a Cas protein a TIF protein or a fusion protein of the disclosure comprising a Cas protein a TIF protein, and (2) a crRNA comprising a targeting nucleotide sequence complimentary to a target region in a mRNA, wherein the mRNA is translated into the protein. In one embodiment, the cell is a modified cell that produces a recombinant protein.

Methods of Treatment

The present disclosure provides methods of treating, reducing the symptoms of, and/or reducing the risk of developing a disease or disorder in a subject. For example, in one embodiment, methods of the disclosure of treat, reduce the symptoms of, and/or reduce the risk of developing a disease or disorder in a mammal. In one embodiment, the methods of the disclosure of treat, reduce the symptoms of, and/or reduce the risk of developing a disease or disorder in a plant. In one embodiment, the methods of the disclosure of treat, reduce the symptoms of, and/or reduce the risk of developing a disease or disorder in a yeast organism.

In one aspect, the disclosure provides a method of treating a disease or disorder associated with reduced or low protein expression or synthesis. In one embodiment, the method comprises administering to the subject (1) a nucleic acid molecule encoding a fusion protein of the disclosure comprising a Cas protein a TIF protein or a fusion protein of the disclosure comprising a Cas protein a TIF protein, and (2) a CRISPR guide RNA (crRNA) comprising a targeting nucleotide sequence complimentary to a target region in a mRNA, wherein the mRNA is translated into the protein.

In one embodiment the disclosure provides a method of treating or prophylactic treatment of heart failure. In one embodiment, the method comprises administering to the subject (1) a nucleic acid molecule encoding a fusion protein of the disclosure comprising a Cas protein a TIF protein or a fusion protein of the disclosure comprising a Cas protein a TIF protein, and (2) a crRNA molecule complementary to a target region in SERCA2 mRNA, wherein the translation of the SERCA2 mRNA is increased thereby increasing the amount of SERCA2 protein.

In one embodiment, the method is a method of treating or prophylactic treatment of a haploinsufficiency disease. For example, in one embodiment, the method comprises administering to the subject (1) a nucleic acid molecule encoding a fusion protein of the disclosure comprising a Cas protein a TIF protein or a fusion protein of the disclosure comprising a Cas protein a TIF protein, and (2) a crRNA molecule complementary to a target region in an mRNA associated with the haploinsufficiency disease, wherein the wherein the translation of the mRNA is increased thereby increasing the amount of the associated protein. For example, in one embodiment, haploinsufficiency diseases include, but are not limited to, 1q21.1 deletion syndrome, 5q-syndrome in myelodysplastic syndrome (MDS), 22q11.2 deletion syndrome, CHARGE syndrome, Cleidocranial dysostosis, Ehlers-Danlos syndrome, Greig syndrome, Frontotemporal dementia caused by mutations in progranulin, GLUT1 deficiency (DeVivo syndrome), Haploinsufficiency of A20, Holoprosencephaly caused by haploinsufficiency in the Sonic Hedgehog gene, Holt-Oram syndrome, Marfan syndrome, Phelan-McDermid syndrome, Polydactyly, and Dravet Syndrome.

In one embodiment, the subject is a cell. In one embodiment, the cell is a prokaryotic cell or eukaryotic cell. In one embodiment, the cell is a eukaryotic cell. In one embodiment, the cell is a plants, animals, or fungi cell. In one embodiment, the cell is a plant cell. In one embodiment, the cell is an animal cell. In one embodiment, the cell is a yeast cell.

In one embodiment, the method comprises administering to the subject (1) a nucleic acid molecule encoding a fusion protein of the disclosure comprising a Cas protein a TIF protein, and (2) two or more crRNA molecules, where each crRNA molecule is complementary to a region of discrete mRNAs. In one embodiment, the discrete mRNAs are related. For example, in one embodiment, the mRNAs encode proteins in a pathway thereby enhancing translation of all required enzymes in a pathway. In one embodiment, the method treats complex disease pathways including, but not limited to, cardiovascular disease, obesity, cancer, diabetes, asthma, epilepsy. In one embodiment, the method generates pharmaceutical compounds, biofuels, or biologicals.

In one embodiment, the subject is a mammal. For example, in one embodiment, the subject is a human, non-human primate, dog, cat, horse, cow, goat, sheep, rabbit, pig, rat, or mouse. In one embodiment, the subject is a non-mammalian subject. For example, in one embodiment, the subject is a zebrafish, fruit fly, or roundworm.

Amino Acid and Nucleic Acid Sequences

Table 2 provides a summary of the amino acid and nucleic acid sequences.

TABLE 2

Summary of sequences

| SEQ ID NO | Type | Description |
|---|---|---|
| 1 | Amino Acid | PspCas13b |
| 2 | Amino Acid | PspCas13b Truncation |
| 3 | Amino Acid | AspCas13b |
| 4 | Amino Acid | AspCas13c |
| 5 | Amino Acid | BmaCas13a |
| 6 | Amino Acid | BzoCas13b |
| 7 | Amino Acid | CamCas13a |
| 8 | Amino Acid | CcaCas13b |
| 9 | Amino Acid | Cga2Cas13a |
| 10 | Amino Acid | CgaCas13a |
| 11 | Amino Acid | EbaCas13a |
| 12 | Amino Acid | EreCas13a |
| 13 | Amino Acid | EsCas13d |
| 14 | Amino Acid | FbrCas13b |
| 15 | Amino Acid | FnbCas13c |
| 16 | Amino Acid | FndCas13c |
| 17 | Amino Acid | FnfCas13c |
| 18 | Amino Acid | FnsCas13c |
| 19 | Amino Acid | FpeCas13c |
| 20 | Amino Acid | FulCas13c |
| 21 | Amino Acid | HheCas13a |
| 22 | Amino Acid | LbfCas13a |
| 23 | Amino Acid | LbmCas13a |
| 24 | Amino Acid | LbnCas13a |
| 25 | Amino Acid | LbuCas13a |
| 26 | Amino Acid | LseCas13a |
| 27 | Amino Acid | LshCas13a |
| 28 | Amino Acid | LspCas13a |
| 29 | Amino Acid | Lwa2cas13a |
| 30 | Amino Acid | LwaCas13a |
| 31 | Amino Acid | LweCas13a |
| 32 | Amino Acid | PauCas13b |
| 33 | Amino Acid | PbuCas13b |
| 34 | Amino Acid | PgiCas13b |
| 35 | Amino Acid | PguCas13b |
| 36 | Amino Acid | Pin2Cas13b |
| 37 | Amino Acid | Pin3Cas13b |
| 38 | Amino Acid | PinCas13b |
| 39 | Amino Acid | Pprcas13a |
| 40 | Amino Acid | PsaCas13b |
| 41 | Amino Acid | PsmCas13b |
| 42 | Amino Acid | RanCas13b |
| 43 | Amino Acid | RcdCas13a |
| 44 | Amino Acid | RcrCas13a |
| 45 | Amino Acid | RcsCas13a |
| 46 | Amino Acid | UrCas13d |
| 47 | Amino Acid | dPspCas13b |
| 48 | Amino Acid | dPspCas13b truncation |
| 49 | Amino Acid | Linker sequence 1 |
| 50 | Amino Acid | Linker sequence 2 |
| 51 | Amino Acid | Linker sequence 3 |
| 52 | Amino Acid | Linker sequence 4 |
| 53 | Amino Acid | Linker sequence 5 |
| 54 | Amino Acid | Linker sequence 6 |
| 55 | Amino Acid | Linker sequence 7 |
| 56 | Amino Acid | 3xFlag |
| 57 | Amino Acid | NES |
| 58 | Amino Acid | Nuclear Export Signal (NES) |
| 59 | Amino Acid | EIF4G1 (712-970) |
| 60 | Amino Acid | EIF4G2 (68-330) |
| 61 | Amino Acid | EIF4G3 (754-1003) |
| 62 | Amino Acid | PAIP1 (150-432) |
| 63 | Amino Acid | Yeast TIF4631 (597-871) |
| 64 | Amino Acid | Yeast TIF4632 (557-832) |
| 65 | Amino Acid | EIF4E |
| 66 | Amino Acid | EIF4E (W102L) CAP-binding mutant |

TABLE 2-continued

Summary of sequences

| SEQ ID NO | Type | Description |
|---|---|---|
| 67 | Amino Acid | EIF4G1 (rrc:565-1085) |
| 68 | Amino Acid | EIF4G1 |
| 69 | Amino Acid | EIF1 (human) |
| 70 | Amino Acid | EIF1AX (human) |
| 71 | Amino Acid | VPg (Feline calicivirus) |
| 72 | Amino Acid | VPg (MNV) |
| 73 | Amino Acid | VPg (Plum pox potyvirus) |
| 74 | Amino Acid | Nucleocapsid (N) Protein |
| 75 | Amino Acid | Nucleocapsid (N) Protein 1-187 |
| 76 | Amino Acid | Bacterial IF1 (*E. Coli*) |
| 77 | Amino Acid | Bacterial IF3 (*E. Coli*) |
| 78 | Amino Acid | Fusion Protein |
| 79 | Nucleic Acid | PspCas13b |
| 80 | Nucleic Acid | PspCas13b Truncation |
| 81 | Nucleic Acid | dPspCas13b |
| 82 | Nucleic Acid | dPspCas13b truncation |
| 83 | Nucleic Acid | Linker sequence 1 |
| 84 | Nucleic Acid | 3xFlag |
| 85 | Nucleic Acid | NES |
| 86 | Nucleic Acid | NES |
| 87 | Nucleic Acid | EIF4G1 (rrc:565-1085) |
| 88 | Nucleic Acid | EIF1 (human) |
| 89 | Nucleic Acid | EIF1AX (human) |
| 90 | Nucleic Acid | VPg (Feline calicivirus) |
| 91 | Nucleic Acid | VPg (MNV) |
| 92 | Nucleic Acid | VPg (Plum pox potyvirus) |
| 93 | Nucleic Acid | Nucleocapsid (N) Protein |
| 94 | Nucleic Acid | Nucleocapsid (N) Protein 1-187 |
| 95 | Nucleic Acid | dCas13-EIF4G1 |

EXPERIMENTAL EXAMPLES

The disclosure is further described in detail by reference to the following experimental examples. These examples are provided for purposes of illustration only and are not intended to be limiting unless otherwise specified. Thus, the disclosure should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present disclosure and practice the claimed methods. The following working examples therefore, specifically point out certain embodiments of the present disclosure, and are not to be construed as limiting in any way the remainder of the disclosure.

Example 1: Targeted Translation of RNA with CRISPR-Cas13 to Enhance Protein Synthesis The data presented herein demonstrates use of RNA binding CRISPR-Cas13 to induce the recruitment of the preinitiation complex on targeted mRNAs to enhance protein synthesis. This approach, termed synthescriptR herein, has the potential to enhance protein synthesis for therapeutic applications in human patients or for enhanced production of proteins in eukaryote cells for drug manufacturing.

Post-transcriptionally, mRNAs are exported to the cytoplasm, where they are first bound by the EIF4F complex, composed of EIF4A, EIF4E, and EIF4G. The large EIF4G protein serves as a scaffold which is required to recruit the 40S ribosome to the 5' CAP and initiate translation. In previous reports, a central fragment of this scaffold was identified as sufficient to act as a ribosome recruitment core (RRC) and in tethering experiments, sufficient to recruit 40S ribosome to mRNAs. To determine if mRNAs could be targeted for translation to enhance protein synthesis using CRISPR-Cas13, fusions between dPspCas13b and several eiFs were generated, including the RRC of EIF4G. An mRNA reporter was targeted that contained an open reading frame of superfolder GFP, which contains an additional 3' open reading frame of luciferase in the 3' UTR. This large 3' UTR containing the luciferase open reading frame results in normally low expression of sfGFP in cells. In cell-based assays, synthescriptR resulted in enhanced translation of the sfGFP-Luc transcripts when guided by a crRNA specific to the sfGFP-Luc mRNA, but not with a non-targeting crRNA (FIG. 1). Further, dPspCas13b fusions to eiFs EIF4E (CAP binding protein) or EIF3D did not show enhanced translation. Thus, synthescriptR has the potential to specifically enhance the translation of mRNAs targeted with crRNAs. This approach could be useful for enhancing the translation of therapeutically beneficial proteins in vivo, such as SERCA2 in heart failure to rescue cardiac contractility. Additionally, this approach could be used to increase the production of proteins in eukaryote cells, which can generate protein modifications not present in bacteria.

What is claimed is:

1. A fusion protein comprising:

a.) a CRISPR-associated (Cas) protein; and b.) a translation initiation factor (TIF) protein, wherein the TIF protein consists of a fragment of EIF4G as represented by SEQ ID NO: 67.

2. The fusion protein of claim 1, wherein the Cas protein is catalytically dead Cas13 (dCas13).

3. The fusion protein of claim 2, wherein dCas13 comprises a sequence selected from SEQ ID NOs: 47-48, or a variant thereof.

4. The fusion protein of claim 1, wherein the fusion protein further comprises a nuclear export signal (NES).

5. The fusion protein of claim 4, wherein the NES comprises an amino acid sequence selected from SEQ ID NOs: 57-58, or a variant thereof.

6. The fusion protein of claim 1, wherein the fusion protein comprises an amino acid sequence of SEQ ID NO: 78, or a variant thereof.

7. A nucleic acid molecule encoding a fusion protein of claim 1.

8. The nucleic acid molecule of claim 7, wherein the nucleic acid molecule comprises a nucleic acid sequence of SEQ ID NO: 95, or a variant thereof.

9. A method of enhancing the synthesis of a protein in a subject, the method comprising administering to the subject: a fusion protein comprising a CRISPR-associated (Cas) protein and an translation initiation factor (TIF) protein, wherein the TIF protein consists of a fragment of EIF4G as represented by SEQ ID NO: 67, or a nucleic acid molecule encoding the fusion protein, and a CRISPR guide RNA (crRNA) comprising a sequence complimentary to a target RNA sequence in a mRNA transcript, wherein the mRNA transcript is translated into the protein.

10. The method of claim 9 being either an in vitro or in vivo method.

* * * * *